United States Patent
Liu et al.

(10) Patent No.: US 11,466,318 B2
(45) Date of Patent: Oct. 11, 2022

(54) SINGLE FLUORESCENT DYE-BASED SEQUENCING METHOD

(71) Applicant: EGI TECH (SHEN ZHEN) CO., LIMITED, Shenzhen (CN)

(72) Inventors: Erkai Liu, Shenzhen (CN); Ao Chen, Shenzhen (CN); Wenwei Zhang, Shenzhen (CN); Xun Xu, Shenzhen (CN)

(73) Assignee: EGI TECH (SHEN ZHEN) CO., LIMITED, Guangdong (CN)

( * ) Notice: Subject to any disclaimer, the term of this patent is extended or adjusted under 35 U.S.C. 154(b) by 397 days.

(21) Appl. No.: 16/474,030

(22) PCT Filed: Dec. 27, 2017

(86) PCT No.: PCT/CN2017/118928
§ 371 (c)(1),
(2) Date: Jun. 26, 2019

(87) PCT Pub. No.: WO2018/121587
PCT Pub. Date: Jul. 5, 2018

(65) Prior Publication Data
US 2019/0330693 A1    Oct. 31, 2019

(30) Foreign Application Priority Data

Dec. 27, 2016 (WO) ................ PCT/CN2016/112402

(51) Int. Cl.
*C12Q 1/68* (2018.01)
*C12Q 1/6869* (2018.01)
*C12Q 1/6816* (2018.01)
*C12Q 1/6818* (2018.01)
*C12Q 1/6853* (2018.01)

(52) U.S. Cl.
CPC ......... *C12Q 1/6869* (2013.01); *C12Q 1/6816* (2013.01); *C12Q 1/6818* (2013.01); *C12Q 1/6853* (2013.01)

(58) Field of Classification Search
CPC .. C12Q 1/6869; C12Q 1/6816; C12Q 1/6818; C12Q 1/6853
See application file for complete search history.

(56) References Cited

U.S. PATENT DOCUMENTS 7,816,503 B2 * 10/2010 Milton .................. C12Q 1/686
536/26.6
2013/0079232 A1    3/2013 Kain et al.
2013/0189743 A1    7/2013 Balasubramanian et al.

FOREIGN PATENT DOCUMENTS

| CN | 1771336 A | 5/2006 |
|---|---|---|
| CN | 101120098 A | 2/2008 |
| CN | 101128601 A | 2/2008 |
| WO | WO 2004/072294 A2 | 8/2004 |
| WO | WO 2005/003375 A2 | 1/2005 |
| WO | WO 2005/123957 A2 | 12/2005 |
| WO | WO 2013191793 A1 | 12/2013 |
| WO | WO 2015/002789 A1 | 1/2015 |
| WO | WO 2016/154038 A1 | 9/2016 |

OTHER PUBLICATIONS

Tan et al., "Design and synthesis of fluorescence-labeled nucleotide with a cleavable azo linker for DNA sequencing", Chem. Commun., 2016, 52: 954-957.
Goodwin et al., "Coming of age: ten years of next-generation sequencing technologies", Nature Reviews | Genetics, 2016, 17: 333-351.
Zhou et al., "The Next-Generation Sequencing Technology: A Technology Review and Future Perspective", Science China: Life Sciences, 2010, 53(1): 44-57.

* cited by examiner

*Primary Examiner* — Jezia Riley
(74) *Attorney, Agent, or Firm* — James S. Keddie; Bozicevic, Field & Francis LLP

(57) ABSTRACT

Provided is a single fluorescent dye based sequencing method. Moreover, the present invention further provide modified nucleosides and nucleotides, and a kit comprising the nucleoside and/or nucleotide, particularly suitable for the sequencing method of the present invention. Additionally, the present invention further provides uses of the nucleoside, the nucleotide and the kit for sequencing.

6 Claims, 1 Drawing Sheet
Specification includes a Sequence Listing.

Photograph 1      Photograph 2

Photograph 1      Photograph 2

Photograph 1      Photograph 2

Photograph 1      Photograph 2

SINGLE FLUORESCENT DYE-BASED SEQUENCING METHOD

CROSS-REFERENCE TO RELATED APPLICATIONS

This application is a § 371 national phase of International Application No. PCT/CN2017/118928, filed on Dec. 27, 2017, which claims benefit of International Application No. PCT/CN2016/112402, filed on Dec. 27, 2016, which applications are incorporated by reference herein.

TECHNICAL FIELD

The present invention relates to the field of nucleic acid sequencing. In particular, the present invention provides a sequencing method based on a single fluorescent dye. Furthermore, the present invention also provides a modified nucleoside and nucleotide and a kit comprising the nucleoside and/or nucleotide, which are particularly suitable for use in the sequencing method of the invention. In addition, the present invention also provides the use of the nucleoside, nucleotide and kit for sequencing.

BACKGROUND TECHNIQUE

DNA sequencing technology includes the first-generation DNA sequencing technology represented by Sanger sequencing process and the second-generation DNA sequencing technology represented by Illumina Hiseq 2500, Roche 454, ABI Solid, BGISEQ-500 and the like. The Sanger sequencing process has the characteristics of simple experimental operation, intuitive and accurate results, short experimental period etc. It has wide application in the fields such as detection of clinical gene mutation and genotyping, which require high timeliness of detection results. However, the disadvantages of the Sanger sequencing process are small throughput and high cost, which limits its application in large-scale gene sequencing.

Compared with the first-generation DNA sequencing technology, the second-generation DNA sequencing technology has the characteristics of large sequencing throughput, low cost, high degree of automation and single molecule sequencing. Taking the sequencing technology of Hiseq 2500V2 as an example, an experimental procedure can generate 10-200 G base data, and the average cost per base is less than 1/1000 of the sequencing cost of the Sanger sequencing method; and the obtained sequencing result can be processed and analyzed directly by computer. Therefore, the second-generation DNA sequencing technology is very suitable for large-scale sequencing.

The second-generation DNA sequencing technology that has been developed mainly involves the techniques of sequencing by ligation (SBL) and sequencing by synthesis (SBS). Typical examples of these sequencing technologies include the SOLiD sequencing method developed by Applied Biosystems, the combined probe anchor ligation method (cPAL) developed by Complete Genomics, and the combined probe anchor synthesis method (cPAS) developed by BGI Gene, and Illumina sequencing process developed by Illumina company and Solexa technology company. Of these sequencing methods, Illumina and Complate Genomics use a method for detecting optical signals. In order to identify and distinguish four bases (A, T/U, C and G), it is usually necessary to use four fluorescent dyes to label these four bases respectively. In this case, in order to read the fluorescent signals carried by the respective bases, the sequencing device must be equipped with at least two monochromatic exciting light sources and at least two cameras, which results in a costly manufacturing and a large volume of the sequencing device.

It has been reported that the identification and discrimination of the four bases can be achieved by using two kinds of fluorescent dyes (Sara Goodwin, et. al. Nature Reviews Genetics 17, 333-351 (2016)). For example, the NextSeq sequencing system and the Mini-Seq sequencing system developed by Illumina Company use a sequencing method based on dual fluorescent dyes. In such sequencing methods, the identification and discrimination of the four bases are achieved by different combinations of two fluorescent dyes. For example, the four bases are distinguished by labeling base A with a first fluorescent dye, labeling base G with a second fluorescent dye, labeling base C with the first and the second fluorescent dyes simultaneously, with base T/U not labeled. In such sequencing methods, the sequencing device requires only one camera, but still requires at least 2 monochromatic exciting light sources. Therefore, the manufacturing cost of the sequencing apparatus using two kinds of fluorescent dyes is still relatively high, and the volume of the apparatus is still relatively large. In addition, the sequencing quality of the sequencing method based on dual fluorescent dyes is significantly reduced compared with the sequencing method using four fluorescent dyes, mainly because it is difficult to distinguish the dual-color fluorescence from the single-color fluorescence, and the accuracy is therefore reduced.

The three-generation sequencer of Oxford Nanopore is very small because of its sequencing principle. It can even be carried into space and then perform sequencing experiments. Compared with the huge second-generation sequencer, the third-generation sequencer demonstrates its superiority in this respect. However, the third-generation sequencer has a high error rate, which limits its application value. Therefore, new sequencing method needs to be developed to further reduce the manufacturing cost and the volume of the sequencing device and ensure high sequencing quality.

SUMMARY OF THE INVENTION

In order to solve the above technical problems, the inventors of the present application have developed a new sequencing method that uses one single fluorescent dye or two fluorescent dyes capable of emitting the same fluorescent signal under the same excitation condition to distinguish four bases. Thus, the sequencing apparatus for carrying out the sequencing method of the present invention requires only one exciting light source and one camera, thereby greatly reducing the manufacturing cost and the volume of the sequencing apparatus. For example, the sequencing device used for the sequencing method of the present invention can be conveniently carried around for immediate/on-site detection. Furthermore, the sequencing method of the present invention has a high sequencing quality comparable to that of sequencing methods based on four fluorescent dyes and can be used in various sequencing applications.

Thus, in one aspect, the invention provides a method of sequencing a nucleic acid molecule comprising the steps of:

(1) providing a nucleic acid molecule to be sequenced attached onto a support, or attaching a nucleic acid molecule to be sequenced onto a support;

(2) adding a primer for initiating a nucleotide polymerization, a polymerase for performing a nucleotide polymerization, and four compounds to form a reaction system containing a solution phase and a solid phase; wherein the four compounds are respectively derivatives of nucleotides A, (T/U), C and G, and have a base complementary pairing ability; and, each of the four compounds has a hydroxyl group (—OH) at 3' position of the ribose or deoxyribose which is protected by a protecting group; and, the first compound and the third compound are incapable of emitting a fluorescent signal (e.g., carrying no fluorophore), the second compound is capable of emitting a fluorescent signal (e.g., carrying a fluorophore), and the fourth compound does not emit a fluorescent signal or emits the same fluorescent signal as the second compound (e.g., carrying a fluorophore, wherein the fluorophore is the same as the fluorophore in the second compound; or the fluorophore has a structure different from, but has the same or substantially the same emission spectrum as the fluorophore in the second compound);

(3) annealing the primer to the nucleic acid molecule to be sequenced, wherein the primer serves as an initial growing nucleic acid strand, and together with the nucleic acid molecule to be sequenced, forms a duplex attached to the support;

(4) performing a nucleotide polymerization reaction using the polymerase under a condition allowing the polymerase to perform the nucleotide polymerization, thereby incorporating one of the four compounds at the 3' end of the growing nucleic acid strand;

(5)(i) if the fourth compound is capable of emitting the same fluorescent signal as the second compound, removing the solution phase of the reaction system in the previous step, retaining the duplex attached to the support, and detecting whether the duplex or the growing nucleic acid strand emits the fluorescent signal; or (ii) if the fourth compound does not emit a fluorescent signal, subjecting the duplex or the growing nucleic acid strand to a treatment in a reaction system comprising a solution phase and a solid phase, wherein the treatment has no effect on the first compound, the second compound and the third compound, and enables the fourth compound to emit the same fluorescent signal as the second compound (e.g., by modifying the fourth compound to carry a fluorophore, wherein the fluorophore is the same as the fluorophore of second compound, or has the same emission spectrum as the fluorophore of the second compound); thereafter, removing the solution phase of the reaction system in the previous step, retaining the duplex attached to the support, and detecting whether the duplex or the growing nucleic acid strand emits the fluorescent signal;

(6) subjecting the duplex or the growing nucleic acid strand to a treatment in a reaction system containing a solution phase and a solid phase, wherein the treatment has no effect on the first compound and the second compound, and enables the third compound to emit the same fluorescent signal as the second compound (for example, by modifying the third compound to carry a fluorophore which is the same to the fluorophore of the second compound or has the same emission spectrum as the fluorophore of the second compound) and is capable of removing the fluorescent signal of the fourth compound (e.g., removing the fluorophore on the fourth compound, or quenching the fluorescent signal emitted by the fluorophore on the fourth compound); and (7) removing the solution phase of the reaction system in the previous step, retaining the duplex attached to the support, and detecting whether the duplex or the growing nucleic acid strand emits the fluorescent signal.

In some preferred embodiments, the method further comprises the steps of:

(8) subjecting the duplex or grown nucleic acid strand in the previous step to a treatment in a reaction system containing a solution phase and a solid phase, wherein the treatment is capable of removing the protecting group at the 3' position of the ribose or deoxyribose in the compound incorporated at the 3' end of the growing nucleic acid strand, and removing the fluorescent signal on the duplex or growing nucleic acid strand, if present; and (9) removing the solution phase of the reaction system in the previous step;

(10) adding a polymerase for performing a nucleotide polymerization reaction, and said four compounds to form a reaction system containing a solution phase and a solid phase, and then conducting steps (4) to (7).

Optionally, the method further comprises the following step (11):

(11) repeating steps (8)-(10) one or more times.

In the method of the present invention, if, in step (4), the first compound is incorporated at the 3' end of the growing nucleic acid strand, then since the first compound itself does not carry a fluorophore, and is not affected by the treatment in step (6), no fluorescent signal will be detected in steps (5) and (7).

If, in step (4), the second compound is incorporated at the 3' end of the growing nucleic acid strand, then since the second compound itself carries a fluorophore and is not affected by the treatment in step (6), the fluorescent signal will be detected in both steps (5) and (7).

If, in step (4), the third compound is incorporated at the 3' end of the growing nucleic acid strand, then (i) since the third compound itself does not carry a fluorophore, it will not be detected in step (5); and (ii) since the third compound has performed the treatment of step (6) and loses its fluorescent signal, a fluorescent signal will be detected in step (7).

If, in step (4), the fourth compound is incorporated at the 3' end of the growing nucleic acid strand, then, (i) since the fourth compound carries a fluorophore itself or carries a fluorophore after the treatment in step (5), a fluorescent signal will be detected in step (5); and (ii) since the fourth compound loses its fluorescent signal due to the treatment of step (6), no fluorescent signal will be detected in step (7).

Therefore, in some preferred embodiments, the type of the compound incorporated at the 3' end of the growing nucleic acid strand in step (4) is determined according to the detection results of steps (5) and (7), wherein, when both of the detection results of steps (5) and (7) are that the duplex does not emit the fluorescent signal, it is determined that the compound incorporated at the 3' end of the growing nucleic acid strand in step (4) is the first compound;

when both of the detection results of steps (5) and (7) are that the duplex emits the fluorescent signal, it is determined that the compound incorporated at the 3' end of the growing nucleic acid strand in step (4) is the second compound;

when the detection result of the step (5) is that the duplex does not emit the fluorescent signal, and the detection result of the step (7) is that the duplex emits the fluorescent signal, it is determined that the compound incorporated at the 3' end of the growing nucleic acid strand in step (4) is the third compound;

when the detection result of the step (5) is that the duplex signal emits the fluorescent signal, and the detection result of the step (7) is that the duplex does not emit the fluorescent signal, it is determined that the compound incorporated at the 3' end of the growing nucleic acid strand in step (4) is the fourth compound;

optionally, based on the base complementary pairing principle, the type of base at the corresponding position of the nucleic acid molecule to be sequenced is determined according to the type of the compound incorporated at the 3' end of the growing nucleic acid strand in step (4).

In some exemplary embodiments, the method of the present invention comprises the steps of:

(1) providing a nucleic acid molecule to be sequenced attached onto a support, or attaching a nucleic acid molecule to be sequenced onto a support;

(2) adding a primer for initiating a nucleotide polymerization, a polymerase for performing the nucleotide polymerization, and the first, second, third and fourth compounds which have structures of formula (I), formula (II), formula (III), and formula (IV), respectively, to form a reaction system comprising a solution phase and a solid phase:

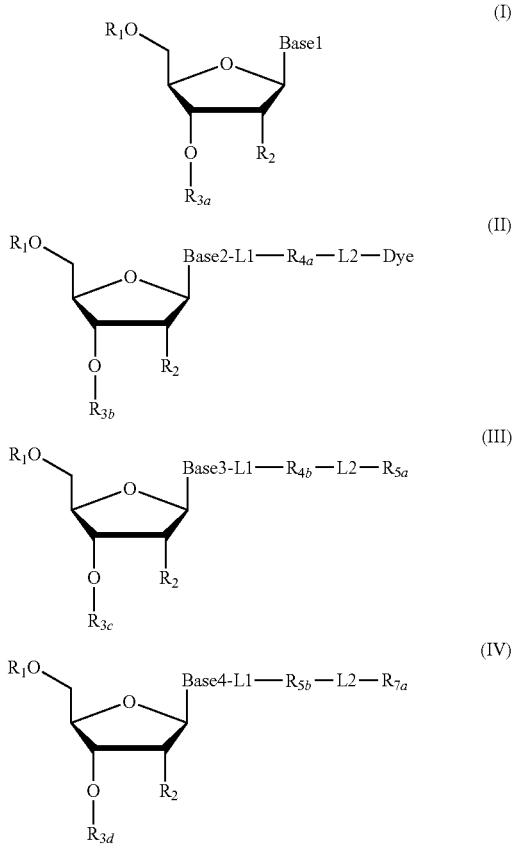

wherein, Base1, Base2, Base3, and Base4 represent 4 different bases, and are selected from A, (T/U), C, and G;

$R_1$ is independently selected from —H, monophosphate group (—$PO_3H_2$), diphosphate group (—$PO_3H$—$PO_3H_2$), triphosphate group (—$PO_3H$—$PO_3H$—$PO_3H_2$) and tetraphosphate group (—$PO_3H$—$PO_3H$—$PO_3H$—$PO_3H_2$);

$R_2$ is independently selected from —H and —OH;

$R_{3a}$, $R_{3b}$, $R_{3c}$, $R_{3d}$, $R_{4a}$, $R_{4b}$, and $R_{5b}$ are independently reactive groups capable of performing a bioorthogonal cleavage reaction;

$R_{5a}$ is a reactive group capable of performing a first bioorthogonal ligation reaction;

L1 is independently a linking group or absent;

L2 is independently a linking group or absent;

Dye represents a fluorophore capable of emitting a fluorescent signal;

$R_{7a}$ is a fluorophore capable of emitting a fluorescent signal ($Dye_1$), or a reactive group capable of performing a second bioorthogonal ligation reaction, or one member of a binding pair;

and, Dye and $Dye_1$ have the same structure, or have different structures but have the same or substantially the same emission spectrum;

optionally, between $R_{5b}$ and $R_{7a}$, there is a reactive group $R_8$ capable of performing a third bioorthogonal ligation reaction;

(3) annealing the primer to the nucleic acid molecule to be sequenced, wherein the primer serves as an initial growing nucleic acid strand, and forms a duplex attached to the support together with the nucleic acid molecule to be sequenced;

(4) performing a nucleotide polymerization reaction using the polymerase under a condition allowing the polymerase to perform the nucleotide polymerization, thereby incorporating one of the four compounds at the 3' end of the growing nucleic acid strand;

(5)(i) if the fourth compound is capable of emitting the same fluorescent signal as the second compound, and $R_{7a}$ is $Dye_1$, removing the solution phase of the reaction system of the previous step, retaining the duplex attached to the support, and detecting whether the duplex or the growing nucleic acid strand emits the fluorescent signal; or (ii) if the fourth compound does not emit a fluorescent signal, and $R_{7a}$ is a reactive group capable of performing the second bioorthogonal ligation reaction or is one member of the binding pair, subjecting the duplex or the growing nucleic acid strand to a treatment in a reaction system containing a solution phase and a solid phase, wherein the treatment has no effect on the first compound, the second compound and the third compound, and enables $R_{7a}$ in the fourth compound to specifically interact with/bind to, or perform the second bioorthogonal ligation reaction with an agent (e.g., the other member of the binding pair, or a compound which is capable of performing the second bioorthogonal ligation reaction with $R_{7a}$) carrying a fluorophore (for example, a fluorophore having the same structure as the fluorophore of the second compound, or a fluorophore having the same emission spectrum as the fluorophore of the second compound); thereafter, removing the solution phase of the reaction system of the previous step, retaining the duplex attached to the support, and detecting whether the duplex or the growing nucleic acid strand emits the fluorescent signal;

wherein the other member of the binding pair carrying the fluorophore has the structure: $R_{7b}$-L-$Dye_1$; wherein $R_{7b}$ is the other member of the binding pair, L is independently a linking group or absent; $Dye_1$ represents a fluorophore that is capable of emitting a fluorescent signal, and has the same structure as Dye, or has a different structure but the same emission spectrum as Dye; or the compound capable of performing the second bioorthogonal ligation reaction with $R_{7a}$ and carrying a fluorophore has the following structure: $R_{7b}$-L-$Dye_1$; wherein $R_{7b}$ is a group capable of performing the second bioorthogonal ligation reaction with $R_{7a}$, L is independently a linking group or absent; $Dye_1$ represents a fluorophore capable of emitting a fluorescent signal, and has the same structure as Dye, or has a different structure but the same emission spectrum as Dye;

(6) subjecting the duplex or the growing nucleic acid strand to a treatment in a reaction system containing a solution phase and a solid phase, wherein the treatment has no effect on the first compound and the second compound, and enables $R_{5a}$ in the third compound to perform the first bioorthogonal ligation reaction with an agent carrying a fluorophore (e.g., a fluorophore having the same structure as the fluorophore of the second compound, or a fluorophore having a structure different from but having the same emission spectrum as the fluorophore of the second compound), thereby the fluorophore in the agent is introduced into the third compound and make the third compound to emit a fluorescent signal; and said treatment (i) enables $R_{5b}$ in the fourth compound to perform the bioorthogonal cleavage reaction, thereby removing the fluorophore in the fourth compound, or (ii) enables $R_8$ in the fourth compound to react with a compound carrying a quenching group to perform a third orthogonal ligation reaction, thereby quenching the fluorescent signal emitted by the fluorophore Dye1 in the fourth compound; and (7) removing the solution phase of the reaction system in the previous step, retaining the duplex attached to the support, and detecting whether the duplex or the growing nucleic acid strand emits the fluorescent signal.

In some preferred embodiments, the method further comprises the steps of:

(8) subjecting the duplex or the growing nucleic acid strand in the previous step to a treatment in a reaction system containing a solution phase and a solid phase, wherein the treatment enables $R_{3a}$, $R_{3b}$, $R_{3c}$, $R_{3d}$, $R_{4a}$ and $R_{4b}$ to perform the bioorthogonal cleavage reaction, thereby allowing the compound incorporated at the 3' end of the growing nucleic acid strand to have a free hydroxyl group at the 3' position of the ribose or deoxyribose (in other words, converting —$OR_{3a}$, —$OR_{3b}$, —$OR_{3c}$ or —$OR_{3d}$ (if present) into a free hydroxyl group), and, removing the fluorophore on the duplex or the growing nucleic acid strand (in other words, removing the fluorophore attached to $R_{4a}$ or $R_{4b}$), if present;

(9) removing the solution phase of the reaction system in the previous step;

(10) adding a polymerase for performing a nucleotide polymerization, and the first compound, the second compound, the third compound, and the fourth compound, thereby forming a reaction system containing a solution phase and a solid phase, and then performing the steps (4)-(7).

In some preferred embodiments, the method further comprises the step of:

(11) repeating steps (8)-(10) one or more times.

In some exemplary embodiments, the method of the present invention comprises the steps of:

(1) providing a nucleic acid molecule to be sequenced attached onto a support, or attaching the nucleic acid molecule to be sequenced onto a support;

(2) adding a primer for initiating a nucleotide polymerization, a polymerase for performing the nucleotide polymerization, and the first, second, third and fourth compounds having structures of formula (I), formula (II), formula (III), and formula (IV), respectively, to form a reaction system comprising a solution phase and a solid phase:

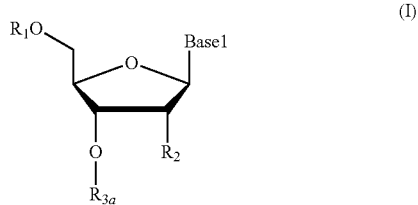

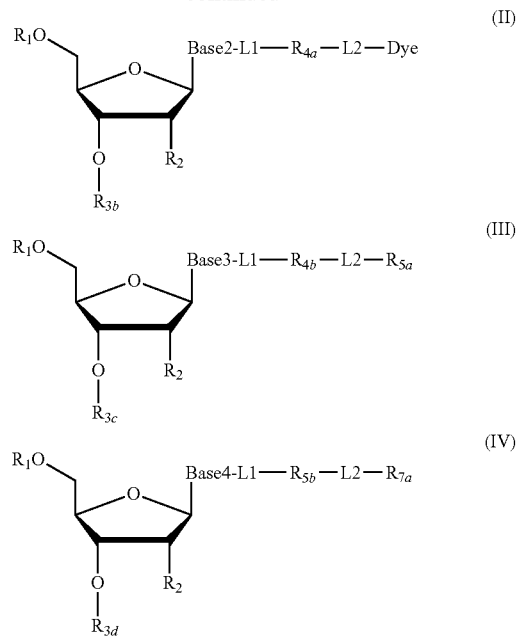

wherein, Base1, Base2, Base3, and Base4 represent 4 different bases, and are selected from A, (T/U), C, and G;

$R_1$ is independently selected from —H, monophosphate group (—$PO_3H_2$), diphosphate group (—$PO_3H$—$PO_3H_2$), triphosphate group (—$PO_3H$—$PO_3H$—$PO_3H_2$) and tetraphosphate group (—$PO_3H$—$PO_3H$—$PO_3H$—$PO_3H_2$);

$R_2$ is independently selected from —H and —OH;

$R_{3a}$, $R_{3b}$, $R_{3c}$, $R_{3d}$, $R_{4a}$, $R_{4b}$, and $R_{4c}$ are independently reactive groups capable of performing a bioorthogonal cleavage reaction;

$R_{5a}$ is one member of the first binding pair;

$R_{6a}$ is (i) one member of the second binding pair and is one member of the third binding pair; or is (ii) only one member of the third binding pair; and, $R_{6a}$ is $Dye_1$, or $R_{6a}$ is also linked with -L3-$Dye_1$;

L1 is independently a linking group or absent;

L2 is independently a linking group or absent;

L3 is a linking group or absent;

Dye and $Dye_1$ represent fluorophores capable of emitting a fluorescent signal; and, both of them have the same structure, or have different structures but have the same or substantially the same emission spectrum;

optionally, there is a reactive group $R_8$ capable of performing a bioorthogonal ligation reaction between $R_{4c}$ and $R_{6a}$;

(3) annealing the primer to the nucleic acid molecule to be sequenced, wherein the primer serves as an initial growing nucleic acid strand, and forms a duplex attached to the support together with the nucleic acid molecule to be sequenced;

(4) performing a nucleotide polymerization reaction using the polymerase under a condition allowing the polymerase to perform the nucleotide polymerization, thereby incorporating one of the four compounds at the 3' end of the growing nucleic acid strand;

(5) (i) if the fourth compound does not emit a fluorescent signal, $R_{6a}$ is one member of the second binding pair, and meanwhile, it is one member of the third binding pair, subjecting the duplex or the growing nucleic acid strand to a treatment in reaction system comprising a solution phase and a solid phase, wherein the treatment has no effect on the first compound, second compound and third compound, and enables $R_{6a}$ in the fourth compound to specifically interact with/bind to an agent (for example, the other member of the second binding pair) carrying a fluorophore (for example, a fluorophore having the same structure as the fluorophore of the second compound, or a fluorophore having a different structure from, but has the same or substantially the same emission spectrum as the fluorophore of the second compound); thereafter, removing the solution phase of the reaction system in the previous step, retaining the duplex attached to the support, and detecting whether the duplex or the growing nucleic acid strand emits the fluorescent signal;

the other member of the second binding pair carrying the fluorophore has the following structure: $R_{6b}$-L4-$Dye_2$; wherein $R_{6b}$ is the other member of the second binding pair, and L4 is independently a linking group or is absent; $Dye_2$ represents a fluorophore which is capable of emitting a fluorescent signal and has the same structure as Dye, or has a different structure from, but has the same or substantially the same emission spectrum as Dye; or (ii) if the fourth compound is capable of emitting the same fluorescent signal as the second compound, $R_{6a}$ is only one member of the third binding pair, and $R_{6a}$ is $Dye_1$ or is also connected to -L3-$Dye_1$, removing the solution phase of the reaction system in the previous step, retaining the duplex attached to the support, and detecting whether the duplex or the growing nucleic acid strand emits the fluorescent signal;

(6) subjecting the duplex or the growing nucleic acid strand to a treatment in a reaction system containing a solution phase and a solid phase, wherein the treatment has no effect on the first compound and the second compound, and enables $R_{5a}$ in the third compound specifically bind to the other member of the first binding pair carrying a fluorophore, introducing the fluorophore into the third compound to make the third compound to emit a fluorescent signal; and said treatment (i) is capable of making $R_{6a}$ in the fourth compound specifically bind to the other member of the third binding pair carrying a quenching group to quench the fluorescent signal emitted by the fluorophore $Dye_1$ or $Dye_2$ in the fourth compound, or (ii) is capable of making $R_8$ in the fourth compound perform an orthogonal ligation reaction with the compound carrying a quenching group to quench the fluorescent signal emitted by the fluorophore $Dye_1$ or $Dye_2$ in the fourth compound, the other member of the first binding pair carrying a fluorophore has the structure: $R_{5b}$-L5-$Dye_3$; wherein $R_{5b}$ is the other member of the first binding pair, and L5 is independently a linking group or absent; $Dye_3$ represents a fluorophore capable of emitting a fluorescent signal, and has the same structure as the fluorophore in the second compound, or has a different structure but the same emission spectrum; and, the other member of the third binding pair carrying the quenching group has the structure: $R_{6c}$-L6-Que; wherein $R_{6c}$ is the other member of the second binding pair, and L6 is independently a linking group or absent; Que represents a quenching group capable of quenching the fluorescent signal emitted by $Dye_1$ or $Dye_2$; and (7) removing the solution phase of the reaction system in the previous step, retaining the duplex attached to the support, and detecting whether the duplex or the growing nucleic acid strand emits the fluorescent signal.

In some preferred embodiments, the method further comprises the steps of:

(8) subjecting the duplex or the growing nucleic acid strand in the previous step to a treatment in a reaction system containing a solution phase and a solid phase, wherein the treatment enables $R_{3a}$, $R_{3b}$, $R_{3c}$, $R_{3d}$, $R_{4a}$, $R_{4b}$, or $R_{4c}$ to perform the bioorthogonal cleavage reaction, making the compound incorporated at the 3' end of the growing nucleic acid strand has a free hydroxyl group at the 3' position of the ribose or deoxyribose (in other words, converting —$OR_{3a}$, —$OR_{3b}$, —$OR_{3c}$ or —$OR_{3d}$ (if present) into free hydroxyl group) and removing the fluorophore on the duplex or the growing nucleic acid strand (in other words, removing the fluorophore attached to $R_{4a}$, $R_{4b}$ or $R_{4c}$), if present;

(9) removing the solution phase of the reaction system in the previous step;

(10) adding a polymerase for performing a nucleotide polymerization, and the first compound, the second compound, the third compound, and the fourth compound, thereby forming a reaction system containing a solution phase and a solid phase, and then performing the steps (4)-(7).

In some preferred embodiments, the method further comprises the steps of:

(11) repeating steps (8)-(10) one or more times.

In some preferred embodiments, the method of the invention comprises the steps of:

(1) providing a nucleic acid molecule to be sequenced attached onto a support, or attaching a nucleic acid molecule to be sequenced onto a support;

(2) adding a primer for initiating a nucleotide polymerization, a polymerase for performing the nucleotide polymerization, and the first compound, the second compound, the third compound and the fourth compound having structures of formula (I), formula (II), formula (III), and formula (IV), respectively to form a reaction system comprising a solution phase and a solid phase:

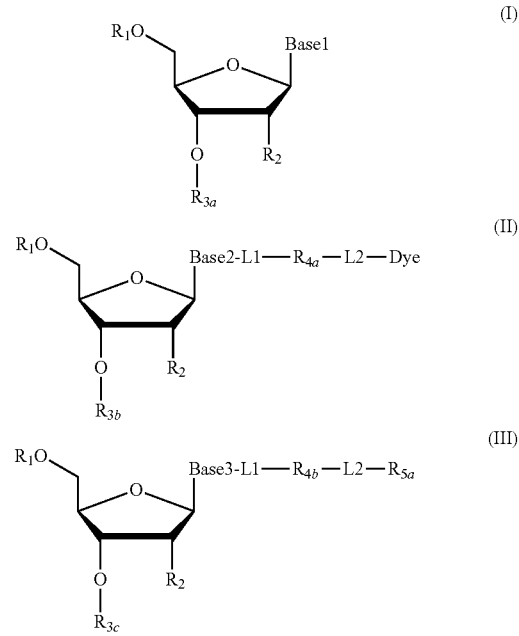

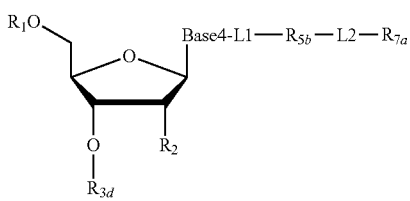

(IV)

wherein, Base1, Base2, Base3, and Base4 represent 4 different bases, and are selected from A, (T/U), C, and G;

$R_1$ is independently selected from —H, monophosphate group (—PO$_3$H$_2$), diphosphate group (—PO$_3$H—PO$_3$H$_2$), triphosphate group (—PO$_3$H—PO$_3$H—PO$_3$H$_2$) and tetraphosphate group (—PO$_3$H—PO$_3$H—PO$_3$H—PO$_3$H$_2$);

$R_2$ is independently selected from —H and —OH;

$R_{3a}$, $R_{3b}$, $R_{3c}$, $R_{3d}$, $R_{4a}$, $R_{4b}$, and $R_{4c}$ are independently reactive groups capable of performing a bioorthogonal cleavage reaction;

$R_{5a}$ is a reactive group capable of performing a first bioorthogonal ligation reaction;

$R_{6a}$ is (i) one member of the first binding pair and is one member of the second binding pair; or is (ii) only one member of the second binding pair, and $R_{6a}$ is Dye$_1$, or $R_{6a}$ is also linked with -L3-Dye$_1$;

L1 is independently a linking group or absent;

L2 is independently a linking group or absent;

L3 is a linking group or absent;

Dye represents a fluorophore capable of emitting a fluorescent signal; Dye and Dye$_1$ have the same structure, or have different structures but have the same or substantially the same emission spectrum;

optionally, there is a reactive group $R_8$ capable of performing the second bioorthogonal ligation reaction between $R_{4c}$ and $R_{6a}$;

(3) annealing the primer to the nucleic acid molecule to be sequenced, wherein the primer serves as an initial growing nucleic acid strand, and forms a duplex attached to the support together with the nucleic acid molecule to be sequenced;

(4) performing a nucleotide polymerization reaction using the polymerase under a condition allowing the polymerase to perform the nucleotide polymerization, thereby incorporating one of the four compounds at the 3' end of the growing nucleic acid strand;

(5) (i) if the fourth compound does not emit a fluorescent signal, $R_{6a}$ is one member of the first binding pair and is one member of the second binding pair, subjecting the duplex or the growing nucleic acid strand to a treatment in a reaction system comprising a solution phase and a solid phase, wherein the treatment has no effect on the first compound, the second compound and the third compound, and enables $R_{6a}$ in the fourth compound to specifically interact with/bind to an agent (for example, the other member of the first binding pair) carrying a fluorophore (for example, a fluorophore having the same structure as the fluorophore of the second compound, or a fluorophore that has a different structure from but has the same or substantially the same emission spectrum as the fluorophore of the second compound); thereafter, removing the solution phase of the reaction system in the previous step, retaining the duplex attached to the support, and detecting whether the duplex or the growing nucleic acid strand emits the fluorescent signal;

the other member of the first binding pair carrying the fluorophore has the structure: $R_{6b}$-L4-Dye$_2$; wherein $R_{6b}$ is the other member of the first binding pair, and L4 is independently a linking group or absent; Dye$_2$ represents a fluorophore capable of emitting a fluorescent signal and has the same structure as Dye, or having a different structure from Dye but having the same or substantially the same emission spectrum as Dye; or (ii) if the fourth compound does not emit the same fluorescent signal as the second compound, $R_{6a}$ is only one member of the second binding pair, and, $R_{6a}$ is Dye$_1$, or $R_{6a}$ is also linked with -L3-Dye$_1$, removing the solution phase of the reaction system in the previous step, retaining the duplex attached to the support, and detecting whether the duplex or the growing nucleic acid strand emits the fluorescent signal;

(6) subjecting the duplex or the growing nucleic acid strand to a treatment in a reaction system containing a solution phase and a solid phase, wherein the treatment has no effect on the first compound and the second compound, and enables $R_{5a}$ in the third compound to perform the first bioorthogonal ligation reaction with an agent carrying a fluorophore (e.g., the same fluorophore as the fluorophore of the second compound, or a fluorophore having a emission spectrum the same or substantially the same as the emission spectrum of the fluorophore of the second compound), thereby introducing a fluorophore in the agent into the third compound to make the third compound emit a fluorescent signal; and said treatment (i) is capable of making $R_{6a}$ in the fourth compound specifically bind to the other member of a second binding pair carrying a quenching group, thereby quenching the fluorescent signal emitted by the fluorophore Dye$_1$ or Dye$_2$ in the fourth compound, or (ii) is capable of making $R_8$ in the fourth compound perform the second orthogonal ligation reaction with a compound carrying a quenching group, thereby quenching the fluorescent signal emitted by the fluorophore Dye$_1$ or Dye$_2$ in the fourth compound; wherein, the other member of the second binding pair carrying the quenching group has the structure: $R_{6c}$-L'-Que; wherein, $R_{6c}$ is the other member of the second binding pair, L' is independently a linking group or absent; Que represents a quenching group capable of quenching the fluorescent signal emitted by Dye$_1$ or Dye$_2$; and (7) removing the solution phase of the reaction system in the previous step, retaining the duplex attached to the support, and detecting whether the duplex or the growing nucleic acid strand emits the fluorescent signal.

In some preferred embodiments, the method further comprises the steps of:

(8) subjecting the duplex or the growing nucleic acid strand in the previous step to a treatment in a reaction system containing a solution phase and a solid phase, wherein the treatment enables $R_{3a}$, $R_{3b}$, $R_{3c}$, $R_{3d}$, $R_{4a}$, $R_{4b}$, $R_{4c}$ to perform the bioorthogonal cleavage reaction, thereby allowing the compound incorporated at the 3' end of the growing nucleic acid strand to have a free hydroxyl group at the 3' position of the ribose or deoxyribose (in other words, converting —OR$_{3a}$, —OR$_{3b}$, —OR$_{3c}$ or —OR$_{3d}$ (if present) into free hydroxyl group) and removing the fluorophore on the duplex or the growing nucleic acid strand (in other words, removing the fluorophore attached to $R_{4a}$, $R_{4b}$ or $R_{4c}$), if present;

(9) removing the solution phase of the reaction system in the previous step;

(10) adding a polymerase for performing a nucleotide polymerization, and the first compound, the second compound, the third compound, and the fourth compound, thereby forming a reaction system containing a solution phase and a solid phase, and then performing the steps of (4)-(7).

In some preferred embodiments, the method further comprises the steps of:

(11) repeating steps (8)-(10) one or more times.

In some preferred embodiments, the method of the invention comprises the steps of:

(1) providing a nucleic acid molecule to be sequenced attached onto a support, or attaching a nucleic acid molecule to be sequenced onto a support;

(2) adding a primer for initiating a nucleotide polymerization, a polymerase for performing the nucleotide polymerization, and the first compound, the second compound, the third compound and the fourth compound having the structures of formula (I), formula (II), formula (III), and formula (IV), respectively, thereby to form a reaction system comprising a solution phase and a solid phase:

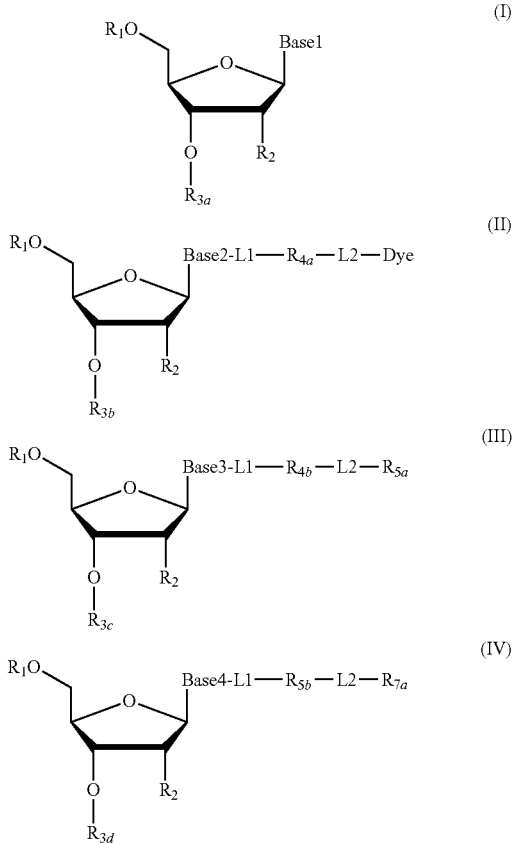

wherein, Base1, Base2, Base3, and Base4 represent 4 different bases, and are selected from A, (T/U), C, and G;

$R_1$ is independently selected from —H, a monophosphate group (—$PO_3H_2$), a diphosphate group (—$PO_3H$—$PO_3H_2$), a triphosphate group (—$PO_3H$—$PO_3H$—$PO_3H_2$) and a tetraphosphate group (—$PO_3H$—$PO_3H$—$PO_3H$—$PO_3H_2$);

$R_2$ is independently selected from —H and —OH;

$R_{3a}$, $R_{3b}$, $R_{3c}$, $R_{3d}$, $R_{4a}$, $R_{4b}$, and $R_{4c}$ are independently reactive groups capable of performing a bioorthogonal cleavage reaction;

$R_{5a}$ is one member of the first binding pair;

$R_{6a}$ is a fluorophore capable of emitting a fluorescent signal ($Dye_1$), a reactive group capable of performing a first bioorthogonal ligation reaction, and/or one member of the second binding pair;

L1 are independently a linking group or absent;

L2 are independently a linking group or absent;

Dye and $Dye_1$ represent fluorophores capable of emitting a fluorescent signal; and, Dye and $Dye_1$ have the same structure, or have different structures but have the same or substantially the same emission spectrum;

optionally, there is a reactive group $R_8$ capable of performing the second bioorthogonal ligation reaction between $R_{4c}$ and $R_{6a}$;

(3) annealing the primer to the nucleic acid molecule to be sequenced, wherein the primer serves as an initial growing nucleic acid strand, and forms a duplex attached to the support together with the nucleic acid molecule to be sequenced;

(4) performing a nucleotide polymerization reaction using the polymerase under a condition allowing the polymerase to perform the nucleotide polymerization, thereby incorporating one of the four compounds at the 3' end of the growing nucleic acid strand;

(5)(i) if the fourth compound is capable of emitting the same fluorescent signal as the second compound, and $R_{6a}$ is $Dye_1$, removing the solution phase of the reaction system of the previous step, retaining the duplex attached to the support, and detecting whether the chain or the growing nucleic acid strand emits the fluorescent signal; or (ii) if the fourth compound does not emit a fluorescent signal, and $R_{6a}$ is a reactive group capable of performing the first bioorthogonal ligation reaction or is one member of the second binding pair, subjecting the duplex or the growing nucleic acid to a treatment in a reaction system containing a solution phase and a solid phase, wherein the treatment has no effect on the first compound, the second compound and the third compound, and enables $R_{6a}$ in the fourth compound to specifically interact with/bind to, or perform the first bioorthogonal ligation reaction with an agent (for example, the other member of the second binding pair, or a compound capable of performing the first bioorthogonal ligation reaction with $R_{6a}$) carrying a fluorophore (for example, a fluorophore having the same structure as the fluorophore of the second compound or a fluorophore having an emission spectrum the same or substantially the same to the emission spectrum of the fluorophore of the second compound); thereafter, removing the solution phase of the reaction system in the previous step, retaining the duplex attached to the support, and detecting whether the duplex or the growing nucleic acid strand emits the fluorescent signal;

the other member of the second binding pair carrying the fluorophore has the following structure: $R_{6b}$-L'-$Dye_1$; wherein $R_{6b}$ is the other member of the second binding pair, L' is independently a linking group or absent; $Dye_1$ represents a fluorophore capable of emitting a fluorescent signal and has the same structure as Dye, or has a different structure from Dye but has the same or substantially the same emission spectrum as Dye; or the compound capable of performing the first bioorthogonal ligation reaction with $R_{6a}$ and carrying a fluorophore has the following structure: $R_{6b}$-L'-$Dye_1$; wherein, $R_{6b}$ is a group capable of performing the first bioorthogonal ligation reaction with $R_{6a}$, L' is independently a linking group or absent; $Dye_1$ represents a fluorophore capable of emitting a fluorescent signal, and has the same structure as Dye, or has a different structure from Dye but has the same or substantially the same emission spectrum as Dye;

(6) subjecting the duplex or the growing nucleic acid strand to a treatment in a reaction system containing a solution phase and a solid phase, wherein the treatment has no effect on the first compound and the second compound, and enables $R_{5a}$ in the third compound to specifically bind to the other member of the first binding pair carrying a fluorophore to introduce the fluorophore into the third compound to make the third compound to emit a fluorescent signal; wherein the treatment (i) enables $R_{4c}$ in the fourth compound to perform the bioorthogonal cleavage reaction to remove the fluorophore in the fourth compound, or (ii) enables $R_8$ in the fourth compound to perform the second orthogonal ligation reaction with a compound carrying a quenching group, thereby quenching the fluorescent signal emitted by the fluorophore $Dye_1$ in the fourth compound; wherein, the other member of the first binding pair carrying a fluorophore has the following structure: $R_{5b}$-L-$Dye_2$; wherein $R_{5b}$ is the other member of the first binding pair, L is independently a linking group or absent; $Dye_2$ represents a fluorophore capable of emitting a fluorescent signal, wherein the fluorophore is the same as the fluorophore of the second compound, or has an emission spectrum the same or substantially the same as the fluorophore of the second compound; and (7) removing the solution phase of the reaction system in the previous step, retaining the duplex attached to the support, and detecting whether the duplex or the growing nucleic acid strand emits the fluorescent signal.

In some preferred embodiments, the method further comprises the steps of:

(8) subjecting the duplex or the growing nucleic acid strand in the previous step to a treatment in a reaction system containing a solution phase and a solid phase, wherein the treatment enables $R_{3a}$, $R_{3b}$, $R_{3c}$, $R_{3d}$, $R_{4a}$ and $R_{4b}$ to perform the bioorthogonal cleavage reaction, thereby allowing the compound incorporated at the 3' end of the growing nucleic acid strand to have a free hydroxyl group at the 3' position of the ribose or deoxyribose (in other words, converting —$OR_{3a}$, —$OR_{3b}$, —$OR_{3c}$ or —$OR_{3d}$ (if present) into a free hydroxyl group) and removing the fluorophore on the duplex or the growing nucleic acid strand (in other words, removing the fluorophore attached to $R_{4a}$ or $R_{4b}$), if present;

(9) removing the solution phase of the reaction system in the previous step;

(10) adding a polymerase for performing a nucleotide polymerization, and the first compound, the second compound, the third compound, and the fourth compound, thereby forming a reaction system containing a solution phase and a solid phase, and then performing the steps (4)-(7).

In some preferred embodiments, the method further comprises the steps of:

(11) repeating steps (8)-(10) one or more times.

In some exemplary embodiments, the method of the present invention comprises the steps of:

(1) providing a nucleic acid molecule to be sequenced attached onto a support, or attaching a nucleic acid molecule to be sequenced onto a support;

(2) adding a primer for initiating a nucleotide polymerization, a polymerase for performing a nucleotide polymerization, and the first, second, third and fourth compounds having the structures of formula (I), formula (II), formula (III), and formula (IV), respectively, to form a reaction system containing a solution phase and a solid phase:

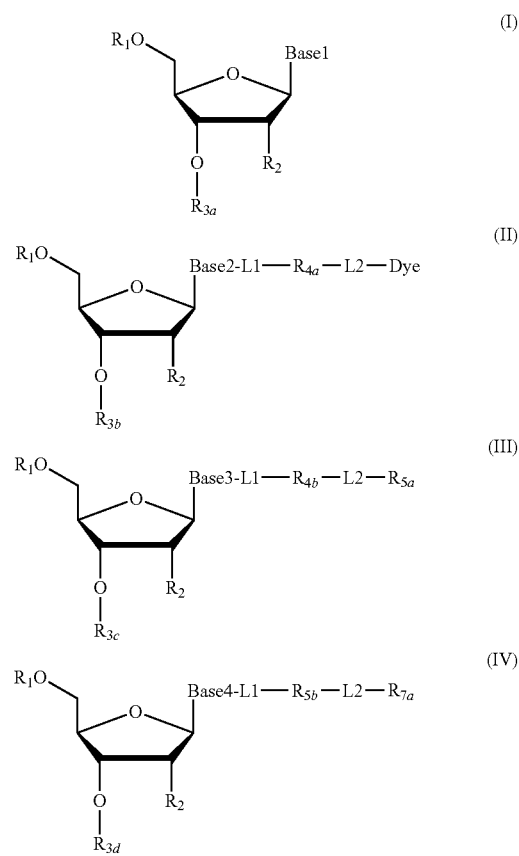

wherein, Base1, Base2, Base3, and Base4 represent 4 different bases, and are selected from A, (T/U), C, and G;

$R_1$ is independently selected from —H, monophosphate group (—$PO_3H_2$), diphosphate group (—$PO_3H$—$PO_3H_2$), triphosphate group (—$PO_3H$—$PO_3H$—$PO_3H_2$) and tetraphosphate group (—$PO_3H$—$PO_3H$—$PO_3H$—$PO_3H_2$);

$R_2$ is independently selected from —H and —OH;

$R_{3a}$, $R_{3b}$, $R_{3c}$, $R_{3d}$, $R_{4a}$, $R_{4b}$, and $R_{4c}$ are independently reactive groups capable of performing a bioorthogonal cleavage reaction;

$R_{5a}$ is one member of the first binding pair;

$R_{6a}$ is one member of the second binding pair, optionally, $R_{6a}$ is $Dye_1$ or is also linked onto -L3-$Dye_1$;

L1 is independently a linking group or absent;

L2 is independently a linking group or absent;

L3 is a linking group or absent;

Dye and $Dye_1$ represent fluorophores capable of emitting a fluorescent signal; and, both of them have the same structure, or have different structures but have the same or substantially the same emission spectrum;

optionally, there is a reactive group $R_8$ capable of performing a bioorthogonal ligation reaction between $R_{4c}$ and $R_{6a}$;

(3) annealing the primer to the nucleic acid molecule to be sequenced, wherein the primer serves as an initial growing nucleic acid strand, and forms a duplex attached to the support together with the nucleic acid molecule to be sequenced;

(4) performing a nucleotide polymerization reaction using the polymerase under a condition allowing the polymerase to perform the nucleotide polymerization, thereby incorporating one of the four compounds at the 3' end of the growing nucleic acid strand;

(5)(i) if the fourth compound does not emit a fluorescent signal, subjecting the duplex or the growing nucleic acid strand to a treatment in a reaction system containing a solution phase and a solid phase, wherein the treatment has no effect on the first compound, the second compound and the third compound, and enables $R_{6a}$ in the fourth compound to specifically interact with/bind to an agent (e.g., the other member of the second binding pair) carrying a fluorophore (for example, a fluorophore having the same structure as the fluorophore of the second compound, or a fluorophore has a structure different from, but has the same or substantially the same emission spectrum as the fluorophore in the second compound); thereafter, removing the solution phase of the reaction system in the previous step, retaining the duplex attached to the support, and detecting whether the duplex or the growing nucleic acid strand emits the fluorescent signal;

wherein the other member of the second binding pair carrying the fluorophore has the following structure: $R_{6b}$-L4-$Dye_2$; wherein $R_{6b}$ is the other member of the second binding pair, and L4 is independently a linking group or absent; $Dye_2$ represents a fluorophore capable of emitting a fluorescent signal, and has the same structure as Dye, or has a structure different from, but has the same or substantially the same emission spectrum as Dye; meanwhile, $R_{6b}$ is one member of the third binding pair; or (ii) if the fourth compound is capable of emitting the same fluorescent signal as the second compound, removing the solution phase of the reaction system in the previous step, retaining the duplex attached to the support, and detecting whether the duplex or growing nucleic acid strand emits the fluorescent signal;

(6) subjecting the duplex or the growing nucleic acid strand to a treatment in a reaction system containing a solution phase and a solid phase, wherein the treatment has no effect on the first compound and the second compound, and enables $R_{5a}$ in the third compound to specifically interact with/bind to the other member of the first binding pair carrying a fluorophore, thereby introducing the fluorophore into the third compound to make the third compound to emit a fluorescent signal; and the treatment (i) enables $R_{6b}$ to specifically interact with/bind to the other member $R_{6c}$ of the third binding pair, thereby dissociating the conjugate between $R_{6b}$ and $R_{6a}$ and making the fourth compound to lose its fluorophore, or (ii) enables $R_8$ in the fourth compound to perform the bioorthogonal ligation reaction with a compound carrying a quenching group, thereby quenching the fluorescent signal emitted by the fluorophore $Dye_1$ or $Dye_2$ in the fourth compound; wherein the other member of the first binding pair carrying a fluorophore has the following structure: $R_{5b}$-L5-$Dye_3$; wherein $R_{5b}$ is the other member of the first binding pair, and L5 is independently a linking group or absent; $Dye_3$ represents a fluorophore capable of emitting a fluorescent signal, wherein the fluorophore has the same structure as the fluorophore in the second compound, or has a structure different from but has the same or substantially the same emission spectrum as the fluorophore in the second compound;

(7) removing the solution phase of the reaction system of the previous step, retaining the duplex attached to the support d, and detecting whether the duplex or the growing nucleic acid strand emits the fluorescent signal.

In some preferred embodiments, the method further comprises the steps of:

(8) subjecting the duplex or the growing nucleic acid strand in the previous step to a treatment in a reaction system containing a solution phase and a solid phase, wherein the treatment enables $R_{3a}$, $R_{3b}$, $R_{3c}$, $R_{3d}$, $R_{4a}$, $R_{4b}$, $R_{4c}$ to perform the bioorthogonal cleavage reaction, thereby allowing the compound incorporated at the 3' end of the growing nucleic acid strand to have free hydroxyl group at the 3' position of the ribose or deoxyribose (in other words, converting —$OR_{3a}$, —$OR_{3b}$, —$OR_{3c}$ or —$OR_{3d}$ (if present) into free hydroxyl group), and removing the fluorophore on the duplex or the growing nucleic acid strand (in other words, removing the fluorophore attached to $R_{4a}$, $R_{4b}$ or $R_{4c}$), if present;

(9) removing the solution phase of the reaction system in the previous step;

(10) adding a polymerase for performing a nucleotide polymerization, and the first compound, the second compound, the third compound, and the fourth compound, thereby forming a reaction system containing a solution phase and a solid phase, and then performing the steps (4)-(7).

In some preferred embodiments, the method further comprises the steps of:

(11) repeating steps (8)-(10) one or more times.

In some preferred embodiments, the method of the invention comprises the steps of:

(1) providing a nucleic acid molecule to be sequenced attached onto a support, or attaching a nucleic acid molecule to be sequenced onto a support;

(2) adding a primer for initiating a nucleotide polymerization, a polymerase for performing a nucleotide polymerization, and the first, second, third and fourth compounds having structures of formula (I), formula (II), formula (III), and formula (IV), respectively, to form a reaction system comprising a solution phase and a solid phase:

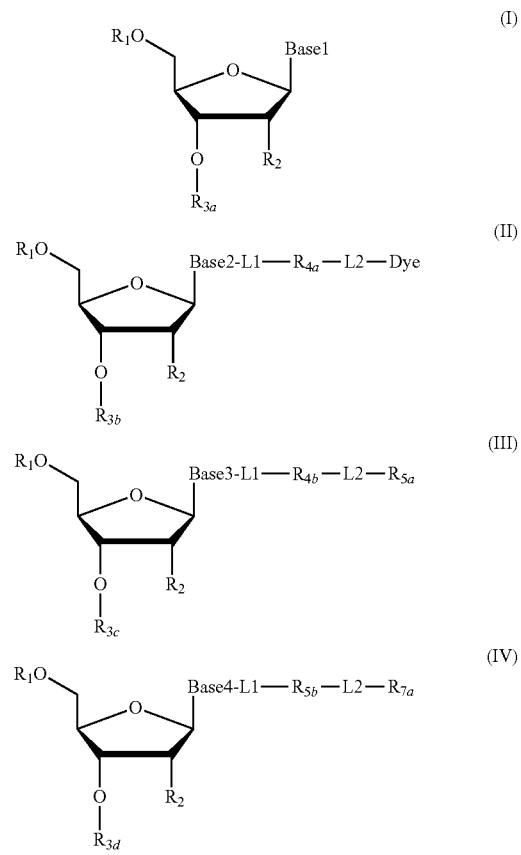

wherein, Base1, Base2, Base3, and Base4 represent 4 different bases, and are selected from A, (T/U), C, and G;

$R_1$ is independently selected from —H, monophosphate group (—PO$_3$H$_2$), diphosphate group (—PO$_3$H—PO$_3$H$_2$), triphosphate group (—PO$_3$H—PO$_3$H—PO$_3$H$_2$) and tetra-phosphate group (—PO$_3$H—PO$_3$H—PO$_3$H—PO$_3$H$_2$);

$R_2$ is independently selected from —H and —OH;

$R_{3a}$, $R_{3b}$, $R_{3c}$, $R_{3d}$, $R_{4a}$, $R_{4b}$, and $R_{4c}$ are independently reactive groups capable of performing a bioorthogonal cleavage reaction;

$R_{5a}$ is a reactive group capable of performing a first bioorthogonal ligation reaction;

$R_{6a}$ is one member of the first binding pair, optionally, $R_{6a}$ is Dye$_1$ or is also linked onto -L3-Dye$_1$;

L1 is independently a linking group or absent;

L2 is independently a linking group or absent;

L3 is a linking group or absent;

Dye represents a fluorophore capable of emitting a fluorescent signal; Dye and Dye$_1$ have the same structure, or have different structures but have the same or substantially the same emission spectrum;

optionally, there is a reactive group $R_8$ capable of performing a second bioorthogonal ligation reaction between $R_{4c}$ and $R_{6a}$;

(3) annealing the primer to the nucleic acid molecule to be sequenced, wherein the primer serves as an initial growing nucleic acid strand, and forms a duplex attached to the support together with the nucleic acid molecule to be sequenced;

(4) performing a nucleotide polymerization reaction using the polymerase under a condition allowing the polymerase to perform the nucleotide polymerization, thereby incorporating one of the four compounds at the 3' end of the growing nucleic acid strand;

(5)(i) if the fourth compound does not emit a fluorescent signal, subjecting the duplex or the growing nucleic acid strand to a treatment in a reaction system containing a solution phase and a solid phase, wherein the treatment has no effect on the first compound, the second compound and the third compound, and enables $R_{6a}$ in the fourth compound to specifically interact with/bind to an agent (for example, the other member of the first binding pair) carrying a fluorophore (for example, a fluorophore which has the same structure as the fluorophore of the second compound, or a fluorophore which has a structure different from, but has the same or substantially the same emission spectrum as the fluorophore of the second compound); thereafter, removing solution phase of the reaction system of the previous step, retaining the duplex attached to the support, and detecting whether the duplex and the growing nucleic acid strand emits the fluorescent signal;

wherein the other member of the first binding pair carrying the fluorophore has the following structure: $R_{6b}$-L4-Dye$_2$; wherein $R_{6b}$ is the other member of the first binding pair, and L4 is independently a linking group or absent; Dye$_2$ represents a fluorophore capable of emitting a fluorescent signal, and has the same structure as Dye, or a fluorophore has a different structure from, but the same or substantially the same emission spectrum as Dye; meanwhile, $R_{6b}$ is one member of the second binding pair; or (ii) if the fourth compound is capable of emitting the same fluorescent signal as the second compound, removing solution phase of the reaction system of the previous step, retaining the duplex attached to the support, and detecting whether the duplex and the growing nucleic acid strand emits the fluorescent signal;

(6) subjecting the duplex or the growing nucleic acid strand to a treatment in a reaction system containing a solution phase and a solid phase, wherein the treatment has no effect on the first compound and the second compound, and enables $R_{5a}$ in the third compound to perform the first bioorthogonal ligation reaction with an agent carrying a fluorophore (for example, a fluorophore the same as the fluorophore of the second compound, or a fluorophore having an emission spectrum the same or substantially the same to the fluorophore of the second compound), thereby introducing the fluorophore in the agent into the third compound to make the third compound to emit a fluorescent signal; and the treatment (i) enables $R_{6b}$ to specifically interact with/bind to the other member $R_6$ of the second binding pair, thereby dissociating the conjugate between $R_{6b}$ and $R_{6a}$ and making the fourth compound to lose its fluorophore, or (ii) enables $R_8$ in the fourth compound to perform the second bioorthogonal ligation reaction with a compound carrying a quenching group, thereby quenching the fluorescent signal emitted by the fluorophore Dye$_1$ or Dye$_2$ in the fourth compound; wherein, the other member of the second binding pair carrying the quenching group has the following structure: $R_{6c}$-L'-Que; wherein $R_{6c}$ is the other member of the second binding pair, L' is independently a linking group or absent; Que represents a quenching group capable of quenching the fluorescent signal emitted by Dye$_1$ or Dye$_2$;

(7) removing the solution phase of the reaction system in the previous step, retaining the duplex attached to the support, and detecting whether the duplex or the growing nucleic acid strand emits the fluorescent signal.

In some preferred embodiments, the method further comprises the steps of:

(8) subjecting the duplex or the growing nucleic acid strand in the previous step to a treatment in a reaction system containing a solution phase and a solid phase, wherein the treatment enables $R_{3a}$, $R_{3b}$, $R_{3c}$, $R_{3d}$, $R_{4a}$, $R_{4b}$, $R_{4c}$ to perform the bioorthogonal cleavage reaction, thereby allowing the compound incorporated at the 3' end of the growing nucleic acid strand to have a free hydroxyl group at the 3' position of the ribose or deoxyribose (in other words, converting —OR$_{3a}$, —OR$_{3b}$, —OR$_{3c}$ or —OR$_{3d}$ (if present) into free a hydroxyl group) and removing the fluorophore on the duplex or the growing nucleic acid strand (in other words, removing the fluorophore attached to $R_{4a}$, $R_{4b}$ or $R_{4c}$), if present;

(9) removing the solution phase of the reaction system in the previous step;

(10) adding a polymerase for performing a nucleotide polymerization, and the first compound, the second compound, the third compound, and the fourth compound, thereby forming a reaction system containing a solution phase and a solid phase, and then performing the steps (4)-(7).

In some preferred embodiments, the method further comprises the steps of:

(11) repeating steps (8)-(10) one or more times.

In another aspect, the invention provides a kit comprising four compounds as defined above. In some preferred embodiments, the kit of the invention comprises four compounds (i.e., the first, second, third, and fourth compounds), wherein:

the four compounds are derivatives of nucleotides A, (T/U), C and G, respectively, and have a base complementary pairing ability; and, each of the four compounds has a hydroxyl group (—OH) at the 3' position of the ribose or deoxyribose which is protected by a protecting group; and, the protecting group can be removed;

the first compound and the third compound are incapable of emitting a fluorescent signal (e.g., carrying no fluorophore), the second compound is capable of emitting a fluorescent signal, and the fourth compound is incapable of emitting a fluorescent signal, or is capable of emitting the same fluorescent signal as the second compound (for example, carrying a fluorophore, wherein the fluorophore is the same as the fluorophore in the second compound, or the fluorophore has a different structure from, but has the same or substantially the same emission spectrum as the fluorophore in the second compound); and, the third compound is capable of emitting the same fluorescent signal as the second compound upon a treatment (e.g., by having the third compound carry the same fluorophore as the fluorophore of the second compound, or by having the third compound carry a fluorophore has the same or substantially the same emission spectrum as the fluorophore of the second compound);

wherein if the fourth compound does not emit the same fluorescent signal as the second compound, the fluorescent of the fourth compound can be removed upon a treatment (e.g., by removing the fluorophore, or by quenching the fluorescent signal emitted by the fluorophore);

if the fourth compound does not emit a fluorescent signal, the fourth compound is capable of emitting the same fluorescent signal as the second compound after the first treatment (for example, by having the fourth compound carry the same fluorophore as the fluorophore of the second compound, or by having the fourth compound carry a fluorophore which has the same or substantially the same emission spectrum as the fluorophore of the second compound); and the fluorescent signal of the fourth compound can be removed after the second treatment (e.g., by removing the fluorophore, or by quenching the fluorescent signal emitted by the fluorophore).

In some preferred embodiments, the kit of the present invention further comprises: an agent and/or device for extracting a nucleic acid molecule from a sample; an agent for pretreating a nucleic acid molecule; a support for attaching a nucleic acid molecule to be sequenced; an agent for attaching (for example, covalently or non-covalently linking) a nucleic acid molecule to be sequenced to a support; a primer for initiating a nucleotide polymerization; a polymerase for performing a nucleotide polymerization reaction; one or more buffer solutions; one or more washing solutions; or any combination thereof.

SEQUENCE INFORMATION

Figure 1:
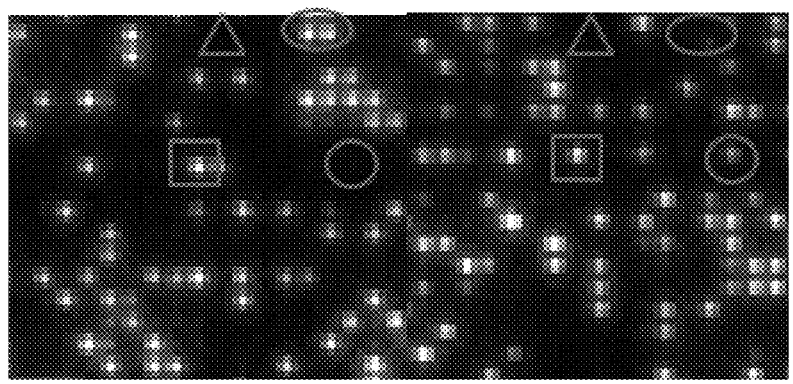
FIG. 1 shows the comparison results of Experimental Photos 1 and 2 obtained in Experimental Example 1.

The information of the sequences involved in the present invention is provided in the following table:

| SEQ ID NO. | Sequence | Length | Description | SEQ ID NO. | Sequence | Length | Description |
| --- | --- | --- | --- | --- | --- | --- | --- |
| 1 | TAGGTCCGAT | 10 bp | Synthetic Oligonucleotide | 19 | TGTCTGCGAA | 10 bp | Synthetic Oligonucleotide |
| 2 | GGACGGAATC | 10 bp | Synthetic Oligonucleotide | 20 | ATTGGTACAA | 10 bp | Synthetic Oligonucleotide |
| 3 | CTTACTGCCG | 10 bp | Synthetic Oligonucleotide | 21 | CGATTGTGGT | 10 bp | Synthetic Oligonucleotide |
| 4 | ACCTAATTGA | 10 bp | Synthetic Oligonucleotide | 22 | ACAGACTTCC | 10 bp | Synthetic Oligonucleotide |
| 5 | TTCGTATCCG | 10 bp | Synthetic Oligonucleotide | 23 | TCCACACTCT | 10 bp | Synthetic Oligonucleotide |
| 6 | GGTAACGAGC | 10 bp | Synthetic Oligonucleotide | 24 | CACCACAAGC | 10 bp | Synthetic Oligonucleotide |
| 7 | CAACGTATAA | 10 bp | Synthetic Oligonucleotide | 25 | TAGAGGACAA | 10 bp | Synthetic Oligonucleotide |
| 8 | ACGTCGCGTT | 10 bp | Synthetic Oligonucleotide | 26 | CCTAGCGAAT | 10 bp | Synthetic Oligonucleotide |
| 9 | TTCTGCTAGC | 10 bp | Synthetic Oligonucleotide | 27 | GTAGTCATCG | 10 bp | Synthetic Oligonucleotide |
| 10 | AGGAAGATAG | 10 bp | Synthetic Oligonucleotide | 28 | GCTGAGCTGT | 10 bp | Synthetic Oligonucleotide |
| 11 | GCTCTTGCTT | 10 bp | Synthetic Oligonucleotide | 29 | AACCTAGATA | 10 bp | Synthetic Oligonucleotide |
| 12 | CAAGCACGCA | 10 bp | Synthetic Oligonucleotide | 30 | TTGCCATCTC | 10 bp | Synthetic Oligonucleotide |

-continued

| SEQ ID NO. | Sequence | Length | Description | SEQ ID NO. | Sequence | Length | Description |
|---|---|---|---|---|---|---|---|
| 13 | CGGCAATCCG | 10 bp | Synthetic Oligonucleotide | 31 | AGATCTTGCG | 10 bp | Synthetic Oligonucleotide |
| 14 | ATCAGGATTC | 10 bp | Synthetic Oligonucleotide | 32 | CGCTATCGGC | 10 bp | Synthetic Oligonucleotide |
| 15 | TCATTCCAGA | 10 bp | Synthetic Oligonucleotide | 33 | GCAACGATGG | 10 bp | Synthetic Oligonucleotide |
| 16 | GATGCTGGAT | 10 bp | Synthetic Oligonucleotide | 34 | TAATCGTTCA | 10 bp | Synthetic Oligonucleotide |
| 17 | GTGAGTGATG | 10 bp | Synthetic Oligonucleotide | 35 | GTTCGCTCTA | 10 bp | Synthetic Oligonucleotide |
| 18 | GAGTCAGCTG | 10 bp | Synthetic Oligonucleotide | 36 | TCTCACACAT | 10 bp | Synthetic Oligonucleotide |

DETAILED DESCRIPTION OF THE INVENTION

In the present invention, all technical and scientific terms used herein have the same meaning as commonly understood by one of ordinary skill in the art to which the invention belongs, unless otherwise defined. In the embodiments of the present invention, methods and materials similar or equivalent to those described herein can be used, and the exemplary suitable methods and materials are described below. All publications, patent applications, patents, and other references are incorporated herein by reference. In addition, the materials, methods, and examples are illustrative only and not limiting. Further, for better understanding of the present invention, definitions and explanations of related terms are provided below.

As used herein, the term "support" refers to any material (solid or semi-solid) that allows for stable attachment of a nucleic acid, such as latex bead, dextran bead, polystyrene, polypropylene, polyacrylamide gel, gold thin layer, glass and silicon wafer. In some exemplary embodiments, the support is optically clear, such as glass. As used herein, "stable attachment" means that the linkage between the nucleic acid molecule and the support is sufficiently strong that the nucleic acid molecule will not be detached from the support due to the condition used in various reactions or treatments (for example, polymerization reaction, bioorthogonal cleavage reaction, bioorthogonal ligation reaction and washing treatment).

As used herein, the term "attach" or "link" is intended to cover any form of linkage, such as covalent linkage and non-covalent linkage. In some exemplary embodiments, the nucleic acid molecule is preferably linked onto the support by covalent linkage.

As used herein, the term "fragmentation" refers to the process of converting a large nucleic acid fragment (for example, a large DNA fragment) into a small nucleic acid fragment (for example, a small DNA fragment). In some embodiments, the term "large nucleic acid fragment" is intended to encompass nucleic acid molecules (for example, DNA) greater than 5 kb, greater than 10 kb, greater than 25 kb (for example, DNA), for example, greater than 500 kb, greater than 1 Mb, greater than 5 Mb or greater nucleic acid molecules (for example, DNA).

As used herein, the term "end-filling" refers to the process of complementing the end of a nucleic acid molecule having an overhanging end to form a nucleic acid molecule having a blunt end.

As used herein, the terms "adapter" and "adapter sequence" are used interchangeably. As used herein, the terms "adapter" and "adapter sequence" refer to a segment of an oligonucleotide sequence introduced artificially at the 5' end and/or 3' end of a nucleic acid molecule. An adapter may generally comprise one or more regions for achieving a particular function. Thus, when an adapter is introduced artificially at the 5' and/or 3' end of the nucleic acid molecule, the adapter will perform the specific function, thereby facilitating a subsequent application. For example, the adapter may comprise one or more primer binding regions to facilitate the binding of primer. In some exemplary embodiments, the adapter may comprise one or more primer binding regions, for example, a primer binding region capable of hybridizing to a primer for amplification, and/or a primer binding region capable of hybridizing to a primer for use in a sequencing reaction. In some preferred embodiments, the adapter comprises a universal adapter sequence capable of hybridizing to a universal primer, for example, a universal adapter sequence capable of hybridizing to a universal amplification primer and/or a universal sequencing primer. Thus, the nucleic acid molecule carrying the adapter may be conveniently amplified and/or sequenced by using a universal amplification primer and/or a universal sequencing primer. In some exemplary embodiments, the adapter may also comprise a tag or tag sequence.

As used herein, the terms "tag" and "tag sequence" may be used interchangeably. As used herein, the terms "tag" and "tag sequence" refer to a segment of an oligonucleotide sequence with a particular base sequence introduced at the 5' and/or 3' end of a nucleic acid molecule. A label is commonly used to identify/distinguish the source of a nucleic acid molecule. For example, different tags can be introduced in different nucleic acid molecules from different sources, thereby when these nucleic acid molecules of different sources are mixed together, the source of each nucleic acid molecule can be accurately determined by the unique tag sequence carried on each nucleic acid molecule. The tag sequence may have any length, such as 2-50 bp, such as 2, 3, 4, 5, 10, 15, 20, 25, 30, 35, 40, 45, 50 bp, according to actual needs.

As used herein, the term "hybridization" generally refers to hybridization under a stringent condition. Hybridization techniques are well known in the field of molecular biology. For illustrative purposes, the stringent condition comprises, for example, moderate stringent condition (for example, hybridization is proceeded at about 45° C. in 6× sodium chloride/sodium citrate (SSC), followed by one or more washing in 0.2×SSC/0.1% SDS at about 50-65° C.); highly stringent condition (for example, hybridization is proceeded at about 45° C. in 6×SSC, followed by one or more washing in 0.1×SSC/0.2% SDS at about 68° C.); and other stringent hybridization conditions known to those skilled in the art (see, for example, Ausubel, F. M., et al., 1989, Current Protocols in Molecular Biology, volume 1, Green Publishing Associates, Inc., and John Wiley & Sons, Inc., New York, pages 6.3.1-6.3.6 and 2.10.3).

As used herein, the expression "a reaction system containing a solution phase and a solid phase" means that the reaction system of the present invention comprises a support and a substance attached to the support (solid phase), and substance (solution phase) dissolved in the solution/solvent. Correspondingly, the expression "removing the solution phase of the reaction system" means removing the solution in the reaction system and the substance (solution phase) contained therein, and retaining only the support in the reaction system and the substance (solid phase) attached to the support. In the context of the present invention, the substance (solid phase) attached to the support may comprise a nucleic acid molecule to be sequenced, a growing nucleic acid strand, and/or a duplex formed by the nucleic acid molecule to be sequenced and the growing nucleic acid strand.

As used herein, the term "primer" refers to an oligonucleotide sequence that hybridizes to a complementary sequence and initiates a specific polymerization reaction. In general, the sequence of the primer is selected/designed to have maximum hybridization activity for the complementary sequence, while having very low non-specific hybridization activity for other sequences, thereby minimizing non-specific amplification. Methods for designing primers are well known to those skilled in the art and can be performed using commercially available software (for example, Primer Premier version 6.0, Oligo version 7.36, etc.).

As used herein, the term "polymerase" refers to an enzyme capable of performing a nucleotide polymerization reaction. Such enzyme is capable of introducing a nucleotide paired with a nucleotide at a position corresponding to a template nucleic acid at the 3' end of a growing nucleic acid strand according to the principle of base complementary pairing.

As used herein, the expressions "A, (T/U), C, and G" are intended to cover two instances: "A, T, C, and G" and "A, U, C, and G." Thus, the expression "the four compounds are derivatives of nucleotides A, (T/U), C and G, respectively" is intended to mean that the four compounds are derivatives of nucleotides A, T, C and G, respectively, or derivatives of nucleotides A, U, C and G, respectively.

As used herein, the expression "a compound having a base complementary pairing ability" means that the compound is capable of pairing with a corresponding base and forming a hydrogen bond according to the principle of base complementary pairing. According to the principle of base complementary pairing, base A can be paired with base T or U, and base G can be paired with base C. Therefore, when a compound having a base complementary pairing ability is a derivative of nucleotide A, it can pair with base T or U; when a compound having a base complementary pairing ability is a derivative of nucleotide T or U, it can pair with base A; when a compound having a base complementary pairing ability is a derivative of nucleotide C, it can pair with base G; when a compound having a base complementary pairing ability is a derivative of nucleotide G, it can pair with base C.

As used herein, the expression "hydroxyl (—OH) is protected by a protecting group" means that H in the free hydroxyl group (—OH) is substituted with a protecting group (P) to form a protected hydroxyl group (—OP). In some preferred embodiments, the protecting group (P) can be removed, thereby the protected hydroxyl group (—OP) is converted into a free hydroxyl group (—OH).

As used herein, the term "binding pair" means a pair of molecules (i.e., two members) that are capable of interacting with each other by specific non-covalent interaction. In general case, the two members of a binding pair rely on their three-dimensional structure to achieve the specific interaction (i.e., specific recognition and binding). Typical binding pairs include, for example, antigen (e.g., small molecule antigen)-antibody, hapten-antibody, hormone-receptor, ligand-receptor, nucleic acid strand-complementary nucleic acid strand, substrate-enzyme, substrate analog-enzyme, inhibitor-enzyme, sugar-plant lectin, biotin-avidin (e.g., avidin and streptavidin), digoxin and digoxin antibody, and 5-position bromo-deoxyguanosine and its antibody, etc.

As used herein, the term "specific interaction/binding" refers to a non-random interaction/binding reaction between two molecules, for example, an interaction between an antibody and the antigen to which it is directed. In some embodiments, the presence of a specific interaction between two members of a binding pair means that one member of the binding pair binds to the other member with $K_D$ less than about $10^{-5}$ M, e.g. less than about $10^{-6}$ M, $10^{-7}$ M, $10^{-8}$ M, $10^{-9}$ M or $10^{-10}$ M or less.

As used herein, the term "$K_D$" refers to the dissociation equilibrium constant of the interaction of two members of a binding pair, which is used to describe the binding affinity between the two members. The smaller the equilibrium dissociation constant, the tighter the binding between the two members, and the higher the affinity between the two members. Typically, one member of the binding pair binds to the other member with the dissociation equilibrium constant ($K_D$) less than about $10^{-5}$ M, e.g. less than about $10^{-6}$ M, $10^{-7}$ M, $10^{-8}$ M, $10^{-9}$ M or $10^{-10}$ M or less. Various known methods can be used to determine the binding affinity of two members of the binding pair, for example, using surface plasmon resonance (SPR).

As used herein, the term "bioorthogonal reaction" refers to a chemical reaction that can occur within an organism (for example, a living cell or tissue) without affecting the biochemical reaction of the organism itself. The bioorthogonal reaction has strong activity and selectivity under physiological conditions, and its substrate and/or reaction mechanism is rare or absent in the organism, therefore, it maintains good inertness to active molecules in the organism and can be performed in vivo without being disturbed. The bioorthogonal reaction can be used to label a biomacromolecule or an active small molecule, and can be applied in molecular imaging, drug screening, and the like.

As used herein, the term "bioorthogonal cleavage reaction" refers to a bioorthogonal reaction in which a reactive group in a substrate performs cleavage of a covalent bond to form a product. Reactions that can be used as bioorthogonal cleavage reaction include, but are not limited to, Ru-catalyzed deallylation reaction, Pd-catalyzed depropargylation reaction, Cu-catalyzed depropargylation reaction, specific IED-DA-induced "click and release" reaction, and strain-promoted alkene-azide cycloaddition-induced aryl azide reduction.

As used herein, the term "bioorthogonal ligation reaction" refers to a bioorthogonal reaction in which a reactive group in a substrate performs the formation of a covalent bond to form a product. Reactions that can be used as bioorthogonal ligation reaction include, but are not limited to, Staudinger Ligation, Cu catalyzed azide-alkyne cycloaddition (AAC), strain-promoted azide-alkyne cycloaddition (SPAAC), inverse electron-demand Diels-Alder reaction (IEDDA), Pd-catalyzed Suzuki cross-coupling, disulfide bond formation reaction of thiol and thiol derivatives.

As used herein, the term "reactive group" refers to a group capable of performing a chemical reaction. The expression "a reactive group capable of performing a bioorthogonal ligation reaction" means that the reactive group is capable of performing a bioorthogonal ligation reaction with another reactive group (complementary group) and forms a covalent bond between the two reactive groups, resulting in a covalent linkage between different compounds respectively comprising the two reactive groups or between different moieties of one compound comprising the two reactive groups. The expression "reactive group capable of performing a bioorthogonal cleavage reaction" means that the reactive group is capable of performing a bioorthogonal cleavage reaction and causes the reactive group or a portion thereof to be cleaved or detached from the compound containing the reactive group.

As used herein, the term "cycloenylidene" includes both a divalent group obtained by eliminating two hydrogen atoms from the same carbon atom on a cycloolefin, and a divalent group obtained by eliminating one hydrogen atom on each of the two carbon atoms on a cycloolefin.

As used herein,

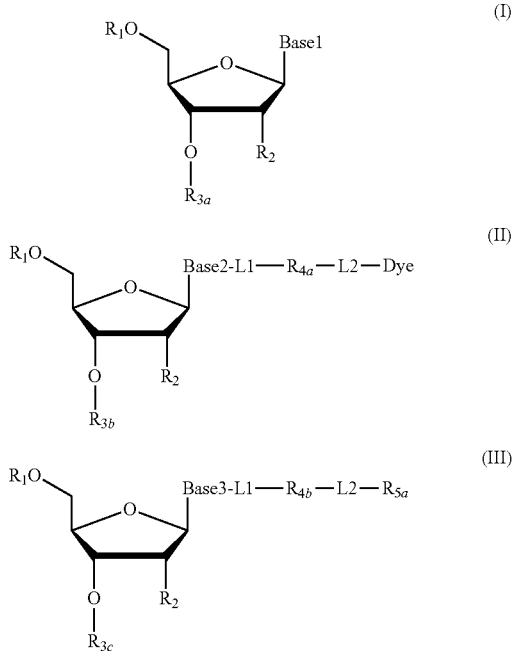

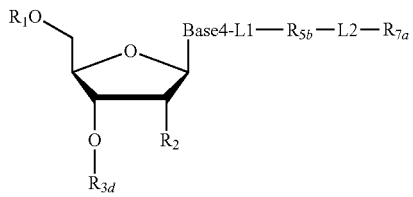

both mean trans-cyclooctene.

(1) Sequencing Method

The inventors of the present application have developed a new sequencing method that uses one fluorescent dye to distinguish four bases.

Thus, in one aspect, the invention provides a method for sequencing a nucleic acid molecule comprising the steps of:

(1) providing a nucleic acid molecule to be sequenced attached onto a support or attaching a nucleic acid molecule to be sequenced onto a support;

(2) adding a primer for initiating a nucleotide polymerization, a polymerase for performing a nucleotide polymerization, and four compounds to form a reaction system containing a solution phase and a solid phase; wherein the four compounds are respectively derivatives of nucleotides A, (T/U), C and G, and have a base complementary pairing ability; and, each of the four compounds has a hydroxyl group (—OH) at 3' position of the ribose or deoxyribose which is protected by a protecting group; and, the first compound and the third compound are incapable of emitting a fluorescent signal (for example, carrying no fluorophore), the second compound is capable of emitting a fluorescent signal (for example, carrying a fluorophore), and the fourth compound does not emit a fluorescent signal, or emits the same fluorescent signal as the second compound (for example, carrying a fluorophore, wherein the fluorophore is the same as the fluorophore in the second compound, or the fluorophore has a structure different from the fluorophore in the second compound, but has the same or substantially the same emission spectrum as the fluorophore in the second compound);

(3) annealing the primer to the nucleic acid molecule to be sequenced, wherein the primer serves as an initial growing nucleic acid strand, and forms a duplex attached to the support together with the nucleic acid molecule to be sequenced;

(4) performing a nucleotide polymerization reaction using a polymerase under a condition allowing the polymerase to perform the nucleotide polymerization, thereby incorporating one of the four compounds into the 3' end of the growing nucleic acid strand;

(5)(i) if the fourth compound is capable of emitting the same fluorescent signal as the second compound, removing the solution phase of the reaction system in the previous step, retaining the duplex attached to the support, and detecting whether the duplex or the growing nucleic acid strand emits the fluorescent signal; or (ii) if the fourth compound does not emit a fluorescent signal, subjecting the duplex or the growing nucleic acid strand to a treatment in a reaction system comprising a solution phase and a solid phase, wherein the treatment has no effect on the first compound, the second compound and the third compound, but is capable of making the fourth compound to emit the same fluorescent signal as the second compound (for example, by modifying the fourth compound to carry a fluorophore, wherein the fluorophore is the same as the fluorophore of the second compound, or has the same emission spectrum as the fluorophore of the second compound); thereafter, removing the solution phase of the reaction system of the previous step, retaining the duplex attached to the support, and detecting whether the duplex or the growing nucleic acid strand emits the fluorescent signal;

(6) subjecting the duplex or the growing nucleic acid strand to a treatment in a reaction system containing a solution phase and a solid phase, wherein the treatment has no affect on the first compound and the second compound, but enables the third compound to emit the same fluorescent signal of the second compound (for example, by modifying the third compound to carry a fluorophore, wherein the fluorophore is the same as the fluorophore in the second compound, or has the same emission spectrum as the fluorophore of the second compound), and is capable of removing the fluorescent signal of the fourth compound (for example, removing the fluorophore on the fourth compound, or quenching the fluorescent signal emitted by the fluorophore on the fourth compound); and (7) removing the solution phase of the reaction system of the previous step, retaining the duplex attached to the support, and detecting whether the duplex or the growing nucleic acid strand emits the fluorescent signal.

In some preferred embodiments, the method further comprises the steps of:

(8) subjecting the duplex or the growing nucleic acid strand in the previous step to a treatment in a reaction system containing a solution phase and a solid phase, wherein the treatment is capable of removing the protecting group at 3' position of ribose or deoxyribose in the compound incorporated at the 3' end of the growing nucleic acid strand, and removing the fluorescent signal on the duplex or growing nucleic acid strand, if present; and (9) removing the solution phase of the reaction system in the previous step;

(10) adding a polymerase for performing a nucleotide polymerization, and the four compounds to form a reaction system containing a solution phase and a solid phase, and then conducting steps (4) to (7).

Optionally, the method further comprises the following step (11):

(11) repeating steps (8)-(10) one or more times.

Nucleic Acid Molecule

In the method of the present invention, the nucleic acid molecule to be sequenced may be any nucleic acid molecule of interest. In some preferred embodiments, the nucleic acid molecule to be sequenced comprises deoxyribonucleotides, ribonucleotides, modified deoxyribonucleotides, modified ribonucleotides, or any combination thereof. In the method of the invention, the nucleic acid molecule to be sequenced is not limited by its type. In some preferred embodiments, the nucleic acid molecule to be sequenced is DNA or RNA. In some preferred embodiments, the nucleic acid molecule to be sequenced may be genomic DNA, mitochondrial DNA, chloroplast DNA, mRNA, cDNA, miRNA, or siRNA. In some preferred embodiments, the nucleic acid molecule to be sequenced is linear or circular. In some preferred embodiments, the nucleic acid molecule to be sequenced is double-stranded or single-stranded. For example, the nucleic acid molecule to be sequenced can be single-stranded DNA (ssDNA), double-stranded DNA (dsDNA), single-stranded RNA (ssRNA), double-stranded RNA (dsRNA), or a hybrid of DNA and RNA. In some preferred embodiments, the nucleic acid molecule to be sequenced is a single stranded DNA. In some preferred embodiments, the nucleic acid molecule to be sequenced is a double stranded DNA.

In the method of the invention, the nucleic acid molecule to be sequenced is not limited by its source. In some preferred embodiments, the nucleic acid molecule to be sequenced can be obtained from any source, for example, any cell, tissue or organism (for example, a virus, a bacterium, a fungus, a plant, or an animal). In some preferred embodiments, the nucleic acid molecule to be sequenced is derived from a mammal (for example, a human, a non-human primate, a rodent or a canine), a plant, a bird, a reptile, a fishe, a fungus, a bacterium or a virus.

Method for extracting or obtaining nucleic acid molecules from cells, tissues or organisms are well known to those skilled in the art. Suitable methods include, but are not limited to, ethanol precipitation, chloroform extraction, and the like. A detailed description of such methods can be found, for example, in J. Sambrook et al., Molecular Cloning: A Laboratory Manual, 2nd Edition, Cold Spring Harbor Laboratory Press, 1989, and F. M. Ausubel et al., Short Protocols in Molecular Biology, 3rd edition, John Wiley & Sons, Inc., 1995. In addition, various commercial kits can be used to extract nucleic acid molecules from a variety of sources, such as cells, tissues or organisms.

In the method of the invention, the nucleic acid molecule to be sequenced is not limited by its length. In some preferred embodiments, the nucleic acid molecule to be sequenced may be at least 10 bp, at least 20 bp, at least 30 bp, at least 40 bp, at least 50 bp, at least 100 bp, at least 200 bp, at least 300 bp, at least 400 bp, at least 500 bp, at least 1000 bp in length, or at least 2000 bp. In some preferred embodiments, the nucleic acid molecule to be sequenced may be $10^{-20}$ bp, 20-30 bp, 30-40 bp, 40-50 bp, 50-100 bp, 100-200 bp, 200-300 bp, 300-400 bp, 400-500 bp, 500-1000 bp, 1000-2000 bp, or more than 2000 bp. In some preferred embodiments, the nucleic acid molecule to be sequenced may have a length of $10^{-1000}$ bp to facilitate high throughput sequencing.

In some preferred embodiments, the nucleic acid molecule may be pretreated prior to attaching the nucleic acid molecule to the support. Such pretreatments include, but are not limited to, fragmentation of nucleic acid molecule, complementation of end, addition of adapter, addition of tag, repair of nick, amplification of nucleic acid molecule, isolation and purification of nucleic acid molecule, and any combination thereof.

For example, in some preferred embodiments, a nucleic acid molecule can be subjected to fragmentation in order to obtain a nucleic acid molecule of suitable length. In the method of the invention, fragmentation of a nucleic acid molecule (e.g., DNA) can be performed by any method known to those of ordinary skill in the art. For example, fragmentation can be carried out by enzymatic or mechanical means. The mechanical method can be ultrasonic or physical shear. The enzymatic method can be carried out by digestion with a nuclease (for example, deoxyribonuclease) or restriction endonuclease. In some preferred embodiments, the fragmentation results in an end with an unknown sequence. In some preferred embodiments, the fragmentation results in an end with a known sequence.

In some preferred embodiments, the enzymatic method uses DNase I to fragment a nucleic acid molecule. DNase I is a universal enzyme that non-specifically cleaves double-stranded DNA (dsDNA) to release 5'-phosphorylated dinucleotide, trinucleotide and oligonucleotide products. DNase I has optimal activity in a buffer containing $Mn^{2+}$, $Mg^{2+}$ and $Ca^{2+}$ but no other salts, and is commonly used to fragment a large DNA genome into small DNA fragments, and the small DNA fragments produced subsequently can be used to construct a DNA library.

The shearing characteristic of DNase I will result in random digestion of DNA molecules (i.e., no sequence bias), and, when used in the presence of a buffer containing manganese ions, predominantly produce blunt-ended dsDNA fragments (Melgar, E. and D. A. Goldthwait. 1968. Deoxyribonucleic acid nucleases. II. The effects of metal on the mechanism of action of deoxyribonuclease I. J. Biol. Chem. 243: 4409). When genomic DNA is treated with DNase I, three factors may be considered: (i) amount of enzyme used (unit); (ii) digestion temperature (° C.); and (iii) incubation time (minute). Generally, large DNA fragments or whole genomic DNA can be digested with DNase I for 1-2 minutes between 10° C. and 37° C. to produce DNA molecules of suitable length.

Thus, in some preferred embodiments, the nucleic acid molecule of interest (the nucleic acid molecule to be sequenced) is fragmented prior to step (1). In some preferred embodiments, the nucleic acid molecule to be sequenced is subjected to fragmentation by enzymatic or mechanical means. In some preferred embodiments, the nucleic acid molecule to be sequenced is fragmented by DNase I. In some preferred embodiments, the nucleic acid molecule to be sequenced is subjected to fragmentation by sonication. In some preferred embodiments, the fragmented nucleic acid molecule is 50-2000 bp in length, such as 50-100 bp, 100-200 bp, 200-300 bp, 300-400 bp, 400-500 bp, 500-1000 bp, 1000-2000 bp, 50-1500 bp, or 50-1000 bp.

Fragmentation of a double-stranded nucleic acid molecule (for example, dsDNA, genomic DNA) can produce nucleic acid fragments having blunt end or overhangs of one or two nucleotides in length. For example, when genomic DNA (gDNA) is treated by sonication or DNase I, the product may comprise a DNA fragment having a blunt end or overhang. In this case, the end of the nucleic acid molecule having an overhang can be filled using a polymerase to form a nucleic acid molecule having a blunt end to facilitate subsequent applications (e.g., to facilitate ligation of the fragmented nucleic acid molecule to the adapter).

Thus, in some preferred embodiments, after fragmentation of a nucleic acid molecule to be sequenced (e.g., dsDNA), the fragmented nucleic acid molecule is treated with a DNA polymerase to produce a DNA fragment having a blunt end. In some preferred embodiments, the DNA polymerase may be any known DNA polymerase, such as T4 DNA polymerase, Pfu DNA polymerase, Klenow DNA polymerase. In some cases, the use of Pfu DNA polymerase may be advantageous because Pfu DNA polymerase cannot only complement the overhang to form a blunt end, but also has 3'-5' exonuclease activity, and can remove single nucleotide and dinucleotide overhangs to further increase the number of DNA fragments with blunt ends (Costa, G. L. and M. P. Weiner. 1994a. Protocols for cloning and analysis of blunt-ended PCR-generated DNA fragments. PCR Methods Appl 3 (5): S95; Costa, G. L. t A. Grafsky and M. P. Wemer. 1994b. Cloning and analysis of PCR-generated DNA fragments. PCR Methods Appl 3 (6): 338; Costa, G. L. and M. P. Weiner. 1994c. Polishing with T4 or Pfu polymerase increases the efficiency of cloning of PCR products. Nucleic Acids Res. 22(12): 2423).

In some preferred embodiments, an adapter/adapters can be introduced at the 5' and/or 3' end of the nucleic acid molecule to be sequenced. In general, the adapter is an oligonucleotide sequence and it can be any sequence, of any length. Adapter of suitable length and sequence can be selected by methods well known in the art. For example, the adapter attached to the end of a nucleic acid molecule to be sequenced is typically a relatively short nucleotide sequence between 5 to 100 nucleotides in length (for example, 5-10 bp, $10^{-20}$ bp, 20-30 bp, 30-40 bp, 40-50 bp, 50-100 bp). In some preferred embodiments, the adapter may have a primer binding region. Such primer binding region can anneal or hybridize to a primer and can be used to initiate a specific polymerase reaction. In some preferred embodiments, the adapter has one or more primer binding regions. In some preferred embodiments, the adapter has one or more regions that are capable of hybridizing to a primer for amplification. In some preferred embodiments, the adapter has one or more regions that are capable of hybridizing to a primer used in the sequencing reaction. In some preferred embodiments, an adapter is introduced at the 5' end of the nucleic acid molecule to be sequenced. In some preferred embodiments, an adapter is introduced at the 3' end of the nucleic acid molecule to be sequenced. In some preferred embodiments, adapters are introduced at the 5' and 3' ends of the nucleic acid molecule to be sequenced. In some embodiments, the adapter comprises a universal adapter sequence that is capable of hybridizing to a universal primer. In some embodiments, the adapter comprises a universal adapter sequence that is capable of hybridizing to a universal amplification primer and/or a universal sequencing primer.

In some preferred embodiments, a tag sequence may be introduced into a nucleic acid molecule to be sequenced, or a tag sequence may be introduced into the adapter described above. A tag sequence refers to a segment of an oligonucleotide having a particular base sequence. According to actual needs, the tag sequence may have any length, such as 2-50 bp, such as 2, 3, 4, 5, 10, 15, 20, 25, 30, 35, 40, 45, 50 bp. In some preferred embodiments, a tag sequence containing a particular sequence is introduced in each nucleic acid molecule to be sequenced to facilitate discriminating the source of each nucleic acid molecule to be sequenced. In some preferred embodiments, a tag sequence can be introduced directly at the 5' and/or 3' end of the nucleic acid molecule to be sequenced. In some preferred embodiments, a tag sequence can be introduced into the adapter and then the adapter is ligated to the 5' and/or 3' end of the nucleic acid molecule to be sequenced. The tag sequence can be located at any position in the adapter sequence, such as the 5' and/or 3' end of the adapter sequence. In some preferred embodiments, the adapter comprises a primer binding region and a tag sequence. In some further preferred embodiments, the primer binding region comprises a universal adapter sequence that is recognized by a universal primer, and preferably, the tag sequence can be located at the 3' end of the primer binding region.

In some preferred embodiments, different tag sequences are used to label/distinguish nucleic acid molecules from different sources. In such embodiments, preferably, the same tag sequences are introduced into nucleic acid molecules of the same source, and for each nucleic acid source, a unique tag sequence is used. Subsequently, nucleic acid molecules of different sources can be combined to form a library, and the source of each nucleic acid molecule in the library can be identified/discriminated by the unique tag sequence carried on each nucleic acid molecule.

The nucleic acid molecule to be sequenced can be linked to an adapter or tag sequence by methods well known in the art (for example, PCR or ligation reaction). For example, if a part of the sequence of the nucleic acid molecule to be sequenced is known, the nucleic acid molecule to be sequenced can be amplified by PCR with suitable a PCR primer (which contains adapter sequence and a sequence which is capable of specifically recognizing the nucleic acid molecule to be sequenced). The amplified product obtained is the nucleic acid molecule to be sequenced which is introduced with an adapter/adapters at the 5' and/or 3' end. In some embodiments, a nucleic acid molecule can be linked onto an adapter using a non-specific ligase (for example, T4 DNA ligase). In some embodiments, a nucleic acid molecule and an adapter can be treated with a restriction endonuclease thereby allowing them to have the same sticky ends, and then the ligase can be used to link the nucleic acid molecule with the adapter having the same sticky ends, thereby obtaining a nucleic acid molecule linked onto the adapter.

In some embodiments, after linking the nucleic acid molecule with the adapter together with a ligase, the resulting product may have a nick at the junction. In this case, a polymerase can be used to repair the nicks. For example, DNA polymerases that lose 3'-5' exonuclease activity but exhibit 5'-3' exonuclease activity can have the ability to recognize nicks and repair nicks (Hamilton, S. C., J. W. Farchaus and M. C. Davis. 2001. DNA polymerases as engines for biotechnology. BioTechniques 31:370). DNA polymerases which can be used for this purpose include, for example, polI of *Thermoanaerobacter thermosulfuricus*, DNA polI of *E. coli*, and phage phi29. In a preferred embodiment, polI of *Bacillus stearothermophilus* is used to repair the nick of dsDNA and form unnotched dsDNA.

In some preferred embodiments, the nucleic acid molecules to be sequenced can also be amplified to increase the amounts or copy numbers of the nucleic acid molecules. Methods for amplifying nucleic acid molecules are well known to those skilled in the art, a typical example of which is PCR. For example, nucleic acid molecules can be amplified using the following methods: (i) polymerase chain reaction (PCR) requiring temperature cycling (see, for example, Saiki et al., 1995. Science 230:1350-1354), ligase chain reaction (see, for example, Barany, 1991. Proc. Natl. Acad. Sci. USA 88: 189-193; Barringer et al., 1990. Gene 89: 117-122), and transcription-based amplification (see, for example, Kwoh et al., 1989. Proc. Natl. Acad. Sci. USA 86:1173-1177); (ii) Isothermal amplification system (see, for example, Guatelli et al., 1990. Proc. Natl. Acad. Sci. USA 87: 1874-1878); QP replicase system (see, for example, Lizardi et al., 1988. BioTechnology 6: 1197-1202); and strand displacement amplification (Nucleic Acids Res. 1992 Apr. 11; 20(7): 1691-6). In some preferred embodiments, the nucleic acid molecule to be sequenced is amplified by PCR, and the primers used for PCR amplification comprise an adapter sequence and/or a tag sequence. The PCR product thus produced will carry an adapter sequence and/or a tag sequence, which can be conveniently used for subsequent applications (e.g., high throughput sequencing).

In some preferred embodiments, the nucleic acid molecules to be sequenced are also isolated and purified before or after various pretreatment steps. Such separation and purification steps may be advantageous. For example, in some preferred embodiments, the isolation and purification steps can be used to obtain nucleic acid molecules of a suitable length (e.g., 50-1000 bp) to be sequenced for subsequent applications (e.g., high throughput sequencing). In some preferred embodiments, agarose gel electrophoresis can be utilized to separate and purify the nucleic acid molecules to be sequenced. In some preferred embodiments, the nucleic acid molecules to be sequenced can be isolated and purified by size exclusion chromatography or sucrose sedimentation.

It should be understood that the pre-treatment steps described above (e.g., fragmentation, ed, addition of adapters, tag addition, nick repair, amplification, separation, and purification) are merely exemplary and not limiting. Those skilled in the art can perform various desired pretreatments on the nucleic acid molecules to be sequenced according to actual needs, and each pretreatment step is not limited by a specific order. For example, in some embodiments, the nucleic acid molecule can be firstly fragmented and an adapter is added prior to amplification. In other embodiments, the nucleic acid molecule can be amplified prior to fragmentation and addition of an adapter. In some embodiments, the nucleic acid molecule is fragmented and an adapter is added without amplification step.

In some exemplary embodiments, prior to step (1), the nucleic acid molecule of interest (e.g., genomic DNA) is subjected to the following pretreatment:

(i) fragmenting the nucleic acid molecule of interest (e.g., a large nucleic acid fragment, e.g., genomic DNA) to produce a fragmented nucleic acid molecule;

(ii) linking the fragmented nucleic acid molecule to an adapter sequence comprising, for example, a primer binding region capable of hybridizing to a universal amplification primer, a primer binding region capable of hybridizing to a universal sequencing primer, and/or a tag sequence, and optionally performing isolation, purification, and denaturation to produce a nucleic acid molecule to be sequenced;

(iii) linking the nucleic acid molecule to be sequenced to a support to obtain a nucleic acid molecule to be sequenced attached to the support.

Support

In most cases, the support for ligation of the nucleic acid molecule to be sequenced is in the solid phase for ease of handling. Therefore, in the present disclosure, "support" is sometimes also referred to as "solid support" or "solid support." However, it should be understood that the "support" referred to herein is not limited to a solid, it may also be a semi-solid (e.g., gel).

In the method of the present invention, the support for ligation of the nucleic acid molecule to be sequenced may be made of various suitable materials. Such materials include, for example, inorganic substances, natural polymers, synthetic polymers, and any combination thereof. Specific examples include, but are not limited to, cellulose, cellulose derivatives (such as nitrocellulose), acrylic resins, glass, silica gel, polystyrene, gelatin, polyvinylpyrrolidone, copolymers of vinyl and acrylamide, and polystyrene crossed with divinylbenzene (see, for example, Merrifield Biochemistry 1964, 3, 1385-1390), polyacrylamide, latex, dextran, rubber, silicon, plastic, natural sponge, metal plastic, cross-linking Dextran (e.g., Sephadex™), agarose gel (Sepharose™), and other supports known to those skilled in the art.

In some preferred embodiments, the support for ligation of the nucleic acid molecule to be sequenced may be a solid support comprising an inert substrate or matrix (e.g., slides, polymer beads, etc.), said inert substrate or matrix has been functionalized, for example, by the use of intermediate materials containing active groups that allow covalent attachment of biomolecules such as polynucleotides. Examples of such supports include, but are not limited to, polyacrylamide hydrogels supported on an inert substrate such as glass, in particular polyacrylamide hydrogels as described in WO 2005/065814 and US 2008/0280773, wherein, the content of the patent application is hereby incorporated by reference in its entirety. In such embodiments, the biomolecule (e.g., a polynucleotide) can be directly and covalently attached to an intermediate material (e.g., a hydrogel), while the intermediate material itself can be non-covalently attached to the substrate or matrix (for example, a glass substrate). In some preferred embodiments, the support is a slide or wafer having a surface modified with a layer of avidin, amino, acrylamide silane or aldehyde based chemical groups.

In the present invention, the support or solid support is not limited by its size, shape and configuration. In some embodiments, the support or solid support is a planar structure, such as a slide, chip, microchip, and/or array. The surface of such a support may be in the form of a planar layer.

In some embodiments, the support or surface thereof is non-planar, such as the inner or outer surface of a tube or container. In some embodiments, the support or solid support comprises microspheres or beads. As used herein, "microsphere" or "bead" or "particle" or grammatical equivalent refers to a small discrete particle. Suitable bead ingredients include, but are not limited to, plastics, ceramics, glass, polystyrene, methyl styrene, acrylic polymers, paramagnetic materials, cerium oxide sol, carbon graphite, titanium dioxide, latex, cross-linked dextran such as Sepharose, cellulose, nylon, crosslinked micelles and teflon, as well as any other materials outlined herein for the preparation of solid supports. In addition, the beads may be spherical or non-spherical. In some embodiments, spherical beads can be used. In some embodiments, irregular particles can be used. In addition, the beads can also be porous.

In some preferred embodiments, the support for ligation of the nucleic acid molecule to be sequenced is an array of beads or wells (also referred to as a chip). The array can be prepared by using any of the materials summarized herein for preparing a solid support, and preferably, the surface of the beads or pores on the array is functionalized to facilitate ligation of the nucleic acid molecules. The number of beads or holes on the array is not limited. For example, each array may include $10$-$10^2$, $10^2$-$10^3$, $10^3$-$10^4$, $10^4$-$10^5$, $10^5$-$10^6$, $10^6$-$10^7$, $10^7$-$10^8$, $10^8$-$10^9$ or more beads or pores. In some exemplary embodiments, one or more nucleic acid molecules can be attached to the surface of each bead or well. Correspondingly, each array can be linked with $10$-$10^2$, $10^2$-$10^3$, $10^3$-$10^4$, $10^4$-$10^5$, $10^5$-$10^6$, $10^6$-$10^7$, $10^7$-$10^8$, $10^8$-$10^9$ or more nucleic acid molecules. Thus, such arrays can be used particularly advantageously for high throughput sequencing of nucleic acid molecules.

As is generally known in the art, a variety of techniques can be utilized to make the support. Such techniques include, but are not limited to, photolithography, stamping techniques, plastic film technology, and microetching techniques. As will be appreciated by those skilled in the art, the techniques used will depend on the composition, structure and shape of the support.

Connection of the Nucleic Acid Molecule to be Sequenced to the Support

In the method of the invention, the nucleic acid molecule to be sequenced can be linked (e.g., covalently or non-covalently linked) to the support by any method known to those of ordinary skill in the art. For example, the nucleic acid molecule to be sequenced can be linked onto a support by covalent attachment, or by irreversible passive adsorption, or by intermolecular affinity (e.g., affinity between biotin and avidin). Preferably, however, the linkage between the nucleic acid molecule to be sequenced and the support is sufficiently strong that the nucleic acid molecule will not be detached from the support due to the conditions used in various reactions and washing of the water or buffer solution.

For example, in some preferred embodiments, the 5' end of the nucleic acid molecule to be sequenced carries a device capable of covalently attaching the nucleic acid molecule to a support, such as a chemically modified functional group. Examples of such functional groups include, but are not limited to, a phosphate group, carboxylic acid molecule, aldehyde molecule, thiol, hydroxyl group, dimethoxytrityl group (DMT), or an amino group.

For example, in some preferred embodiments, the 5' end of the nucleic acid molecule to be sequenced may be modified with a chemical functional group (e.g., phosphoric acid, thiol or amino group), and the support (e.g., porous glass bead) may be derivatized by amino-alkoxysilane (for example, aminopropyltrimethoxysilane, aminopropyltriethoxysilane, 4-aminobutyltriethoxysilane, etc.), thereby covalently linking the nucleic acid molecule to the support by the chemical reaction between the active groups. In some preferred embodiments, the 5' end of the nucleic acid molecule to be sequenced can be modified with a carboxylic acid or an aldehyde group, and the support (e.g., latex beads) is derivatized with hydrazine, thereby covalently linking the nucleic acid molecule to the support by the chemical reaction between the active groups (Kremsky et al., 1987).

Alternatively, a cross-linking agent can be used to link the nucleic acid molecule of interest to the support. Such crosslinking agents include, for example, succinic anhydride, phenyl diisothiocyanate (Guo et al., 1994), maleic anhydride (Yang et al., 1998), 1-ethyl-3-(3-dimethylaminopropyl)-carbodiimide hydrochloride (EDC), m-maleimidobenzoic acid-N-hydroxysuccinimide ester (MBS), N-succinimidyl [4-iodoacetyl]aminobenzoic acid (SIAB), 4-(N-maleimidomethyl)cyclohexane-1-carboxylic acid succinimide (SMCC), N-γ-maleimidobutyryloxy-succinimidyl ester (GMBS), 4-(p-maleimidophenyl)butyric acid succinimide (SMPB), and corresponding thio compounds (water soluble).

In addition, the support can also be derivatized with a bifunctional cross-linker such as homobifunctional cross-linker and a heterobifunctional cross-linker to provide a modified functionalized surface. Subsequently, a nucleic acid molecule having a 5'-phosphate, thiol or amino group is capable of interacting with a functionalized surface to form a covalent linkage between the nucleic acid and the support. A large number of bifunctional crosslinkers and methods of use thereof are well known in the art (see, for example, Pierce Catalog and Handbook, pages 155-200).

Primer, Polymerase and Base Derivative

In some preferred embodiments, in step (2), a primer for initiating nucleotide polymerization, a polymerase for performing nucleotide polymerization, and four base derivatives are added to the nucleic acid molecule to be sequenced, to form a reaction system containing a solution phase and a solid phase.

In the method of the present invention, the primer may be of any length and may comprise any sequence or any base as long as it is capable of specifically annealing to a region of the target nucleic acid molecule. In other words, in the method of the present invention, the primer is not limited to its length, structure and composition. For example, in some exemplary embodiments, the primers may be 5-50 bp in length, such as 5-10, 10-15, 15-20, 20-25, 25-30, 30-35, 35-40, 40-45, 45-50 bp. In some exemplary embodiments, the primers are capable of forming a secondary structure (e.g., a hairpin structure). In some exemplary embodiments, the primer does not form any secondary structure (e.g., a hairpin structure). In some exemplary embodiments, the primers may comprise naturally occurring or non-naturally occurring nucleotides. In some exemplary embodiments, the primer comprises or consists of a naturally occurring nucleotide. In some exemplary embodiments, the primer comprises a modified nucleotide, such as a locked nucleic acid (LNA). In some exemplary embodiments, the primer is capable of hybridizing to a nucleic acid of interest under stringent conditions, such as moderately stringent conditions or highly stringent conditions. In some exemplary embodiments, the primer has a sequence that is fully complementary to a target sequence in a nucleic acid molecule of interest. In some exemplary embodiments, the primer is partially complementary to a target sequence in a nucleic acid molecule of interest (e.g., a mismatch is present). In some exemplary embodiments, the primer comprises a universal primer sequence. In some exemplary embodiments, the nucleic acid molecule to be sequenced comprises an adapter, and the adapter comprises a sequence capable of hybridizing to a universal primer, and the primer used is a universal primer.

In the method of the present invention, various known polymerases can be used for nucleotide polymerization. In some exemplary embodiments, the polymerase is capable of synthesizing a new DNA strand (for example, a DNA polymerase) using DNA as a template. In some exemplary embodiments, the polymerase is capable of synthesizing a new DNA strand (for example, a reverse transcriptase) using RNA as a template. In some exemplary embodiments, the polymerase is capable of synthesizing a new RNA strand (for example, RNA polymerase) using DNA or RNA as a template. Accordingly, in some preferred embodiments, the polymerase is selected from the group consisting of a DNA polymerase, an RNA polymerase, and a reverse transcriptase. A suitable polymerase can be selected for nucleotide polymerization according to actual needs. In some preferred embodiments, the polymerization reaction is a polymerase chain reaction (PCR). In some preferred embodiments, the polymerization reaction is a reverse transcription reaction.

Further, as described above, in the method of the present invention, steps (4)-(7) may be repeated. Therefore, in some preferred embodiments of the invention, one or more rounds of nucleotide polymerization can be carried out. In other words, in some preferred embodiments of the invention, the nucleotide polymerization can be carried out in one or more steps. In this case, the same or different polymerases can be used for each round of nucleotide polymerization. For example, a first DNA polymerase can be used in the first round of nucleotide polymerization, and a second DNA polymerase can be used in the second round of nucleotide polymerization. However, in some exemplary embodiments, the same polymerase (for example, the same DNA polymerase) is used in all nucleotide polymerizations.

In the method of the present invention, the four compounds used in the step (2) are derivatives of nucleotides A, (T/U), C and G, respectively. In some exemplary embodiments, the four compounds are derivatives of ribose or deoxyribonucleotides A, T, C, and G, respectively. In some exemplary embodiments, the four compounds are derivatives of ribose or deoxyribonucleotides A, U, C, and G, respectively. It is particularly advantageous that the four compounds do not perform a chemical reaction with each other during the nucleotide polymerization.

In addition, the four compounds described have a base complementary pairing ability. For example, when the compound is a derivative of nucleotide A, it will be capable of pairing with the base T or U. When the compound is a derivative of nucleotide T or U, it will be able to pair with base A. When the compound is a derivative of nucleotide C, it will be able to pair with base G. When the compound is a derivative of nucleotide G, it will be able to pair with base C. Thus, in step (4), the polymerase (for example, DNA polymerase) will incorporate a compound capable of complementary pairing with a base at a corresponding position in the template nucleic acid into 3' end of the growing nucleic acid strand according to the principle of base complementary pairing. Accordingly, after determining the type of compound incorporated into the 3' end of the growing nucleic acid strand by the fluorescent signal, the type of the base at the corresponding position in the template nucleic acid can be determined according to the principle of base complementary pairing. For example, if a compound incorporated at the 3' end of the growing nucleic acid strand is identified as a derivative of nucleotide A, then the base at the corresponding position in the template nucleic acid can be determined to be T or U. If a compound incorporated at the 3' end of the growing nucleic acid strand is identified as a derivative of nucleotide T or U, then it is determined that the base at the corresponding position in the template nucleic acid is A. If a compound incorporated at the 3' end of the growing nucleic acid strand is identified as a derivative of nucleotide C, then it is determined that the base at the corresponding position in the template nucleic acid is G. If a compound incorporated at the 3' end of the growing nucleic acid strand is identified as a derivative of nucleotide G, then it is determined that the base at the corresponding position in the template nucleic acid is C.

In some preferred embodiments, the hydroxy groups (—OH) at the 3' position of the ribose or deoxyribose of the four compounds are protected. In other words, in some preferred embodiments, the hydroxyl groups (—OH) at the 3' position of the ribose or deoxyribose of the four compounds are protected by a protecting group, thus they are capable of terminating the polymerization of a polymerase (for example, DNA polymerase). For example, when any of the four compounds is introduced into the 3' end of the growing nucleic acid strand, the polymerase is incapable of performing the next round of polymerization due to free hydroxyl group (—OH) is not present at the 3' position of the ribose or deoxyribose of the compound, and the polymerization reaction will be terminated thereby. In this case, in each round of polymerization, one and only one base will be incorporated into the growing nucleic acid strand.

Particularly advantageously, the protecting groups at the 3' position of the ribose or deoxyribose of the four compounds can be removed. In some preferred embodiments, after step (7) (for example, in step (8)), the protecting group is removed and converted to a free hydroxyl group (—OH). Subsequently, the polymerase and the four compounds can be used to carry out the next round of polymerization of the grown nucleic acid strand and introduce one more base.

Thus, the four compounds used in step (2) have reversible termination properties: when they are incorporated into the 3' end of the growing nucleic acid strand (for example, in step (4)), they will terminate the polymerase and continue the polymerization, to terminate further extension of the growing nucleic acid strand; and, after the comprised protecting group is removed, the polymerase will be able to continue to polymerize the growing nucleic acid strand (for example, in step (10)), continuing to extend the nucleic acid chain.

Fluorescent Signal and Fluorophore

In the method of the invention, any material capable of emitting a fluorescent signal (e.g., a fluorophore) can be used. Examples of fluorophores include, but are not limited to, various known fluorescent labels such as AF532, ALEX-350, FAM, VIC, TET, CAL Fluor® Gold 540, JOE, HEX, CAL Fluor Orange 560, TAMRA, CAL Fluor Red 590, ROX, CAL Fluor Red 610, TEXAS RED, CAL Fluor Red 635, Quasar 670, CY3, CY5, CY5.5, Quasar 705, and the like. Such fluorophores and their detection methods are well known in the art and can be selected according to actual needs.

Different fluorophores may have the same or substantially the same emission spectrum under the same or near excitation conditions, thereby emitting the same or substantially the same fluorescent signal. For example, CY3 is capable of emitting fluorescence at a wavelength of about 560 nm under exciting light with a wavelength of about 550 nm, and AF532 is capable of emitting fluorescence at a wavelength of about 555 nm under exciting light having a wavelength of about 530 nm. Choosing the appropriate exciting light conditions allows the two to produce the same or substantially the same emitting spectrum. In the present invention, emitting spectrum means that under the same excitation condition, the maximum emission wavelength of the emission spectrum is close (e.g., the phase difference is less than 20 nm), so that the same signal is given on the optical filter to be considered to be substantially the same spectrum.

In some embodiments, a fluorophore can be one member of a binding pair, and/or is capable of performing a bioorthogonal reaction (for example, a bioorthogonal ligation reaction or a bioorthogonal cleavage reaction). For example, the fluorophore Cy3, as one member of the binding pair, is capable of specifically binding to the other member Cy3 antibody of the binding pair.

Determination of a Compound Incorporated into a Growing Nucleic Acid Strand

In the method of the invention, the type of compound incorporated into the growing nucleic acid strand is identified/determined by only one fluorophore (or a different fluorophore capable of emitting the same fluorescent signal). For this purpose, in the method of the invention, the fluorescent signal detection on the duplex or the growing nucleic acid strand is carried out twice after each round of polymerization. Briefly, in the method of the present invention, firstly, one of the four compounds is incorporated into 3' end (step 4) of a growing nucleic acid strand according to the principle of base complementary pairing by using a polymerase, a nucleic acid molecule to be sequenced is used as a template; subsequently, if the fourth compound itself is capable of emitting a fluorescent signal, the growing nucleic acid strand is first detected to determine whether it emits a fluorescent signal; if the fourth compound does not carry a fluorophore, the duplex or the growing nucleic acid strand is subjected to a treatment in a reaction system containing a solution phase and a solid phase, the treatment has no effect on the first compound, the second compound, and the third compound, but enables the fourth compound to emit the same fluorescent signal as the second compound (step 5); after detection, the growing nucleic acid strand is treated, the treatment has no effect on the first compound and the second compound, but enables the third compound to emit the same fluorescent signal as the second compound, and is capable of removing the fluorescent signal of the fourth compound (step 6); then, the growing nucleic acid strand is subjected to a second detection to determine whether it emits fluorescence signal (step 7). Based on the results of the two detections of fluorescent signal, the type of the compound incorporated into the 3' end of the growing nucleic acid strand can be accurately determined.

In particular, if the first compound is incorporated into 3' end of the growing nucleic acid strand in step (4), then, since the first compound itself does not carry fluorophore, and is not affected by the treatment in step (6), no fluorescent signal will be detected in steps (5) and (7). In other words, if no fluorescent signal is detected in both of steps (5) and (7), it can be determined that the compound incorporated at the 3' end of the growing nucleic acid strand is the first compound.

If the second compound is incorporated into the 3' end of the growing nucleic acid strand in step (4), then since the second compound itself carries a fluorophore and is not affected by the treatment in step (6), a fluorescent signal will be detected in both steps (5) and (7). In other words, if a fluorescent signal is detected in both of steps (5) and (7), then it can be determined that the compound incorporated at the 3' end of the growing nucleic acid strand is the second compound.

If the third compound is incorporated into the 3' end of the growing nucleic acid strand in step (4), then (i) since the third compound itself does not carry a fluorophore, no fluorescent signal will be detected in step (5); and, (ii) since the third compound performs the treatment of step (6) and emits a fluorescent signal a fluorescent signal will be detected in step (7). In other words, if a fluorescent signal is not detected in the step (5) and a fluorescent signal is detected in the step (7), it can be determined that the compound incorporated at the 3' end of the growing nucleic acid strand is the third compound.

If the fourth compound is incorporated into the 3' end of the growing nucleic acid strand in step (4), then (i) since the fourth compound carries fluorophore itself, or carries a fluorophore upon the treatment in step (5), a fluorescent signal will be detected in step (5); and, (ii) since the fourth compound loses its fluorescent signal upon the treatment of step (6), no fluorescent signal will be detected in step (7). In other words, if a fluorescent signal is detected in step (5) and no fluorescent signal is detected in step (7), it can be determined that the compound incorporated at the 3' end of the growing nucleic acid strand is the fourth compound.

Therefore, in some preferred embodiments, the method of the present invention further comprises, after step (7), determining the types of the compounds incorporated at the 3' end of the growing nucleic acid strand in step (4) according to the detection results in steps (5) and (7), wherein, when the detection results of steps (5) and (7) are both, when the duplex or the growing nucleic acid strand does not emit the fluorescent signal, it is determined the compound incorporated at the 3' end of the growing nucleic acid strand in step (4) as the first compound;

When the detection results of steps (5) and (7) are both, when the duplex or the growing nucleic acid strand emits the fluorescent signal, determining the compound incorporated at the 3' end of the growing nucleic acid strand in step (4) as the second compound;

when the detection result in step (5) is that the duplex or the growing nucleic acid strand does not emit the fluorescent signal, and the detection result in step (7) is that when the duplex or the growing nucleic acid strand emit the fluorescent signal, determining the compound incorporated at the 3' end of the growing nucleic acid strand in step (4) as the third compound; and when the detection result in step (5) is that the duplex or the growing nucleic acid strand emit the fluorescent signal, and the detection result in step (7) is that when the duplex or the growing nucleic acid strand does not emit the fluorescent signal, determining the compound incorporated at the 3' end of the growing nucleic acid strand in step (4) as the fourth compound.

In some preferred embodiments, the method of the present invention further comprises, after step (7), determining the types of bases at the corresponding position in the nucleic acid molecule to be sequenced according to the type of compound incorporated in the 3' end of the growing nucleic acid strand in step (4), based on the base complementary pairing principle. For example, if a compound incorporated at the 3' end of the growing nucleic acid strand is identified as a first compound (for example, a derivative of nucleotide A), then it can be determined that the base at the corresponding position in the nucleic acid molecule to be sequenced can be determined is a base capable of pairing with the first compound (for example, T or U).

More specifically, if a compound incorporated at the 3' end of the growing nucleic acid strand is identified as a derivative of nucleotide A, then it can be determined that the base at the corresponding position in the nucleic acid molecule to be sequenced is T or U. If the compound incorporated at the 3' end of the growing nucleic acid strand is determined as a derivative of nucleotide T or U, then it can be determined that the base at the corresponding position in the nucleic acid molecule to be sequenced is A. If the compound incorporated at the 3' end of the growing nucleic acid strand is determined to be a derivative of nucleotide C, then it can be determined that the base at the corresponding position in the nucleic acid molecule to be sequenced is G. If the compound incorporated at the 3' end of the growing nucleic acid strand is determined as a derivative of nucleotide G, then it is determined that the base at the corresponding position in the nucleic acid molecule to be sequenced is C.

Treatment for the Duplex or the Growing Nucleic Acid Strand

In some preferred embodiments of the methods of the invention, each round of polymerization may involve two detections of fluorescent signal, as well as two or three treatments of the duplex or the growing nucleic acid strand, wherein, the treatment in step (6) can be used to alter the fluorescent signal of the third compound and the fourth compound (so that it is convenient to distinguish/identify the type of compound incorporated into the 3' end of the growing nucleic acid strand); the treatment in step (8) can be used to remove the protecting group at the 3' position of the ribose or deoxyribose in the compound incorporated at the 3' end of the growing nucleic acid strand (so that a new round of polymerization can be initiated), and remove the fluorescent signal that may be carried on the duplex or the growing nucleic acid strand (thereby avoiding interference with subsequent fluorescence detection); optionally, if the fourth compound itself cannot emit a fluorescent signal, then step (5) comprises treatment enabling the fourth compound to carry the fluorophore.

Suitable treatment can be designed and selected according to the structure and type of the four compounds used. For example, in some exemplary embodiments, a reactive group capable of performing a bioorthogonal cleavage reaction and/or a bioorthogonal ligation reaction may be introduced in one or more of the four compounds so as to control (e.g., maintain or change) the ability of the four compounds to emit the fluorescent signal in step (6). In some exemplary embodiments, members of the binding pair may be introduced in one or more of the four compounds so as to control (for example, maintain or change) the ability of the four compounds to emit fluorescent signals in step (6).

For example, in some exemplary embodiments, a reactive group capable of performing a bioorthogonal ligation reaction can be introduced into the third compound and the fluorophore can be introduced in the third compound by bioorthogonal ligation reaction in step (6) to enable the third compound to emit a fluorescent signal. In some exemplary embodiments, in step (6), one member of the binding pair can be introduced into the third compound and a fluorophore can be introduced into the third compound by the specific interaction between the member and the other member (carrying the fluorophore) of the binding pair to enable the compound to emit the fluorescent signal. In some exemplary embodiments, a reactive group capable of performing a bioorthogonal cleavage reaction can be introduced into the fourth compound, and the fluorophore in the fourth compound can be cleaved off by a bioorthogonal cleavage reaction in step (6) to enable the fourth compound to lose its ability to emit a fluorescent signal. In some exemplary embodiments, one member of the binding pair can be introduced into the fourth compound, and a quenching group which is capable of quenching the fluorescence can be introduced into the fourth compound by the specific interaction between the member and the other member (carrying the quenching group) of the binding pair to enable the fourth compound to lose the ability of emitting the fluorescent signal. In some exemplary embodiments, a reactive group capable of performing a bioorthogonal cleavage reaction can be introduced into the four compounds so as to remove the protecting group at the 3' position of ribose or deoxyribose and the fluorescent signal that may be present in step (8).

Washing Step

In the method of the invention, the washing step can be increased as needed. The washing step can be increased at any desired stage, and optionally, the washing step can be performed one or more times.

For example, one or more washings may be performed in step (5) after removing the solution phase of the reaction system to sufficiently remove the residual solution phase. Such a washing step may be advantageous, which can be used to fully remove the free (i.e., not incorporated into the growing nucleic acid strand) compound carrying the fluorophore, to reduce the non-specific fluorescent signal as much as possible.

Similarly, one or more washings may be performed in step (7) after removing the solution phase of the reaction system to sufficiently remove the residual solution phase. Such a washing step may be advantageous, which can be used to fully remove the agents (which may carry the fluorescence) used in step (6) to reduce the non-specific fluorescent signal as much as possible.

Similarly, one or more washings may be performed in step (9) after removing the solution phase of the reaction system to sufficiently remove the residual solution phase. Such a washing step may be advantageous, which can be used to fully remove the agents and the produced products (which may carry the fluorescence) in step (8) to reduce the non-specific fluorescent signal as much as possible, and avoid adverse effects on subsequent polymerization reaction as much as possible.

The washing step can be carried out using a variety of suitable washing solutions. Examples of such washing solutions include, but are not limited to, phosphate buffer, citrate buffer, Tris-HCl buffer, acetate buffer, carbonate buffer, and the like. It is within the ability of those skilled in the art to select suitable washing solution (including suitable ingredients, concentration, ionic strength, pH, etc.) according to the actual needs.

Two exemplary embodiments of the method of the invention are described in detail below. However, it is to be understood that the embodiments described in detail below are merely illustrative and not restrictive. Modifications and modifications of the embodiments described in detail below are apparent to those skilled in the art.

Exemplary Embodiment 1

In some exemplary embodiments, the ability of the four compounds to emit fluorescent signals is controlled (for example, maintained or changed) in step (6) by using a reactive group capable of performing a bioorthogonal cleavage reaction and/or a bioorthogonal ligation reaction; and preferably, the removal of the protecting group and the fluorescent signal can be achieved in step (8) by using a reactive group capable of performing a bioorthogonal cleavage reaction. For example, in some exemplary embodiments, the first, second, third, and fourth compounds may have the structures of formulas (I), (11), (III), and (IV), respectively:

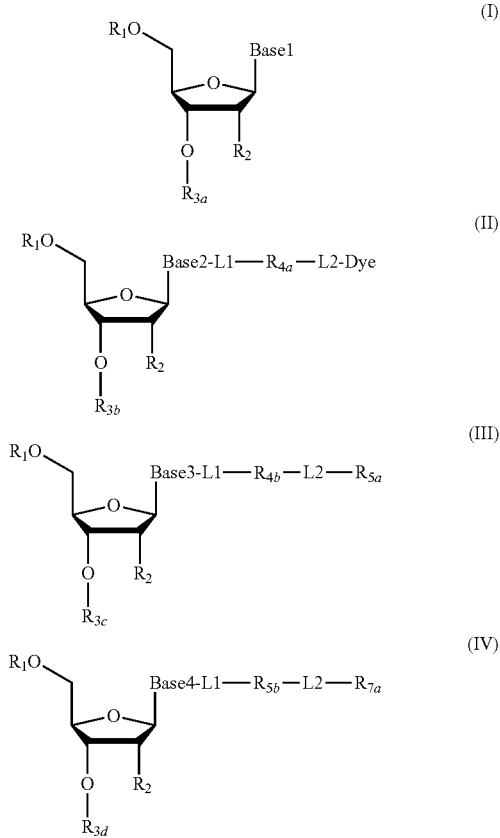

wherein, Base1, Base2, Base3, and Base4 represent 4 different bases, and are selected from A, (T/U), C, and G;

$R_1$ is independently selected from —H, a monophosphate group (—PO$_3$H$_2$), a diphosphate group (—PO$_3$H—PO$_3$H$_2$), a triphosphate group (—PO$_3$H—PO$_3$H—PO$_3$H$_2$) and a tetraphosphate group (—PO$_3$H—PO$_3$H—PO$_3$H—PO$_3$H$_2$);

$R_2$ is independently selected from —H and —OH;

$R_{3a}$, $R_{3b}$, $R_{3c}$, $R_{3d}$, $R_{4a}$, $R_{4b}$, and $R_{5b}$ are independently a reactive group capable of performing a bioorthogonal cleavage reaction;

$R_{5a}$ is a reactive group capable of performing a first bioorthogonal ligation reaction;

L1 is independently a linking group or absent;

L2 is independently a linking group or absent;

Dye represents a fluorophore capable of emitting a fluorescent signal;

$R_{7a}$ is a fluorophore capable of emitting a fluorescent signal (Dye$_1$), or a reactive group capable of performing a second bioorthogonal ligation reaction, or one member of a binding pair;

further, Dye and Dye$_1$ have the same structure, or have different structures but have the same or substantially the same emission spectrum;

optionally, a reactive group $R_8$ capable of performing a third bioorthogonal ligation reaction is present between $R_{5b}$ and $R_{7a}$.

In such exemplary embodiment, the fourth compound itself may carry a fluorophore capable of emitting the same fluorescent signal as the second compound, or may not carry a fluorophore but specifically interact with/bind to an agent (for example, the other member of the binding pair, or a compound capable of performing the second bioorthogonal ligation reaction with $R_{7a}$) carrying a fluorophore (for example, a fluorophore having the same structure as the fluorophore of the second compound, or a fluorophore having the same emission spectrum as the fluorophore of the second compound) in step (5), to introduce the fluorophore into the fourth compound, and enables the fourth compound to emit the same fluorescent signal as that of the second compound. Further, a fluorophore (for example, a fluorophore the same as the fluorophore of the second compound, or a fluorophore having a different structure but the same or substantially the same emission spectrum as that of the second compound) can be introduced into the third compound by making $R_{5a}$ to perform the first bioorthogonal ligation reaction with an agent carrying the fluorophore; and, (1) the fluorophore in the fourth compound can be removed by making $R_{5b}$ in the fourth compound to perform the bioorthogonal cleavage reaction, or (ii) the fluorescent signal of the fourth compound can be quenched by making $R_8$ in the fourth compound to perform the third bioorthogonal ligation reaction with a compound carrying a quenching group. Therefore, in some preferred embodiments, in step (6), the duplex or the growing nucleic acid strand is subjected to a treatment which has no effect on the first compound and the second compound, but enables $R_{5a}$ to perform the first bioorthogonal ligation reaction with an agent carrying a fluorophore (for example, a fluorophore the same as the fluorophore of the second compound, or a fluorophore having a different structure but the same or substantially the same emission spectrum as that of the second compound) (thereby introducing the fluorophore carried by the agent into the third compound, and making the third compound to carry the fluorophore and emit a fluorescent signal); moreover, the treatment enables $R_{5b}$ to perform the bioorthogonal cleavage reaction (thereby removing the fluorophore in the fourth compound, and making the fourth compound no longer to emit the fluorescent signal), or enables $R_8$ in the fourth compound to perform the second bioorthogonal ligation reaction with a compound carrying a quenching group, thereby quenching the fluorescent signal emitted by the fluorophore in the fourth compound. In such exemplary embodiments, prior to the treatment of the step (6), the first compound and the third compound, if present, do not emit fluorophore, and the second compound and the fourth compound, if present, fluoresce; further, after the treatment of step (6), the first compound (if present) still does not fluoresce, the second compound (if present) still fluoresces, the third compound (if present) changes to fluoresce, and the fourth compound (if present) changes to not fluoresce. Therefore, the type of compound incorporated into the 3' end of the growing nucleic acid strand can be determined by detecting and comparing the fluorescent signal.

Further, in such exemplary embodiments, by enabling $R_{3a}$, $R_{3b}$, $R_{3c}$, $R_{3d}$, $R_{4a}$, $R_{4b}$ to perform a bioorthogonal cleavage reaction, the protecting group at the 3' position of the ribose or deoxyribose in the compound incorporated into the 3' end of the growing nucleic acid strand is removed, and the fluorophore (if present) on the duplex or the growing nucleic acid strand is removed. Therefore, in some preferred embodiments, in step (8), the duplex or the growing nucleic acid strand is subjected to a treatment which enables $R_{3a}$, $R_{3b}$, $R_{3c}$, $R_{3d}$, $R_{4a}$, $R_{4b}$ to perform the bioorthogonal cleavage reaction. In such exemplary embodiments, after the treatment of step (8), the growing nucleic acid strand will have no fluorophore, and the ribose or deoxyribose at the 3' end of the growing nucleic acid strand will have a free hydroxyl group at the 3' position, wherein the free hydroxyl group can be used to initiate the next round of polymerization.

Therefore, in some preferred embodiments, the method of the invention comprises the steps of:

(1) providing a nucleic acid molecule to be sequenced attached onto a support or attaching the nucleic acid molecule to be sequenced onto a support;

(2) adding a primer for initiating a nucleotide polymerization, a polymerase for performing a nucleotide polymerization, and the first, second, third and fourth compounds having structures of formula (I), formula (II), formula (III), and formula (IV), respectively, to form a reaction system comprising a solution phase and a solid phase:

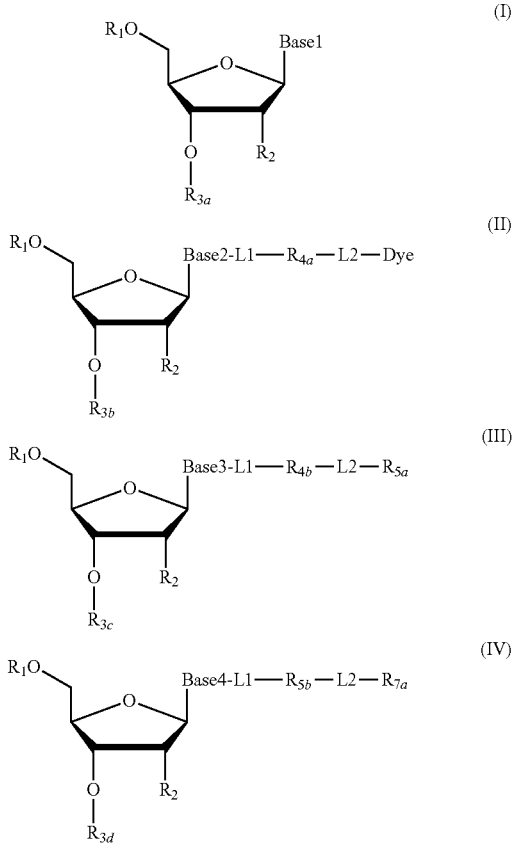

wherein, Base1, Base2, Base3, and Base4 represent 4 different bases, and are selected from A, (T/U), C, and G;

$R_1$ is independently selected from —H, a monophosphate group (—PO$_3$H$_2$), a diphosphate group (—PO$_3$H—PO$_3$H$_2$), a triphosphate group (—PO$_3$H—PO$_3$H—PO$_3$H$_2$) and a tetraphosphate group (—PO$_3$H—PO$_3$H—PO$_3$H—PO$_3$H$_2$);

$R_2$ is independently selected from —H and —OH;

$R_{3a}$, $R_{3b}$, $R_{3c}$, $R_{3d}$, $R_{4a}$, $R_{4b}$, and $R_{5b}$ are independently a reactive group capable of performing a bioorthogonal cleavage reaction;

$R_{5a}$ is a reactive group capable of performing a first bioorthogonal ligation reaction;

L1 is independently a linking group or absent;
L2 is independently a linking group or absent;

Dye represents a fluorophore capable of emitting a fluorescent signal;

$R_{7a}$ is a fluorophore capable of emitting a fluorescent signal (Dye$_1$), or a reactive group capable of performing a second bioorthogonal ligation reaction, or one member of a binding pair;

also, Dye and Dye$_1$ have the same structure, or have different structures but have the same or substantially the same emission spectrum;

optionally, there is a reactive group $R_8$ capable of performing a third bioorthogonal ligation reaction between $R_{5b}$ and $R_{7a}$;

(3) annealing the primer to the nucleic acid molecule to be sequenced, wherein the primer serves as an initial growing nucleic acid strand, and together with the nucleic acid molecule to be sequenced, forms a duplex attached to the support;

(4) performing a nucleotide polymerization reaction using the polymerase under a condition allowing the polymerase to perform the nucleotide polymerization, thereby incorporating one of the four compounds into the 3' end of the growing nucleic acid strand;

(5)(i) if the fourth compound is capable of emitting the same fluorescent signal as the second compound, and $R_{7a}$ is Dye$_1$, removing the solution phase of the reaction system of the previous step, retaining the duplex attached to the support, and detecting whether the duplex or the growing nucleic acid strand emits the fluorescent signal; or (ii) if the fourth compound does not emit a fluorescent signal, and $R_{7a}$ is a reactive group capable of performing the second bioorthogonal ligation reaction or is one member of the binding pair, subjecting the duplex or the growing nucleic acid strand to a treatment in a reaction system containing a solution phase and a solid phase, wherein the treatment has no effect on the first compound, the second compound and the third compound, and enables $R_{7a}$ in the fourth compound to specifically interact with/bind to, or perform the second bioorthogonal ligation reaction with an agent (e.g., the other member of the binding pair, or a compound which is capable of performing the second bioorthogonal ligation reaction with $R_{7a}$) carrying a fluorophore (for example, a fluorophore having the same structure as the fluorophore of the second compound, or a fluorophore having the same or substantially the same emission spectrum as the fluorophore of the second compound); thereafter, removing the solution phase of the reaction system of the previous step, retaining the duplex attached to the support, and detecting whether the duplex or the growing nucleic acid strand emits the fluorescent signal;

wherein the other member of the binding pair carrying the fluorophore has the structure: $R_{7b}$-L-Dye$_1$; wherein $R_{7b}$ is the other member of the binding pair, L is independently a linking group or absent; Dye$_1$ represents a fluorophore that is capable of emitting a fluorescent signal, and has the same structure as Dye, or has a different structure but the same emission spectrum as Dye; or the compound capable of performing the second bioorthogonal ligation reaction with $R_{7a}$ and carrying a fluorophore has the following structure: $R_{7b}$-L-$Dye_1$; wherein $R_{7b}$ is a group capable of performing the second bioorthogonal ligation reaction with $R_{7a}$, L is independently a linking group or absent; $Dye_1$ represents a fluorophore capable of emitting a fluorescent signal, and has the same structure as Dye, or has a different structure but the same emission spectrum as Dye;

(6) subjecting the duplex or the growing nucleic acid strand to a treatment in a reaction system containing a solution phase and a solid phase, wherein the treatment has no effect on the first compound and the second compound, and enables $R_{5a}$ in the third compound to perform the first bioorthogonal ligation reaction with an agent carrying a fluorophore (e.g., a fluorophore having the same structure as the fluorophore of the second compound, or a fluorophore having a structure different from but having the same or substantially the same emission spectrum as the fluorophore of the second compound), thereby introducing the fluorophore carried by the agent into the third compound and making the third compound to emit a fluorescent signal; and said treatment (i) enables $R_{5b}$ in the fourth compound to perform the bioorthogonal cleavage reaction, thereby removing the fluorophore in the fourth compound, or (ii) enables $R_8$ in the fourth compound to react with a compound carrying a quenching group to perform a third orthogonal ligation reaction, thereby quenching the fluorescent signal emitted by the fluorophore Dye1 in the fourth compound; and (7) removing the solution phase of the reaction system in the previous step, retaining the duplex attached to the support, and detecting whether the duplex or the growing nucleic acid strand emits the fluorescent signal.

In some preferred embodiments, the method further comprises the steps of:

(8) subjecting the duplex or the growing nucleic acid strand in the previous step to a treatment in a reaction system containing a solution phase and a solid phase, wherein the treatment enables $R_{3a}$, $R_{3b}$, $R_{3c}$, $R_{3d}$, $R_{4a}$ and $R_{4b}$ to perform the bioorthogonal cleavage reaction, thereby allowing the compound incorporated at the 3' end of the growing nucleic acid strand to have a free hydroxyl group at the 3' position of the ribose or deoxyribose (in other words, converting —$OR_{3a}$, —$OR_{3b}$, —$OR_{3c}$ or —$OR_{3d}$ (if present) into a free hydroxyl group), and, removing the fluorophore on the duplex or the growing nucleic acid strand (in other words, removing the fluorophore attached to $R_{4a}$ or $R_{4b}$), if present;

(9) removing the solution phase of the reaction system in the previous step;

(10) adding a polymerase for performing a nucleotide polymerization, and the first compound, the second compound, the third compound, and the fourth compound, thereby forming a reaction system containing a solution phase and a solid phase, and then performing the steps (4)-(7).

In some preferred embodiments, the method further comprises the step of:

(11) repeating steps (8)-(10) one or more times.

In some exemplary embodiments, in step (4), if the compound of formula (I) is incorporated into the 3' end of the growing nucleic acid strand, since the compound of formula (I) does not carry a fluorophore itself, and it does not react at step (6), no fluorescent signal will be detected in steps (5) and (7). In other words, if no fluorescent signal is detected in both of steps (5)-(7), it can be determined that the compound incorporated at the 3' end of the growing nucleic acid strand is a compound of formula (I).

In step (4), if the compound of formula (II) is incorporated into the 3' end of the growing nucleic acid strand, since the compound of formula (II) carries a fluorophore itself and it does not perform any reaction in step (6), a fluorescent signal will be detected in both steps (5) and (7). In other words, if a fluorescent signal is detected in both of steps (5) and (7), it can be determined that the compound incorporated at the 3' end of the growing nucleic acid strand is a compound of formula (II).

In step (4), if the compound of formula (III) is incorporated into the 3' end of the growing nucleic acid strand, (i) since the compound of formula (III) does not carry a fluorophore, no fluorescent signal will be detected in step (5); and (ii) the compound of formula (III) performs a bioorthogonal ligation reaction with the agent carrying a fluorophore in step (6), introducing the fluorophore into the growing nucleic acid strand, therefore, a fluorescent signal will be detected in step (7). In other words, if no fluorescent signal is detected in step (5) and a fluorescent signal is detected in step (7), it can be determined that the compound incorporated at the 3' end of the growing nucleic acid strand is a compound of the formula (III).

In step (4), if the compound of formula (IV) is incorporated into the 3' end of the growing nucleic acid strand, (i) since the compound of formula (IV) carries a fluorophore itself or carries a fluorophore after the treatment in step (5), a fluorescent signal will be detected in step (5); and (ii) since the compound of formula (IV) performs a bioorthogonal cleavage reaction or a third bioorthogonal ligation reaction in step (6) to loss the fluorophore or the fluorescent signal is quenched, the fluorescent signal will not be detected in step (7) thereby. In other words, if a fluorescent signal is detected in step (5) and a fluorescent signal is not detected in step (7), it can be determined that the compound incorporated at the 3' end of the growing nucleic acid strand is a compound of the formula (IV).

Therefore, in some preferred embodiments, the method of the present invention further comprises: after step (7), determining the type of the compound incorporated into 3' end of the growing nucleic acid strand in step (4) according to the detection results in steps (5) and (7), wherein, when both of the detection results of steps (5) and (7) are that the duplex or the growing nucleic acid strand does not emit the fluorescent signal, it is determined that the compound incorporated into 3' end of the growing nucleic acid strand in step (4) is the compound of formula (I);

when both of the detection results of steps (5) and (7) are that the duplex or the growing nucleic acid strand emits the fluorescent signal, it is determined that the compound incorporated into 3' end of the growing nucleic acid strand in step (4) is the compound of formula (II);

when the detection result of step (5) is that the duplex or the growing nucleic acid strand does not emit the fluorescent signal, and the detection result of step (7) is that the duplex or the growing nucleic acid strand emits the fluorescent signal, it is determined that the compound incorporated into 3' end of the growing nucleic acid strand in step (4) is the compound of formula (III); and, when the detection result of step (5) is that the duplex or the growing nucleic acid strand emits the fluorescent signal, and the detection result of step (7) is that the duplex or the growing nucleic acid strand does not emit the fluorescent signal, it is determined that the compound incorporated into 3' end of the growing nucleic acid strand in step (4) is the compound of formula (IV).

In some preferred embodiments, the method of the present invention further comprises that, after step (7), based on the base complementary pairing principle, the type of base at the corresponding position in the nucleic acid molecule to be sequenced is determined according to the type of the compound incorporated at the 3' end of the growing nucleic acid strand in step (4).

In some preferred embodiments, the compound of formula (I), the compound of formula (II), the compound of formula (III) and the compound of formula (IV) do not react with each other during the nucleotide polymerization reaction.

In some preferred embodiments, Base1 and Base2 are purine bases, and Base3 and Base4 are pyrimidine bases. In some preferred embodiments, Base1 is base G, Base2 is base A, Base3 is base C, and Base4 is base T or U. In some preferred embodiments, Base1 is base G, Base2 is base A, Base3 is base T or U, and Base4 is base C. In some preferred embodiments, Base1 is base A, Base2 is base G, Base3 is base C, and Base4 is base T or U. In some preferred embodiments, Base1 is base A, Base2 is base G, Base3 is base T or U, and Base4 is base C.

In some preferred embodiments, Base1 and Base2 are pyrimidine bases, and Base3 and Base4 are purine bases. In some preferred embodiments, Base1 is base C, Base2 is base T or U, Base3 is base G, and Base4 is base A. In some preferred embodiments, Base1 is base C, Base2 is base T or U, Base3 is base A, and Base4 is base G. In some preferred embodiments, Base1 is base T or U, Base2 is base C, Base3 is base G, and Base4 is base A. In some preferred embodiments, Base1 is base T or U, Base2 is base C, Base3 is base A, and Base4 is base G.

In some preferred embodiments, the compound of formula (I), the compound of formula (II), the compound of formula (III) and the compound of formula (IV) have the same $R_1$. In some preferred embodiments, $R_1$ is independently —H. In some preferred embodiments, $R_1$ is independently monophosphate group (—$PO_3H_2$). In some preferred embodiments, $R_1$ is independently diphosphate group (—$PO_3H$—$PO_3H_2$). In some preferred embodiments, $R_1$ is independently triphosphate group (—$PO_3H$—$PO_3H$—$PO_3H_2$). In some preferred embodiments, $R_1$ is independently tetraphosphate group (—$PO_3H$—$PO_3H$—$PO_3H$—$PO_3H_2$).

In some preferred embodiments, the compound of formula (I), the compound of formula (II), the compound of formula (III) and the compound of formula (IV) have the same $R_2$. In some preferred embodiments, $R_2$ is independently —H. In some preferred embodiments, $R_2$ is independently —OH.

In some preferred embodiments, $R_{3a}$, $R_{3b}$, $R_{3c}$, $R_{3d}$, $R_{4a}$, $R_{4b}$, $R_{5a}$, $R_{5b}$ are independently capable of performing a bioorthogonal cleavage or ligation reaction. As used herein, the expression "independently capable of performing bioorthogonal cleavage or ligation reaction" means that the reactive groups, agents, or molecules, etc., are capable of performing bioorthogonal cleavage or ligation reactions, respectively, and do not interfere with or affect each other. For example, the expression "$R_{3a}$ and $R_{3b}$ are capable of performing bioorthogonal cleavage or ligation reaction independently" means that both $R_{3a}$ and $R_{3b}$ are capable of performing a bioorthogonal cleavage or ligation reaction, $R_{3a}$ does not affect the bioorthogonal cleavage or ligation reaction of $R_{3b}$, and $R_{3b}$ does not affect the bioorthogonal cleavage or ligation reaction of $R_{3a}$.

In some exemplary embodiments, $R_{3a}$ is a first reactive group capable of performing a bioorthogonal cleavage reaction in the presence of a first agent; $R_{3b}$ is a second reactive group capable of performing a bioorthogonal cleavage reaction in the presence of a second agent; $R_{3c}$ is a third reactive group capable of performing a bioorthogonal cleavage reaction in the presence of a third agent; $R_{3d}$ is a fourth reactive group capable of performing a bioorthogonal cleavage reaction in the presence of a fourth agent; $R_{4a}$ is a fifth reactive group capable of performing a bioorthogonal cleavage reaction in the presence of a fifth agent; $R_{4b}$ is a sixth reactive group capable of performing a bioorthogonal cleavage reaction in the presence of a sixth agent; $R_{5a}$ is a seventh reactive group capable of performing a bioorthogonal ligation reaction in the presence of a seventh agent; and, $R_{5b}$ is an eighth reactive group capable of performing a bioorthogonal cleavage reaction in the presence of an eighth agent.

Preferably, in such embodiments, in step (6), a seventh agent and an eighth agent may be added, thereby allowing $R_{5a}$ (if present) in the compound of formula (III) to perform a first bioorthogonal ligation reaction, and allowing $R_{5b}$ (if present) in the compound of formula (IV) to perform a bioorthogonal cleavage reaction. For example, the seventh agent may comprise compound M which carries a fluorophore the same as the fluorophore of the second compound and the fourth compound (or a fluorophore having a different structure but having the same or substantially the same emission spectrum), and the compound M is capable of performing the first bioorthogonal ligation reaction with $R_{5a}$, thereby introducing the fluorophore in compound M into the compound of formula (III). Further, the eighth agent enables $R_{5b}$ in compound of formula (IV) to perform the bioorthogonal cleavage reaction, thereby removing $R_{5b}$ and the fluorophore attached to it in compound of formula (IV). In such embodiments, it is particularly preferred that, in step (6), the seventh agent does not react with the first compound or with the second compound, and further preferably, the eighth agent does not react with the first compound or with the second compound. Therefore, in some preferred embodiments, in step (6), the seventh agent and the eighth agent may be added to form a reaction system comprising a solution phase and a solid phase, wherein the seventh agent comprises compound M, and the compound M carries the same fluorophore (or a fluorophore having a different structure but the same or substantially the same emission spectrum) as the second compound and the fourth compound, and the compound M is capable of performing a bioorthogonal ligation reaction with $R_{5a}$, thereby introducing a fluorophore in compound M into the third compound; then, the duplex is incubated with the seventh agent and the eighth agent under a condition that allows compound M to perform the bioorthogonal ligation reaction with $R_{5a}$ and allow $R_{5b}$ to perform the bioorthogonal cleavage reaction.

More preferably, in such embodiments, in step (8), a first agent, a second agent, a third agent, a fourth agent, a fifth agent and a sixth agent may be added, thereby making $R_{3a}$, $R_{3b}$, $R_{3c}$, $R_{3d}$, $R_{4a}$, $R_{4b}$ (if present) to perform the bioorthogonal cleavage reaction respectively. Therefore, $R_{3a}$, $R_{3b}$, $R_{3c}$, $R_{3d}$ (if present) will be removed from the 3' position of ribose or deoxyribose (in other words, —$OR_{3a}$, —$OR_{3b}$, —$OR_{3c}$ or —$OR_{3d}$ (if present) will be converted to free hydroxyl group), and $R_{4a}$ and the fluorophore attached thereto (if present) and $R_{4b}$ and the fluorophore attached thereto (if present) will also be removed. Thus, after step (8), the growing nucleic acid strand will not carry a fluorophore and will have a free hydroxyl group at the 3' end, which can be used for the next round of polymerization. Therefore, in some preferred embodiments, in step (8), a first agent, a second agent, a third agent, a fourth agent, a fifth agent and a sixth agent are added to form a reaction system comprising a solution phase and a solid phase, and the duplex is incubated with the first agent, the second agent, the third agent, the fourth agent, the fifth agent and the sixth agent under a condition that allows $R_{3a}$, $R_{3b}$, $R_{3c}$, $R_{3d}$, $R_{4a}$ and $R_{4b}$ to perform a bioorthogonal cleavage reaction, respectively.

In some preferred embodiments, $R_{3a}$, $R_{3b}$, $R_{3c}$ and $R_{3d}$ are capable of performing a bioorthogonal cleavage reaction respectively in the presence of the same agent. In this case, preferably, in step (8), the first agent, the second agent, the third agent, and the fourth agent are the same agent.

In some preferred embodiments, $R_{3a}$, $R_{3b}$, $R_{3c}$, and $R_{3d}$ are the same reactive group. In this case, preferably, in step (8), the first agent, the second agent, the third agent, and the fourth agent are the same agent. In other words, in step (8), the same $R_{3a}$, $R_{3b}$, $R_{3c}$, and $R_{3d}$ (if present) will each perform the bioorthogonal cleavage reaction in the presence of the same agent (i.e., the first agent), and are removed from the growing nucleic acid strand.

In some preferred embodiments, $R_{4a}$ and $R_{4b}$ are capable of performing the bioorthogonal cleavage reaction respectively in the presence of the same agent. In this case, preferably, in step (8), the fifth agent and the sixth agent are the same agent.

In some preferred embodiments, $R_{4a}$ and $R_{4b}$ are the same reactive group. In this case, preferably, in step (8), the fifth agent and the sixth agent are the same agent. In other words, in step (8), the same $R_{4a}$ and $R_{4b}$ (if present) will perform the bioorthogonal cleavage reaction respectively in the presence of the same agent (i.e., the fifth agent), and are removed from the growing nucleic acid strand.

In some preferred embodiments, $R_{3a}$, $R_{3b}$, $R_{3c}$, $R_{3d}$, $R_{4a}$ and $R_{4b}$ are capable of performing the bioorthogonal cleavage reaction respectively in the presence of the same agent. In this case, preferably, in step (8), the first agent, the second agent, the third agent, the fourth agent, the fifth agent, and the sixth agent are the same agent. In other words, in step (8), an agent (i.e., the first agent) is added to make $R_{3a}$, $R_{3b}$, $R_{3c}$, $R_{3d}$, $R_{4a}$ and $R_{4b}$ (if present) to perform the bioorthogonal cleavage reaction and removed from the growing nucleic acid strand respectively in the presence of said agent (i.e., the first agent).

In some exemplary embodiments, $R_{7a}$ is a fluorophore $Dye_1$ which is capable of emitting a fluorescent signal, wherein $Dye_1$ has the same structure as Dye, or has a different structure but the same emission spectrum as Dye. Therefore, the fourth compound itself is capable of emitting the same fluorescent signal as the one of the second compound.

In some exemplary embodiments, the fourth compound does not carry a fluorophore, and $R_{7a}$ is a reactive group capable of performing a second bioorthogonal ligation reaction.

In such embodiments, step (5) comprises: adding a ninth agent to make $R_{7a}$ (if present) in the compound of formula (IV) to perform a second bioorthogonal ligation reaction. For example, the ninth agent may comprise a compound M', which has the structure $R_{7b}$-L-$Dye_1$, wherein $R_{7b}$ is a group capable of performing a second bioorthogonal ligation reaction with $R_{7a}$, and L is independently a linking group or absent; $Dye_1$ represents a fluorophore capable of emitting a fluorescent signal, and has the same structure as Dye or has a different structure but the same emission spectrum as Dye.

In some exemplary embodiments, the fourth compound does not carry a fluorophore and $R_{7a}$ is one member of a binding pair. In such embodiments, step (5) comprises adding a ninth agent to make $R_{7a}$ (if present) in the compound of formula (IV) to specifically interact with and/or bind to the other member of the binding pair. For example, the ninth agent may comprise a compound M" which has the structure $R_{7b}$-L-$Dye_1$, wherein $R_{7b}$ is the other member of the binding pair, L is independently a linking group or absent; $Dye_1$ represents a fluorophore which is capable of emitting a fluorescent signal, and has the same structure as Dye, or has a different structure but the same emission spectrum as Dye.

In some exemplary embodiments, a reactive group $R_8$ capable of performing a third bioorthogonal ligation reaction is present between $R_{5b}$ and $R_{7a}$ of the fourth compound. In some preferred embodiments, $R_{3a}$, $R_{3b}$, $R_{3c}$, $R_{3d}$, $R_{4a}$, $R_{4b}$, $R_{5a}$ and $R_8$ are independently capable of performing a bioorthogonal cleavage or ligation reaction. In some exemplary embodiments, $R_{8a}$ is capable of performing a third bioorthogonal ligation reaction in the presence of a tenth agent.

Preferably, in such embodiments, in step (6), a seventh agent and a tenth agent may be added, thereby enabling $R_{5a}$ (if present) in the compound of formula (III) to perform a first bioorthogonal ligation reaction, and enabling $R_8$ (if present) in the compound of formula (IV) to perform a third bioorthogonal ligation reaction. For example, the seventh agent may comprise a compound M which carries a fluorophore the same as the fluorophore of the second compound and the fourth compound (or a fluorophore having a different structure but the same or substantially the same emission spectrum as the fluorophore of the second compound and the fourth compound), and the compound M is capable of performing the first bioorthogonal ligation reaction with $R_{5a}$, and thereby introducing the fluorophore in compound M into the compound of formula (III). Furthermore, the tenth agent enables $R_8$ in the compound of formula (IV) to perform the third bioorthogonal ligation reaction, thereby quenching the fluorescent signal in compound of formula (IV). In such embodiments, it is particularly preferred that in step (6), the seventh agent does not react with the first compound or with the second compound, and further preferably, the tenth agent does not react with the first compound or with the second compound. Therefore, in some preferred embodiments, in step (6), a seventh agent and a tenth agent may be added to form a reaction system comprising a solution phase and a solid phase, wherein the seventh agent comprises compound M, wherein the compound M carries a fluorophore the same as the fluorophore of the second compound and the fourth compound (or a fluorophore having a different structure but the same or substantially the same emission spectrum as the fluorophore of the second compound and the fourth compound), and the compound M is capable of performing a first bioorthogonal ligation reaction with $R_{5a}$, thereby introducing the fluorophore in compound M into the third compound; the tenth agent comprises compound M'" which carries a quencher, and said compound M'" is capable of performing a third bioorthogonal ligation reaction with $R_8$, thereby introducing the quencher in compound M'" into the fourth compound; then, the duplex is incubated with the seventh agent and the tenth agent under a condition that allows compound M'" to perform the first bioorthogonal ligation reaction with $R_{5a}$ and allows M4 to perform the third bioorthogonal ligation reaction with $R_8$.

In some preferred embodiments, $R_{3a}$, $R_{3b}$, $R_{3c}$ and $R_{3d}$ are independently selected from the group consisting of —CH$_2$CH=CH$_2$, —CH$_2$N$_3$, C$_{3-8}$ cycloalkenyl (e.g., C$_3$ cycloalkenyl, C$_4$ cycloalkenyl, C$_5$ cycloalkenyl, C$_6$ cycloalkenyl, C$_7$ cycloalkenyl or C$_8$ cycloalkenyl). In some preferred embodiments, the C$_{3-8}$ cycloalkenyl is selected from the group consisting of C$_3$ cycloalkenyl and C$_8$ cycloalkenyl. In some preferred embodiments, the C$_{3-8}$ cycloalkenyl group is

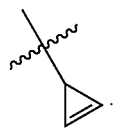

In some preferred embodiments, the C$_{3-8}$ cycloalkenyl group is

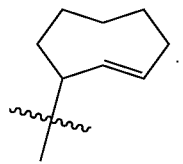 [SMILES: *C1/C=C/CCCCC1]

In some preferred embodiments, R$_{3a}$, R$_{3b}$, R$_{3c}$ and R$_{3d}$ are the same reactive group and are selected from the group consisting of —CH$_2$CH=CH$_2$, —CH$_2$N$_3$, C$_{3-8}$ cycloalkenyl (e.g., C$_3$ cycloalkenyl, C$_4$ cycloalkenyl, C$_5$ cycloalkenyl, C$_6$ cycloalkenyl, C$_7$ cycloalkenyl or C$_8$ cycloalkenyl). In some preferred embodiments, the C$_{3-8}$ cycloalkenyl is selected from the group consisting of C$_3$ cycloalkenyl and C$_8$ cycloalkenyl. In some preferred embodiments, the C$_{3-8}$ cycloalkenyl is

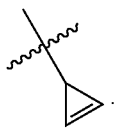

In some preferred embodiments, the C$_{3-8}$ cycloalkenyl is

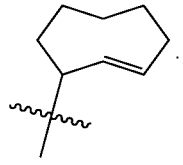 [SMILES: *C1/C=C/CCCCC1]

In some preferred embodiments, R$_{3a}$, R$_{3b}$, R$_{3c}$ and R$_{3d}$ are the same reactive group and are —CH$_2$N$_3$.

In some preferred embodiments, R$_{4a}$ and R$_{4b}$ are independently selected from the group consisting of:

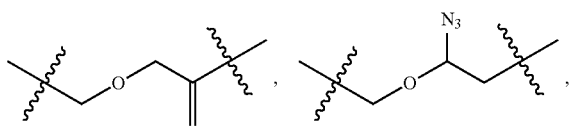

—O—C$_{3-8}$ cycloalkenylene. In some preferred embodiments, the "—O—C$_{3-8}$ cycloalkenylene" is selected from the group consisting of —O—C$_3$ cycloalkenylene, —O—C$_4$ cycloalkenylene, —O—C$_5$ cycloalkenylene, —O—C$_6$ cycloalkenylene, —O—C$_7$ cycloalkenylene, and —O—C$_8$ cycloalkenylene. In some preferred embodiments, the "—O—C$_{3-8}$ cycloalkenylene" is

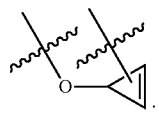

In some preferred embodiments, the "—O—C$_{3-8}$ cycloalkenylene" is

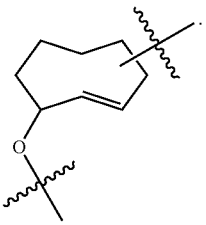

In some preferred embodiments, R$_{4a}$ and R$_{4b}$ are the same reactive group and are selected from the group consisting of:

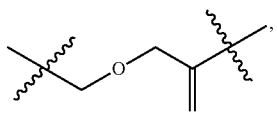

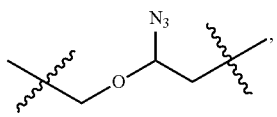 [SMILES: *COC(C*)N=[N+]=[N-]]

—O—C$_{3-8}$ cycloalkenylene. In some preferred embodiments, the "—O—C$_{3-8}$ cycloalkenylene" is selected from the group consisting of —O—C$_3$ cycloalkenylene, —O—C$_4$ cycloalkenylene, —O—C$_5$ cycloalkenylene, —O—C$_6$ cycloalkenylene, —O—C$_7$ cycloalkenylene, and —O—C$_8$ cycloalkenylene. In some preferred embodiments, the "—O—C$_{3-8}$ cycloalkenylene" is

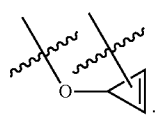

In some preferred embodiments, the "—O—$C_{3-8}$ cycloalkenylene" is

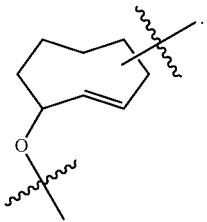

In some preferred embodiments, both $R_{4a}$ and $R_{4b}$ are

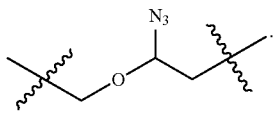

In some preferred embodiments, the first agent, the second agent, the third agent, the fourth agent, the fifth agent, and the sixth agent independently comprise a material selected from the group consisting of:

a complex of palladium (for example, a complex of palladium with four triphenylphosphine 3,3',3''-trisulfonic acids);

a complex of ruthenium (for example, a complex of ruthenium with quinoline carboxylate (or a derivative thereof), allyl or cyclopentadiene);

a phosphide (e.g., a carboxyphosphine or hydroxyphosphine such as $P(CH_2CH_2COOH)_3$ or $P(CH_2CH_2OH)_3$); and compound Q which has the structural formula

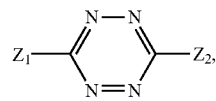

wherein $Z_1$ and $Z_2$ are independently selected from a modified or unmodified alkyl group (e.g., $C_1$-$C_6$ alkyl group such as $C_1$ alkyl group, $C_2$ alkyl group, $C_3$ alkyl group, $C_4$ alkyl group, $C_5$ alkyl group or $C_6$ alkyl group) and a modified or unmodified aryl (for example, 6-10 membered aryl such as 6-membered aryl, 7-membered aryl, 8-membered aryl, 9-membered aryl or 10-membered aryl such as phenyl or pyridyl).

In some preferred embodiments, $R_{3a}$, $R_{3b}$, $R_{3c}$ and $R_{3d}$ are —$CH_2CH$=$CH_2$. In this case, preferably, $R_{4a}$ and $R_{4b}$ are

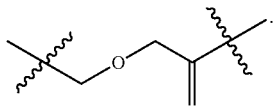 [SMILES: *COCC(*)=C]

Further preferably, the first agent, the second agent, the third agent, the fourth agent, the fifth agent, and the sixth agent comprise a complex of palladium or a complex of ruthenium. Preferably, the first agent, the second agent, the third agent, the fourth agent, the fifth agent, and the sixth agent are the same agent, and comprise a complex of palladium or a complex of ruthenium.

In some preferred embodiments, $R_{3a}$, $R_{3b}$, $R_{3c}$, and $R_{3d}$ are —$CH_2$—$N_3$. In this case, preferably, $R_{4a}$ and $R_{4b}$ are

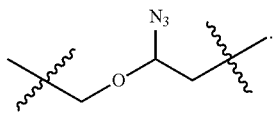 [SMILES: *COC(C*)N=[N+]=[N-]]

Further preferably, the first agent, the second agent, the third agent, the fourth agent, the fifth agent, and the sixth agent comprise phosphonate such as carboxyl phosphonate or hydroxyl phosphonate, e.g. $P(CH_2CH_2COOH)_3$ or $P(CH_2CH_2OH)_3$. Preferably, the first agent, the second agent, the third agent, the fourth agent, the fifth agent, and the sixth agent are the same agent, and comprise phosphonate such as carboxyl phosphonate or hydroxyl phosphonate, e.g. $P(CH_2CH_2COOH)_3$ or $P(CH_2CH_2OH)_3$.

In some preferred embodiments, $R_{3a}$, $R_{3b}$, $R_{3c}$ and $R_{3d}$ are

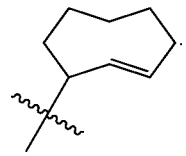 [SMILES: *C1/C=C/CCCCC1]

In this case, preferably, $R_{4a}$ and $R_{4b}$ are

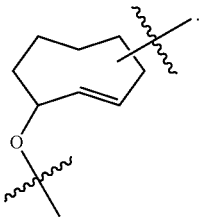

Further preferably, the first agent, the second agent, the third agents, the fourth agent, the fifth agent, and the sixth agent comprise the compound Q as defined above. Further preferably, in compound Q, $Z_1$ is methyl; and $Z_2$ is modified or unmodified pyridyl. More preferably, compound Q is

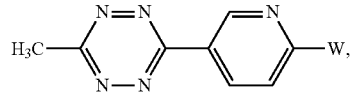

wherein W is hydrogen or a modifying group. Preferably, the first agent, the second agent, the third agent, the fourth agent, the fifth agent, and the sixth agent are the same agent and comprise the compound Q as defined above.

In some preferred embodiments, the linking groups L1 and L2 in the first compound, the second compound, the third compound and the fourth compound, and L in $R_{7b}$-L-Dye$_1$ are independent from each other and are not particularly limited. A person skilled in the art can select suitable linking groups L1, L2 and L according to the bases (Base1, Base2, Base3 or Base4) in the compounds and the reactive groups ($R_{4a}$, $R_{4b}$, $R_{5a}$ or $R_{5b}$).

In some exemplary embodiments, L1 and L2 in the first compound, the second compound, the third compound and the fourth compound, and L in $R_{7b}$-L-$Dye_1$ are independently selected from the group consisting of:

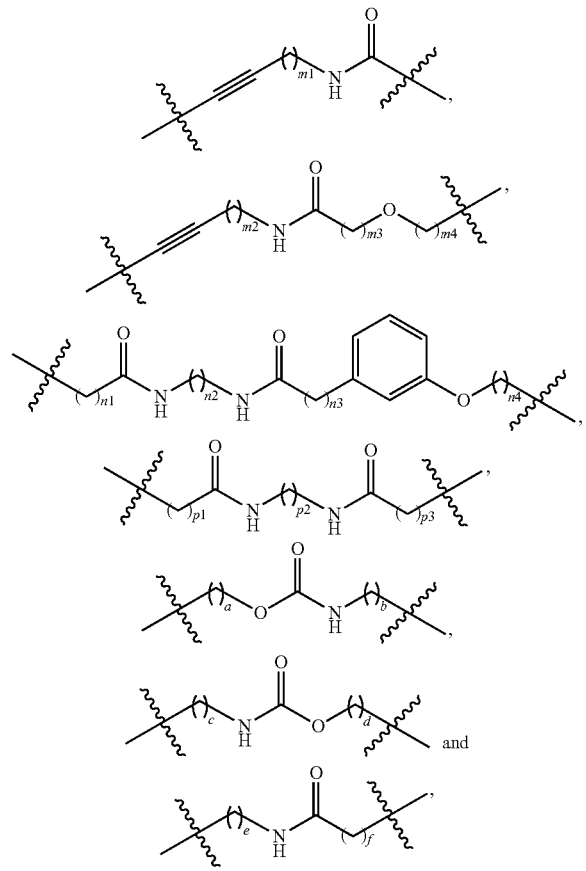

wherein m1, m2, m3, m4, n1, n2, n3, n4, p1, p2, p3, a, b, c, d, e and f are independently selected from 0, 1, 2, 3, 4, 5 or 6.

In some exemplary embodiments, L1 in the first compound, the second compound, the third compound or the fourth compound is independently selected from the group consisting of:

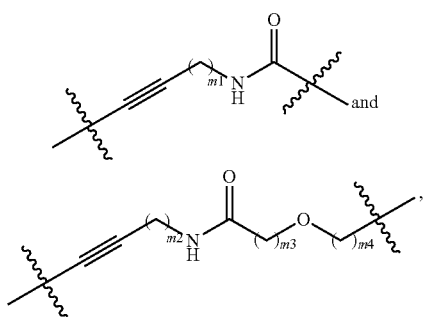

wherein m1, m2, m3, and m4 are independently selected from 0, 1, 2, 3, 4, 5 or 6.

In some preferred embodiments, L1 in the first compound, the second compound, the third compound or the fourth compound is independently selected from the group consisting of:

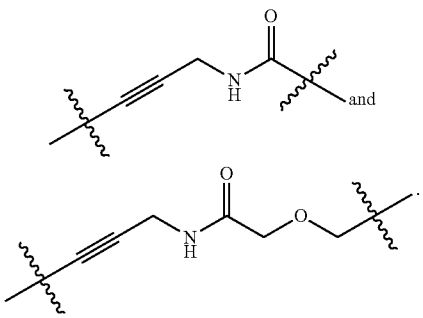

In some preferred embodiments, L2 in the first compound, the second compound, the third compound or the fourth compound is independently selected from the group consisting of:

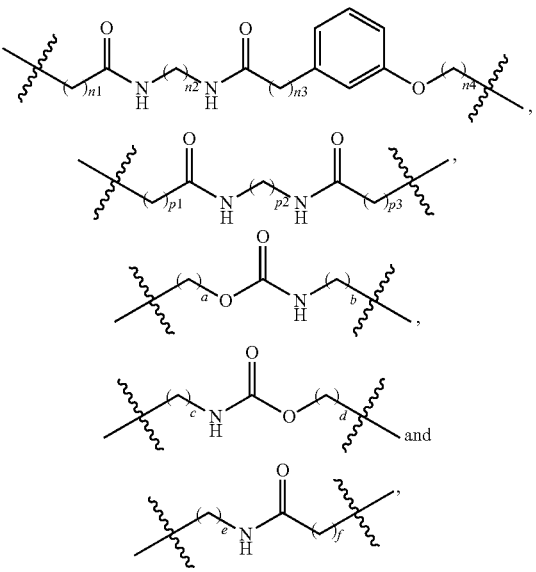

wherein n1, n2, n3, n4, p1, p2, p3, a, b, c, d, e, and f are independently selected from 0, 1, 2, 3, 4, 5, or 6.

In some preferred embodiments, L2 in the first compound, the second compound, the third compound or the fourth compound is independently selected from the group consisting of:

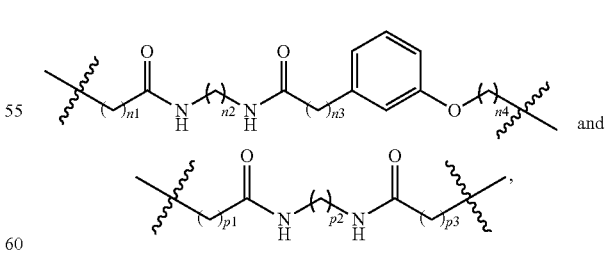

wherein n1, n2, n3, n4, p1, p2, p3 are independently selected from 0, 1, 2, 3, 4, 5 or 6.

In some preferred embodiments, L2 in the first compound, the second compound, the third compound or the fourth compound is independently selected from the group consisting of:

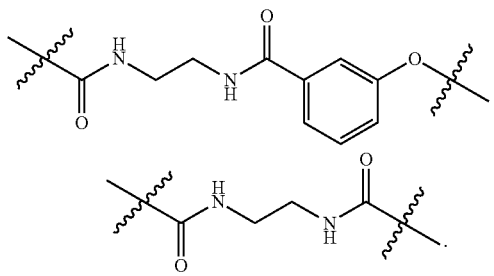 and

In some preferred embodiments, $R_{5a}$ is selected from the group consisting of:

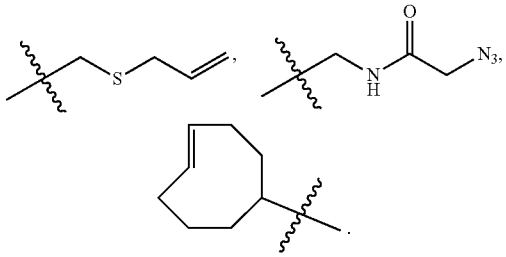

In some preferred embodiments, $R_{5b}$ is selected from the group consisting of:

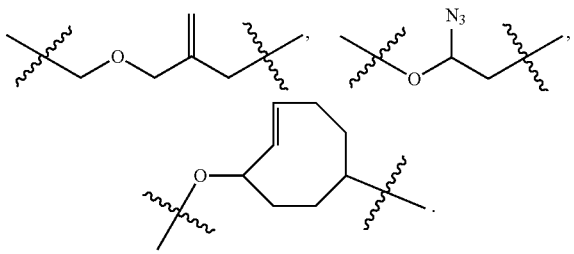

In some preferred embodiments, the seventh agent comprises compound M which is selected from the group consisting of:

compound M1, which has the structural formula

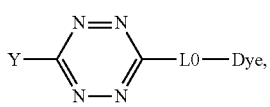

wherein Y is selected from alkyl group (e.g., a $C_1$-$C_6$ alkyl group, e.g., $C_1$ alkyl group, $C_2$ alkyl group, $C_3$ alkyl group, $C_4$ alkyl group, $C_5$ alkyl group or $C_6$ alkyl group) and aryl (e.g., a 6-10 membered aryl, e.g., a 6-membered aryl, a 7-membered aryl, an 8-membered aryl, a 9-membered aryl or a 10-membered aryl, e.g., phenyl group), L0 is absent or is a linking group, Dye is a fluorophore, wherein the fluorophore is the same as the fluorophore in the second compound and in the fourth compound (or the fluorophore has a different structure but the same or substantially the same emission spectrum as that of the second compound and the fourth compound);

compound M2, which has the structural formula

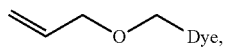

wherein, Dye is a fluorophore which is the same as the fluorophore of the second compound and of the fourth compound (or has a different structure but the same or substantially the same emission spectrum as that of the second compound and the fourth compound); and compound M3, which has the formula

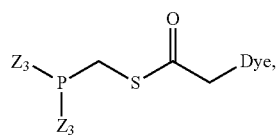

wherein $Z_3$ is independently selected from alkyl (for example $C_1$-$C_6$ alkyl, e.g. $C_1$ alkyl, $C_2$ alkyl, $C_3$ alkyl, $C_4$ alkyl, $C_5$ alkyl or $C_6$ alkyl) and aryl (for example, a 6-10 membered aryl such as a 6-membered aryl, a 7-membered aryl, an 8-membered aryl, a 9-membered aryl or a 10-membered aryl, e.g. phenyl), and Dye is a fluorophore which is the same as that of the second compound and of the fourth compound (or has a different structure but the same or substantially the same emission spectrum as that of the second compound and the fourth compound).

In the embodiment of the present invention, the linking group L0 is not particularly limited. A person skilled in the art can select a suitable linking group L0 according to actual needs. For example, in some preferred embodiments, L0 may be

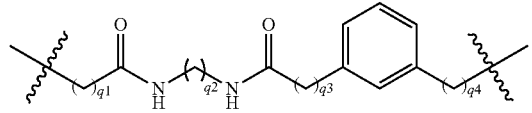

wherein, q1, q2, q3, q4 are independently selected from 0, 1, 2, 3, 4, 5 or 6.

In some preferred embodiments, the seventh agent comprises compound M1, and Y is $C_1$-$C_6$ alkyl, such as methyl.

In some preferred embodiments, L0 in compound M1 is

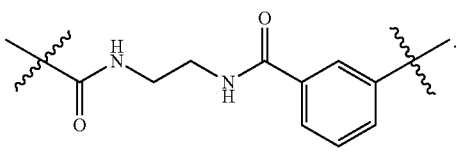 [SMILES: *C(=O)NCCNC(=O)c1cccc(*)c1]

In some preferred embodiments, Dye in compound M1 is AF532. In some preferred embodiments, compound M1 has the structure:

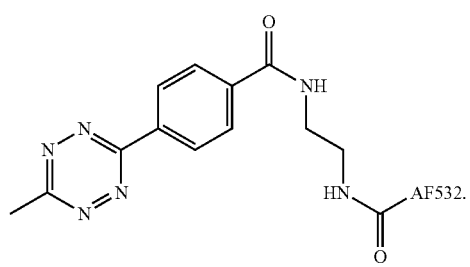

In some preferred embodiments, in addition to compound M, the seventh agent further comprises a complex of ruthenium. In some preferred embodiments, the seventh agent comprises compound M2 and a complex of ruthenium.

In some preferred embodiments, the eighth agent comprises compound M as defined above, and, compound M is selected from compounds M1, M2 and M3 as defined above.

In some preferred embodiments, in addition to compound M, the eighth agent further comprises a complex of ruthenium. In some preferred embodiments, the eighth agent comprises compound M2 and a complex of ruthenium.

In some preferred embodiments, in the presence of the same agent, $R_{5a}$ is capable of performing a bioorthogonal ligation reaction, and $R_{5b}$ is capable of performing a bioorthogonal cleavage reaction. In this case, preferably, in step (7), the seventh agent and the eighth agent are the same agent.

In some preferred embodiments, $R_{5a}$ is

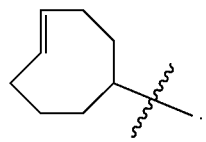 [SMILES: *C1CC/C=C/CCC1]

In this case, preferably, $R_{5b}$ is

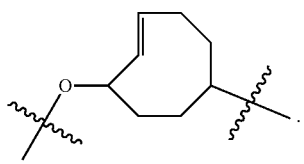 [SMILES: *OC1/C=C/CCC(*)CC1]

Further preferably, the seventh agent and the eighth agent comprise compound M1. Preferably, the seventh agent and the eighth agent are the same agent and comprise the compound M1 as defined above.

In some preferred embodiments, $R_{5a}$ is

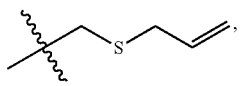 [SMILES: *CSCC=C]

In this case, preferably, $R_{5b}$ is

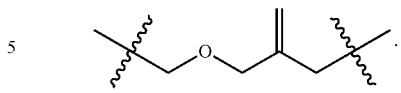

Further preferably, the seventh agent and the eighth agent comprise compound M2. More preferably, both the seventh agent and the eighth agent comprise compound M2 and a complex of ruthenium. Preferably, the seventh agent and the eighth agent are the same agent and comprise compound M2 and a complex of ruthenium as defined above.

In some preferred embodiments, $R_{5a}$ is

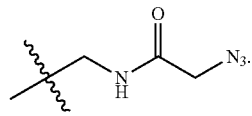

In this case, preferably, $R_{5b}$ is

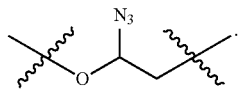 [SMILES: *CC(N=[N+]=[N-])O*]

Further preferably, the seventh agent and the eighth agent comprise compound M3. Preferably, the seventh agent and the eighth agent are the same agent and comprise the compound M3 as defined above.

In some preferred embodiments, $R_{3a}$, $R_{3b}$, $R_{3c}$ and $R_{3d}$ are —CH$_2$CH=CH$_2$; $R_{4a}$ and $R_{4b}$ are

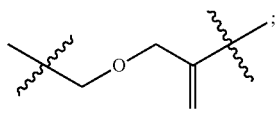 [SMILES: *COCC(*)=C]

the first agent, second agent, third agent, fourth agent, fifth agent, and six agents comprise a complex of palladium or a complex of ruthenium; $R_{5a}$ is

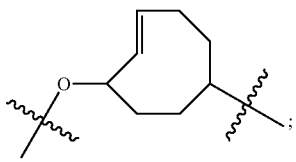 [SMILES: *OC1/C=C/CCC(*)CC1]

$R_{5b}$ is

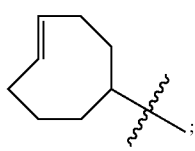 [SMILES: *C1CC/C=C/CCC1]

the seventh agent and the eighth agent comprise compound M1.

Preferably, the first agent, the second agent, the third agent, the fourth agent, the fifth agent, and the sixth agent are the same agent, and comprise a complex of palladium or a complex of ruthenium. Preferably, the seventh agent and the eighth agent are the same agent and comprise the compound M1 as defined above.

In some preferred embodiments, $R_{3a}$, $R_{3b}$, $R_{3c}$, and $R_{3d}$ are —$CH_2$—$N_3$; $R_{4a}$ and $R_{4b}$ are

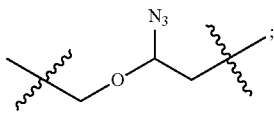 [SMILES: *COC(C*)N=[N+]=[N-]]

the first agent, second agent, third agent, fourth agent, fifth agent, and six agents comprise a phosphide such as a carboxyl phosphide or a hydroxyl phosphide, e.g. $P(CH_2CH_2COOH)_3$ or $P(CH_2CH_2OH)_3$; $R_{5a}$ is

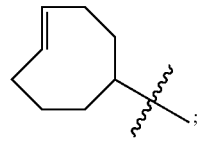 [SMILES: *C1CC/C=C/CCC1]

$R_{5b}$ is

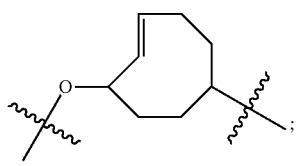 [SMILES: *OC1/C=C/CCC(*)CC1]

the seventh agent and the eighth agent comprise compound M1. Preferably, the first agent, the second agent, the third agent, the fourth agent, the fifth agent and the sixth agent are the same agent and comprise a phosphide such as a carboxyl phosphide or a hydroxyl phosphide, e.g. $P(CH_2CH_2COOH)_3$ or $P(CH_2CH_2OH)_3$. Preferably, the seventh agent and the eighth agent are the same agent and comprise the compound M1 as defined above.

In some preferred embodiments, $R_{3a}$, $R_{3b}$, $R_{3c}$, and $R_{3d}$ are —$CH_2$—$N_3$; $R_{4a}$ and $R_{4b}$ are

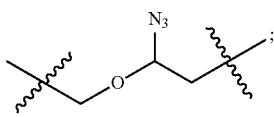 [SMILES: *COC(C*)N=[N+]=[N-]]

the first agent, second agent, third agent, fourth agent, fifth agent, and sixth agent comprise a phosphide such as a carboxyl phosphide or a hydroxyl phosphide, e.g. $P(CH_2CH_2COOH)_3$ or $P(CH_2CH_2OH)_3$; $R_{5a}$ is

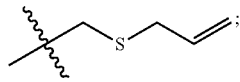 [SMILES: *CSCC=C]

$R_{5b}$ is

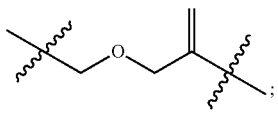 [SMILES: *COCC(*)=C]

the seventh agent and the eighth agent comprise compound M2 and a complex of ruthenium. Preferably, the first agent, the second agent, the third agent, the fourth agent, the fifth agent and the sixth agent are the same agent and comprise a phosphide such as a carboxyl phosphide or a hydroxyl phosphide, e.g. $P(CH_2CH_2COOH)_3$ or $P(CH_2CH_2OH)_3$. Preferably, the seventh agent and the eighth agent are the same agent and comprise compound M2 and a complex of ruthenium.

In some preferred embodiments, $R_{3a}$, $R_{3b}$, $R_{3c}$, and $R_{3d}$ are —$CH_2CH=CH_2$; $R_{4a}$ and $R_{4b}$ are

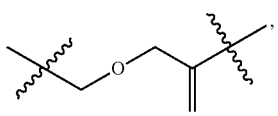 [SMILES: *COCC(*)=C]

the first agent, the second agent, the third agent, the fourth agent, the fifth agent, and the six agents comprise a complex of palladium or a complex of ruthenium; $R_{5a}$ is

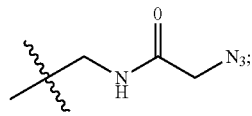

$R_{5b}$ is

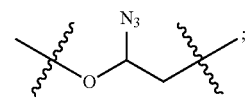 [SMILES: *CC(N=[N+]=[N-])O*]

the seventh agent and the eighth agent comprise compound M3. Preferably, the first agent, the second agent, the third agent, the fourth agent, the fifth agent, and the sixth agent are the same agent, and comprise a complex of palladium or a complex of ruthenium. Preferably, the seventh agent and the eighth agent are the same agent and comprise the compound M3.

In some preferred embodiments, $R_{3a}$, $R_{3b}$, $R_{3c}$, and $R_{3d}$ are

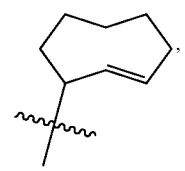

$R_{4a}$ and $R_{4b}$ are

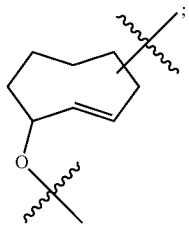

the first agent, second agent, third agent, fourth agent, fifth agent, and sixth agent comprise compound Q (for example, the compound Q as defined above); $R_{5a}$ is

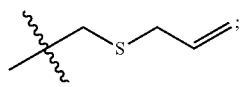

$R_{5b}$ is

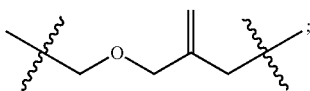 [SMILES: *COCC(=C)C*]

the seventh agent and the eighth agent comprise compound M2 and a complex of ruthenium. Preferably, the first agent, the second agent, the third agent, the fourth agent, the fifth agent, and the sixth agent are the same agent, and comprise compound Q (e.g., the compound Q as defined above). Preferably, the seventh agent and the eighth agent are the same agent and comprise compound M2 and a complex of ruthenium.

In some preferred embodiments, $R_{3a}$, $R_{3b}$, $R_{3c}$, and $R_{3d}$ are

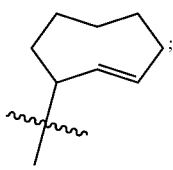 [SMILES: *C1/C=C/CCCCC1]

$R_{4a}$ and $R_{4b}$ are

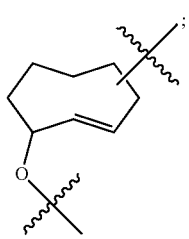

the first agent, the second agent, the third agent, the fourth agent, the fifth agent, and the sixth agent comprise compound Q (for example, the compound Q as defined above); $R_{5a}$ is

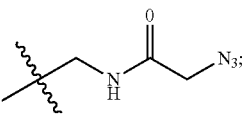

$R_{5b}$ is

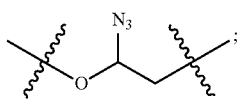 [SMILES: *CC(N=[N+]=[N-])O*]

the seventh agent and the eighth agent comprise compound M3. Preferably, the first agent, the second agent, the third agent, the fourth agent, the fifth agent, and the sixth agent are the same agent, and comprise compound Q (e.g., the compound Q as defined above). Preferably, the seventh agent and the eighth agent are the same agent and comprise the compound M3.

In some preferred embodiments, the Dye in the third compound is Cy3 or AF532.

In some preferred embodiments, $R_{7a}$ in the fourth compound is $Dye_1$. In some preferred embodiments, $Dye_1$ is Cy3 or AF532.

In some preferred embodiments, Dye in the third compound is AF532, and $R_{7a}$ in the fourth compound is Cy3.

In some preferred embodiments, Dye in the third compound is Cy3 and $R_{7a}$ in the fourth compound is AF532.

In some exemplary embodiments, the fourth compound itself does not carry a fluorophore and $R_{7a}$ is a reactive group capable of performing a second bioorthogonal ligation reaction. In some preferred embodiments, $R_{7a}$ is selected from the group consisting of:

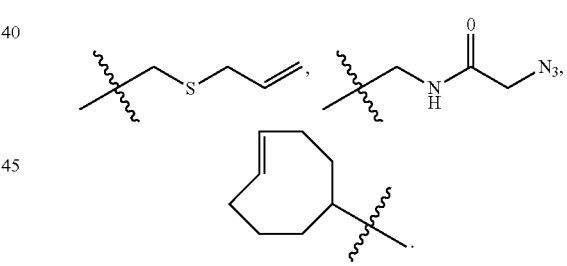

In some exemplary embodiments, the compound M capable of performing a second bioorthogonal ligation reaction with $R_{7a}$ is selected from the group consisting of the compounds M1, M2 and M3 as defined above.

In some exemplary embodiments, the fourth compound itself does not carry a fluorophore and $R_{7a}$ is one member of a binding pair. In some preferred embodiments, the binding pair is selected from the group consisting of: antigen (e.g., small molecule antigen)-antibody, hapten-antibody, hormone-receptor, ligand-receptor, nucleic acid strand-complementary nucleic acid strand, substrate-enzyme, substrate analog-enzyme, inhibitor-enzyme, sugar-lectin, biotin-avidin (e.g., avidin and streptavidin), digoxin and digoxin antibody, as well as 5-position bromodeoxyguanosine and its antibody. In some preferred embodiments, the two members of the binding pair are selected from the group consisting of: (a) biotin and avidin (e.g., streptavidin), (b)

desthiobiotin and avidin (for example, streptavidin) and (c) digoxin and digoxin antibody.

In some preferred embodiments, the first compound has the structure shown in formula (Ia):

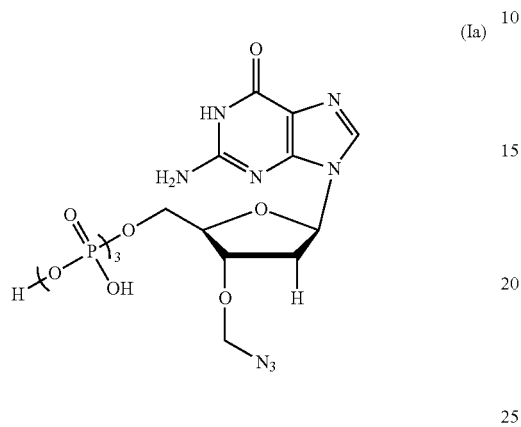

(Ia)

In some preferred embodiments, the second compound has the structure shown in formula (IIa):

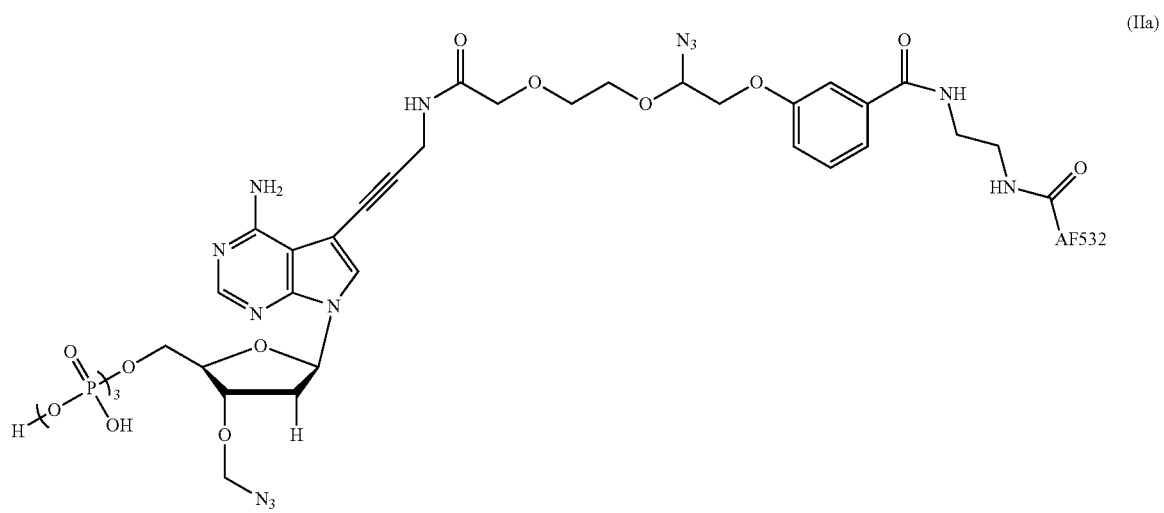

(IIa)

In some preferred embodiments, the third compound has the structure shown in formula (IIIa):

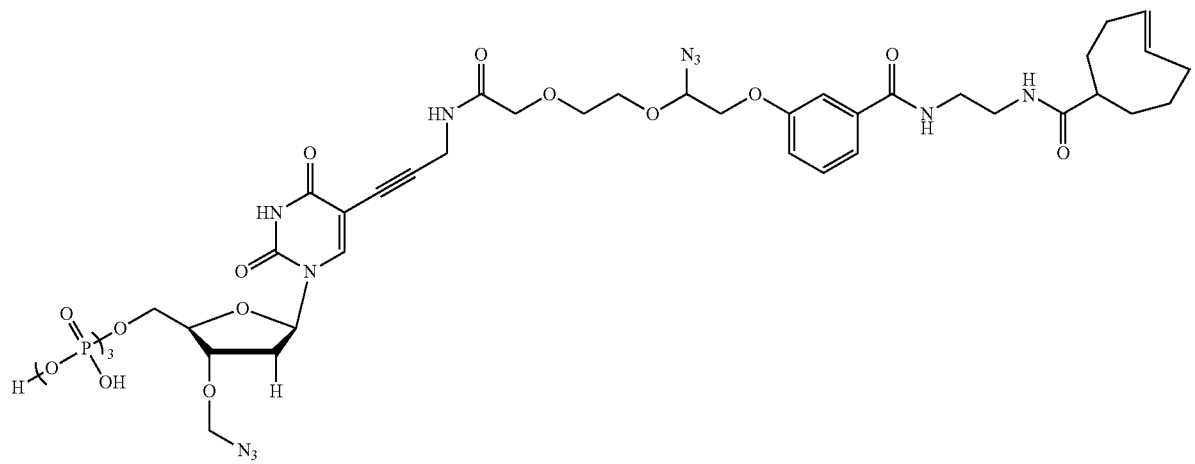

(IIIa)

In some preferred embodiments, the fourth compound has the structure shown in formula (IVa):

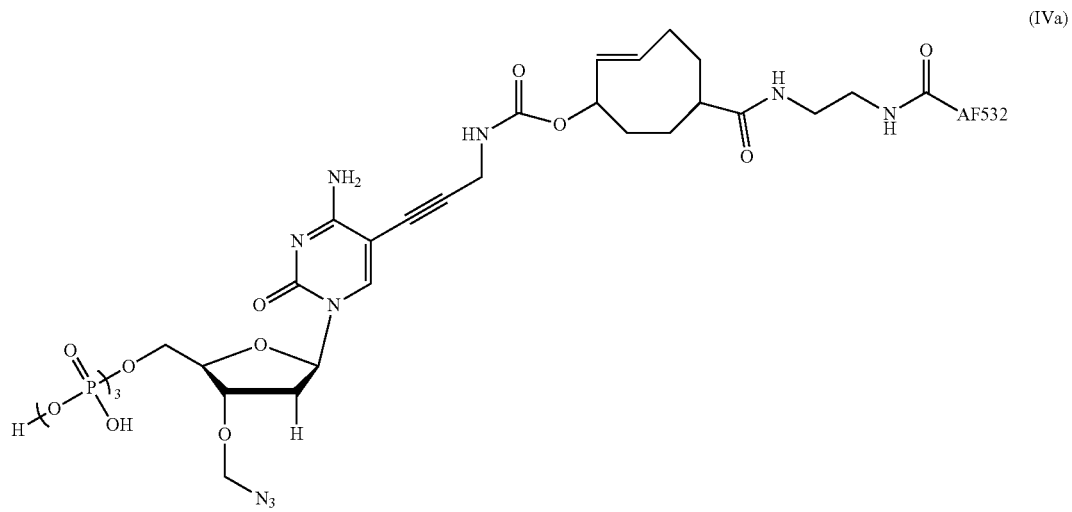

(IVa)

Additionally, as described above, the method of the present invention may comprise a washing step as needed. The washing step can be added at any desired stage, and optionally, the washing step can be performed one or more times.

For example, in step (5), after removing the solution phase of the reaction system, one or more washings may be performed to sufficiently remove the residual solution phase. Such a washing step may be advantageous for sufficiently removing a fluorophore-bearing compound (e.g., compound of formula (II) or compound of formula (IV)) which is free (i.e., not incorporated into the nucleic acid strand), thereby minimizing non-specific fluorescent signal as much as possible.

Similarly, in step (7), after removing the solution phase of the reaction system, one or more washings may be performed to sufficiently remove the residual solution phase. Such a washing step may be advantageous for sufficiently removing the fluorescent-carrying agent used in step (6), thereby minimizing non-specific fluorescent signal as much as possible. Similarly, in step (9), after removing the solution phase of the reaction system, one or more washings may be performed to sufficiently remove the residual solution phase. Such a washing step may be advantageous for sufficiently removing the agents used in step (8) and the products produced (which may carry fluorescence), thereby minimizing non-specific fluorescent signal and avoiding adverse effect on the subsequent polymerization reaction as much as possible.

The washing step can be carried out using a variety of suitable washing solutions. Examples of such washing solutions include, but are not limited to, phosphate buffer, citrate buffer, Tris-HCl buffer, acetate buffer, carbonate buffer, and the like. It is within the ability of those skilled in the art to select a suitable washing solution (including suitable ingredient, concentration, ionic strength, pH value, etc.) according to the actual needs.

Exemplary Embodiment 2

In some exemplary embodiments, the ability of the four compounds to emit fluorescent signals is controlled (for example, maintained or changed) in step (6) by using a binding pair (which comprises two members that interact with each other by specific non-covalent interaction); and preferably, the removal of the protecting group and the fluorescent signal can be achieved in step (8) by using a reactive group capable of performing a bioorthogonal cleavage reaction. For example, in some exemplary embodiments, the first, second, third, and fourth compounds may have the structures of formulas (I), (II), (III), and (IV), respectively:

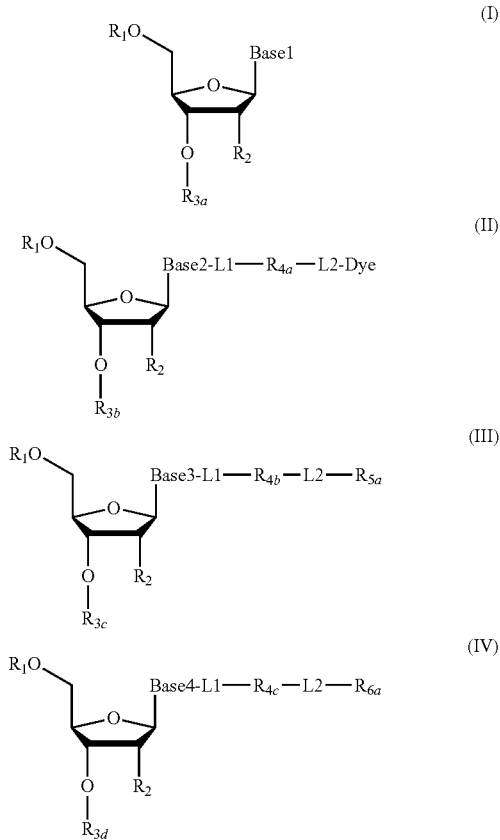

wherein, Base1, Base2, Base3, and Base4 represent 4 different bases, and are selected from A, (T/U), C, and G;

$R_1$ is independently selected from —H, monophosphate group (—$PO_3H_2$), diphosphate group (—$PO_3H$—$PO_3H_2$), triphosphate group (—$PO_3H$—$PO_3H$—$PO_3H_2$) and tetraphosphate group (—$PO_3H$—$PO_3H$—$PO_3H$—$PO_3H_2$);

$R_2$ is independently selected from —H and —OH;

$R_{3a}$, $R_{3b}$, $R_{3c}$, $R_{3d}$, $R_{4a}$, $R_{4b}$ and $R_{4c}$ are independently a reactive group capable of performing a bioorthogonal cleavage reaction;

$R_{5a}$ is one member of the first binding pair;

$R_{6a}$ is (i) one member of the second binding pair, and is also one member of the third binding pair; or is (ii) just one member of the third binding pair; and, $R_{6a}$ is $Dye_1$ or $R_{6a}$ is linked with -L3-$Dye_1$;

L1 is independently a linking group or absent;
L2 is independently a linking group or absent;
L3 is a linking group or absent;

Dye and $Dye_1$ represent a fluorophore capable of emitting a fluorescent signal; and, both of them have the same structure, or have different structures but have the same or substantially the same emission spectrum;

optionally, a reactive group $R_8$ capable of performing the bioorthogonal ligation reaction is present between $R_{4c}$ and $R_{6a}$.

In such exemplary embodiment, the fourth compound itself may carry a fluorophore capable of emitting the same fluorescent signal as the second compound, or may not carry a fluorophore but specifically interact with/bind to the agent (for example, the other member of the second binding pair, or a compound capable of performing the second bioorthogonal ligation reaction with $R_{6a}$) carrying a fluorophore (for example, a fluorophore having the same structure as the fluorophore of the second compound, or a fluorophore having the same or substantially the same emission spectrum as the fluorophore of the second compound) in step (5), to introduce the fluorophore into the fourth compound, and enables the fourth compound to emit the same fluorescent signal as that of the second compound. Further, a fluorophore may be introduced into the third compound by specific interaction/binding between $R_{5a}$ and the other member (represented as "$R_{5b}$-L-$Dye_3$" herein, wherein $R_{5b}$ is the other member of the first binding pair, L is a linking group or absent; $Dye_3$ represents a fluorophore that is capable of emitting a fluorescent signal, preferably a fluorophore which is the same as the fluorophore of the second compound, or a fluorophore which has a different structure but the same or substantially the same emission spectrum as that of the second compound) of the first binding pair carrying the fluorophore. Further, (i) the fluorescent signal emitted by the fourth compound can be quenched by specific interaction/binding between $R_{6a}$ with the other member of the third binding pair carrying a quenching group (represented as "$R_{6c}$-L6-Que" herein, wherein $R_6$ is the other member of the third binding pair, L6 is a linking group or absent; Que represents a quenching group which is capable of quenching the fluorescent signal emitted by Dye); or, (ii) the fluorescent signal in the fourth compound can be quenched by enabling $R_8$ in the fourth compound to perform a bioorthogonal ligation reaction with a compound carrying a quenching group. In such exemplary embodiments, $R_{6a}$ can be a member of two binding pairs (the second binding pair $R_{6a}$ and $R_{6b}$, and the third binding pair $R_{6a}$ and $R_{6c}$). Particularly preferably, the two members of the first binding pair ($R_{5a}$ and $R_{5b}$) do not interact with the two members of the third binding pair ($R_{6a}$ and $R_{6b}$). In addition, particularly preferably, $R_{5a}$ and $R_{5b}$ do not affect the specific interaction between $R_{6a}$ and $R_{6c}$, and, $R_{6a}$ and $R_{6c}$ do not affect the specific interaction between $R_{5a}$ and $R_{5b}$.

Therefore, in some preferred embodiments, in step (6), the duplex or the growing nucleic acid strand is subjected to a treatment which has no effect on the first compound and the second compound, but enables $R_{5a}$ to perform specific interaction/binding with the other member ($R_{5b}$-L5-$Dye_3$) of the first binding pair carrying a fluorophore (thereby introducing the fluorophore into the third compound to enable it to carry the fluorophore and emit a fluorescent signal), and enables $R_{6a}$ to perform the specific interaction/binding with the other member ($R_{6c}$-L6-Que) of the second binding pair carrying a quenching group (thereby quenching the fluorescent signal emitted by the fluorophore in the fourth compound), or enables $R_8$ in the fourth compound to perform a bioorthogonal ligation reaction with a compound carrying a quenching group (thereby quenching the fluorescent signal emitted by the fluorophore in the fourth compound). In such exemplary embodiments, prior to the treatment of the step (6), the first compound and the third compound, if present, do not emit fluorophore, and the second compound and the fourth compound, if present, fluoresce; further, after the treatment of step (6), the first compound (if present) still does not fluoresce, the second compound (if present) still fluoresces, the third compound (if present) changes to fluoresce, and the fourth compound (if present) changes to not fluoresce. Therefore, the type of compound incorporated into the 3' end of the growing nucleic acid strand can be determined by detecting and comparing the fluorescent signal. In the method of the present invention, a suitable quenching group can be selected according to the fluorophore used. The quenching groups for various fluorophores are well known in the art, and examples thereof include, but are not limited to, DABCYL, BHQ quenchers (such as BHQ-1 or BHQ-2), ECLIPSE, and/or TAMRA.

Further, in such exemplary embodiments, by enabling $R_{3a}$, $R_{3b}$, $R_{3c}$, $R_{3d}$, $R_{4a}$, $R_{4b}$, $R_{4c}$ to perform a bioorthogonal cleavage reaction, the protecting group at the 3' position of the ribose or deoxyribose in the compound incorporated into the 3' end of the growing nucleic acid strand is removed, and the fluorophore (if present) on the duplex or the growing nucleic acid strand is removed. Therefore, in some preferred embodiments, in step (8), the duplex or the growing nucleic acid strand is subjected to a treatment which enables $R_{3a}$, $R_{3b}$, $R_{3c}$, $R_{3d}$, $R_{4a}$, $R_{4b}$, $R_{4c}$ to perform the bioorthogonal cleavage reaction. In such exemplary embodiments, after the treatment of step (8), the growing nucleic acid strand will have no fluorophore, and the ribose or deoxyribose at the 3' end of the growing nucleic acid strand will have a free hydroxyl group at the 3' position, wherein the free hydroxyl group can be used to initiate the next round of polymerization.

Therefore, in some embodiments, the method of the invention comprises the steps of:

(1) providing a nucleic acid molecule to be sequenced attached onto a support or attaching the nucleic acid molecule to be sequenced onto a support;

(2) adding a primer for initiating a nucleotide polymerization, a polymerase for performing a nucleotide polymerization, and the first, second, third and fourth compounds having structures of formula (I), formula (II), formula (III), and formula (IV), respectively, to form a reaction system comprising a solution phase and a solid phase:

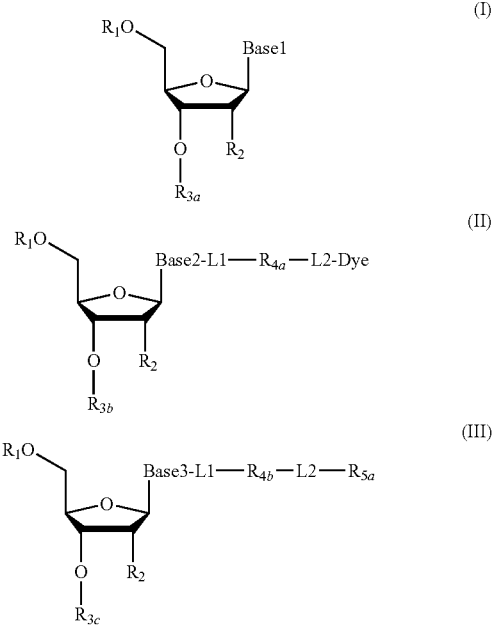

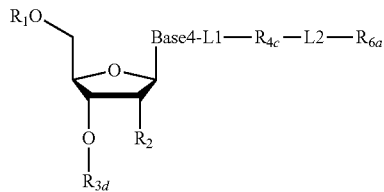

wherein, Base1, Base2, Base3, and Base4 represent 4 different bases, and are selected from A, (T/U), C, and G;

$R_1$ is independently selected from —H, monophosphate group (—PO$_3$H$_2$), diphosphate group (—PO$_3$H—PO$_3$H$_2$), triphosphate group (—PO$_3$H—PO$_3$H—PO$_3$H$_2$) and tetraphosphate group (—PO$_3$H—PO$_3$H—PO$_3$H—PO$_3$H$_2$);

$R_2$ is independently selected from —H and —OH;

$R_{3a}$, $R_{3b}$, $R_{3c}$, $R_{3d}$, $R_{4a}$, $R_{4b}$ and $R_{4c}$ are independently a reactive group capable of performing a bioorthogonal cleavage reaction;

$R_{5a}$ is one member of the first binding pair;

$R_{6a}$ is (i) one member of the second binding pair, and is also one member of the third binding pair; or is (ii) just one member of the third binding pair; and, $R_{6a}$ is Dye$_1$, or $R_{6a}$ is linked with -L3-Dye$_1$;

L1 is independently a linking group or absent;

L2 is independently a linking group or absent;

L3 is a linking group or absent;

Dye and Dye$_1$ represent fluorophore capable of emitting a fluorescent signal; and, both of them have the same structure, or have different structures but have the same or substantially the same emission spectrum;

optionally, a reactive group $R_8$ capable of performing the bioorthogonal ligation reaction is present between $R_{4c}$ and $R_{6a}$.

(3) annealing the primer to the nucleic acid molecule to be sequenced, wherein the primer serves as an initial growing nucleic acid strand, and together with the nucleic acid molecule to be sequenced, forms a duplex attached to the support;

(4) performing a nucleotide polymerization reaction using the polymerase under a condition allowing the polymerase to perform the nucleotide polymerization, thereby incorporating one of the four compounds into the 3' end of the growing nucleic acid strand;

(5) (i) if the fourth compound is incapable of emitting a fluorescent signal, $R_{6a}$ is one member of the second binding pair, and is also one member of the third binding pair, then the duplex or the growing nucleic acid strand is subjected to a treatment in a reaction system containing a solution phase and a solid phase, wherein the treatment has no effect on the first compound, the second compound and the third compound, but enables $R_{6a}$ in the fourth compound to perform specific interaction/binding with an agent (for example, the other member of the second binding pair) carrying a fluorophore (for example, a fluorophore having the same structure as the fluorophore of the second compound, or a fluorophore having different structure from, but the same or substantially the same emission spectrum as that of the second compound); after that, removing the solution phase of the reaction system in the previous step, retaining the duplex attached to the support, and detecting whether the duplex or the growing nucleic acid strand emits the fluorescent signal;

wherein the other member of the second binding pair carrying the fluorophore has the following structure: $R_{6b}$-

L4-Dye$_2$; wherein, R$_{6b}$ is the other member of the second binding pair, and L4 is independently a linking group or absent; Dye$_2$ represents a fluorophore capable of emitting a fluorescent signal, and has the same structure as Dye, or has a different structure but the same or substantially the same emission spectrum as Dye;

(ii) if the fourth compound is capable of emitting the same fluorescent signal as the second compound, R$_{6a}$ is only one member of the third binding pair, and R$_{6a}$ is Dye$_1$ or is also linked with -L3-Dye$_1$, then removing the solution phase of the reaction system in the previous step, retaining the duplex attached to the support, and detecting whether the duplex or the growing nucleic acid strand emits the fluorescent signal;

(6) subjecting the duplex or the growing nucleic acid strand to a treatment in a reaction system containing a solution phase and a solid phase, wherein the treatment has no effect on the first compound and the second compound, but it enables R$_{5a}$ in the third compound to specifically bind to the other member of the first binding pair carrying a fluorophore, thereby introducing the fluorophore into the third compound to make the third compound to emit a fluorescent signal; and, the treatment (i) enables R$_{6a}$ in the fourth compound to specifically bind to the other member of the third binding pair carrying a quenching group, thereby quenching the fluorescent signal emitted by the fluorophore Dye$_1$ or Dye$_2$ in the fourth compound, or (ii) enables R$_8$ in the fourth compound to perform a bioorthogonal ligation reaction with a compound carrying a quenching group, thereby quenching the fluorescent signal emitted by the fluorophore Dye$_1$ or Dye$_2$ in the fourth compound; wherein the other member of the first binding pair carrying a fluorophore has the structure: R$_{5b}$-L5-Dye$_3$; wherein, R$_{5b}$ is the other member of the first binding pair, and L5 is independently a linking group or absent; Dye$_3$ represents a fluorophore capable of emitting a fluorescent signal, having the same structure as the fluorophore in the second compound, or having a different structure but having the same emission spectrum as that of the second compound; and, the other member of the third binding pair carrying the quenching group has the structure: R$_{6c}$-L6-Que; wherein R$_{6c}$ is the other member of the second binding pair, and L6 is independently a linking group or absent; Que represents a quenching group capable of quenching the fluorescent signal emitted by Dye$_1$ or Dye$_2$;

(7) removing the solution phase of the reaction system in the previous step, retaining the duplex attached to the support, and detecting whether the duplex or the growing nucleic acid strand emits the fluorescent signal.

In some preferred embodiments, the method further comprises the steps of:

(8) subjecting the duplex or the growing nucleic acid strand in the previous step to a treatment in a reaction system containing a solution phase and a solid phase, wherein the treatment enables R$_{3a}$, R$_{3b}$, R$_{3c}$, R$_{3d}$, R$_{4a}$, R$_{4b}$, R$_{4c}$ to perform the bioorthogonal cleavage reaction, thereby allowing the compound incorporated at the 3' end of the growing nucleic acid strand to have a free hydroxyl group at the 3' position of the ribose or deoxyribose (in other words, converting —OR$_{3a}$, —OR$_{3b}$, —OR$_{3c}$ or —OR$_{3d}$ (if present) into a free hydroxyl group), and, removing the fluorophore on the duplex or the growing nucleic acid strand (in other words, removing the fluorophore attached to R$_{4a}$, R$_{4b}$ or R$_{4c}$), if present;

(9) removing the solution phase of the reaction system in the previous step;

(10) adding a polymerase for performing a nucleotide polymerization, and the first compound, the second compound, the third compound, and the fourth compound, thereby forming a reaction system containing a solution phase and a solid phase, and then performing the steps (4)-(7).

In some preferred embodiments, the method further comprises the step of:

(11) repeating steps (8)-(10) one or more times.

In some exemplary embodiments, in step (4), if the compound of formula (I) is incorporated into the 3' end of the growing nucleic acid strand, since the compound of formula (I) does not carry a fluorophore itself, and it does not react at step (6), no fluorescent signal will be detected in steps (5) and (7). In other words, if no fluorescent signal is detected in both of steps (5)-(7), it can be determined that the compound incorporated at the 3' end of the growing nucleic acid strand is a compound of formula (I).

In step (4), if the compound of formula (II) is incorporated into the 3' end of the growing nucleic acid strand, since the compound of formula (II) carries a fluorophore itself and it does not perform any reaction in step (6), a fluorescent signal will be detected in both steps (5) and (7). In other words, if a fluorescent signal is detected in both of steps (5) and (7), it can be determined that the compound incorporated at the 3' end of the growing nucleic acid strand is a compound of formula (II).

In step (4), if the compound of formula (III) is incorporated into the 3' end of the growing nucleic acid strand, (i) since the compound of formula (III) does not carry a fluorophore, no fluorescent signal will be detected in step (5); and (ii) the compound of formula (III) performs a bioorthogonal ligation reaction with the agent carrying a fluorophore in step (6), introducing the fluorophore into the growing nucleic acid strand, therefore, a fluorescent signal will be detected in step (7). In other words, if no fluorescent signal is detected in step (5) and a fluorescent signal is detected in step (7), it can be determined that the compound incorporated at the 3' end of the growing nucleic acid strand is a compound of the formula (III).

In step (4), if the compound of formula (IV) is incorporated into the 3' end of the growing nucleic acid strand, (i) since the compound of formula (IV) carries a fluorophore itself or carries a fluorophore after the treatment in step (5), a fluorescent signal will be detected in step (5); and (ii) since the compound of formula (IV) performs a bioorthogonal cleavage reaction or a third bioorthogonal ligation reaction in step (6) to loss the fluorophore or the fluorescent signal is quenched, the fluorescent signal will not be detected in step (7) thereby. In other words, if a fluorescent signal is detected in step (5) and a fluorescent signal is not detected in step (7), it can be determined that the compound incorporated at the 3' end of the growing nucleic acid strand is a compound of the formula (IV).

Therefore, in some preferred embodiments, the method of the present invention further comprises: after step (7), determining the type of the compound incorporated into 3' end of the growing nucleic acid strand in step (4) according to the detection results in steps (5) and (7), wherein, when both of the detection results of steps (5) and (7) are that the duplex or the growing nucleic acid strand does not emit the fluorescent signal, it is determined that the compound incorporated into 3' end of the growing nucleic acid strand in step (4) is the compound of formula (I);

when both of the detection results of steps (5) and (7) are that the duplex or the growing nucleic acid strand emits the fluorescent signal, it is determined that the compound incorporated into 3' end of the growing nucleic acid strand in step (4) is the compound of formula (II);

when the detection result of step (5) is that the duplex or the growing nucleic acid strand does not emit the fluorescent signal, and the detection result of step (7) is that the duplex or the growing nucleic acid strand emits the fluorescent signal, it is determined that the compound incorporated into 3' end of the growing nucleic acid strand in step (4) is the compound of formula (III); and, when the detection result of step (5) is that the duplex or the growing nucleic acid strand emits the fluorescent signal, and the detection result of step (7) is that the duplex or the growing nucleic acid strand does not emit the fluorescent signal, it is determined that the compound incorporated into 3' end of the growing nucleic acid strand in step (4) is the compound of formula (IV).

In some preferred embodiments, the method of the present invention further comprises that, after step (7), based on the base complementary pairing principle, the type of base at the corresponding position in the nucleic acid molecule to be sequenced is determined according to the type of the compound incorporated at the 3' end of the growing nucleic acid strand in step (4).

In some preferred embodiments, the compound of formula (I), the compound of formula (II), the compound of formula (III) and the compound of formula (IV) do not react with each other during the nucleotide polymerization reaction.

In some preferred embodiments, Base1 and Base2 are purine bases, and Base3 and Base4 are pyrimidine bases. In some preferred embodiments, Base1 is base G, Base2 is base A, Base3 is base C, and Base4 is base T or U. In some preferred embodiments, Base1 is base G, Base2 is base A, Base3 is base T or U, and Base4 is base C. In some preferred embodiments, Base1 is base A, Base2 is base G, Base3 is base C, and Base4 is base T or U. In some preferred embodiments, Base1 is base A, Base2 is base G, Base3 is base T or U, and Base4 is base C.

In some preferred embodiments, Base1 and Base2 are pyrimidine bases, and Base3 and Base4 are purine bases. In some preferred embodiments, Base1 is base C, Base2 is base T or U, Base3 is base G, and Base4 is base A. In some preferred embodiments, Base1 is base C, Base2 is base T or U, Base3 is base A, and Base4 is base G. In some preferred embodiments, Base1 is base T or U, Base2 is base C, Base3 is base G, and Base4 is base A. In some preferred embodiments, Base1 is base T or U, Base2 is base C, Base3 is base A, and Base4 is base G.

In some preferred embodiments, the compound of formula (I), the compound of formula (II), the compound of formula (III) and the compound of formula (IV) have the same $R_1$. In some preferred embodiments, $R_1$ is independently —H. In some preferred embodiments, $R_1$ is independently monophosphate group (—PO$_3$H$_2$). In some preferred embodiments, $R_1$ is independently diphosphate group (—PO$_3$H—PO$_3$H$_2$). In some preferred embodiments, $R_1$ is independently triphosphate group (—PO$_3$H—PO$_3$H—PO$_3$H$_2$). In some preferred embodiments, $R_1$ is independently tetraphosphate group (—PO$_3$H—PO$_3$H—PO$_3$H—PO$_3$H$_2$).

In some preferred embodiments, the compound of formula (I), the compound of formula (II), the compound of formula (III) and the compound of formula (IV) have the same $R_2$. In some preferred embodiments, $R_2$ is independently —H. In some preferred embodiments, $R_2$ is independently —OH.

In some preferred embodiments, each one of $R_{3a}$, $R_{3b}$, $R_{3c}$, $R_{3d}$, $R_{4a}$, $R_{4b}$, $R_{4c}$ is independently capable of performing a bioorthogonal cleavage reaction. As used herein, the expression "each independently capable of performing bioorthogonal cleavage reaction" means that the reactive groups, agents, or molecules, etc., are capable of performing bioorthogonal cleavage reaction, respectively, and do not interfere with or affect each other. For example, the expression "each one of $R_{3a}$ and $R_{3b}$ is independently capable of performing bioorthogonal cleavage reaction" means that both $R_{3a}$ and $R_{3b}$ are capable of performing the bioorthogonal cleavage reaction, and $R_{3a}$ does not affect the bioorthogonal cleavage reaction of $R_{3b}$, $R_{3b}$ does not affect the bioorthogonal cleavage reaction of $R_{3a}$.

In some exemplary embodiments, $R_{3a}$ is a first reactive group capable of performing a bioorthogonal cleavage reaction in the presence of a first agent; $R_{3b}$ is a second reactive group capable of performing a bioorthogonal cleavage reaction in the presence of a second agent; $R_{3c}$ is a third reactive group capable of performing a bioorthogonal cleavage reaction in the presence of a third agent; $R_{3d}$ is a fourth reactive group capable of performing a bioorthogonal cleavage reaction in the presence of a fourth agent; $R_{4a}$ is a fifth reactive group capable of performing a bioorthogonal cleavage reaction in the presence of a fifth agent; $R_{4b}$ is a sixth reactive group capable of performing a bioorthogonal cleavage reaction in the presence of a sixth agent; and $R_{4c}$ is a seventh reactive group capable of performing a bioorthogonal cleavage reaction in the presence of a seventh agent.

Preferably, in such embodiments, in step (8), a first agent, a second agent, a third agent, a fourth agent, a fifth agent, a sixth agent and a seventh agent may be added to make $R_{3a}$, $R_{3b}$, $R_{3c}$, $R_{3d}$, $R_{4a}$, $R_{4b}$, $R_{4c}$ (if present) to perform the bioorthogonal cleavage reaction respectively. Therefore, $R_{3a}$, $R_{3b}$, $R_{3c}$, $R_{3d}$ (if present) will be removed from the 3' position of ribose or deoxyribose (in other words, —OR$_{3a}$, —OR$_{3b}$, —OR$_{3c}$ or —OR$_{3d}$ (if present) will be converted to free hydroxyl group), and $R_{4a}$ and the fluorophore attached thereto (if present), $R_{4b}$ and the fluorophore attached thereto (if present) and $R_{4c}$ and the fluorophore attached thereto (if present) will also be removed. Thus, after step (8), the growing nucleic acid strand will not carry a fluorophore and will have a free hydroxyl group at the 3' end, which can be used for the next round of polymerization. Therefore, in some preferred embodiments, in step (8), a first agent, a second agent, a third agent, a fourth agent, a fifth agent, a sixth agent and a seventh agent are added to form a reaction system comprising a solution phase and a solid phase, and the duplex is incubated with the first agent, the second agent, the third agent, the fourth agent, the fifth agent, the sixth agent and the seventh agent under a condition that allow $R_{3a}$, $R_{3b}$, $R_{3c}$, $R_{3d}$, $R_{4a}$, $R_{4b}$, $R_{4c}$ to perform a bioorthogonal cleavage reaction, respectively.

In some preferred embodiments, $R_{3a}$, $R_{3b}$, $R_{3c}$ and $R_{3d}$ are capable of performing a bioorthogonal cleavage reaction respectively in the presence of the same agent. In this case, preferably, in step (8), the first agent, the second agent, the third agent, and the fourth agent are the same agent.

In some preferred embodiments, $R_{3a}$, $R_{3b}$, $R_{3c}$, and $R_{3d}$ are the same reactive group. In this case, preferably, in step (8), the first agent, the second agent, the third agent, and the fourth agent are the same agent. In other words, in step (8), the same $R_{3a}$, $R_{3b}$, $R_{3c}$, and $R_{3d}$ (if present) will each perform the bioorthogonal cleavage reaction in the presence of the same agent (i.e., the first agent), and are removed from the growing nucleic acid strand.

In some preferred embodiments, $R_{4a}$, $R_{4b}$ and $R_{4c}$ are capable of performing the bioorthogonal cleavage reaction respectively in the presence of the same agent. In this case, preferably, in step (8), the fifth agent, the sixth agent and the seventh agent are the same agent.

In some preferred embodiments, $R_{4a}$, $R_{4b}$ and $R_{4c}$ are the same reactive group. In this case, preferably, in step (8), the fifth agent, the sixth agent and the seventh agent are the same agent. In other words, in step (8), the same $R_{4a}$, $R_{4b}$ and $R_{4c}$ (if present) will perform the bioorthogonal cleavage reaction respectively in the presence of the same agent (i.e., the fifth agent), and are removed from the growing nucleic acid strand.

In some preferred embodiments, $R_{3a}$, $R_{3b}$, $R_{3c}$, $R_{3d}$, $R_{4a}$, $R_{4b}$ and $R_{4c}$ are capable of performing the bioorthogonal cleavage reaction respectively in the presence of the same agent. In this case, preferably, in step (8), the first agent, the second agent, the third agent, the fourth agent, the fifth agent, the sixth agent and the seventh agent are the same agent. In other words, in step (8), an agent (i.e., the first agent) is added to make $R_{3a}$, $R_{3b}$, $R_{3c}$, $R_{3d}$, $R_{4a}$, $R_{4b}$ and $R_{4c}$ (if present) to perform the bioorthogonal cleavage reaction and removed from the growing nucleic acid strand respectively in the presence of said agent (i.e., the first agent).

In some exemplary embodiments, it is particularly preferred that the two members of the first binding pair ($R_{5a}$ and $R_{5b}$) do not react with the two members of the third binding pair ($R_{6a}$ and $R_{6c}$). Furthermore, it is particularly preferred that $R_{5a}$ and $R_{5b}$ do not affect the specific interaction between $R_{6a}$ and $R_{6c}$, and that $R_{6a}$ and $R_{6c}$ do not affect the specific interaction between $R_{5a}$ and $R_{5b}$. In such embodiments, preferably, $R_{5b}$-L5-$Dye_3$ and $R_{6c}$-L6-Que may be added in step (6), thereby enabling $R_{5a}$ (if present) in compound of formula (III) to specifically bind to $R_{5b}$ in $R_{5b}$-L5-D3, and enabling $R_{6a}$ (if present) in compound of formula (IV) to specifically bind to $R_{6c}$ in $R_{6c}$-L6-Que. Therefore, the fluorophore Dye linked with $R_{5b}$ is introduced into the compound of formula (III) by the specific interaction between the two members ($R_{5a}$ and $R_{5b}$) of the first binding pair, thereby enabling the compound of formula (III) to emit a fluorescent signal. Meanwhile, the quenching group Que linked with $R_{6c}$ is introduced into the compound of formula (IV) by the specific interaction between the two members ($R_{6a}$ and $R_{6c}$) of the third binding pair thereby quenching the fluorescent signal emitted by Dye in the compound of formula (IV), and the compound of formula (IV) do not fluoresce any more. In such embodiments, it is particularly preferred that, $R_{5b}$-L5-$Dye_3$ does not react with the first compound and the second compound in step (6), and further preferably, $R_{6c}$-L6-Que does not react with the first compound and the second compound. Therefore, in some preferred embodiments, in step (6), $R_{5b}$-L5-$Dye_3$ and $R_{6c}$-L6-Que may be added to form a reaction system comprising a solution phase and a solid phase, wherein $R_{5b}$ is the other member of the first binding pair, L5 is a linking group or absent; $Dye_3$ represents a fluorophore capable of emitting a fluorescent signal, $R_{6c}$ is the other member of the third binding pair, L6 is a linking group or absent, and Que represents a quenching group of the fluorescent signal emitted by $Dye_1$ or $Dye_2$; then, the duplex is incubated with $R_{5b}$-L5-$Dye_3$ and $R_{6c}$-L6-Que under a condition that allows specific binding between $R_{5a}$ and $R_{5b}$ and allows specific binding between $R_{6a}$ and $R_{6c}$.

In some exemplary embodiments, $R_{6a}$ is one member of the third binding pair; and $R_{6a}$ is $Dye_1$, or $R_{6a}$ is further linked with -L3-$Dye_1$, wherein $Dye_1$ has the same structure as Dye or has different structure but the same emission spectrum as Dye, therefore, the fourth compound itself is capable of emitting the same fluorescent signal as the second compound. In such embodiments, step (6) comprises adding the eighth agent, thereby enabling $R_{6a}$ (if present) in the compound of formula (IV) to specifically interact with and/or specifically bind to the other member of the third binding pair. For example, the eighth agent may comprise the other member of a third binding pair carrying a fluorophore, which has the structure of $R_{60}$-L6-Que, wherein, $R_{6c}$ is the other member of the third binding pair, L6 is independently a linking group or absent, and Que represents a quenching group capable of quenching the fluorescent signal emitted by $Dye_1$ or $Dye_2$.

In some exemplary embodiments, the fourth compound does not carry a fluorophore, and $R_{6a}$ is one member of the second binding pair and is one member of the third binding pair. In such embodiments, step (5) comprises adding a ninth agent thereby enabling $R_{6a}$ (if present) in the compound of formula (IV) to specifically interact with and/or specifically bind to the other member of the second binding pair. For example, the ninth agent may comprise the other member of the second binding pair carrying a fluorophore, which has the structure of $R_{6b}$-L4-$Dye_2$, wherein, $R_{6b}$ is the other member of the second binding pair, and L4 is independently a linking group or absent; $Dye_2$ represents a fluorophore capable of emitting a fluorescent signal, having the same structure as Dye, or having a different structure but having the same emission spectrum as Dye. In such embodiments, step (6) comprises adding a tenth agent thereby enabling $R_{6a}$ (if present) in the compound of formula (IV) to specifically interact with and/or bind to the other member of the third binding pair. For example, the tenth agent may comprise the other member of a third binding pair carrying a fluorophore, which has the structure of $R_{6c}$-L6-Que, wherein, $R_{6c}$ is the other member of the third binding pair, and L6 is independently a linking group or absent; Que represents a quenching group capable of quenching the fluorescent signal emitted by $Dye_1$ or $Dye_2$.

Preferably, in the above two kinds of embodiments, an eleventh agent and a tenth agent may be added in step (6), thereby enabling $R_{5a}$ (if present) in the compound of formula (III) to specifically interact with and/or specifically bind to the other member of the first binding pair, and enabling $R_{6a}$ (if present) in the compound of formula (IV) to specifically interact with and/or specifically bind to the other member of the third binding pair. For example, the eleventh agent may comprise the other member of the first binding pair, wherein the other member of the first binding pair carries the same fluorophore (or a fluorophore has different structure but the same or substantially the same fluorophore) as the second compound and the fourth compound, and the other member of the first binding pair is capable of specifically binding to $R_{5a}$ thereby introducing the carried fluorophore into the compound of formula (III). Furthermore, the tenth agent comprises the other member of the third binding pair carrying a quencher, where the other member of the third binding pair is capable of specifically interacting with and/or specifically binding to $R_{6a}$ (if present), thereby the fluorescent signal in compound of formula (IV) is quenched. In such embodiments, it is particularly preferred that, in step (6), the eleventh agent does not react with the first compound and the second compound, and further preferably, the tenth agent does not react with the first compound and the second compound. Therefore, in some preferred embodiments, the eleventh agent and the tenth agent can be added to form a reaction system comprising a solution phase and a solid phase in step (6), wherein, the eleventh agent comprises the other member of the first binding pair, and the other member of the first binding pair may carry the same fluorophore (or a fluorophore has different structure but the same or substantially the same emission spectrum) as the fluorophore of the second compound and of the fourth compound, and the other member of the first binding pair is capable of specifically interacting with and/or specifically binding to $R_{5a}$, thereby introducing the carried fluorophore into the third compound; the tenth agent comprises the other member of the third binding pair, wherein the other member of the third binding pair carries a quencher, and is capable of specifically interacting with and/or specifically binding to $R_{6a}$, thereby introducing the carried quencher into the fourth compound; then, the duplex is incubated with the eleventh agent and the tenth agent under a condition, wherein the condition allows $R_{5a}$ to specifically interact with and/or specifically bind to the other member of the first binding pair, and allows $R_{6a}$ to specifically interact with and/or specifically bind to the other member of the third binding pair.

In some exemplary embodiments, a reactive group $R_8$ capable of performing a third bioorthogonal ligation reaction exists between $R_{5b}$ and $R_{7a}$ of the fourth compound. In some preferred embodiments, each one of $R_{3a}$, $R_{3b}$, $R_{3c}$, $R_{3d}$, $R_{4a}$, $R_{4b}$, $R_{5a}$ and $R_8$ is independently capable of performing the bioorthogonal cleavage or ligation reaction. In some exemplary embodiments, $R_{8a}$ is capable of performing the third bioorthogonal ligation reaction in the presence of a twelfth agent.

Preferably, in such embodiments, an eleventh agent and a twelfth agent can be added in step (6) making $R_{5a}$ (if present) in the compound of formula (III) to perform the first bioorthogonal ligation reaction, and $R_8$ (if present) in compound of formula (IV) is enabled to perform the third bioorthogonal ligation reaction. For example, the eleventh agent can comprise the other member of the first binding pair, and the other member of the first binding pair carries the same fluorophore as the second compound and the fourth compound (or the fluorophore has different structure but the same or substantially the same fluorophore), and the other member of the first binding pair is capable of specifically binding to $R_{5a}$ and thereby introducing the carried fluorophore into the compound of formula (III). Furthermore, the twelfth agent enables $R_8$ in the compound of formula (IV) to perform a third bioorthogonal ligation reaction and thereby quenching the fluorescent signal in the compound of formula (IV). In such embodiments, it is also particularly preferred that, the eleventh agent does not react with the first compound and the second compound in step (6), and further preferably, the twelfth agent does not react with the first compound and the second compound. Therefore, in some preferred embodiments, the eleventh agent and the twelfth agent can be added to form a reaction system comprising a solution phase and a solid phase in step (6), wherein, the eleventh agent comprises the other member of the first binding pair, and the other member of the first binding pair can carry the same fluorophore (or the fluorophore has different structure but the same or substantially the same fluorophore) as the second compound and the fourth compound, and, the other member of the first binding pair is capable of specifically interacting with and/or specifically binding to $R_{5a}$, thereby the carried fluorophore can be introduced in the third compound; the twelfth agent comprises compound M, said compound M carries a quencher, and the compound M is capable of performing the third bioorthogonal ligation reaction with $R_8$ to introduce the quencher in compound M into the fourth compound; then, the duplex is incubated with the eleventh agent and the twelfth agent under conditions that allow $R_{5a}$ to specifically interact with and/or specifically bind to the other member of the first binding pair, and conditions that allow M to perform the third bioorthogonal ligation reaction with $R_8$.

In some preferred embodiments, $R_{3a}$, $R_{3b}$, $R_{3c}$ and $R_{3d}$ are independently selected from the group consisting of —$CH_2CH=CH_2$, —$CH_2N_3$, $C_{3-8}$ cycloalkenyl (e.g., $C_3$ cycloalkenyl, $C_4$ cycloalkenyl, $C_5$ cycloalkenyl, $C_6$ cycloalkenyl, $C_7$ cycloalkenyl or $C_8$ cycloalkenyl). In some preferred embodiments, the $C_{3-8}$ cycloalkenyl is selected from the group consisting of $C_3$ cycloalkenyl and $C_8$ cycloalkenyl. In some preferred embodiments, the $C_{3-8}$ cycloalkenyl group is

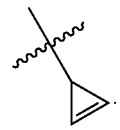

In some preferred embodiments, the $C_{3-8}$ cycloalkenyl group is

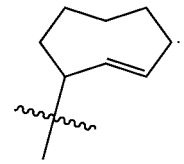

In some preferred embodiments, $R_{3a}$, $R_{3b}$, $R_{3c}$ and $R_{3d}$ are the same reactive group and are selected from the group consisting of —$CH_2CH=CH_2$, —$CH_2N_3$, $C_{3-8}$ cycloalkenyl (e.g., $C_3$ cycloalkenyl, $C_4$ cycloalkenyl, $C_5$ cycloalkenyl, $C_6$ cycloalkenyl, $C_7$ cycloalkenyl or $C_8$ cycloalkenyl). In some preferred embodiments, the $C_{3-8}$ cycloalkenyl is selected from the group consisting of $C_3$ cycloalkenyl and $C_8$ cycloalkenyl. In some preferred embodiments, the $C_{3-8}$ cycloalkenyl is

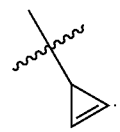 [SMILES: *C1C=C1]

In some preferred embodiments, the $C_{3-8}$ cycloalkenyl is

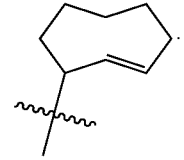 [SMILES: *C1/C=C/CCCCC1]

In some preferred embodiments, $R_{3a}$, $R_{3b}$, $R_{3c}$ and $R_{3d}$ are the same reactive group and are —$CH_2N_3$.

In some preferred embodiments, $R_{4a}$, $R_{4b}$ and $R_{4c}$ are independently selected from the group consisting of:

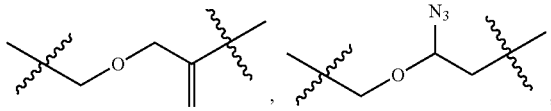

—O—$C_{3-8}$ cycloalkenylene. In some preferred embodiments, the "—O—$C_{3-8}$ cycloalkenylene" is selected from the group consisting of —O—$C_3$ cycloalkenylene, —O—$C_4$ cycloalkenylene, —O—$C_5$ cycloalkenylene, —O—$C_6$ cycloalkenylene, —O—$C_7$ cycloalkenylene, and —O—$C_8$ cycloalkenylene. In some preferred embodiments, the "—O—$C_{3-8}$ cycloalkenylene" is

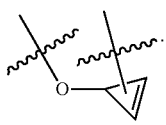

In some preferred embodiments, the "—O—$C_3$-8 cycloalkenylene" is

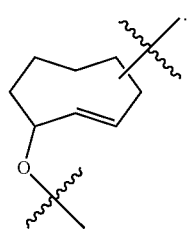

In some preferred embodiments, $R_{4a}$, $R_{4b}$ and $R_{4c}$ are the same reactive group and are selected from the group consisting of:

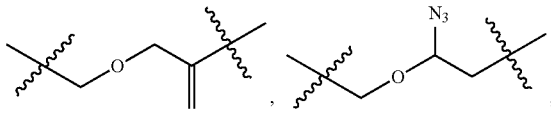

—O—$C_{3-8}$ cycloalkenylene. In some preferred embodiments, the "—O—$C_{3-8}$ cycloalkenylene" is selected from the group consisting of —O—$C_3$ cycloalkenylene, —O—$C_4$ cycloalkenylene, —O—$C_5$ cycloalkenylene, —O—$C_6$ cycloalkenylene, —O—$C_7$ cycloalkenylene, and —O—$C_8$ cycloalkenylene. In some preferred embodiments, the "—O—$C_{3-8}$ cycloalkenylene" is

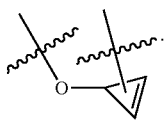

In some preferred embodiments, the "—O—$C_{3-8}$ cycloalkenylene" is

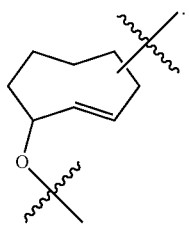

In some preferred embodiments, $R_{4a}$, $R_{4b}$ and $R_{4c}$ are

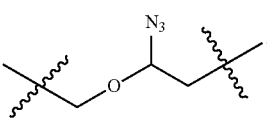

In some preferred embodiments, the first agent, the second agent, the third agent, the fourth agent, the fifth agent, the sixth agent and the seventh agent independently comprise a material selected from the group consisting of:

a complex of palladium (for example, a complex of palladium with four triphenylphosphine 3,3',3"-trisulfonic acids);

a complex of ruthenium (for example, a complex of ruthenium with quinoline carboxylate (or a derivative thereof), allyl or cyclopentadiene);

a phosphide (e.g., a carboxyphosphine or hydroxyphosphine such as $P(CH_2CH_2COOH)_3$ or $P(CH_2CH_2OH)_3$); and compound Q which has the structural formula

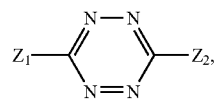

wherein $Z_1$ and $Z_2$ are independently selected from a modified or unmodified alkyl group (e.g., $C_1$-$C_{06}$ alkyl group such as $C_1$ alkyl group, $C_2$ alkyl group, $C_3$ alkyl group, $C_4$ alkyl group, $C_5$ alkyl group or $C_6$ alkyl group) and a modified or unmodified aryl (for example, 6-10 membered aryl such as 6-membered aryl, 7-membered aryl, 8-membered aryl, 9-membered aryl or 10-membered aryl such as phenyl or pyridyl).

In some preferred embodiments, $R_{3a}$, $R_{3b}$, $R_{3c}$ and $R_{3d}$ are —$CH_2CH$=$CH_2$. In this case, preferably, $R_{4a}$, $R_{4b}$ and $R_{4c}$ are

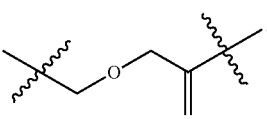

Further preferably, the first agent, the second agent, the third agent, the fourth agent, the fifth agent, the sixth agent and the seventh agent comprise a complex of palladium or a complex of ruthenium. Preferably, the first agent, the second agent, the third agent, the fourth agent, the fifth agent, the sixth agent and the seventh agent are the same agent, and comprise a complex of palladium or a complex of ruthenium.

In some preferred embodiments, $R_{3a}$, $R_{3b}$, $R_{3c}$, and $R_{3d}$ are —$CH_2$—$N_3$. In this case, preferably, $R_{4a}$, $R_{4b}$ and $R_{4c}$ are

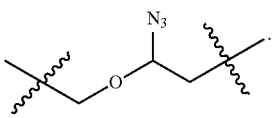 [SMILES: *COC(C*)N=[N+]=[N-]]

Further preferably, the first agent, the second agent, the third agent, the fourth agent, the fifth agent, the sixth agent and the seventh agent comprise phosphonate such as carboxyl phosphonate or hydroxyl phosphonate, e.g. $P(CH_2CH_2COOH)_3$ or $P(CH_2CH_2OH)_3$. Preferably, the first agent, the second agent, the third agent, the fourth agent, the fifth agent, the sixth agent and the seventh agent are the same agent, and comprise phosphonate such as carboxyl phosphonate or hydroxyl phosphonate, e.g. $P(CH_2CH_2COOH)_3$ or $P(CH_2CH_2OH)_3$.

In some preferred embodiments, $R_{3a}$, $R_{3b}$, $R_{3c}$ and $R_{3d}$ are

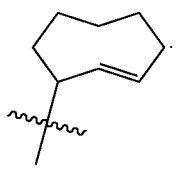 [SMILES: *C1/C=C/CCCCC1]

In this case, preferably, $R_{4a}$, $R_{4b}$ and $R_{4c}$ are

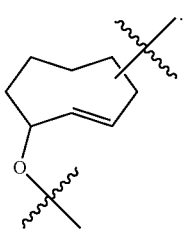

Further preferably, the first agent, the second agent, the third agents, the fourth agent, the fifth agent, the sixth agent and the seventh agent comprise the compound Q as defined above. Further preferably, in compound Q, $Z_1$ is methyl; and $Z_2$ is modified or unmodified pyridyl. More preferably, compound Q is

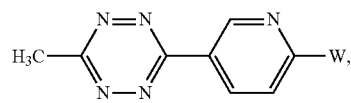

wherein is hydrogen or a modifying group. Preferably, the first agent, the second agent, the third agent, the fourth agent, the fifth agent, the sixth agent and the seventh agent are the same agent and comprise the compound Q as defined above.

In some preferred embodiments, the linking groups L1, L2 and L3 in the first compound, the second compound, the third compound and the fourth compound, and L4, L5 and L6 in $R_{6b}$-L4-Dye$_2$, $R_{5b}$-L5-Dye$_3$ and $R_{6c}$-L6-Que are independent from each other and are not particularly limited. A person skilled in the art can select suitable linking groups L1, L2, L3, L4, L5 and L6 according to the bases (Base1, Base2, Base3 or Base4) in the compounds, the reactive groups ($R_{4a}$, $R_{4b}$ and $R_{4c}$) and the members ($R_{5a}$, $R_{5b}$, $R_{6a}$ and $R_{6b}$) of the first binding pair and the second binding pair.

In some exemplary embodiments, the linking groups L1, L2, L3, L4, L5 and L6 are independently selected from the group consisting of:

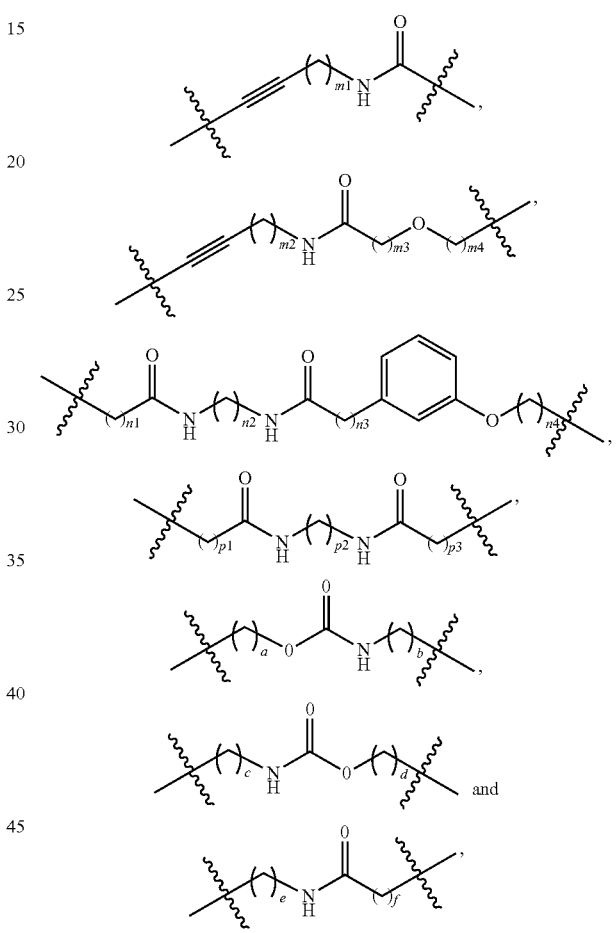

wherein m1, m2, m3, m4, n1, n2, n3, n4, p1, p2, p3, a, b, c, d, e and f are independently selected from 0, 1, 2, 3, 4, 5 or 6.

In some exemplary embodiments, L1 in the first compound, the second compound, the third compound or the fourth compound is independently selected from the group consisting of:

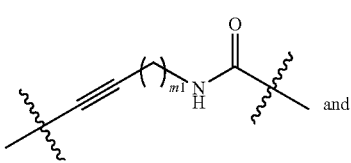

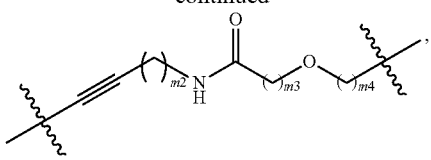

wherein m1, m2, m3, and m4 are independently selected from 0, 1, 2, 3, 4, 5 or 6.

In some preferred embodiments, L1 in the first compound, the second compound, the third compound or the fourth compound is independently selected from the group consisting of:

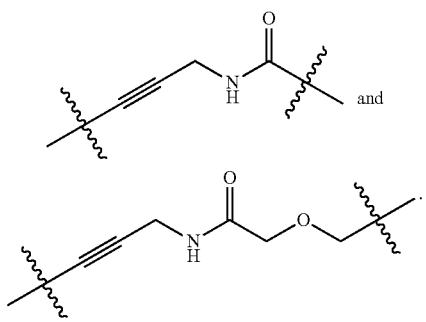

In some preferred embodiments, L2 in the first compound, the second compound, the third compound or the fourth compound is independently selected from the group consisting of:

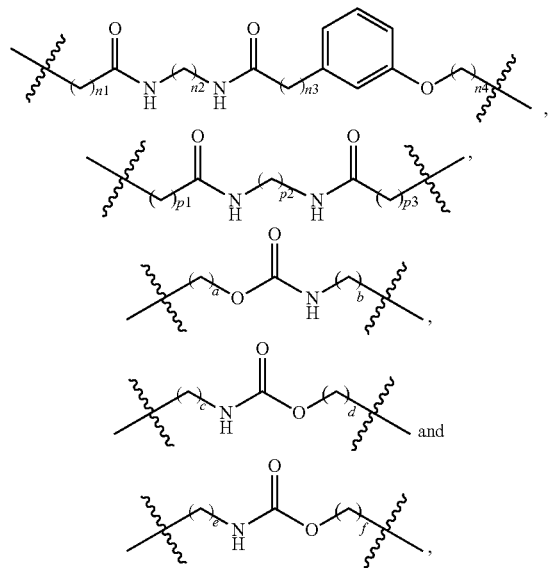

wherein n1, n2, n3, n4, p1, p2, p3, a, b, c, d, e, and f are independently selected from 0, 1, 2, 3, 4, 5, or 6.

In some preferred embodiments, L2 in the first compound, the second compound, the third compound or the fourth compound is independently selected from the group consisting of:

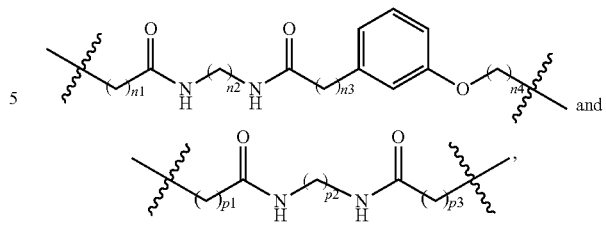

wherein n1, n2, n3, n4, p1, p2, p3 are independently selected from 0, 1, 2, 3, 4, 5 or 6.

In some preferred embodiments, L2 in the first compound, the second compound, the third compound or the fourth compound is independently selected from the group consisting of:

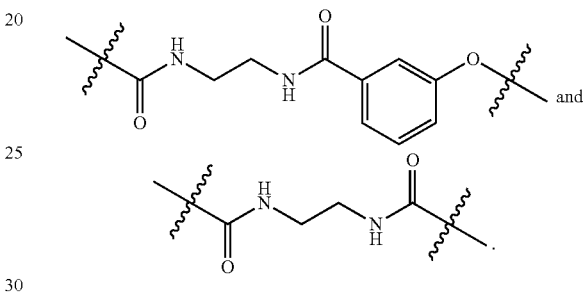

In some preferred embodiments, $R_{5a}$ and $R_{5b}$ are two members of the first binding pair, $R_{6a}$ and $R_{6b}$ are two members of the second binding pair, and $R_{6a}$ and $R_{6c}$ are two members of the third binding pair. In some preferred embodiments, the first binding pair and the second binding pair are independently selected from the group consisting of: antigen (e.g., small molecule antigen)-antibody, hapten-antibody, hormone-receptor, ligand-receptor, nucleic acid strand-complementary nucleic acid strand, substrate-enzyme, substrate analog-enzyme, inhibitor-enzyme, sugar-plant lectin, biotin-avidin (for example, avidin and streptavidin), digoxin and digoxin antibody, and 5-position bromodeoxyguanosine and its antibody.

In some preferred embodiments, the two members of the first binding pair are selected from the group consisting of: (a) biotin and avidin (for example, streptavidin), (b) desthiobiotin and avidin (e.g., streptavidin) and (c) digoxin and digoxin antibody. In some preferred embodiments, $R_{5a}$ is biotin or desthiobiotin, and $R_{5b}$ is avidin (for example, streptavidin). In some preferred embodiments, $R_{5a}$ is digoxin and $R_{5b}$ is a digoxin antibody.

In some preferred embodiments, the two members of the second binding pair are selected from the group consisting of: (a) biotin and avidin (for example, streptavidin), (b) desthiobiotin and avidin (e.g., streptavidin) and (c) digoxin and digoxin antibody. In some preferred embodiments, $R_{6a}$ is biotin or desthiobiotin, and $R_{6b}$ is avidin (for example, streptavidin). In some preferred embodiments, $R_{6a}$ is digoxin and $R_{6b}$ is a digoxin antibody.

In some preferred embodiments, the two members of the third binding pair are selected from the group consisting of: (a) biotin and avidin (for example, streptavidin), (b) desthiobiotin and avidin (for example, streptavidin), (c) digoxin and digoxin antibody, (d) Cy3 and Cy3 antibody. In some preferred embodiments, $R_{6a}$ is Cy3 and $R_{6c}$ is a Cy3 antibody. It is particularly preferred that the two members of the first binding pair ($R_{5a}$ and $R_{5b}$) do not interact with the two members of the third binding pair ($R_{6a}$ and $R_{6c}$). Furthermore, it is particularly preferred that $R_{5a}$ and $R_{5b}$ do not affect the specific interaction between $R_{6a}$ and $R_{6c}$, and that $R_{6a}$ and $R_{6c}$ do not affect the specific interaction between $R_{5a}$ and $R_{5b}$. Thus, in some preferred embodiments, the two members of the first binding pair are biotin and avidin (for example, streptavidin), and the two members of the third binding pair are digoxin and digoxin antibody. In some preferred embodiments, the two members of the first binding pair are digoxin and digoxin antibody, and the two members of the third binding pair are biotin and avidin (for example, streptavidin). In some preferred embodiments, the two members of the first binding pair are biotin and avidin (for example, streptavidin), and the two members of the third binding pair are Cy3 and Cy3 antibody.

In some preferred embodiments, $R_{3a}$, $R_{3b}$, $R_{3c}$, and $R_{3d}$ are —$CH_2CH=CH_2$; $R_{4a}$, $R_{4b}$ and $R_{4c}$ are

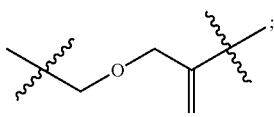 [SMILES: *COCC(*)=C]

the first, second, third, fourth, fifth, sixth and seventh agent comprise a complex of palladium or a complex of ruthenium; $R_{5a}$ is biotin; $R_{5b}$ is avidin (for example, streptavidin); $R_{6a}$ is digoxin; $R_{6b}$ is digoxin antibody. Preferably, the first, second, third, fourth, fifth, sixth and seventh agent are the same agents, and comprise a complex of palladium or a complex of ruthenium.

In some preferred embodiments, $R_{3a}$, $R_{3b}$, $R_{3c}$, and $R_{3d}$ are —$CH_2$—$N_3$; $R_{4a}$, $R_{4b}$ and $R_{4c}$ are

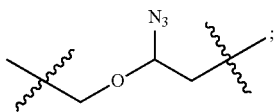 [SMILES: *COC(C*)N=[N+]=[N-]]

the first, second, third, fourth, fifth, sixth and seventh agent comprise a phosphide such as a carboxyl phosphide or a hydroxyl phosphide such as $P(CH_2CH_2COOH)_3$ or $P(CH_2CH_2OH)_3$; $R_{5a}$ is biotin; $R_{5b}$ is avidin (for example, streptavidin); $R_{6a}$ is digoxin; $R_{6b}$ is digoxin antibody. Preferably, the first, second, third, fourth, fifth, sixth and seventh agent are the same agents and comprise a phosphide such as a carboxyl phosphide or a hydroxyl phosphide such as $P(CH_2CH_2COOH)_3$ or $P(CH_2CH_2OH)_3$.

In some preferred embodiments, $R_{3a}$, $R_{3b}$, $R_{3c}$, and $R_{3d}$ are —$CH_2$—$N_3$; $R_{4a}$, $R_{4b}$ and $R_{4c}$ are

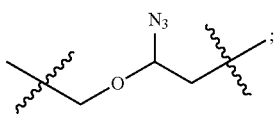 [SMILES: *COC(C*)N=[N+]=[N-]]

the first, second, third, fourth, fifth, sixth and seventh agent comprise a phosphide such as a carboxyl phosphide or a hydroxyl phosphide, such as $P(CH_2CH_2COOH)_3$ or $P(CH_2CH_2OH)_3$; $R_{5a}$ is digoxin; $R_{5b}$ is digoxin antibody; $R_{6a}$ is biotin; $R_{6b}$ is avidin (for example, streptavidin). Preferably, the first, second, third, fourth, fifth, sixth and seventh agents are the same agents and comprise a phosphide such as a carboxyl phosphide or a hydroxyl phosphide such as $P(CH_2CH_2COOH)_3$ or $P(CH_2CH_2OH)_3$.

In some preferred embodiments $R_{3a}$, $R_{3b}$, $R_{3c}$, and $R_{3d}$ are —$CH_2CH=CH_2$; $R_{4a}$, $R_{4b}$ and $R_{4c}$ are

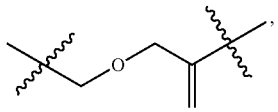 [SMILES: *COCC(*)=C]

the first, second, third, fourth, fifth, sixth and seventh agent comprise a complex of palladium or a complex of ruthenium; $R_{5a}$ is digoxin; $R_{5b}$ is digoxin antibody; $R_{6a}$ is biotin; $R_{6b}$ is avidin (for example, streptavidin). Preferably, the first, second, third, fourth, fifth, sixth and seventh agents are the same agents, and comprise a complex of palladium or a complex of ruthenium.

In some preferred embodiments, $R_{3a}$, $R_{3b}$, $R_{3c}$, and $R_{3d}$ are

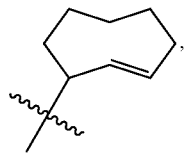 [SMILES: *C1/C=C/CCCCC1]

$R_{4a}$, $R_{4b}$ and $R_{4c}$ are

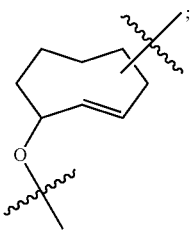

the first, second, third, fourth, fifth, sixth and seventh agent comprises compound Q (for example, the compound Q as defined above); $R_{5a}$ is biotin; $R_{5b}$ is avidin (for example, streptavidin); $R_{6a}$ is digoxin; $R_{6b}$ is digoxin antibody. Preferably, the first, second, third, fourth, fifth, sixth and seventh agent are the same agents, and comprise compound Q (e.g., the compound Q as defined above).

In some preferred embodiments, $R_{3a}$, $R_{3b}$, $R_{3c}$, and $R_{3d}$ are

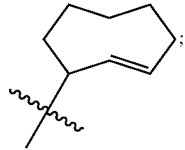

$R_{4a}$, $R_{4b}$ and $R_{4c}$ are

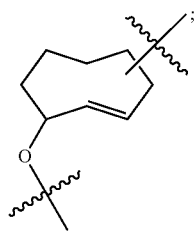

the first, second, third, fourth, fifth, sixth and seventh agent comprises compound Q (for example, the compound Q as defined above); $R_{5a}$ is digoxin; $R_{5b}$ is digoxin antibody; $R_{6a}$ is biotin; $R_{6b}$ is avidin (for example, streptavidin). Preferably, the first, second, third, fourth, fifth, sixth and seventh agent are the same agents, and comprise compound Q (e.g., the compound Q as defined above).

In some preferred embodiments, $R_{3a}$, $R_{3b}$, $R_{3c}$, and $R_{3d}$ are —CH$_2$CH=CH$_2$; $R_{4a}$, $R_{4b}$ and $R_{4c}$ are

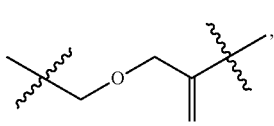 [SMILES: *COCC(*)=C]

the first, second, third, fourth, fifth, sixth and seventh agent comprise a complex of palladium or a complex of ruthenium; $R_{5a}$ is biotin; $R_{5b}$ is avidin (for example, streptavidin); $R_{6a}$ is Cy3; $R_{6b}$ is Cy3 antibody. Preferably, the first, second, third, fourth, fifth, sixth and seventh agents are the same agents, and comprise a complex of palladium or a complex of ruthenium.

In some preferred embodiments, $R_{3a}$, $R_{3b}$, $R_{3c}$, and $R_{3d}$ are

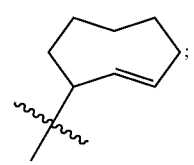

$R_{4a}$, $R_{4b}$ and $R_{4c}$ are

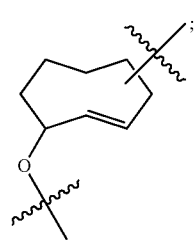

the first, second, third, fourth, fifth, sixth and seventh agent comprises compound Q (for example, the compound Q as defined above); $R_{5a}$ is biotin; $R_{5b}$ is avidin (for example, streptavidin); $R_{6a}$ is Cy3; $R_{6b}$ is Cy3 antibody. Preferably, the first, second, third, fourth, fifth, sixth and seventh agent are the same agents, and comprise compound Q (e.g., the compound Q as defined above).

In some preferred embodiments, $R_{3a}$, $R_{3b}$, $R_{3c}$, and $R_{3d}$ are

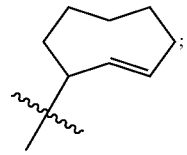

$R_{4a}$, $R_{4b}$ and $R_{4c}$ are

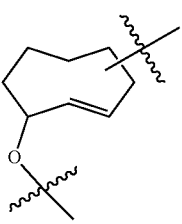

the first, second, third, fourth, fifth, sixth and seventh agent comprises compound Q (for example, the compound Q as defined above); $R_{5a}$ is biotin; $R_{5b}$ is avidin (for example, streptavidin); $R_{6a}$ is Cy3; $R_{6b}$ is Cy3 antibody. Preferably, the first, second, third, fourth, fifth, sixth and seventh agent are the same agents, and comprise the compound Q (e.g., the compound Q as defined above).

In some preferred embodiments, the first compound has the structure shown in formula (Ib):

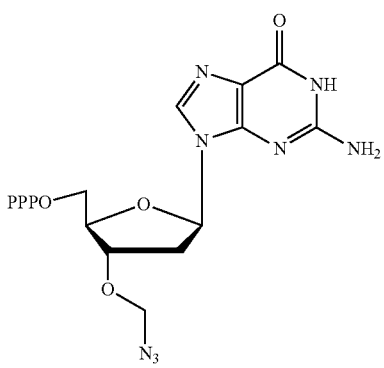

(Ib)

In some preferred embodiments, the second compound has the structure shown in formula (IIb):

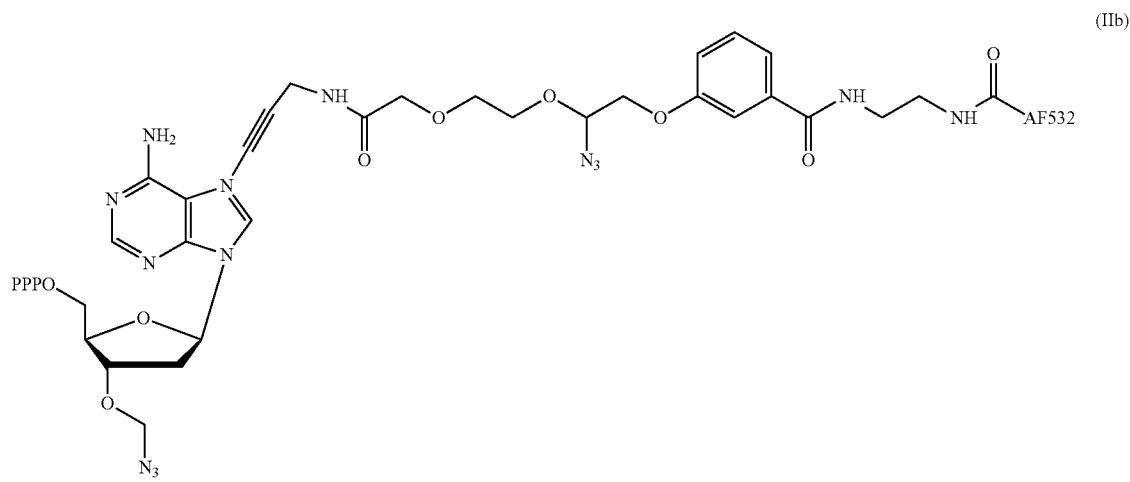

(IIb)

In some preferred embodiments, the third compound has the structure shown in formula (IIIb):

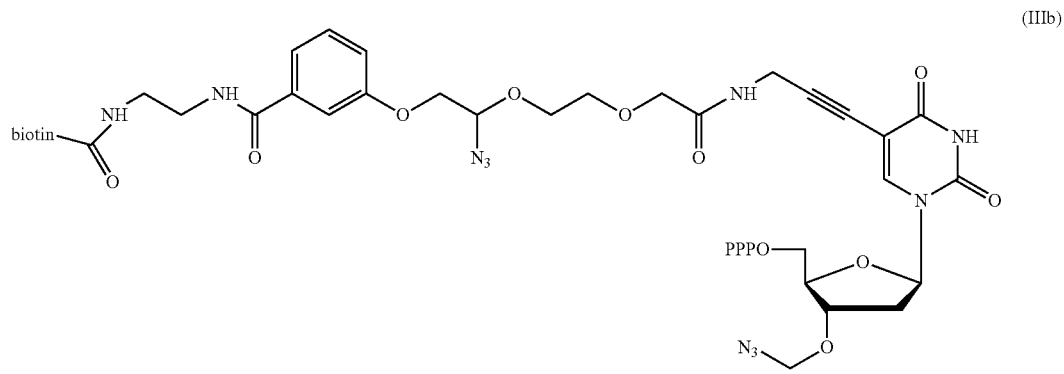

(IIIb)

In some preferred embodiments, the fourth compound has the structure shown in formula (IVb):

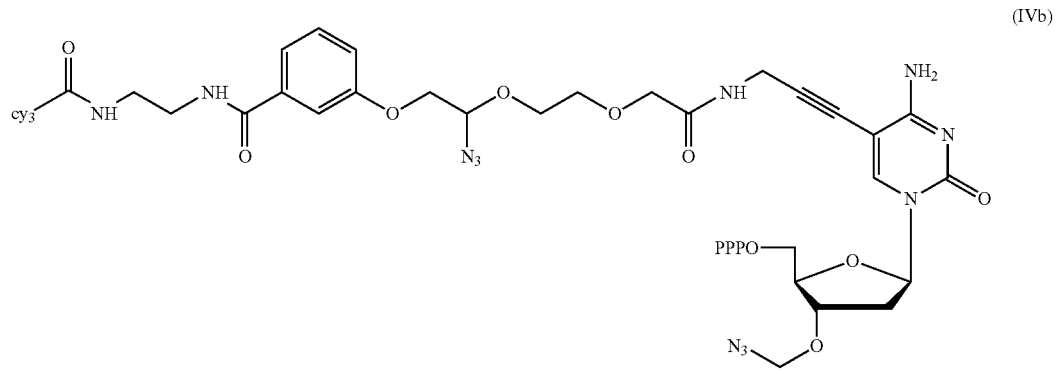

(IVb)

Additionally, as described above, the method of the present invention may comprise a washing step as needed. The washing step can be added at any desired stage, and optionally, the washing step can be performed one or more times.

For example, in step (5), after removing the solution phase of the reaction system, one or more washings may be performed to sufficiently remove the residual solution phase. Such a washing step may be advantageous for sufficiently removing a fluorophore-bearing compound (e.g., $R_{6b}$-L4-$Dye_2$, the compound of formula (II) or compound of formula (IV)) which is free (i.e., not incorporated into the nucleic acid strand), thereby minimizing non-specific fluorescent signal as much as possible.

Similarly, in step (7), after removing the solution phase of the reaction system, one or more washings may be performed to sufficiently remove the residual solution phase. Such a washing step may be advantageous for sufficiently removing the fluorescent-carrying agent (e.g. $R_{5b}$-L5-$Dye_3$) used in step (6), thereby minimizing non-specific fluorescent signal as much as possible.

Similarly, in step (9), after removing the solution phase of the reaction system, one or more washings may be performed to sufficiently remove the residual solution phase. Such a washing step may be advantageous for sufficiently removing the agents used in step (8) and the products produced (which may carry fluorescence), thereby minimizing non-specific fluorescent signal and avoiding adverse effect on the subsequent polymerization reaction as much as possible.

The washing step can be carried out using a variety of suitable washing solutions. Examples of such washing solutions include, but are not limited to, phosphate buffer, citrate buffer, Tris-HCl buffer, acetate buffer, carbonate buffer, and the like. It is within the ability of those skilled in the art to select a suitable washing solution (including suitable ingredient, concentration, ionic strength, pH value, etc.) according to the actual needs.

Exemplary Embodiment 3

In some exemplary embodiments, the ability of the four compounds to emit fluorescent signals is controlled (for example, maintained or changed) in step (6) by using a binding pair (which comprises two members that interact with each other by specific non-covalent interaction); and preferably, the removal of the protecting group and the fluorescent signal can be achieved in step (8) by using a reactive group capable of performing a bioorthogonal cleavage reaction. For example, in some exemplary embodiments, the first, second, third, and fourth compounds may have the structures of formulas (I), (II), (III), and (IV), respectively:

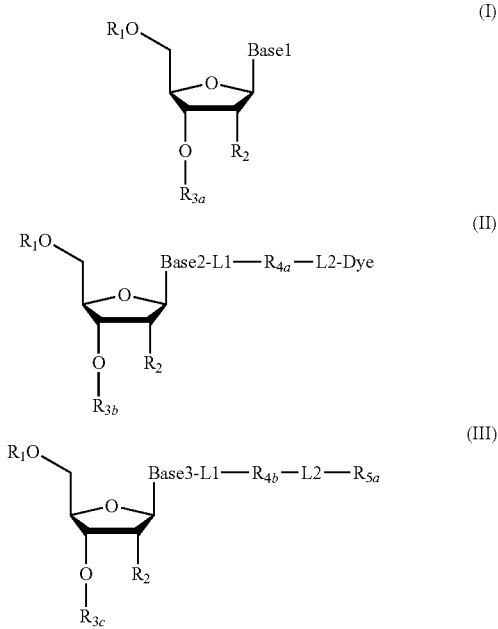

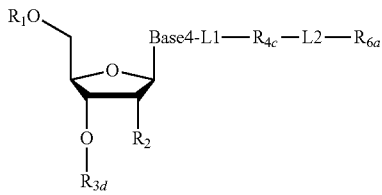

wherein, Base1, Base2, Base3 and Base4 represent 4 different bases, and are selected from A, (T/U), C, and G;

$R_1$ is independently selected from —H, monophosphate group (—$PO_3H_2$), diphosphate group (—$PO_3H$—$PO_3H_2$), triphosphate group (—$PO_3H$—$PO_3H$—$PO_3H_2$) and tetraphosphate group (—$PO_3H$—$PO_3H$—$PO_3H$—$PO_3H_2$);

$R_2$ is independently selected from —H and —OH;

$R_{3a}$, $R_{3b}$, $R_{3c}$, $R_{3d}$, $R_{4a}$, $R_{4b}$, and $R_{4c}$ are independently a reactive group capable of performing a bioorthogonal cleavage reaction;

$R_{5a}$ is a reactive group capable of performing a first bioorthogonal ligation reaction;

$R_{6a}$ is (i) one member of the first binding pair and is one member of the second binding pair; or is (ii) only one member of the second binding pair, and, $R_{6a}$ is $Dye_1$, or $R_{6a}$ is also linked with -L3-$Dye_1$;

L1 is independently a linking group or absent;
L2 is independently a linking group or absent;
L3 is a linking group or absent;

Dye represents a fluorophore capable of emitting a fluorescent signal; Dye and $Dye_1$ have the same structure, or have different structures but have the same or substantially the same emission spectrum;

optionally, a reactive group $R_8$ capable of performing a second bioorthogonal ligation reaction is present between $R_{4c}$ and $R_{6a}$.

In such exemplary embodiments, the fourth compound itself may carry a fluorophore capable of emitting the same fluorescent signal as that of the second compound, or may not carry a fluorophore but specifically interact with/bind to an agent (for example, the other member of the first binding pair) carrying a fluorophore (for example, a fluorophore having the same structure as the second compound, or a fluorophore having the same or substantially the same emission spectrum as the fluorophore of the second compound) in step (5), thereby introducing the fluorophore into compound IV and making compound IV to emit the same fluorescent signal as the second compound. Further, by enabling $R_{5a}$ to perform the first bioorthogonal ligation reaction with an agent carrying a fluorophore (for example, a fluorophore the same as that of the second compound, or a fluorophore having a different structure but having the same or substantially the same emission spectrum as that of the second compound), the fluorophore is introduced into the third compound. In addition, (i) the fluorescent signal emitted by the fourth compound can be quenched by enabling $R_{6a}$ to specific interact with/specific bind to the other member (represented herein as "$R_{6c}$-L'-Que", wherein $R_{60}$ is the other member of the second binding pair, L' is a linking group or absent; Que represents a quenching group which is capable of quenching the fluorescent signal emitted by Dye) of the second binding pair carrying the quenching group; or (ii) the fluorescent signal emitted by the fourth compound can be quenched by enabling $R_8$ in the fourth compound to perform the second bioorthogonal ligation reaction with a compound carrying a quenching group. In such exemplary embodiments, it is particularly preferred that $R_{5a}$ and the agent carrying the fluorophore do not react with the two members of the second binding pair ($R_{6a}$ and $R_{6b}$). Further, it is particularly preferred that the $R_{5a}$ and the agent carrying the fluorophore do not affect the specific interaction between $R_{6a}$ and $R_{6b}$, and $R_{6a}$ and $R_{6b}$ do not affect the bioorthogonal ligation reaction between $R_{5a}$ and the agent carrying the fluorophore.

Therefore, in some preferred embodiments, in step (6), the duplex or the growing nucleic acid strand is subjected to a treatment which has no effect on the first compound and the second compound, but enables $R_{5a}$ to perform the first bioorthogonal ligation reaction with an agent carrying a fluorophore (for example, a fluorophore the same as the fluorophore of the second compound, or a fluorophore having a different structure but the same or substantially the same emission spectrum as that of the second compound) (thereby introducing the fluorophore carried by the agent into the third compound, and making the third compound to carry the fluorophore and emit a fluorescent signal); moreover, the treatment enables $R_{6a}$ to specifically interact with/bind to the other member ($R_{6b}$-L'-Que) of the binding pair carrying a quenching group (thereby quenching the fluorophore in the fourth compound, and making the fourth compound no longer to emit the fluorescent signal), or enables $R_8$ in the fourth compound to perform the second bioorthogonal ligation reaction with a compound carrying a quenching group (thereby quenching the fluorescent signal emitted by the fluorophore in the fourth compound). In such exemplary embodiments, prior to the treatment of the step (6), the first compound and the third compound, if present, do not emit fluorophore, and the second compound and the fourth compound, if present, fluoresce; further, after the treatment of step (6), the first compound (if present) still does not fluoresce, the second compound (if present) still fluoresces, the third compound (if present) changes to fluoresce, and the fourth compound (if present) changes to not fluoresce. Therefore, the type of compound incorporated into the 3' end of the growing nucleic acid strand can be determined by detecting and comparing the fluorescent signal.

In the method of the present invention, a suitable quenching group can be selected according to the fluorophore used. Quenching groups for various fluorophores are well known in the art, and typical examples thereof include, but are not limited to, DABCYL, BHQ quenchers (such as BHQ-1 or BHQ-2), ECLIPSE, and/or TAMRA.

Further, in such exemplary embodiments, by enabling $R_{3a}$, $R_{3b}$, $R_{3c}$, $R_{3d}$, $R_{4a}$, $R_{4b}$, $R_{4c}$ to perform a bioorthogonal cleavage reaction, the protecting group at the 3' position of the ribose or deoxyribose in the compound incorporated into the 3' end of the growing nucleic acid strand is removed, and the fluorophore (if present) on the duplex or the growing nucleic acid strand is removed. Therefore, in some preferred embodiments, in step (8), the duplex or the growing nucleic acid strand is subjected to a treatment which enables $R_{3a}$, $R_{3b}$, $R_{3c}$, $R_{3d}$, $R_{4a}$, $R_{4b}$, $R_{4c}$ to perform the bioorthogonal cleavage reaction. In such exemplary embodiments, after the treatment of step (8), the growing nucleic acid strand will have no fluorophore, and the ribose or deoxyribose at the 3' end of the growing nucleic acid strand will have a free hydroxyl group at the 3' position, wherein the free hydroxyl group can be used to initiate the next round of polymerization.

Therefore, in some preferred embodiments, the method of the invention comprises the steps of:

(1) providing a nucleic acid molecule to be sequenced attached onto a support or attaching the nucleic acid molecule to be sequenced onto a support;

(2) adding a primer for initiating a nucleotide polymerization, a polymerase for performing a nucleotide polymerization, and the first, second, third and fourth compounds having structures of formula (I), formula (II), formula (III), and formula (IV), respectively, to form a reaction system comprising a solution phase and a solid phase:

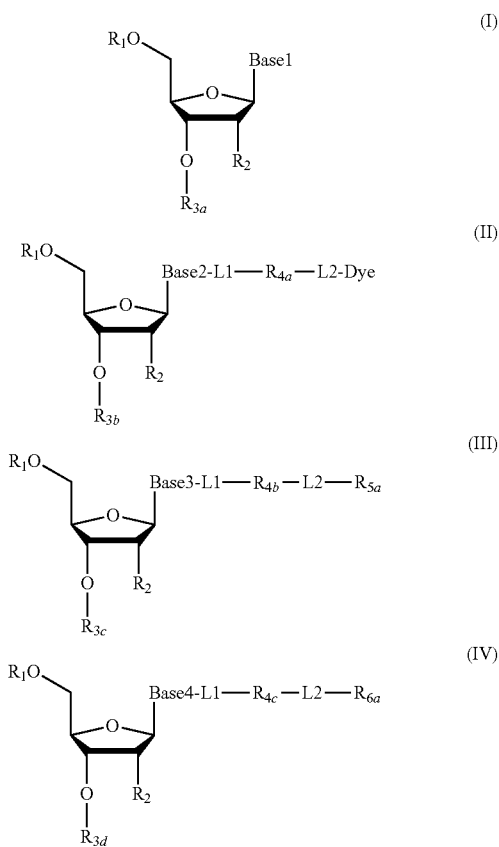

wherein, Base1, Base2, Base3, and Base4 represent 4 different bases, and are selected from A, (T/U), C, and G;

$R_1$ is independently selected from —H, monophosphate group (—PO$_3$H$_2$), diphosphate group (—PO$_3$H—PO$_3$H$_2$), triphosphate group (—PO$_3$H—PO$_3$H—PO$_3$H$_2$) and tetraphosphate group (—PO$_3$H—PO$_3$H—PO$_3$H—PO$_3$H$_2$);

$R_2$ is independently selected from —H and —OH;

$R_{3a}$, $R_{3b}$, $R_{3c}$, $R_{3d}$, $R_{4a}$, $R_{4b}$, and $R_{4c}$ are independently a reactive group capable of performing a bioorthogonal cleavage reaction;

$R_{5a}$ is a reactive group capable of performing a first bioorthogonal ligation reaction;

$R_{6a}$ is (i) one member of the first binding pair, and is one member of the second binding pair; or is (ii) only one member of the second binding pair, and, $R_{6a}$ is Dye$_1$, or $R_{6a}$ is also linked with -L3-Dye$_1$;

L1 is independently a linking group or absent;

L2 is independently a linking group or absent;

L3 is a linking group or absent;

Dye represents a fluorophore capable of emitting a fluorescent signal; Dye and Dye$_1$ have the same structure, or have different structures but have the same or substantially the same emission spectrum;

optionally, there is a reactive group $R_8$ capable of performing a second bioorthogonal ligation reaction between $R_{4c}$ and $R_{6a}$;

(3) annealing the primer to the nucleic acid molecule to be sequenced, and the primer serves as an initial growing nucleic acid strand, and forms a duplex attached to the support together with the nucleic acid molecule to be sequenced;

(4) performing a nucleotide polymerization reaction using a polymerase under a condition allowing the polymerase to perform nucleotide polymerization, thereby incorporating one of the four compounds into the 3' end of the growing nucleic acid strand;

(5) (i) if the fourth compound is incapable of emitting a fluorescent signal, $R_{6a}$ is one member of the first binding pair and is one member of the second binding pair, then subjecting the duplex or the growing nucleic acid strand to a treatment in a reaction system containing a solution phase and a solid phase, wherein the treatment has no effect on the first compound, the second compound and the third compound, and enables $R_{6a}$ in the fourth compound to specifically interact with/bind to an agent (e.g., the other member of the first binding pair) carrying a fluorophore (for example, a fluorophore having the same structure as the fluorophore of the second compound, or a fluorophore having a different structure but having the same or substantially the same emission spectrum as the fluorophore of the second compound); thereafter, removing the solution phase of the reaction system of the previous step, retaining the duplex attached to the support, and detecting whether the duplex or the growing nucleic acid strand emits the fluorescent signal;

wherein the other member of the first binding pair carrying the fluorophore has the following structure: $R_{6b}$-L4-$Dye_2$; wherein, $R_{6b}$ is the other member of the first binding pair, and L4 is independently a linking group or absent; $Dye_2$ represents a fluorophore capable of emitting a fluorescent signal, and has the same structure as Dye or has a different structure but the same or substantially the same emission spectrum as Dye;

(ii) if the fourth compound is capable of emitting the same fluorescent signal as the second compound, $R_{6a}$ is only one member of the second binding pair, and $R_{6a}$ is $Dye_1$, or $R_{6a}$ is also linked with -L3-$Dye_1$, then removing the solution phase of the reaction system of the previous step, retaining the duplex attached to the support, and detecting whether the duplex or the growing nucleic acid strand emits the fluorescent signal;

(6) subjecting the duplex or the growing nucleic acid strand to a treatment in a reaction system comprising a solution phase and a solid phase, wherein the treatment has no effect on the first compound and the second compound, but is capable of enabling $R_{5a}$ in the third compound to perform the first bioorthogonal ligation reaction with an agent carrying a fluorophore (for example, a fluorophore having the same structure as the fluorophore of the second compound, or a fluorophore having a different structure but having the same or substantially the same emission spectrum as the fluorophore of the second compound), thereby introducing the fluorophore in the agent into the third compound to make the third compound to emit a fluorescent signal; and the treatment (i) is capable of enabling $R_{6a}$ in the fourth compound to specific bind with the other member of the second binding pair carrying a quenching group, thereby quenching the fluorescent signal emitted by the fluorophore $Dye_1$ or $Dye_2$ in the fourth compound, or (ii) is capable of enabling $R_8$ in the fourth compound to perform the second bioorthogonal ligation reaction with a compound carrying a quenching group, thereby quenching the fluorescent signal emitted by the fluorophore $Dye_1$ or $Dye_2$ in the fourth compound; wherein, the other member of the second binding pair carrying the quenching group has the following structure: $R_{6c}$-L'-Que; wherein $R_{6c}$ is the other member of the second binding pair, L' is independently a linking group or absent; Que represents a quenching group capable of quenching the fluorescent signal emitted by $Dye_1$ or $Dye_2$;

(7) removing the solution phase of the reaction system of the previous step, retaining the duplex attached to the support, and detecting whether the duplex or the growing nucleic acid strand emits the fluorescent signal.

In some preferred embodiments, the method further comprises the steps of:

(8) subjecting the duplex or the growing nucleic acid strand in the previous step to a treatment in a reaction system containing a solution phase and a solid phase, wherein the treatment enables $R_{3a}$, $R_{3b}$, $R_{3c}$, $R_{3d}$, $R_{4a}$, $R_{4b}$ and $R_{4c}$ to perform the bioorthogonal cleavage reaction, thereby allowing the compound incorporated at the 3' end of the growing nucleic acid strand to have a free hydroxyl group at the 3' position of the ribose or deoxyribose (in other words, converting $-OR_{3a}$, $-OR_{3b}$, $-OR_{3c}$ or $-OR_{3d}$ (if present) into a free hydroxyl group), and, removing the fluorophore on the duplex or the growing nucleic acid strand (in other words, removing the fluorophore attached to $R_{4a}$, $R_{4b}$ or $R_{4c}$), if present;

(9) removing the solution phase of the reaction system in the previous step;

(10) adding a polymerase for performing a nucleotide polymerization, and the first compound, the second compound, the third compound, and the fourth compound, thereby forming a reaction system containing a solution phase and a solid phase, and then performing the steps (4)-(7).

In some preferred embodiments, the method further comprises the step of:

(11) repeating steps (8)-(10) one or more times.

In some exemplary embodiments, in step (4), if the compound of formula (I) is incorporated into the 3' end of the growing nucleic acid strand, since the compound of formula (I) does not carry a fluorophore itself, and it does not react at step (6), no fluorescent signal will be detected in steps (5) and (7). In other words, if no fluorescent signal is detected in both of steps (5)-(7), it can be determined that the compound incorporated at the 3' end of the growing nucleic acid strand is a compound of formula (I).

In step (4), if the compound of formula (II) is incorporated into the 3' end of the growing nucleic acid strand, since the compound of formula (II) carries a fluorophore itself and it does not perform any reaction in step (6), a fluorescent signal will be detected in both steps (5) and (7). In other words, if a fluorescent signal is detected in both of steps (5) and (7), it can be determined that the compound incorporated at the 3' end of the growing nucleic acid strand is a compound of formula (II).

In step (4), if the compound of formula (III) is incorporated into the 3' end of the growing nucleic acid strand, (i) since the compound of formula (III) does not carry a fluorophore, no fluorescent signal will be detected in step (5); and (ii) the compound of formula (III) performs a bioorthogonal ligation reaction with the agent carrying a fluorophore in step (6), introducing the fluorophore into the growing nucleic acid strand, therefore, a fluorescent signal will be detected in step (7). In other words, if no fluorescent signal is detected in step (5) and a fluorescent signal is detected in step (7), it can be determined that the compound incorporated at the 3' end of the growing nucleic acid strand is a compound of the formula (III).

In step (4), if the compound of formula (IV) is incorporated into the 3' end of the growing nucleic acid strand, (i) since the compound of formula (IV) carries a fluorophore itself or carries a fluorophore after the treatment in step (5), a fluorescent signal will be detected in step (5); and (ii) since the compound of formula (IV) specifically bind with the binding pair carrying the quenching group ($R_{6b}$-L'-Que) or performs a bioorthogonal cleavage reaction or a third bioorthogonal ligation reaction in step (6), thereby introducing the quenching group into the growing nucleic acid strand or quenching the fluorescent signal, the fluorescent signal will not be detected in step (7) thereby. In other words, if a fluorescent signal is detected in step (5) and a fluorescent signal is not detected in step (7), it can be determined that the compound incorporated at the 3' end of the growing nucleic acid strand is a compound of the formula (IV).

Therefore, in some preferred embodiments, the method of the present invention further comprises: after step (7), determining the type of the compound incorporated into 3' end of the growing nucleic acid strand in step (4) according to the detection results in steps (5) and (7), wherein, when both of the detection results of steps (5) and (7) are that the duplex or the growing nucleic acid strand does not emit the fluorescent signal, it is determined that the compound incorporated into 3' end of the growing nucleic acid strand in step (4) is the compound of formula (I);

when both of the detection results of steps (5) and (7) are that the duplex or the growing nucleic acid strand emits the fluorescent signal, it is determined that the compound incorporated into 3' end of the growing nucleic acid strand in step (4) is the compound of formula (II);

when the detection result of step (5) is that the duplex or the growing nucleic acid strand does not emit the fluorescent signal, and the detection result of step (7) is that the duplex or the growing nucleic acid strand emits the fluorescent signal, it is determined that the compound incorporated into 3' end of the growing nucleic acid strand in step (4) is the compound of formula (III); and, when the detection result of step (5) is that the duplex or the growing nucleic acid strand emits the fluorescent signal, and the detection result of step (7) is that the duplex or the growing nucleic acid strand does not emit the fluorescent signal, it is determined that the compound incorporated into 3' end of the growing nucleic acid strand in step (4) is the compound of formula (IV).

In some preferred embodiments, the method of the present invention further comprises that, after step (7), based on the base complementary pairing principle, the type of base at the corresponding position in the nucleic acid molecule to be sequenced is determined according to the type of the compound incorporated at the 3' end of the growing nucleic acid strand in step (4).

In some preferred embodiments, the compound of formula (I), the compound of formula (II), the compound of formula (III) and the compound of formula (IV) do not react with each other during the nucleotide polymerization reaction.

In some preferred embodiments, Base1 and Base2 are purine bases, and Base3 and Base4 are pyrimidine bases. In some preferred embodiments, Base1 is base G, Base2 is base A, Base3 is base C, and Base4 is base T or U. In some preferred embodiments, Base1 is base G, Base2 is base A, Base3 is base T or U, and Base4 is base C. In some preferred embodiments, Base1 is base A, Base2 is base G, Base3 is base C, and Base4 is base T or U. In some preferred embodiments, Base1 is base A, Base2 is base G, Base3 is base T or U, and Base4 is base C.

In some preferred embodiments, Base1 and Base2 are pyrimidine bases, and Base3 and Base4 are purine bases. In some preferred embodiments, Base1 is base C, Base2 is base T or U, Base3 is base G, and Base4 is base A. In some preferred embodiments, Base1 is base C, Base2 is base T or U, Base3 is base A, and Base4 is base G. In some preferred embodiments, Base1 is base T or U, Base2 is base C, Base3 is base G, and Base4 is base A. In some preferred embodiments, Base1 is base T or U, Base2 is base C, Base3 is base A, and Base4 is base G.

In some preferred embodiments, the compound of formula (I), the compound of formula (II), the compound of formula (III) and the compound of formula (IV) have the same $R_1$. In some preferred embodiments, $R_1$ is independently —H. In some preferred embodiments, $R_1$ is independently monophosphate group (—$PO_3H_2$). In some preferred embodiments, $R_1$ is independently diphosphate group (—$PO_3H$—$PO_3H_2$). In some preferred embodiments, $R_1$ is independently triphosphate group (—$PO_3H$—$PO_3H$—$PO_3H_2$). In some preferred embodiments, $R_1$ is independently tetraphosphate group (—$PO_3H$—$PO_3H$—$PO_3H$—$PO_3H_2$).

In some preferred embodiments, the compound of formula (I), the compound of formula (II), the compound of formula (III) and the compound of formula (IV) have the same $R_2$. In some preferred embodiments, $R_2$ is independently —H. In some preferred embodiments, $R_2$ is independently —OH.

In some preferred embodiments, $R_{3a}$, $R_{3b}$, $R_{3c}$, $R_{3d}$, $R_{4a}$, $R_{4b}$, $R_{4c}$ are independently capable of performing a bioorthogonal cleavage reaction. As used herein, the expression "independently capable of performing bioorthogonal cleavage reaction" means that the reactive groups, agents, or molecules, etc., are capable of performing bioorthogonal cleavage reactions, respectively, and do not interfere with or affect each other. For example, the expression "$R_{3a}$ and $R_{3b}$ are capable of performing bioorthogonal cleavage reaction independently" means that both $R_{3a}$ and $R_{3b}$ are capable of performing a bioorthogonal cleavage reaction, $R_{3a}$ does not affect the bioorthogonal cleavage reaction of $R_{3b}$, and $R_{3b}$ does not affect the bioorthogonal cleavage reaction of $R_{3a}$.

In some exemplary embodiments, $R_{3a}$ is a first reactive group capable of performing a bioorthogonal cleavage reaction in the presence of a first agent; $R_{3b}$ is a second reactive group capable of performing a bioorthogonal cleavage reaction in the presence of a second agent; $R_{3c}$ is a third reactive group capable of performing a bioorthogonal cleavage reaction in the presence of a third agent; $R_{3d}$ is a fourth reactive group capable of performing a bioorthogonal cleavage reaction in the presence of a fourth agent; $R_{4a}$ is a fifth reactive group capable of performing a bioorthogonal cleavage reaction in the presence of a fifth agent; $R_{4b}$ is a sixth reactive group capable of performing a bioorthogonal cleavage reaction in the presence of a sixth agent; $R_{4c}$ is a seventh reactive group capable of performing a bioorthogonal cleavage reaction in the presence of a seventh agent; and, $R_{5a}$ is an eighth reactive group capable of performing a bioorthogonal ligation reaction in the presence of an eighth agent.

Preferably, in such embodiments, in step (8), a first agent, a second agent, a third agent, a fourth agent, a fifth agent, a sixth agent and a seventh agent may be added, thereby making $R_{3a}$, $R_{3b}$, $R_{3c}$, $R_{3d}$, $R_{4a}$, $R_{4b}$, $R_{4c}$ (if present) to perform the bioorthogonal cleavage reaction respectively. Therefore, $R_{3a}$, $R_{3b}$, $R_{3c}$, $R_{3d}$ (if present) will be removed from the 3' position of ribose or deoxyribose (in other words, $-OR_{3a}$, $-OR_{3b}$, $-OR_{3c}$ or $-OR_{3d}$ (if present) will be converted to free hydroxyl group), and $R_{4a}$ and the fluorophore attached thereto (if present), $R_{4b}$ and the fluorophore attached thereto (if present) and $R_{4c}$ and the fluorophore attached thereto (if present) will also be removed. Thus, after step (8), the growing nucleic acid strand will not carry a fluorophore and will have a free hydroxyl group at the 3' end, which can be used for the next round of polymerization. Therefore, in some preferred embodiments, in step (8), a first agent, a second agent, a third agent, a fourth agent, a fifth agent, a sixth agent and a seventh agent are added to form a reaction system comprising a solution phase and a solid phase, and the duplex is incubated with the first agent, the second agent, the third agent, the fourth agent, the fifth agent, the sixth agent and the seventh agent under a condition that allows $R_{3a}$, $R_{3b}$, $R_{3c}$, $R_{3d}$, $R_{4a}$, $R_{4b}$ and $R_{4c}$ to perform a bioorthogonal cleavage reaction, respectively.

In some preferred embodiments, $R_{3a}$, $R_{3b}$, $R_{3c}$ and $R_{3d}$ are capable of performing a bioorthogonal cleavage reaction respectively in the presence of the same agent. In this case, preferably, in step (8), the first agent, the second agent, the third agent, and the fourth agent are the same agent.

In some preferred embodiments, $R_{3a}$, $R_{3b}$, $R_{3c}$, and $R_{3d}$ are the same reactive group. In this case, preferably, in step (8), the first agent, the second agent, the third agent, and the fourth agent are the same agent. In other words, in step (8), the same $R_{3a}$, $R_{3b}$, $R_{3c}$, and $R_{3d}$ (if present) will each perform the bioorthogonal cleavage reaction in the presence of the same agent (i.e., the first agent), and are removed from the growing nucleic acid strand.

In some preferred embodiments, $R_{4a}$, $R_{4b}$ and $R_{4c}$ are capable of performing the bioorthogonal cleavage reaction respectively in the presence of the same agent. In this case, preferably, in step (8), the fifth agent, the sixth agent and the seventh agent are the same agent.

In some preferred embodiments, $R_{4a}$, $R_{4b}$ and $R_{4c}$ are the same reactive group. In this case, preferably, in step (8), the fifth agent, the sixth agent and the seventh agent are the same agent. In other words, in step (8), the same $R_{4a}$, $R_{4b}$ and $R_{4c}$ (if present) will perform the bioorthogonal cleavage reaction respectively in the presence of the same agent (i.e., the fifth agent), and are removed from the growing nucleic acid strand.

In some preferred embodiments, $R_{3a}$, $R_{3b}$, $R_{3c}$, $R_{3d}$, $R_{4a}$, $R_{4b}$ and $R_{4c}$ are capable of performing the bioorthogonal cleavage reaction respectively in the presence of the same agent. In this case, preferably, in step (8), the first agent, the second agent, the third agent, the fourth agent, the fifth agent, the sixth agent and the seventh agent are the same agent.

In other words, in step (8), an agent (i.e., the first agent) is added to make $R_{3a}$, $R_{3b}$, $R_{3c}$, $R_{3d}$, $R_{4a}$, $R_{4b}$ and $R_{4c}$ (if present) to perform the bioorthogonal cleavage reaction and removed from the growing nucleic acid strand respectively in the presence of said agent (i.e., the first agent).

In some exemplary embodiments, it is particularly preferred that $R_{5a}$ and the agent carrying fluorophore do not interact with the two members of the second binding pair ($R_{6a}$ and $R_{6b}$). Further, it is particularly preferred that the $R_{5a}$ and the agent carrying fluorophore do not influence the specific interaction between $R_{6a}$ and $R_{6b}$, and $R_{6a}$ and $R_{6b}$ do not influence the bioorthogonal ligation reaction between the $R_{5a}$ and the agent carrying the fluorophore.

In such embodiments, preferably, in step (6), an eighth agent and $R_{6c}$-L'-Que can be added to enable $R_{5a}$ (if present) in compound of formula (III) to perform the bioorthogonal ligation reaction, and enable $R_{6a}$ (if present) in the compound of formula (IV) to specifically bind to $R_{6c}$ in $R_{6c}$-L'-Que. For example, the eighth agent may comprise compound M carrying a fluorophore which is same (or different in structure but having the same or substantially the same emission spectrum) as that of the second compound and the fourth compound, and the compound M is capable of performing a bioorthogonal ligation reaction with $R_{5a}$, and thereby a fluorophore in compound M is introduced into the compound of formula (III) to make the compound of formula (III) to emit a fluorescent signal. Furthermore, by the specific interaction between the two members of the binding pair ($R_{6a}$ and $R_{6c}$), the quenching group Que linked onto $R_{6c}$ is introduced into the compound of formula (IV) to make the fluorescent signal emitted by compound of formula (IV) quenched and the compound of formula (IV) no longer emits fluorescence. In such embodiments, it is also particularly preferred that in the step (6), the eighth agent does not react with the first compound and the second compound, and further preferably, $R_{6c}$-L'-Que does not react with the first compound and the second compound. Therefore, in some preferred embodiments, in step (6), an eighth agent and $R_{6c}$-L'-Que can be added to form a reaction system comprising a solution phase and a solid phase, wherein the eighth agent comprises the compound M carrying a fluorophore which is same (or has a different structure but has the same or substantially the same emission spectrum) as the second compound and the fourth compound, and the compound M is capable of performing a bioorthogonal ligation reaction with $R_{5a}$, thereby the fluorophore in compound M can be introduced into the third compound; and $R_{6c}$ is the other member of the second binding pair, L' is a linking group or absent; Que represents a quenching group capable of quenching the fluorescent signal emitted by Dye; then, the duplex is incubated with the eighth agent and the $R_{60}$-L'-Que agent under a condition allowing the compound M to perform the bioorthogonal ligation reaction with $R_{5a}$ and allowing $R_{6a}$ to specifically bind to $R_{6c}$.

In some exemplary embodiments, $R_{6a}$ is a fluorophore $Dye_1$ capable of emitting a fluorescent signal, $Dye_1$ has the same structure as Dye, or has a different structure but the same emission spectrum, so that the fourth compound itself is capable of emitting the same fluorescent signal as the second compound.

In some exemplary embodiments, the fourth compound does not carry a fluorophore itself and $R_{7a}$ is one member of the first binding pair. In such embodiments, step (5) comprises adding a ninth agent enabling $R_{6a}$ (if present) in the compound of formula (IV) to specifically interact with and/or bind to the other member of the binding pair. For example, the ninth agent may comprise a compound M' having the structure $R_{6b}$-L4-$Dye_2$, wherein $R_{6b}$ is the other member of the first binding pair, L4 is independently a linking group or absent; $Dye_2$ represents a fluorophore which is capable of emitting fluorescent signal, having the same structure as Dye, or having a different structure from Dye but having the same or substantially the same emission spectrum as Dye.

In some exemplary embodiments, a reactive group $R_8$ capable of performing a third bioorthogonal ligation reaction exists between $R_{4c}$ and $R_{6a}$ of the fourth compound. In some preferred embodiments, each one of $R_{3a}$, $R_{3b}$, $R_{3c}$, $R_{3d}$, $R_{4a}$, $R_{4b}$, $R_{5a}$ and $R_8$ is independently capable of performing a bioorthogonal cleavage or ligation reaction. In some exemplary embodiments, $R_{8a}$ is capable of performing a second bioorthogonal ligation reaction in the presence of a tenth agent.

Preferably, in such embodiments, in step (6), a seventh agent and a tenth agent may be added to enable $R_{5a}$ (if present) in the compound of formula (III) to perform a first bioorthogonal ligation reaction, and enable $R_8$ (if present) in the compound of formula (IV) to perform a second bioorthogonal ligation reaction. For example, the seventh agent may comprise a compound M carrying a fluorophore the same (or having a different structure but having the same or substantially the same emission spectrum) as the second compound and the fourth compound, and the compound M is capable of performing the first bioorthogonal ligation reaction with $R_{5a}$, and thereby the fluorophore in compound M is introduced into the compound of formula (III). Furthermore, the tenth agent enables $R_8$ in the compound of formula (IV) to perform the second bioorthogonal ligation reaction and thereby the fluorescent signal in the compound of formula (IV) is quenched. In such embodiments, it is also particularly preferred that the seventh agent does not react with the first compound and the second compound in step (6), and further preferably, the tenth agent does not react with the first compound and the second compound. Therefore, in some preferred embodiments, in step (6), a seventh agent and a tenth agent can be added to form a reaction system comprising a solution phase and a solid phase, wherein, the seventh agent comprises the compound M which carries a fluorophore the same (or having different structure but the same or substantially the same emission spectrum) as the second compound and the fourth compound, and the compound M is capable of performing a first bioorthogonal ligation reaction with $R_{5a}$, thereby the fluorophore in compound M is introduced into the third compound; the tenth agent comprises a compound M" carrying a quencher, and the compound M" is capable of performing a second bioorthogonal ligation reaction with $R_8$, thereby the quencher in compound M" is introduced into the fourth compound; then, the duplex is incubated with a seventh agent and a tenth agent under a condition allowing the compound M" to perform the first bioorthogonal ligation reaction with $R_{5a}$, and allowing M" to perform the second bioorthogonal ligation reaction with $R_8$.

In some preferred embodiments, $R_{3a}$, $R_{3b}$, $R_{3c}$, and $R_{3d}$ are each independently selected from the group consisting of —CH$_2$CH=CH$_2$, —CH$_2$N$_3$, C$_{3-8}$ cycloalkenyl (e.g., C$_3$ cycloalkenyl, C$_4$ cycloalkenyl, C$_5$ membered cycloalkenyl, C$_6$ cycloalkenyl, C$_7$ cycloalkenyl or C$_8$ cycloalkenyl). In some preferred embodiments, the C$_{3-8}$ cycloalkenyl is selected from the group consisting of C$_3$ cycloalkenyl and C$_8$ cycloalkenyl. In some preferred embodiments, the C$_{3-8}$ cycloalkenyl group is

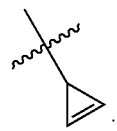

In some preferred embodiments, the C$_{3-8}$ cycloalkenyl group is

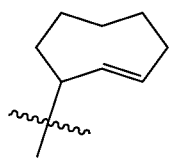

In some preferred embodiments, $R_{3a}$, $R_{3b}$, $R_{3c}$, and $R_{3d}$ are the same reactive groups and are selected from the group consisting of —CH$_2$CH=CH$_2$, —CH$_2$N$_3$, C$_{3-8}$ cycloalkenyl (e.g., C$_3$ cycloalkenyl, C$_4$ cycloalkenyl, C$_5$ membered cycloalkenyl, C$_6$ cycloalkenyl, C$_7$ cycloalkenyl or C$_8$ cycloalkenyl). In some preferred embodiments, the C$_{3-8}$ cycloalkenyl is selected from the group consisting of C$_3$ cycloalkenyl and C$_8$ cycloalkenyl. In some preferred embodiments, the C$_{3-8}$ cycloalkenyl group is

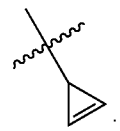

In some preferred embodiments, the C$_{3-8}$ cycloalkenyl group is

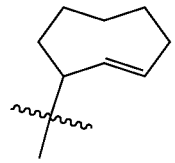

In some preferred embodiments, $R_{3a}$, $R_{3b}$, $R_{3c}$, and $R_{3d}$ are the same reactive groups and are all —CH$_2$N$_3$.

In some preferred embodiments, $R_{4a}$, $R_{4b}$, and $R_{4c}$ are each independently selected from the group consisting of:

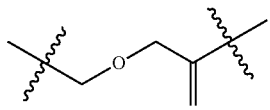

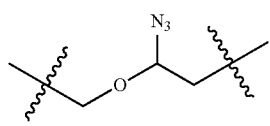

—O—C$_{3-8}$ cycloalkenylene. In some preferred embodiments, the "—O—C$_{3-8}$ cycloalkenylene" is selected from the group consisting of —O—C$_3$ cycloalkenylene, —O—C$_4$ cycloalkenylene, —O—C$_5$ cycloalkenylene, —O—C$_6$ cycloalkenylene, —O—C$_7$ cycloalkenylene, and —O—C$_8$ cycloalkenylene. In some preferred embodiments, said "—O—C$_{3-8}$ cycloalkenylene" is

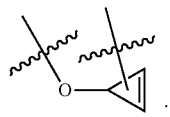

In some preferred embodiments, said "—O—C$_{3-8}$ cycloalkenylene" is

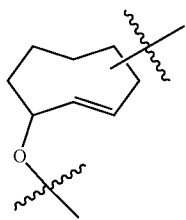

In some preferred embodiments, $R_{4a}$, $R_{4b}$, and $R_{4c}$ are the same reactive groups and are selected from the group consisting of:

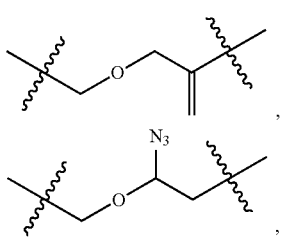

and —O—$C_{3-8}$ cycloalkenylene. In some preferred embodiments, said "—O—$C_{3-8}$ cycloalkenylene" is selected from the group consisting of —O—$C_3$ cycloalkenylene, —O—$C_4$ cycloalkenylene, —O—$C_5$ cycloalkenylene, —O—$C_6$ cycloalkenylene, —O—$C_7$ cycloalkenylene, and —O—$C_8$ cycloalkenylene. In some preferred embodiments, said "—O—$C_{3-8}$ cycloalkenylene" is

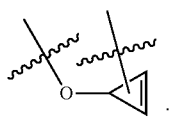

In some preferred embodiments, said "—O—$C_3$-8 cycloalkenylene" is

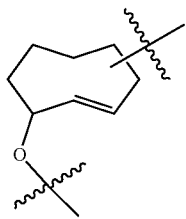

In some preferred embodiments, $R_{4a}$, $R_{4b}$, and $R_{4c}$ are both

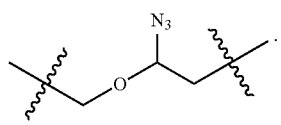

In some preferred embodiments, the first agent, the second agent, the third agent, the fourth agent, the fifth agent, the sixth agent, and the seventh agent each independently comprise substance selected from the group consisting of:

a complex of palladium (for example, a complex of palladium with four triphenylphosphine 3,3',3''-trisulfonic acids);

a complex of ruthenium (for example, a complex of ruthenium with quinoline carboxylate (or a derivative thereof), allyl or cyclopentadiene);

a phosphide (e.g., a carboxyphosphine or hydroxyphosphine such as $P(CH_2CH_2COOH)_3$ or $P(CH_2CH_2OH)_3$); and compound Q having the structural formula

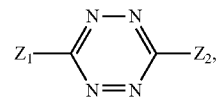

wherein, $Z_1$ and $Z_2$ are each independently selected from a modified or unmodified alkyl (e.g., a $C_1$-$C_6$ alkyl such as $C_1$ alkyl, $C_2$ alkyl, $C_3$ alkyl, $C_4$ alkyl, $C_5$ alkyl or $C_6$ alkyl group) and a modified or unmodified aryl (for example, 6-10 membered aryl such as 6-membered aryl, 7-membered aryl, 8-membered aryl, 9-membered aryl or 10-membered aryl such as phenyl or pyridyl).

In some preferred embodiments, $R_{3a}$, $R_{3b}$, $R_{3c}$ and $R_{3d}$ are —$CH_2CH=CH_2$. In this case, preferably, $R_{4a}$, $R_{4b}$ and $R_{4c}$ are

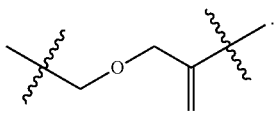

Further preferably, the first agent, the second agent, the third agent, the fourth agent, the fifth agent, the sixth agent and the seventh agent comprise a complex of palladium or a complex of ruthenium. Preferably, the first agent, the second agent, the third agent, the fourth agent, the fifth agent, the sixth agent and the seventh agent are the same agents, and comprise a complex of palladium or a complex of ruthenium.

In some preferred embodiments $R_{3a}$, $R_{3b}$, $R_{3c}$ and $R_{3d}$ are —$CH_2$—$N_3$. In this case, preferably, $R_{4a}$, $R_{4b}$ and $R_{4c}$ are

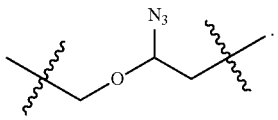

Further preferably, the first agent, the second agent, the third agent, the fourth agent, the fifth agent, the sixth agent and the seventh agent comprise phosphonate such as carboxyl phosphonate or hydroxyl phosphonate such as $P(CH_2CH_2COOH)_3$ or $P(CH_2CH_2OH)_3$. Preferably, the first agent, the second agent, the third agent, the fourth agent, the fifth agent, the sixth agent and the seventh agent are the same agents, and they comprise phosphonate such as carboxyl phosphonate or hydroxyl phosphonate such as $P(CH_2CH_2COOH)_3$ or $P(CH_2CH_2OH)_3$.

In some preferred embodiments, $R_{3a}$, $R_{3b}$, $R_{3c}$, and $R_{3d}$ are

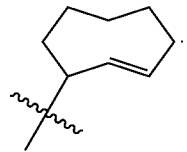

In this case, preferably, $R_{4a}$, $R_{4b}$ and $R_{4c}$ are

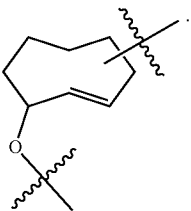

Further preferably, the first agent, the second agent, the third agents, the fourth agent, the fifth agent, the sixth agent and the seventh agent comprise the compound Q as defined above. Further preferably, in compound Q, $Z_1$ is a methyl group; and $Z_2$ is a modified or unmodified pyridyl group. More preferably, compound Q is

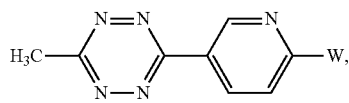

wherein, W is hydrogen or a modifying group. Preferably, the first agent, the second agent, the third agent, the fourth agent, the fifth agent, the sixth agent and the seventh agent are the same agents and comprise the compound Q as defined above.

In some preferred embodiments, the linking groups L1, L2 and L3 in the first compound, the second compound, the third compound, and the fourth compound, L4 in $R_{6b}$-L4-$Dye_2$ and linking group L' in $R_{6b}$-L'-Que are each independent and are not particularly limited. A person skilled in the art can select suitable linking groups L1, L2, L3, L4 and L' according to the bases (Base1, Base2, Base3 and Base4), the reactive groups ($R_{4a}$, $R_{4b}$, $R_{4c}$ and $R_{5a}$) used in the compounds and members ($R_{6a}$ and $R_{6b}$) of the binding pair.

In some exemplary embodiments, the linking groups L1, L2, L3, L4 and L' are each independently selected from the group consisting of:

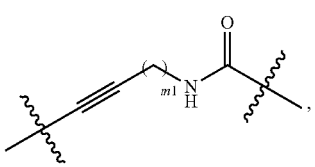

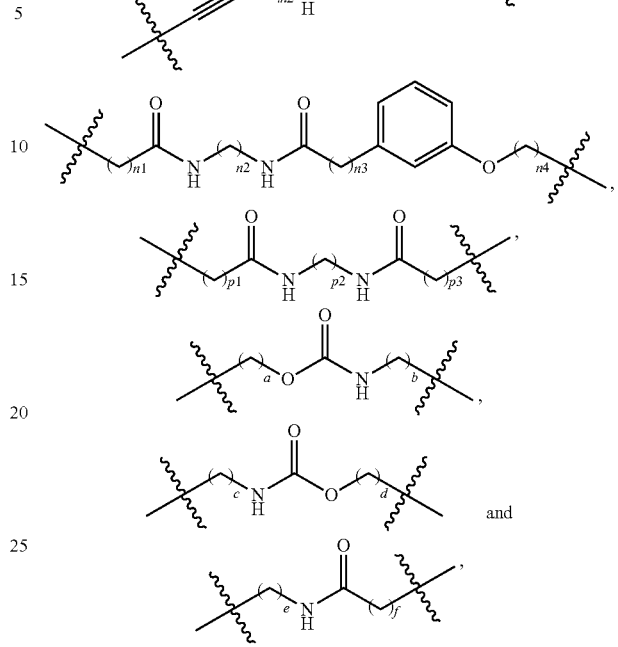

wherein m1, m2, m3, m4, n1, n2, n3, n4, p1, p2, p3, a, b, c, d, e and f are each independently selected from 0, 1, 2, 3, 4, 5 or 6.

In some exemplary embodiments, L1 in the first compound, the second compound, the third compound, and the fourth compound are each independently selected from the group consisting of:

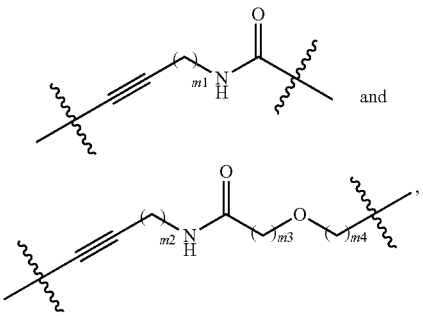

wherein m1, m2, m3, and m4 are each independently selected from 0, 1, 2, 3, 4, 5 or 6.

In some preferred embodiments, L1 in the first compound, the second compound, the third compound, and the fourth compound are each independently selected from the group consisting of:

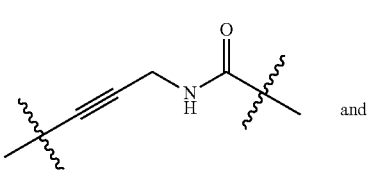

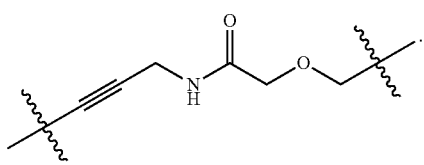

In some preferred embodiments, L2 in the first compound, the second compound, the third compound, and the fourth compound are each independently selected from the group consisting of:

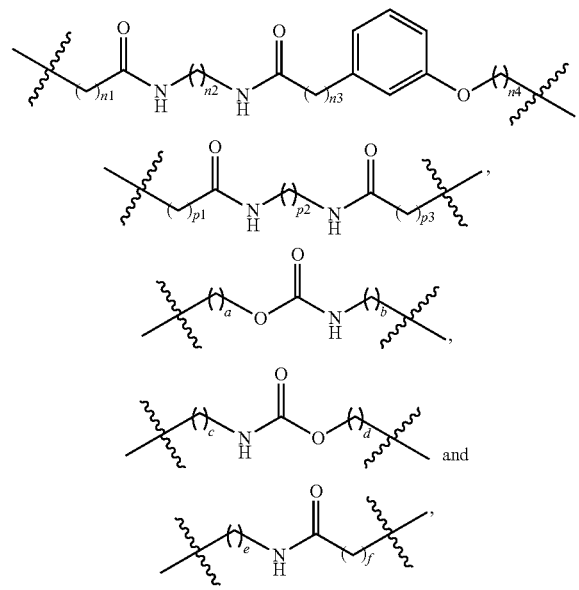

wherein n1, n2, n3, n4, p1, p2, p3, a, b, c, d, e, and f are each independently selected from 0, 1, 2, 3, 4, 5, or 6.

In some preferred embodiments, L2 in the first compound, the second compound, the third compound, and the fourth compound are each independently selected from the group consisting of:

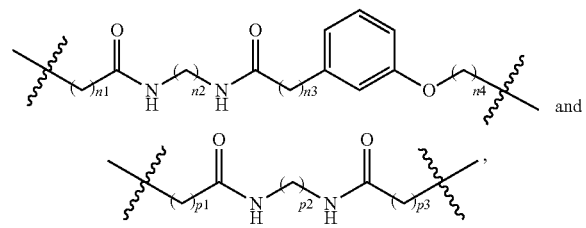

wherein n1, n2, n3, n4, p1, p2, p3 are each independently selected from 0, 1, 2, 3, 4, 5 or 6.

In some preferred embodiments, L2 in the first compound, the second compound, the third compound, and the fourth compound are each independently selected from the group consisting of:

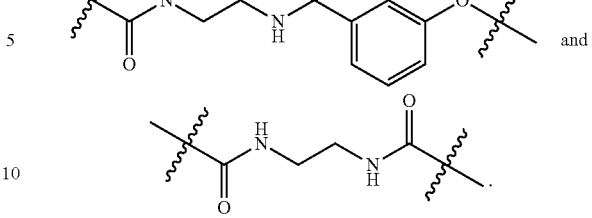

In some preferred embodiments, $R_{5a}$ is selected from the group consisting of:

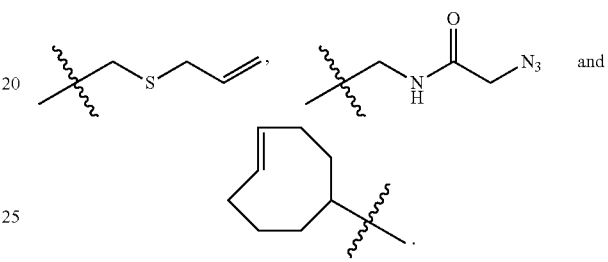

In some preferred embodiments, the eighth agent comprises a compound M selected from the group consisting of:
compound M1, which has the structural formula

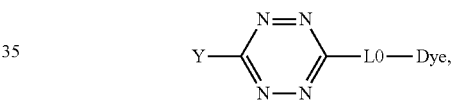

wherein, Y is selected from alkyl (for example, $C_1$-$C_6$ alkyl such as $C_1$ alkyl, $C_2$ alkyl, $C_3$ alkyl, $C_4$ alkyl, $C_5$ alkyl or $C_6$ alkyl) and aryl (for example, 6-10 membered aryl such as 6-membered aryl, 7-membered aryl, 8-membered aryl, 9-membered aryl or 10-membered aryl such as a phenyl group), Dye is a fluorophore, and the fluorophore is the same as the fluorophore in the second compound and the fourth compound (or the fluorophore has a different structure but the same or substantially the same emission spectrum);
compound M2, which has the structural formula wherein Dye is a fluorophore, and the fluorophore is the same as the fluorophore in the second compound and the fourth compound (or the fluorophore has a different structure but the same or substantially the same emission spectrum);
compound M3, which has the structural formula

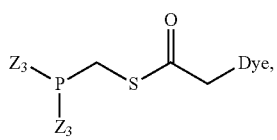

wherein $Z_3$ is independently selected from alkyl (for example, $C_1$-$C_6$ alkyl, such as $C_1$ alkyl, $C_2$ alkyl, $C_3$ alkyl, $C_4$ alkyl, $C_5$ alkyl or $C_6$ alkyl) and aryl (for example, 6-10 membered aryl such as a 6-membered aryl, 7-membered aryl, 8-membered aryl, 9-membered aryl or 10-membered aryl such as phenyl group), and Dye is a fluorophore. wherein the fluorophore is the same as the fluorophore in the second compound and the fourth compound (or the fluorophore has a different structure but the same or substantially the same the emission spectra).

In the embodiment of the present invention, the linking group L0 is not particularly limited. A person skilled in the art can select a suitable linking group L0 according to actual needs. For example, in some preferred embodiments, L0 can be

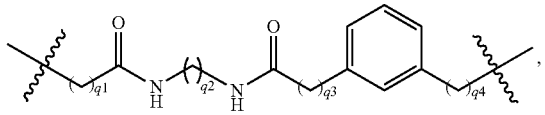

wherein q1, q2, q3, q4 are each independently selected from 0, 1, 2, 3, 4, 5 or 6.

In some preferred embodiments, the eighth agent comprises compound M1, wherein Y is $C_1$-$C_6$ alkyl, such as methyl.

In some preferred embodiments, L0 in compound M1 is

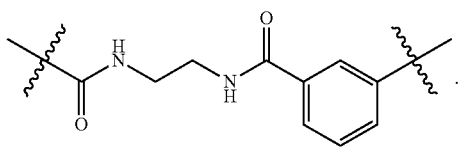 [SMILES: *C(=O)NCCNC(=O)c1cccc(*)c1]

In some preferred embodiments, Dye in compound M1 is AF532. In some preferred embodiments, compound M1 has the following structure:

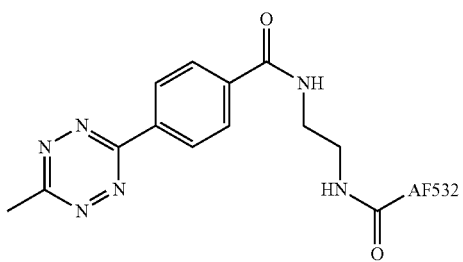

In some preferred embodiments, in addition to compound M, the eighth agent further comprises a complex of ruthenium. In some preferred embodiments, the eighth agent comprises compound M2 and a complex of ruthenium.

In some preferred embodiments, $R_{5a}$ is

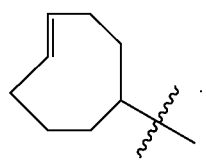 [SMILES: *C1CC/C=C/CCC1]

In this case, preferably, the eighth agent comprises compound M1.

In some preferred embodiments, $R_{5a}$ is

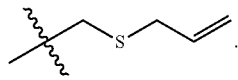

In this case, preferably, the eighth agent comprises compound M2. More preferably, the eighth agents each comprise compound M2 and a complex of ruthenium.

In some preferred embodiments, $R_{5a}$ is

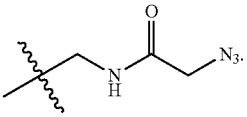 [SMILES: *CNC(=O)CN=[N+]=[N-]]

In this case, preferably, the eighth agent comprises compound M3.

In some preferred embodiments, $R_{6a}$ and $R_{6b}$ are two members of the first binding pair. In some preferred embodiments, $R_{6a}$ and $R_{6c}$ are two members of the second binding pair. In some preferred embodiments, the first binding pair and the second binding pair are each independently selected from the group consisting of: antigen (for example, a small molecule antigen)-antibody, hapten-antibody, hormone-receptor, ligand-receptor, nucleic acid strand-complementary nucleic acid strand, substrate-enzyme, substrate analog-enzyme, inhibitor-enzyme, sugar-plant lectin, biotin-avidin (for example, avidin and streptavidin), digoxin and digoxin antibody, and 5-position bromohydroxydeoxyguanosine and its antibody.

In some preferred embodiments, the two members of the first binding pair are selected from the group consisting of: (a) biotin and avidin (for example, streptavidin), (b) desthiobiotin and avidin (for example, streptavidin) and (c) digoxin and digoxin antibody. In some preferred embodiments, the two members of the second binding pair are selected from the group consisting of: (a) biotin and avidin (for example, streptavidin), (b) desthiobiotin and avidin (for example, streptavidin) and (c) digoxin and digoxin antibody. In some preferred embodiments, $R_{6a}$ is biotin or desthiobiotin, and $R_{6b}$ is avidin (for example, streptavidin). In some preferred embodiments, $R_{6a}$ is digoxin, and $R_{6b}$ is digoxin antibody.

It is particularly preferred that the $R_{5a}$ and the agent carrying the fluorophore do not interact with the two members ($R_{6a}$ and $R_{6c}$) of the second binding pair. Further, it is particularly preferred that the $R_{5a}$ and the agent carrying the fluorophore do not affect the specific interaction between $R_{6a}$ and $R_{6c}$, and, $R_{6a}$ and $R_6$ do not affect the bioorthogonal ligation reaction between the $R_{5a}$ and the agent carrying the fluorophore.

In some preferred embodiments, $R_{3a}$, $R_{3b}$, $R_{3c}$ and $R_{3d}$ are —$CH_2CH=CH_2$; and $R_{4a}$, $R_{4b}$ and $R_{4c}$ are

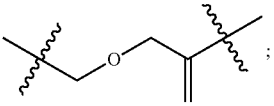 [SMILES: *COCC(*)=C]

the first, second, third, fourth, fifth, sixth and seventh agents comprise complex of palladium or complex of ruthenium; $R_{5a}$ is

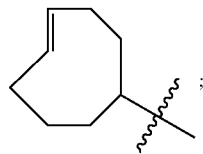 [SMILES: *C1CC/C=C/CCC1]

the eighth agent comprises compound M1; $R_{6a}$ is biotin; and $R_{6b}$ is avidin (for example, streptavidin). Preferably, the first, second, third, fourth, fifth, sixth and seventh agents are the same agent, and comprise complex of palladium or a complex of ruthenium.

In some preferred embodiments, $R_{3a}$, $R_{3b}$, $R_{3c}$ and $R_{3d}$ are —CH$_2$—N$_3$; $R_{4a}$, $R_{4b}$, and $R_{4c}$ are

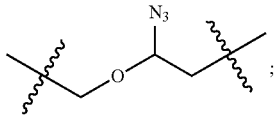 [SMILES: *COC(C*)N=[N+]=[N-]]

the first, second, third, fourth, fifth, sixth and seventh agents comprise a phosphonide such as carboxyphosphine or hydroxyphosphine such as P(CH$_2$CH$_2$COOH)$_3$ or P(CH$_2$CH$_2$OH)$_3$; $R_{5a}$ is

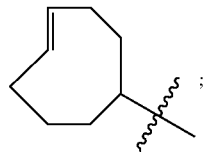 [SMILES: *C1CC/C=C/CCC1]

the eighth agent comprises the compound M1; and the $R_{6a}$ is biotin; $R_{6b}$ is an avidin (such as streptavidin). Preferably, the first, second, third, fourth, fifth, sixth and seventh agents are the same agents, and comprise a phosphine such as carboxyphosphine or hydroxyphosphine, for example P(CH$_2$CH$_2$COOH)$_3$ or P(CH$_2$CH$_2$OH)$_3$.

In some preferred embodiments, $R_{3a}$, $R_{3b}$, $R_{3c}$, and $R_{3d}$ are —CH$_2$—N$_3$; $R_{4a}$, $R_{4b}$, and $R_{4c}$ are

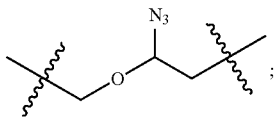 [SMILES: *COC(C*)N=[N+]=[N-]]

the first, second, third, fourth, fifth, sixth and seventh agents comprise a phosphonide such as carboxyphosphine or hydroxyphosphine such as P(CH$_2$CH$_2$COOH)$_3$ or P(CH$_2$CH$_2$OH)$_3$; $R_{5a}$ is

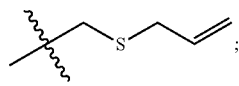 [SMILES: *CSCC=C]

the eighth agent comprises compound M2 and a complex of ruthenium; $R_{6a}$ is biotin; $R_{6b}$ is avidin (for example, streptavidin). Preferably, the first, second, third, fourth, fifth, sixth and seventh agents are the same agents, and comprise a phosphine such as carboxyphosphine or hydroxyphosphine, for example P(CH$_2$CH$_2$COOH)$_3$ or P(CH$_2$CH$_2$OH)$_3$.

In some preferred embodiments, $R_{3a}$, $R_{3b}$, $R_{3c}$, and $R_{3d}$ are —CH$_2$CH=CH$_2$; and $R_{4a}$, $R_{4b}$, and $R_{4c}$ are

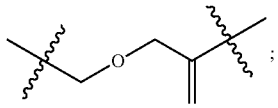 [SMILES: *COCC(*)=C]

the first, second, third, fourth, fifth, sixth and seventh agents comprise a complex of palladium or a complex of ruthenium; $R_{5a}$ is

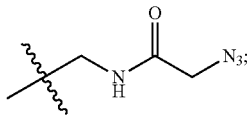 [SMILES: *CNC(=O)CN=[N+]=[N-]]

the eighth agent comprises compound M3; $R_{6a}$ is biotin; and $R_{6b}$ is avidin (for example, streptavidin). Preferably, the first, second, third, fourth, fifth, sixth and seventh agents are the same agents, and comprise a complex of palladium or a complex of ruthenium.

In some preferred embodiments, $R_{3a}$, $R_{3b}$, $R_{3c}$, and $R_{3d}$ are

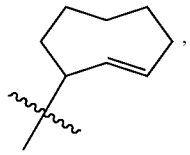 [SMILES: *C1/C=C/CCCCC1]

$R_{4a}$, $R_{4b}$, and $R_{4c}$ are

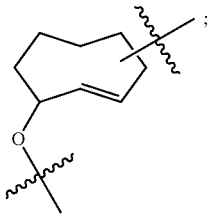

the first, second, third, fourth, fifth, sixth and seventh agents comprise compound Q (for example, the compound Q as defined above); $R_{5a}$ is

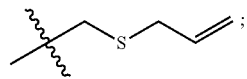 [SMILES: *CSCC=C]

the eighth agent comprises compound M2 and a complex of ruthenium; $R_{6a}$ is biotin; $R_{6b}$ is avidin (for example, streptavidin). Preferably, the first, second, third, fourth, fifth, sixth and seventh agents are the same agents, and comprise compound Q (for example, the compound Q as defined above).

In some preferred embodiments, $R_{3a}$, $R_{3b}$, $R_{3c}$, and $R_{3d}$ are

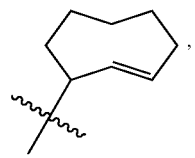 [SMILES: *C1/C=C/CCCCC1]

$R_{4a}$, $R_{4b}$, and $R_{4c}$ are

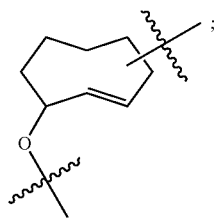

the first, second, third, fourth, fifth, sixth and seventh agents comprise compound Q (for example, the compound Q as defined above); $R_{5a}$ is

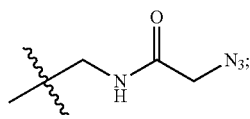 [SMILES: *CNC(=O)CN=[N+]=[N-]]

the eighth agent comprises compound M3; $R_{6a}$ is biotin; $R_{6b}$ is avidin (for example, streptavidin). Preferably, the first, second, third, fourth, fifth, sixth and seventh agents are the same agents, and comprise compound Q (for example, the compound Q as defined above).

Additionally, as described above, the method of the present invention may comprise a washing step as needed. The washing step can be added at any desired stage, and optionally, the washing step can be performed one or more times.

For example, in step (5), after removing the solution phase of the reaction system, one or more washings may be performed to sufficiently remove the residual solution phase. Such a washing step may be advantageous for sufficiently removing a fluorophore-bearing compound (e.g., compound of formula (II) or compound of formula (IV)) which is free (i.e., not incorporated into the nucleic acid strand), thereby minimizing non-specific fluorescent signal as much as possible.

Similarly, in step (7), after removing the solution phase of the reaction system, one or more washings may be performed to sufficiently remove the residual solution phase. Such a washing step may be advantageous for sufficiently removing the fluorescent-carrying agent used in step (6), thereby minimizing non-specific fluorescent signal as much as possible.

Similarly, in step (9), after removing the solution phase of the reaction system, one or more washings may be performed to sufficiently remove the residual solution phase. Such a washing step may be advantageous for sufficiently removing the agents used in step (8) and the products produced (which may carry fluorescence), thereby minimizing non-specific fluorescent signal and avoiding adverse effect on the subsequent polymerization reaction as much as possible.

The washing step can be carried out using a variety of suitable washing solutions. Examples of such washing solutions include, but are not limited to, phosphate buffer, citrate buffer, Tris-HCl buffer, acetate buffer, carbonate buffer, and the like. It is within the ability of those skilled in the art to select a suitable washing solution (including suitable ingredient, concentration, ionic strength, pH value, etc.) according to the actual needs.

Exemplary Embodiment 4

In some exemplary embodiments, the ability of the four compounds to emit the fluorescent signal is controlled (for example, maintained or changed) in step (6) by using reactive group capable of performing bioorthogonal cleavage reaction and a binding pair (containing two members which can interact with each other through specific non-covalent action); and preferably, the removal of the protecting group and the fluorescent signal can be achieved in step (8) by using a reactive group capable of performing a bioorthogonal cleavage reaction. For example, in some exemplary embodiments, the first, second, third, and fourth compounds may have the structures of formulas (I), (II), (III), and (IV), respectively:

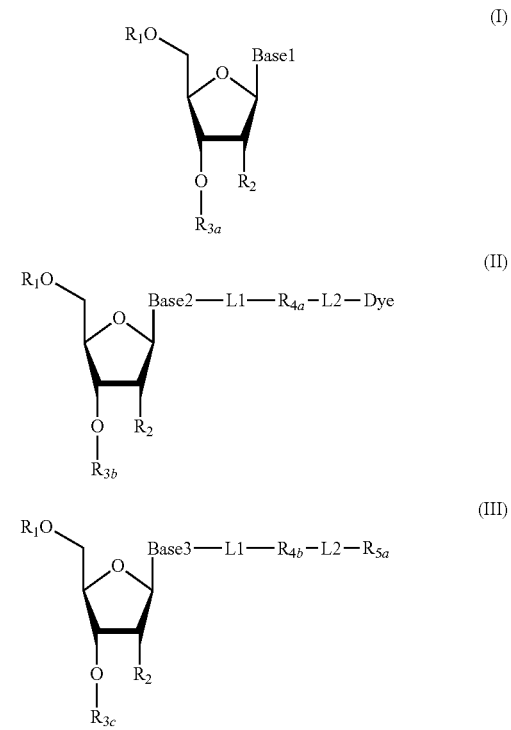

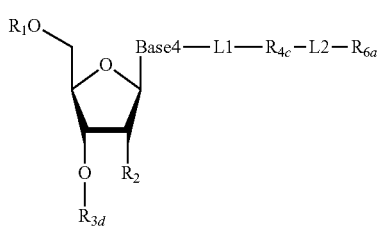

(IV)

wherein, Base1, Base2, Base3, and Base4 represent 4 different bases, and are selected from A, (T/U), C, and G;

$R_1$ is independently selected from —H, monophosphate group (—$PO_3H_2$), diphosphate group (—$PO_3H$—$PO_3H_2$), triphosphate group (—$PO_3H$—$PO_3H$—$PO_3H_2$) and tetraphosphate group (—$PO_3H$—$PO_3H$—$PO_3H$—$PO_3H_2$);

$R_2$ is independently selected from —H and —OH;

$R_{3a}$, $R_{3b}$, $R_{3c}$, $R_{3d}$, $R_{4a}$, $R_{4b}$, and $R_6$ are each independently a reactive group capable of performing a bioorthogonal cleavage reaction;

$R_{5a}$ is one member of the first binding pair;

$R_{6a}$ is a fluorophore ($Dye_1$) capable of emitting a fluorescent signal; a reactive group capable of performing the first bioorthogonal ligation reaction, and/or one member of the second binding pair;

L1 is independently a linking group or absent;

L2 is independently a linking group or absent;

Dye and $Dye_1$ represent a fluorophore capable of emitting a fluorescent signal; and, Dye and $Dye_1$ have the same structure, or have different structures but have the same or substantially the same emission spectrum; optionally, a reactive group $R_8$ capable of performing the second bioorthogonal ligation reaction is present between $R_{4c}$ and $R_{6a}$.

In such exemplary embodiment, the fourth compound itself may carry a fluorophore capable of emitting the same fluorescent signal as the second compound, or may not carry a fluorophore, but specifically interact with/bind to the agent (for example, the other member of the second binding pair, or compound capable of performing the first bioorthogonal ligation reaction with $R_{6a}$) carrying a fluorophore (for example, a fluorophore having the same structure as the second compound, or a fluorophore having the same or substantially the same emission spectrum as the fluorophore of the second compound) in step (5), to introduce the fluorophore into the fourth compound, and it is capable of emitting the same fluorescent signal as the second compound. Further, the third compound can be enabled to carry a fluorophore by specific interaction/binding between $R_{5a}$ and the other member (it is represented as "$R_{5b}$-L-$Dye_2$" herein, wherein $R_{5b}$ is the other member of the first binding pair, L is a linking group or absent; $Dye_2$ represents a fluorophore that is capable of emitting a fluorescent signal, it is preferably a fluorescent signal which is the same as the second compound, or a fluorescent signal which has the same or substantially the same emission spectrum as the second compound) of the first binding pair carrying the fluorophore. Further, (i) subjecting $R_{4c}$ in the fourth compound to a bioorthogonal cleavage reaction to remove the fluorophore in the fourth compound, or (ii) enabling $R_8$ in the fourth compound to perform the second bioorthogonal ligation reaction with a compound carrying the quenching group, thereby quenching the fluorescent signal emitted by fluorophore in the fourth compound. In such exemplary embodiments, it is particularly preferred that the two members ($R_{5a}$ and $R_{5b}$) of the first binding pair do not interact with $R_{4c}$. Furthermore, it is particularly preferred that $R_{5a}$ and $R_{5b}$ do not influence the bioorthogonal cleavage reaction of $R_{4c}$, and $R_{4c}$ does not influence the specific interaction between $R_{5a}$ and $R_{5b}$. Particularly preferably, the two members ($R_{5a}$ and $R_{5b}$) of the first binding pair do not interact with $R_8$. Furthermore, it is particularly preferred that $R_{5a}$ and $R_{5b}$ do not influence the bioorthogonal ligation reaction of $R_8$, and $R_8$ does not influence on the specific interaction between $R_{5a}$ and $R_{5b}$.

Thus, in some preferred embodiments, in step (6), the duplex or the growing nucleic acid strand is subjected to a treatment which has no influence on the first compound and the second compound, but the treatment enables specific interaction/specific binding between $R_{5a}$ with the other member ($R_{5b}$-L-$Dye_2$) of the binding pair carrying the fluorophore, (thus introducing the fluorophore into the third compound, allowing it to carry a fluorophore and emit a fluorescent signal), and enables $R_{4c}$ to perform a bioorthogonal cleavage reaction (thus removing the fluorophore in the fourth compound so that it no longer emits a fluorescent signal), or enable $R_8$ in the fourth compound to perform the second bioorthogonal ligation reaction with the compound carrying the quenching group, (thereby quenching the fluorescent signal emitted by the fluorophore in the fourth compound). In such exemplary embodiments, prior to the treatment of step (6), the first compound and the third compound (if present) do not fluoresce, and the second compound and the fourth compound (if present) fluoresce; also, after the treatment of step (6), the first compound (if present) still does not fluoresce, the second compound (if present) still fluoresces, the third compound (if present) changes to fluoresce, and the fourth compound (if present) changes to not fluoresce. Thus, the type of compound incorporated into the 3' end of the growing nucleic acid strand can be determined by the results of two fluorescent signal detections.

Further, in such exemplary embodiments, the protecting group at 3' position of the ribose or deoxyribose in the compound incorporated into the 3' end of the growing nucleic acid strand, and the fluorophore (if present) on the duplex or the growing nucleic acid strand can be removed by subjecting $R_{3a}$, $R_{3b}$, $R_{3c}$, $R_{3d}$, $R_{4a}$, $R_{4b}$ to a bioorthogonal cleavage reaction. Therefore, in some preferred embodiments, the duplex or the growing nucleic acid strand is subjected to a treatment in step (8), and such treatment enables $R_{3a}$, $R_{3b}$, $R_{3c}$, $R_{3d}$, $R_{4a}$, $R_{4b}$ to perform the bioorthogonal cleavage reaction. In such exemplary embodiments, after the treatment of step (8), the growing nucleic acid strand will not have any fluorophore, and its 3'-end nucleotide will have free hydroxyl at 3' position of the ribose or deoxyribose, and the free hydroxyl can be used for next round of polymerization.

Therefore, in some preferred embodiments, the method of the present invention comprises the following steps:

(1) providing a nucleic acid molecule to be sequenced attached onto a support or attaching the nucleic acid molecule to be sequenced onto a support;

(2) adding a primer for initiating a nucleotide polymerization, a polymerase for performing a nucleotide polymerization, and the first, second, third and fourth compounds having structures of formula (I), formula (II), formula (III), and formula (IV), respectively, to form a reaction system comprising a solution phase and a solid phase:

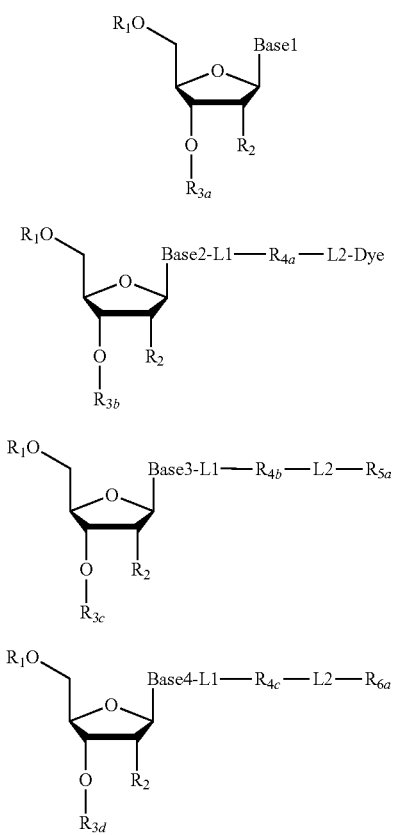

wherein, Base1, Base2, Base3, and Base4 represent 4 different bases, and are selected from A, (T/U), C and G;

$R_1$ is each independently selected from —H, monophosphate group (—$PO_3H_2$), diphosphate group (—$PO_3H$—$PO_3H_2$), triphosphate group (—$PO_3H$—$PO_3H$—$PO_3H_2$) and tetraphosphate group (—$PO_3H$—$PO_3H$—$PO_3H$—$PO_3H_2$);

$R_2$ is each independently selected from —H and —OH;

$R_{3a}$, $R_{3b}$, $R_{3c}$, $R_{3d}$, $R_{4a}$, $R_{4b}$ and $R_{4c}$ are each independently reactive groups capable of performing a bioorthogonal cleavage reaction;

$R_{5a}$ is one member of the first binding pair;

$R_{6a}$ is a fluorophore ($Dye_1$) capable of emitting a fluorescent signal, a reactive group capable of performing the first bioorthogonal ligation reaction, and/or one member of the second binding pair;

L1 is independently a linking group or absent;

L2 is independently a linking group or absent;

Dye and $Dye_1$ represent a fluorophore capable of emitting a fluorescent signal; and, Dye and $Dye_1$ have the same structure, or have different structures but have the same or substantially the same emission spectrum; optionally, a reactive group $R_8$ capable of performing the second bioorthogonal ligation reaction is present between $R_{4c}$ and $R_{6a}$;

(3) annealing the primer to the nucleic acid molecule to be sequenced, and the primer serves as an initial growing nucleic acid strand, and forms a duplex attached to the support together with the nucleic acid molecule to be sequenced;

(4) performing a nucleotide polymerization reaction using a polymerase under a condition allowing the polymerase to perform nucleotide polymerization, thereby incorporating one of the four compounds into the 3' end of the growing nucleic acid strand;

(5)(i) if the fourth compound is capable of emitting the same fluorescent signal as the second compound, and $R_{6a}$ is $Dye_1$, removing the solution phase of the reaction system of the previous step, retaining the duplex attached to the support, and detecting whether the duplex or the growing nucleic acid strand emits the fluorescent signal; or (ii) if the fourth compound does not emit a fluorescent signal, and $R_{6a}$ is a reactive group capable of performing the first bioorthogonal ligation reaction or is one member of the second binding pair, subjecting the duplex or the growing nucleic acid strand to a treatment in a reaction system containing a solution phase and a solid phase, wherein the treatment has no effect on the first compound, the second compound and the third compound, and enables $R_{6a}$ in the fourth compound to specifically interact with/bind to, or perform the first bioorthogonal ligation reaction with an agent (e.g., the other member of the second binding pair, or a compound which is capable of performing the first bioorthogonal ligation reaction with $R_{6a}$) carrying a fluorophore (for example, a fluorophore having the same structure as the fluorophore of the second compound, or a fluorophore having the same or substantially the same emission spectrum as the fluorophore of the second compound); thereafter, removing the solution phase of the reaction system of the previous step, retaining the duplex attached to the support, and detecting whether the duplex or the growing nucleic acid strand emits the fluorescent signal;

wherein the other member of the second binding pair carrying the fluorophore has the structure: $R_{6b}$-L'-$Dye_1$; wherein $R_{6b}$ is the other member of the second binding pair, L' is independently a linking group or absent; $Dye_1$ represents a fluorophore that is capable of emitting a fluorescent signal, and has the same structure as Dye, or has a different structure but the same or substantially the same emission spectrum as Dye; or the compound capable of performing the first bioorthogonal ligation reaction with $R_{6a}$ and carrying a fluorophore has the following structure: $R_{6b}$-L'-$Dye_1$; wherein $R_{6b}$ is a group capable of performing the second bioorthogonal ligation reaction with $R_{6a}$, L' is independently a linking group or absent; $Dye_1$ represents a fluorophore capable of emitting a fluorescent signal, and has the same structure as Dye, or has a different structure but the same emission spectrum as Dye;

(6) subjecting the duplex or the growing nucleic acid strand to a treatment in a reaction system containing a solution phase and a solid phase, wherein the treatment has no effect on the first compound and the second compound, but enables $R_{5a}$ in the third compound to specifically bind to the other member of the first binding pair carrying the fluorophore, thereby introducing the fluorophore into the third compound to make the third compound to emit a fluorescent signal; and, the treatment (i) enables $R_{4c}$ in the fourth compound to perform the bioorthogonal cleavage reaction to remove the fluorophore in the fourth compound, or (ii) enables $R_8$ in the fourth compound to perform a second bioorthogonal ligation reaction with the compound carrying the quenching group, thereby quenching the fluorescent signal emitted by fluorophore $Dye_1$ in the fourth compound; wherein, the other member of the first binding pair carrying the fluorophore has the following structure: $R_{5b}$-L'-$Dye_2$; wherein $R_{5b}$ is the other member of the first binding pair, L is independently a linking group or is absent; $Dye_2$ represents a fluorophore which is capable of emitting a fluorescent signal, and it is the same as fluorophore in the second compound, or it has the same or substantially the same emission spectrum; and (7) removing the solution phase of the reaction system in the previous step, retaining the duplex attached to the support, and detecting whether the duplex or the growing nucleic acid strand emits the fluorescent signal.

In some preferred embodiments, the method further comprises the steps of:

(8) subjecting the duplex or the growing nucleic acid strand in the previous step to a treatment in a reaction system comprising a solution phase and a solid phase, wherein the treatment enables $R_{3a}$, $R_{3b}$, $R_{3c}$, $R_{3d}$, $R_{4a}$, $R_{4b}$ to perform the bioorthogonal cleavage reaction, thereby allowing the compound incorporated at the 3' end of the growing nucleic acid strand to have a free hydroxyl group at the 3' position of the ribose or deoxyribose (in other words, converting —$OR_{3a}$, —$OR_{3b}$, —$OR_{3c}$ or —$OR_{3d}$ (if present) into a free hydroxyl group and removing the fluorophore on the duplex or the growing nucleic acid strand (in other words, removing the fluorophore attached to $R_{4a}$ or $R_{4b}$), if present;

(9) removing the solution phase of the reaction system in the previous step;

(10) adding a polymerase for performing nucleotide polymerization, and the first compound, the second compound, the third compound, and the fourth compound, thereby forming a reaction system comprising a solution phase and a solid phase, and then performing the steps (4)-(7);

In some preferred embodiments, the method further comprises the step of:

(11) repeating steps (8)-(10) one or more times.

In some exemplary embodiments, in step (4), if the compound of formula (I) is incorporated into the 3' end of the growing nucleic acid strand, then since the compound of formula (I) does not carry a fluorophore itself, and it does not react in step (6), no fluorescent signal will be detected in steps (5) and (7). In other words, if no fluorescent signal is detected in both of steps (5)-(7), it can be determined that the compound incorporated at the 3' end of the growing nucleic acid strand is the compound of formula (I).

In step (4), if the compound of formula (II) is incorporated into the 3' end of the growing nucleic acid strand, then since the compound of formula (II) itself carries a fluorophore and it does not perform any reaction in step (6), the fluorescent signal will be detected in both steps (5) and (7). In other words, if a fluorescent signal is detected in both of steps (5) and (7), it can be determined that the compound incorporated at the 3' end of the growing nucleic acid strand is the compound of formula (II).

In step (4), if the compound of formula (III) is incorporated into the 3' end of the growing nucleic acid strand, then (i) since the compound of formula (III) does not carry a fluorophore, no fluorescent signal will be detected in step (5); and (ii) because the compound of formula (III) specifically binds to the other member ($R_{5b}$-L-Dye$_2$) of the binding pair carrying the fluorophore, introducing the fluorophore into the growing nucleic acid strand, a fluorescent signal will be detected in step (7). In other words, if a fluorescent signal is not detected in step (5) and a fluorescent signal is detected in step (7), it can be determined that the compound incorporated at the 3' end of the growing nucleic acid strand is a compound of the formula (III).

In step (4), if the compound of formula (IV) is incorporated into the 3' end of the growing nucleic acid strand, then (i) since the compound of formula (IV) itself carries a fluorophore or is treated in step (5) to carry a fluorophore, a fluorescent signal will be detected in step (5); and (ii) since the compound of formula (IV) performs a bioorthogonal cleavage reaction or a second bioorthogonal ligation reaction in step (6) to loss the fluorophore or the fluorescent signal is quenched, the fluorescent signal will not be detected in step (7). In other words, if the fluorescent signal is detected in step (5) and no fluorescent signal is detected in step (7), it can be determined that the compound incorporated at the 3' end of the growing nucleic acid strand is a compound of the formula (IV).

Therefore, in some preferred embodiments, the method of the present invention further comprises, after step (7), determining the type of the compound incorporated into 3' end of the growing nucleic acid strand in step (4) according to the detection results in steps (5) and (7), wherein, when the detection results in steps (5) and (7) are both, the duplex or the growing nucleic acid strand does not emit the fluorescent signal, it is determined that the compound incorporated into 3' end of the growing nucleic acid strand in step (4) is a compound of formula (I);

when the detection results in steps (5) and (7) are both, the duplex or the growing nucleic acid strand emits the fluorescent signal, it is determined that the compound incorporated into 3' end of the growing nucleic acid strand in step (4) is a compound of formula (II);

when the detection result in step (5) is that the duplex or the growing nucleic acid strand does not emit the fluorescent signal, and the detection result in step (7) is that the duplex or the growing nucleic acid strand emits the fluorescent signal, it is determined that the compound incorporated into 3' end of the growing nucleic acid strand in step (4) is the compound of formula (III); and, when the detection result in step (5) is that the duplex or the growing nucleic acid strand emits the fluorescent signal, and the detection result in step (7) is that the duplex or the growing nucleic acid strand does not emit the fluorescent signal, it is determined that the compound incorporated into 3' end of the growing nucleic acid strand in step (4) is the compound of formula (IV);

in some preferred embodiments, the method of the present invention further comprises, after step (7), based on the base complementary pairing principle, according to the type of compound incorporated in the 3' end of the growing nucleic acid strand in step (4), the type of base at the corresponding position in the nucleic acid molecule to be sequenced is determined.

In some preferred embodiments, the compound of formula (I), the compound of formula (II), the compound of formula (III) and the compound of formula (IV) do not perform a chemical reaction with each other in the process of the nucleotide polymerization reaction.

In some preferred embodiments, Base1 and Base2 are purine bases, and Base3 and Base4 are pyrimidine bases. In some preferred embodiments, Base1 is base G, Base2 is base A, Base3 is base C, and Base4 is base T or U. In some preferred embodiments, Base1 is base G, Base2 is base A, Base3 is base T or U, and Base4 is base C. In some preferred embodiments, Base1 is base A, Base2 is base G, Base3 is base C, and Base4 is base T or U. In some preferred embodiments, Base1 is base A, Base2 is base G, Base3 is base T or U, and Base4 is base C.

In some preferred embodiments, Base1 and Base2 are purine bases, and Base3 and Base4 are pyrimidine bases. In some preferred embodiments, Base1 is base C, Base2 is base T or U, Base3 is base G and Base4 is base A. In some preferred embodiments, Base1 is base C, Base2 is base T or U, Base3 is base A, and Base4 is base G. In some preferred embodiments, Base1 is base T or U, Base2 is base C, Base3 is base G, and Base4 is base A. In some preferred embodiments, Base1 is base T or U, Base2 is base C, Base3 is base A, and Base4 is base G.

In some preferred embodiments, the compound of formula (I), the compound of formula (II), the compound of formula (III) and the compound of formula (IV) have the same $R_1$. In some preferred embodiments, $R_1$ is each independently —H. In some preferred embodiments, $R_1$ is each independently a monophosphate group (—PO$_3$H$_2$). In some preferred embodiments, $R_1$ is each independently a diphosphate group (—PO$_3$H—PO$_3$H$_2$). In some preferred embodiments, $R_1$ is each independently a triphosphate group (—PO$_3$H—PO$_3$H—PO$_3$H$_2$). In some preferred embodiments, $R_1$ is each independently a tetraphosphate group (—PO$_3$H—PO$_3$H—PO$_3$H—PO$_3$H$_2$).

In some preferred embodiments, the compound of formula (I), the compound of formula (II), the compound of formula (III) and the compound of formula (IV) have the same $R_2$. In some preferred embodiments, $R_2$ is each independently —H. In some preferred embodiments, $R_2$ is each independently —OH.

In some preferred embodiments, $R_{3a}$, $R_{3b}$, $R_{3c}$, $R_{3d}$, $R_{4a}$, $R_{4b}$ are each independently capable of performing a bioorthogonal cleavage reaction. As used herein, the expression "each independently capable of performing bioorthogonal cleavage reaction" means that the reactive groups, agents, or molecules, etc., are capable of performing bioorthogonal cleavage reaction, respectively, and they do not interfere with or affect each other. For example, the expression "$R_{3a}$ and $R_{3b}$ are each independently capable of performing bioorthogonal cleavage reaction" means that both $R_{3a}$ and $R_{3b}$ are capable of performing the bioorthogonal cleavage reaction, and $R_{3a}$ does not affect the bioorthogonal cleavage reaction of $R_{3b}$, $R_{3b}$ does not influence the progress of the bioorthogonal cleavage reaction of $R_{3a}$.

In some exemplary embodiments, $R_{3a}$ is a first reactive group capable of performing a bioorthogonal cleavage reaction in the presence of a first agent; $R_{3b}$ is a second reactive group capable of performing a bioorthogonal cleavage reaction in the presence of a second agent; $R_{3c}$ is a third reactive group capable of performing a bioorthogonal cleavage reaction in the presence of a third agent; $R_{3d}$ is a fourth reactive group capable of performing a bioorthogonal cleavage reaction in the presence of a fourth agent; $R_{4a}$ is a fifth reactive group capable of performing a bioorthogonal cleavage reaction in the presence of a fifth agent; $R_{4b}$ is a sixth reactive group capable of performing a bioorthogonal cleavage reaction in the presence of a sixth agent; and $R_{4c}$ is a seventh reactive group capable of performing a bioorthogonal cleavage reaction in the presence of a seventh agent.

In some exemplary embodiments, it is particularly preferred that the two members of the first binding pair ($R_{5a}$ and $R_{5b}$) do not interact with $R_{4c}$. Furthermore, it is particularly preferred that $R_{5a}$ and $R_{5b}$ do not influence the bioorthogonal cleavage reaction of $R_{4c}$, and that $R_{4c}$ do not influence the specific interaction between $R_{5a}$ and $R_{5b}$. Preferably, in such embodiments, $R_{5b}$-L-Dye$_2$ and the seventh agent are added in step (6), enabling $R_{5a}$ (if present) in compound of formula (III) to specifically bind to $R_{5b}$ in $R_{5b}$-L-Dye$_2$, and enabling $R_{4c}$ (if present) in compound of formula (IV) to perform the bioorthogonal cleavage reaction, thereby, by the specific interaction between the two members ($R_{5a}$ and $R_{5b}$) of the binding pair, the fluorophore Dye$_2$ linked with $R_{5b}$ is introduced into the compound of formula (III) to enable compound of formula (III) to emit a fluorescent signal. At the same time, the seventh agent is capable of enabling $R_{4c}$ to perform a bioorthogonal cleavage reaction in the compound of formula (IV), and thereby removing $R_6$ in the compound of formula (IV) and a fluorophore linked thereto. In such embodiments, it is also particularly preferred that, in step (6), $R_{5b}$-L-Dye$_2$ does not react with the first compound and the second compound, and further preferably, the seventh agent does not react with the first compound and the second compound. Therefore, in some preferred embodiments, in step (6), $R_{5b}$-L-Dye$_2$ and a seventh agent can be added to form a reaction system comprising a solution phase and a solid phase, wherein, $R_{5b}$ is the other member of the first binding pair, L is a linking group or absent; Dye represents a fluorophore capable of emitting a fluorescent signal; then, under conditions that allow $R_{5a}$ to specifically bind to $R_{5b}$ and allow $R_{4c}$ to perform the bioorthogonal cleavage reaction, the duplex is incubated with $R_{5b}$-L-Dye$_2$ and a seventh agent.

In some exemplary embodiments, a reactive group $R_8$ capable of performing a second bioorthogonal ligation reaction is present between $R_{5b}$ and $R_{7a}$ in the fourth compound. In some preferred embodiments, $R_{3a}$, $R_{3b}$, $R_{3c}$, $R_{3d}$, $R_{4a}$, $R_{4b}$, $R_{5a}$ and $R_8$ are each independently capable of performing a bioorthogonal cleavage or ligation reaction. In some preferred embodiments, $R_{8a}$ is capable of performing a third bioorthogonal ligation reaction in the presence of an eighth agent.

In such embodiments, it is particularly preferred that the two members ($R_{5a}$ and $R_{5b}$) of the first binding pair do not interact with $R_8$. Furthermore, it is particularly preferred that $R_{5a}$ and $R_{5b}$ do not affect the bioorthogonal ligation reaction of $R_8$, and $R_8$ does not affect the specific interaction between $R_{5a}$ and $R_{5b}$. Preferably, in such embodiments, in step (6), $R_{5b}$-L-Dye$_2$ and an eighth agent may be added such that $R_{5a}$ (if present) in the compound of formula (III) specifically binds to $R_{5b}$ in $R_{5b}$-L-Dye$_2$ such that $R_8$ (if present) in the compound of formula (IV) performs a bioorthogonal ligation reaction. Thus, by the specific interaction between the two members of the binding pair ($R_{5a}$ and $R_{5b}$), the fluorophore Dye$_2$ linked onto $R_{5b}$ is introduced into the compound of formula (III), such that the compound of formula (III) emits the fluorescent signal. At the same time, the eighth agent is capable of enabling $R_{4c}$ in the compound of formula (IV) to perform the bioorthogonal ligation reaction, thereby the fluorophore is quenched in the compound of formula (IV). In such embodiments, it is also particularly preferred that, in step (6), $R_{5b}$-L-Dye$_2$ does not react with the first compound and the second compound, and further preferably, the eighth agent does not react with the first compound and the second compound. Therefore, in some preferred embodiments, in step (6), $R_{5b}$-L-Dye$_2$ and the eighth agent may be added to form a reaction system comprising a solution phase and a solid phase, wherein, $R_{5b}$ is the other member of the first binding pair, L is a linking group or absent; Dye$_2$ represents a fluorophore capable of emitting a fluorescent signal; then, under conditions that allow $R_{5a}$ to specifically bind to $R_{5b}$ and allow $R_8$ to perform the bioorthogonal ligation reaction, the duplex is incubated with $R_{5b}$-L-Dye$_2$ and the eighth agent.

Further preferably, in such embodiments, in step (8), a first agent, a second agent, a third agent, a fourth agent, a fifth agent and a sixth agent may be added such that $R_{3a}$, $R_{3b}$, $R_{3c}$, $R_{3d}$, $R_{4a}$, $R_{4b}$ (if present) each performs a bioorthogonal cleavage reaction. Thus, $R_{3a}$, $R_{3b}$, $R_{3c}$, $R_{3d}$ (if present) will be removed from the 3' position of ribose or deoxyribose (in other words, —OR$_{3a}$, —OR$_{3b}$, —OR$_{3c}$ or —OR$_{3d}$ (if present) will be converted into free hydroxyl), and $R_{4a}$ and the fluorophore linked thereto (if present) and $R_{4b}$ and the fluorophore linked thereto (if present) will also be removed. Thus, after step (8), the growing nucleic acid strand will not carry the fluorophore and will have a free hydroxyl group at the 3' end, which can be used for the next round of polymerization. Therefore, in some preferred embodiments, in step (8), a first agent, a second agent, a third agent, a fourth agent, a fifth agent and a sixth agent are added to form a reaction system comprising a solution phase and a solid phase, and the duplex and the first agent, the second agent, the third agent, the fourth agent, the fifth agent and the sixth agent are incubated under the conditions that allow $R_{3a}$, $R_{3b}$, $R_{3c}$, $R_{3d}$, $R_{4a}$ and $R_{4b}$ to perform a bioorthogonal cleavage reaction.

In some preferred embodiments, $R_{3a}$, $R_{3b}$, $R_{3c}$ and $R_{3d}$ are each capable of performing the bioorthogonal cleavage reaction in the presence of the same agent. In this case, preferably, in step (8), the first agent, the second agent, the third agent and the fourth agent are the same agents.

In some preferred embodiments, $R_{3a}$, $R_{3b}$, $R_{3c}$ and $R_{3d}$ are the same reactive groups. In this case, preferably, in step (8), the first agent, the second agent, the third agent and the fourth agent are the same agents. In other words, in step (8), the same $R_{3a}$, $R_{3b}$, $R_{3c}$ and $R_{3d}$ (if present) will each perform the bioorthogonal cleavage reaction and be excised from the growing nucleic acid strand in the presence of the same agent (i.e., the first agent).

In some preferred embodiments, $R_{4a}$ and $R_{4b}$ are each capable of performing a bioorthogonal cleavage reaction in the presence of the same agent. In this case, preferably, in step (8), the fifth agent and the sixth agent are the same agents.

In some preferred embodiments, $R_{4a}$ and $R_{4b}$ are the same reactive groups. In this case, preferably, in step (8), the fifth agent and the sixth agent are the same agents. In other words, in step (8), in the presence of the same agent (i.e., the fifth agent), the same $R_{4a}$ and $R_{4b}$ (if present) will each perform a bioorthogonal cleavage reaction and be excised from the growing nucleic acid strand.

In some preferred embodiments, $R_{3a}$, $R_{3b}$, $R_{3c}$, $R_{3d}$, $R_{4a}$ and $R_{4b}$ are each capable of performing a bioorthogonal cleavage reaction in the presence of the same agent. In this case, preferably, in step (8), the first agent, the second agent, the third agent, the fourth agent, the fifth agent and the sixth agent are the same agents. In other words, in step (8), it is only necessary to add the same agent (i.e., the first agent), and in the presence of the same agent (i.e., the first agent), the $R_{3a}$, $R_{3b}$, $R_{3c}$, $R_{3d}$, $R_{4a}$ and $R_{4b}$ (if present), will each perform the bioorthogonal cleavage reaction and be excised from the growing nucleic acid strand.

In some exemplary embodiments, $R_{6a}$ is fluorophore $Dye_1$ capable of emitting the fluorescent signal, $Dye_1$ has the same structure as Dye, or is structurally different but has the same emission spectrum, so that the fourth compound itself is capable of emitting a fluorescent signal as the second compound.

In some exemplary embodiments, the fourth compound itself does not carry fluorophore and $R_{6a}$ is a reactive group capable of performing the first bioorthogonal ligation reaction. In such embodiments, step (5) comprises adding a ninth agent such that $R_{6a}$ (if present) in the compound of formula (IV) performs the first bioorthogonal ligation reaction. For example, the ninth agent may comprise a compound M' having the structure $R_{6b}$-L'-$Dye_1$, wherein, $R_{6b}$ is a group capable of performing a first bioorthogonal ligation reaction with $R_{6a}$, and L is independently a linking group or absent; $Dye_1$ represents a fluorophore capable of emitting a fluorescent signal and has the same structure as Dye, or has a different structure but the same emission spectrum.

In some exemplary embodiments, the fourth compound does not carry a fluorophore and $R_{6a}$ is one member of the second binding pair. In such embodiments, step (5) comprises adding a ninth agent such that $R_{6a}$ (if present) in the compound of formula (IV) specifically interacts with and/or binds to the other member of the second binding pair. For example, the ninth agent may comprise a compound M" having the structure $R_{6b}$-L'-$Dye_1$, wherein $R_{6b}$ is the other member of the second binding pair, L is independently a linking group or absent; $Dye_1$ represents the fluorophore which is capable of emitting the fluorescent signal, and has the same structure as Dye, or a different structure but the same emission spectrum.

In some preferred embodiments, $R_{3a}$, $R_{3b}$, $R_{3c}$ and $R_{3d}$ are each independently selected from the group consisting of —$CH_2CH=CH_2$, —$CH_2N_3$, $C_{3-8}$ cycloalkenyl (e.g., $C_3$ cycloalkenyl, $C_4$ cycloalkenyl, $C_5$ membered cycloalkenyl, $C_6$ cycloalkenyl, $C_7$ cycloalkenyl or $C_8$ cycloalkenyl). In some preferred embodiments, the $C_{3-8}$ cycloalkenyl is selected from the group consisting of $C_3$ cycloalkenyl and $C_8$ cycloalkenyl. In some preferred embodiments, the $C_{3-8}$ cycloalkenyl group is

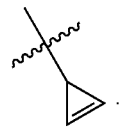

In some preferred embodiments, the $C_{3-8}$ cycloalkenyl group is

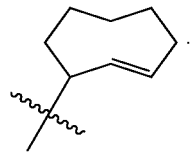 [SMILES: *C1/C=C/CCCCC1]

In some preferred embodiments, $R_{3a}$, $R_{3b}$, $R_{3c}$, and $R_{3d}$ are the same reactive groups and are selected from the group consisting of —$CH_2CH=CH_2$, —$CH_2N_3$, $C_{3-8}$ cycloalkenyl (e.g., $C_3$ cycloalkenyl, $C_4$ cycloalkenyl, $C_5$ membered cycloalkenyl, $C_6$ cycloalkenyl, $C_7$ cycloalkenyl or $C_8$ cycloalkenyl). In some preferred embodiments, the $C_{3-8}$ cycloalkenyl is selected from the group consisting of $C_3$ cycloalkenyl and $C_8$ cycloalkenyl. In some preferred embodiments, the $C_{3-8}$ cycloalkenyl group is

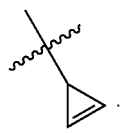 [SMILES: *C1C=C1]

In some preferred embodiments, the $C_{3-8}$ cycloalkenyl group is

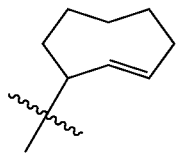

In some preferred embodiments, $R_{3a}$, $R_{3b}$, $R_{3c}$, and $R_{3d}$ are the same reactive groups and are all —$CH_2N_3$.

In some preferred embodiments, $R_{4a}$ and $R_{4b}$ are each independently selected from the group consisting of:

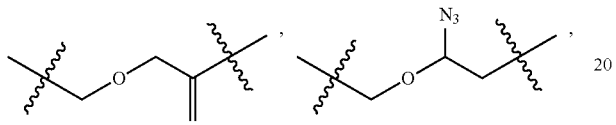

—O—$C_{3-8}$ cycloalkenylene. In some preferred embodiments, the "—O—$C_{3-8}$ cycloalkenylene" is selected from the group consisting of —O—$C_3$ cycloalkenylene, —O—$C_4$ cycloalkenylene, —O—$C_5$ cycloalkenylene, —O—$C_6$ cycloalkenylene, —O—$C_7$ cycloalkenylene, and —O—$C_8$ cycloalkenylene. In some preferred embodiments, said "—O—$C_{3-8}$ cycloalkenylene" is

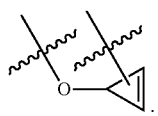

In some preferred embodiments, said "—O—$C_{3-8}$ cycloalkenylene" is

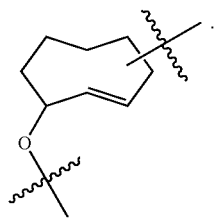

In some preferred embodiments, $R_{4a}$ and $R_{4b}$ are the same reactive groups and are selected from the group consisting of:

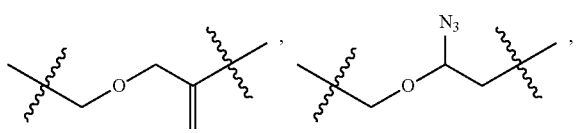

and —O—$C_{3-8}$ cycloalkenylene. In some preferred embodiments, said "—O—$C_{3-8}$ cycloalkenylene" is selected from the group consisting of —O—$C_3$ cycloalkenylene, —O—$C_4$ cycloalkenylene, —O—$C_5$ cycloalkenylene, —O—$C_6$ cycloalkenylene, —O—$C_7$ cycloalkenylene, and —O—$C_8$ cycloalkenylene. In some preferred embodiments, said "—O—$C_{3-8}$ cycloalkenylene" is

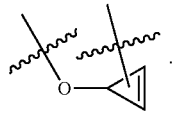

In some preferred embodiments, said "—O—$C_{3-8}$ cycloalkenylene" is

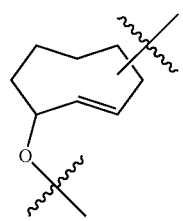

In some preferred embodiments, $R_{4a}$ and $R_{4b}$ are both

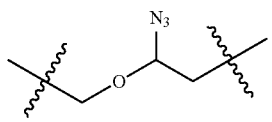

In some preferred embodiments, the first agent, the second agent, the third agent, the fourth agent, the fifth agent and the sixth agent each independently comprise substance selected from the group consisting of:

a complex of palladium (for example, a complex of palladium with four triphenylphosphine 3,3',3"-trisulfonic acids);

a complex of ruthenium (for example, a complex of ruthenium with quinoline carboxylate (or a derivative thereof), allyl or cyclopentadiene);

a phosphide (e.g., a carboxyphosphine or hydroxyphosphine such as $P(CH_2CH_2COOH)_3$ or $P(CH_2CH_2OH)_3$); and compound Q having the structural formula

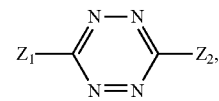

wherein, $Z_1$ and $Z_2$ are each independently selected from a modified or unmodified alkyl group (e.g., $C_1$-$C_{06}$ alkyl group such as $C_1$ alkyl group, $C_2$ alkyl group, $C_3$ alkyl group, $C_4$ alkyl group, $C_5$ alkyl group or $C_6$ alkyl group) and a modified or unmodified aryl (for example, 6-10 membered aryl such as 6-membered aryl, 7-membered aryl, 8-membered aryl, 9-membered aryl or 10-membered aryl such as phenyl or pyridyl).

In some preferred embodiments, $R_{3a}$, $R_{3b}$, $R_{3c}$ and $R_{3d}$ are —$CH_2CH=CH_2$. In this case, preferably, $R_{4a}$ and $R_{4b}$ are

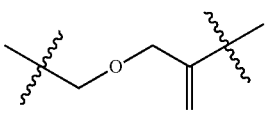

Further preferably, the first agent, the second agent, the third agent, the fourth agent, the fifth agent and the sixth agent comprise a complex of palladium or a complex of ruthenium. Preferably, the first agent, the second agent, the third agent, the fourth agent, the fifth agent and the sixth agent are the same agents, and comprise a complex of palladium or a complex of ruthenium.

In some preferred embodiments, $R_{3a}$, $R_{3b}$, $R_{3c}$ and $R_{3d}$ are —$CH_2$—$N_3$. In this case, preferably, $R_{4a}$ and $R_{4b}$ are

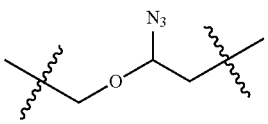

Further preferably, the first agent, the second agent, the third agent, the fourth agent, the fifth agent and the sixth agent comprise phosphonate such as carboxyl phosphonate or hydroxyl phosphonate such as $P(CH_2CH_2COOH)_3$ or $P(CH_2CH_2OH)_3$. Preferably, the first agent, the second agent, the third agent, the fourth agent, the fifth agent and the sixth agent are the same agents, and they comprise phosphonate such as carboxyl phosphonate or hydroxyl phosphonate such as $P(CH_2CH_2COOH)_3$ or $P(CH_2CH_2OH)_3$.

In some preferred embodiments, $R_{3a}$, $R_{3b}$, $R_{3c}$ and $R_{3d}$ are

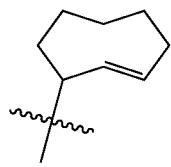

In this case, preferably, $R_{4a}$ and $R_{4b}$ are

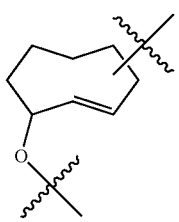

Further preferably, the first agent, the second agent, the third agents, the fourth agent, the fifth agent and the sixth agent comprise the compound Q as defined above. Further preferably, in compound Q, $Z_1$ is a methyl group; and $Z_2$ is a modified or unmodified pyridyl group. More preferably, compound Q is

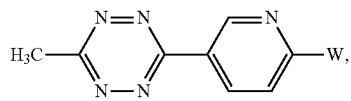

wherein, W is hydrogen or a modifying group. Preferably, the first agent, the second agent, the third agent, the fourth agent, the fifth agent and the sixth agent are the same agents and comprise the compound Q as defined above.

In some preferred embodiments, the linking groups L1 and L2 in the first compound, the second compound, the third compound, and the fourth compound, linking group L in $R_{5b}$-L-Dye and linking group L' in $R_{6b}$-L'-$Dye_1$ are each independent and are not particularly limited. A person skilled in the art can select suitable linking groups L1, L2, L and L' according to the bases (Base1, Base2, Base3 and Base4), the reactive groups ($R_{4a}$, $R_{4b}$ and $R_6$) used in the compounds and members ($R_{5a}$ and $R_{5b}$) of the binding pair.

In some exemplary embodiments, the linking groups L1, L2, L and L' are each independently selected from the group consisting of:

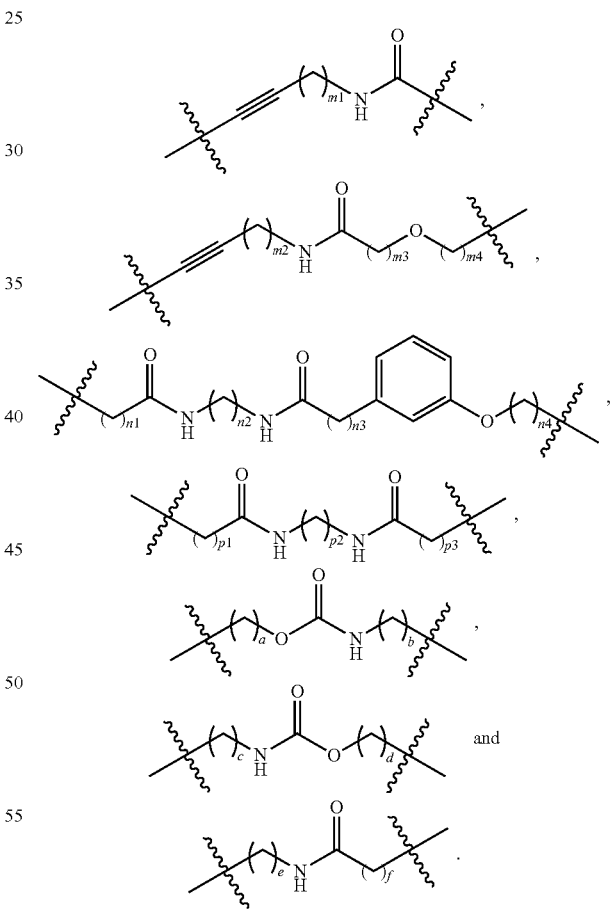

Wherein, m1, m2, m3, m4, n1, n2, n3, n4, p1, p2, p3, a, b, c, d, e and f are each independently selected from 0, 1, 2, 3, 4, 5 or 6.

In some exemplary embodiments, L1 in the first compound, the second compound, the third compound, and the fourth compound are each independently selected from the group consisting of:

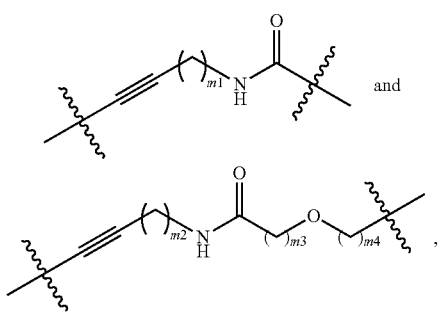

wherein m1, m2, m3, and m4 are each independently selected from 0, 1, 2, 3, 4, 5 or 6.

In some preferred embodiments, L1 in the first compound, the second compound, the third compound, and the fourth compound are each independently selected from the group consisting of:

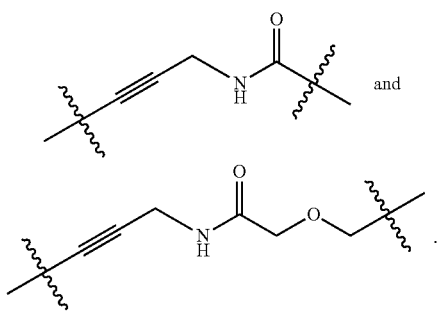

In some preferred embodiments, L2 in the first compound, the second compound, the third compound, and the fourth compound are each independently selected from the group consisting of:

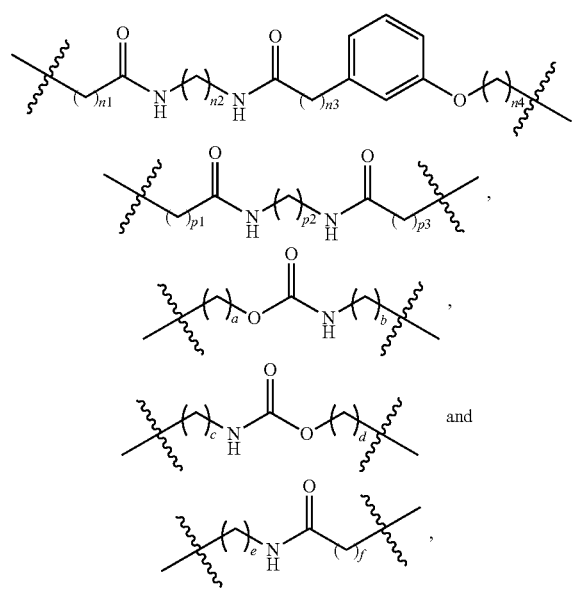

wherein, n1, n2, n3, n4, p1, p2, p3, a, b, c, d, e, and f are each independently selected from 0, 1, 2, 3, 4, 5, or 6.

In some preferred embodiments, L2 in the first compound, the second compound, the third compound, and the fourth compound are each independently selected from the group consisting of:

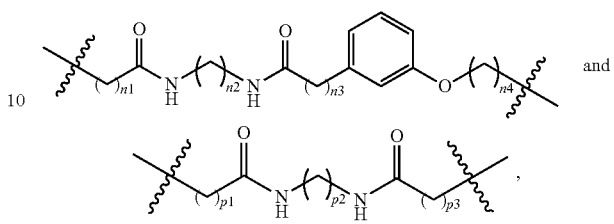

wherein, n1, n2, n3, n4, p1, p2, p3 are each independently selected from 0, 1, 2, 3, 4, 5 or 6.

In some preferred embodiments, L2 in the first compound, the second compound, the third compound, and the fourth compound are each independently selected from the group consisting of:

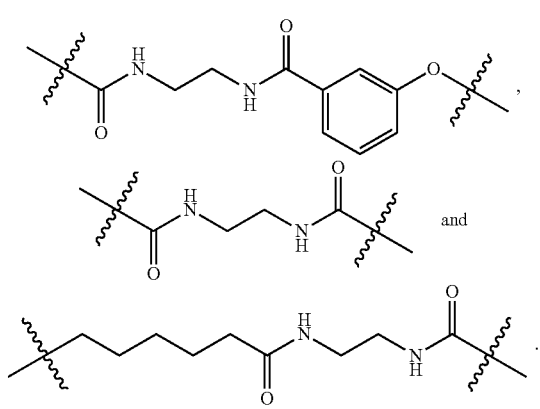

In some preferred embodiments, $R_{5a}$ and $R_{5b}$ are two members of a first binding pair. In some preferred embodiments, $R_{6a}$ and $R_{6b}$ are two members of the second binding pair. In some preferred embodiments, the binding pair is selected from the group consisting of: an antigen (e.g., a small molecule antigen)-antibody, a hapten-antibody, a hormone-receptor, a ligand-receptor, nucleic acid strand-complementary nucleic acid strand, substrate-enzyme, substrate analog-enzyme, inhibitor-enzyme, sugar-plant lectin, biotin-avidin (for example, avidin and streptavidin), digoxin and digoxin antibody, and 5-position bromodeoxyguanosine and its antibody.

In some preferred embodiments, the two members of the first binding pair are selected from the group consisting of: (a) biotin and avidin (for example, streptavidin), (b) desthiobiotin and avidin (e.g., streptavidin) and (c) digoxin and digoxin antibody. In some preferred embodiments, the two members of the second binding pair are selected from the group consisting of: (a) biotin and avidin (for example, streptavidin), (b) desthiobiotin and avidin (e.g., streptavidin) and (c) digoxin and digoxin antibody. In some preferred embodiments, $R_{5a}$ is digoxin or desthiobiotin, and $R_{5b}$ is avidin (for example, streptavidin). In some preferred embodiments, $R_{5a}$ is digoxin, and $R_{5b}$ is digoxin antibody. In some preferred embodiments, $R_{4c}$ is selected from the group consisting of:

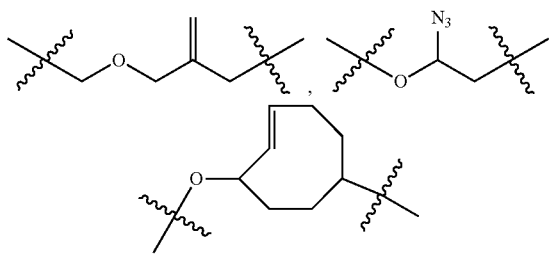

In some preferred embodiments, the seventh agent comprises a compound M selected from the group consisting of:
compound M1, which has the structural formula

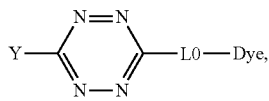

wherein, Y is selected from alkyl (for example, $C_1$-$C_6$ alkyl such as $C_1$ alkyl, $C_2$ alkyl, $C_3$ alkyl, $C_4$ alkyl, $C_5$ alkyl or $C_6$ alkyl) and aryl (for example, 6-10 membered aryl such as 6-membered aryl, 7-membered aryl, 8-membered aryl, 9-membered aryl or 10-membered aryl, for example, phenyl group), L0 is absent or linking group, Dye is a fluorophore, and the fluorophore is the same as the fluorophore in the second compound and the fourth compound (or the fluorophore has a different structure but the same or substantially the same emission spectrum as that of the second compound and the fourth compound);
compound M2, which has a structural formula

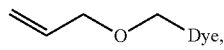

wherein Dye is a fluorophore, and the fluorophore is the same as the fluorophore in the second compound and the fourth compound (or different in structure but the same or substantially the same emission spectrum);
compound M3, which has a structural formula

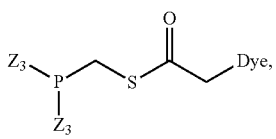

wherein, $Z_3$ is independently selected from alkyl (for example, $C_1$-$C_6$ alkyl, such as $C_1$ alkyl, $C_2$ alkyl, $C_3$ alkyl, $C_4$ alkyl, $C_5$ alkyl or $C_6$ alkyl) and aryl (for example, 6-10 membered aryl such as a 6-membered aryl, 7-membered aryl, 8-membered aryl, 9-membered aryl or 10-membered aryl such as phenyl group), and Dye is a fluorophore. The fluorophore is the same as the fluorophore in the second compound and the fourth compound (or the structures are different but the emission spectra are the same or substantially the same).

In the embodiment of the present invention, the linking group L0 is not particularly limited. A person skilled in the art can select a suitable linking group L0 according to actual needs. For example, in some preferred embodiments, L0 can be

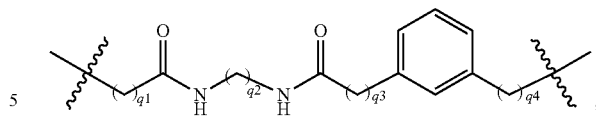

wherein q1, q2, q3, q4 are each independently selected from 0, 1, 2, 3, 4, 5 or 6.

In some preferred embodiments, the seventh agent comprises compound M1, wherein, Y is $C_1$-$C_{06}$ alkyl, such as methyl.

In some preferred embodiments, L0 in compound M1 is

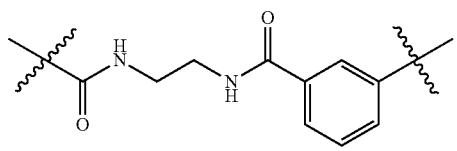

In some preferred embodiments, Dye in compound M1 is AF532. In some preferred embodiments, compound M1 has the following structure:

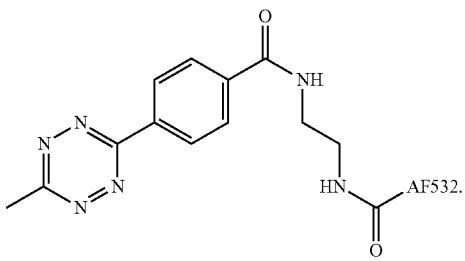

In some preferred embodiments, in addition to compound M, the seventh agent further comprises a complex of ruthenium. In some preferred embodiments, the seventh agent comprises compound M2 and a complex of ruthenium.

In some preferred embodiments, $R_{4c}$ is

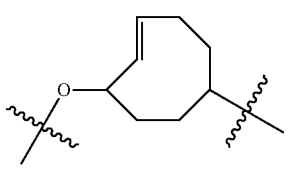

In this case, preferably, the seventh agent comprises compound M1.

In some preferred embodiments, $R_{4c}$ is

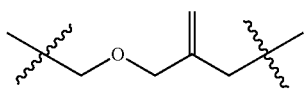

In this case, preferably, the seventh agent comprises compound M2. More preferably, the seventh agents each comprise compound M2 and a complex of ruthenium.

In some preferred embodiments, $R_{4c}$ is

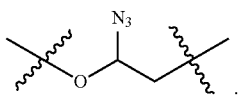 [SMILES: *CC(N=[N+]=[N-])O*]

In this case, preferably, the seventh agent comprises compound M3.

Particularly preferably, the two members of the binding pair ($R_{5a}$ and $R_{5b}$) do not interact with $R_{4c}$. Furthermore, it is particularly preferred that $R_{5a}$ and $R_{5b}$ do not affect the bioorthogonal cleavage reaction of $R_{4c}$, and $R_{4c}$ does not affect the specific interaction between $R_{5a}$ and $R_{5b}$. In some exemplary embodiments, the fourth compound comprises a reactive group $R_8$ capable of performing a second bioorthogonal ligation reaction. In some preferred embodiments, $R_8$ is selected from the groups consisting of:

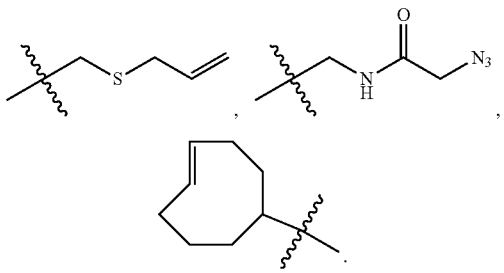

In some exemplary embodiments, the compound capable of performing a second bioorthogonal ligation reaction with $R_8$ is N, N comprises the following groups:

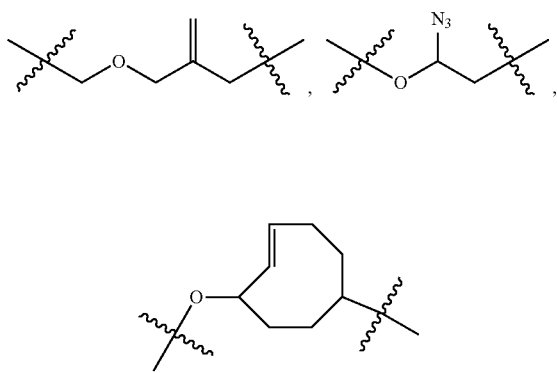

In some preferred embodiments, compound N is selected from the groups consisting of the following compounds:
compound N1 having the structural formula

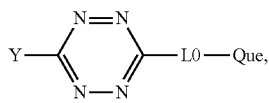

wherein Y is selected from alkyl (e.g., $C_1$-$C_6$ alkyl such as $C_1$ alkyl, $C_2$ alkyl, $C_3$ alkyl, $C_4$ alkyl, $C_5$ alkyl or $C_6$ alkyl) and aryl (e.g., 6-10 membered aryl such as 6-membered aryl, 7-membered aryl, 8-membered aryl, 9-membered aryl or 10-membered aryl such as phenyl), L0 is absent or is a linking group, Que is a quencher capable of quenching the fluorescent signal on the fourth compound;

Compound $N_2$ having a structural formula

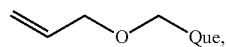

wherein Que is a quencher capable of quenching the fluorescent signal on the fourth compound;

Compound $N_3$ having a structural formula

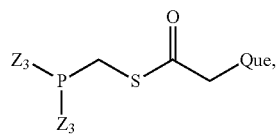

wherein $Z_3$ are each independently selected from an alkyl (e.g., $C_1$-$C_6$ alkyl such as $C_1$ alkyl, $C_2$ alkyl, $C_3$ alkyl, $C_4$ alkyl, $C_5$ alkyl or $C_6$ alkyl) and aryl (e.g., 6-10 membered aryl such as 6-membered aryl, 7-membered aryl, 8-membered aryl, 9-membered aryl or 10-membered aryl such as phenyl), Que is a quencher capable of quenching the fluorescent signal on the fourth compound;

In the embodiment of the present invention, the linking group L0 is not particularly limited. A person skilled in the art can select a suitable linking group L0 according to actual needs. For example, in some preferred embodiments, L0 can be

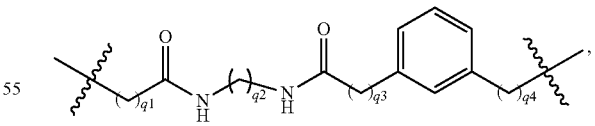

wherein q1, q2, q3, q4 are each independently selected from 0, 1, 2, 3, 4, 5 or 6.

In some embodiments, the compound N is 1, 2, 4, 5-tetrazine BHQ2, having a structure of:

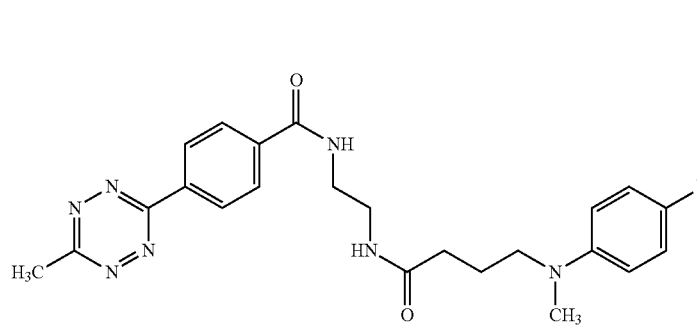

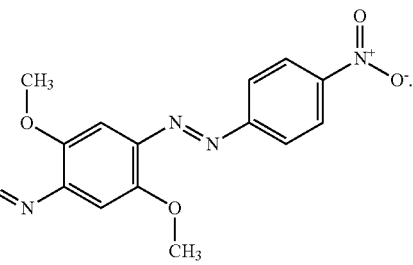

In some preferred embodiments, $R_{3a}$, $R_{3b}$, $R_{3c}$ and $R_{3d}$ are —$CH_2CH=CH_2$; and $R_{4a}$ and $R_{4b}$ are

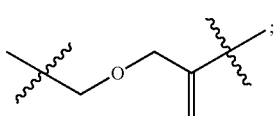 [SMILES: *COCC(*)=C]

the first, second, third, fourth, fifth and sixth agents comprise complex of palladium or complex of ruthenium; $R_{5a}$ is biotin; and $R_{5b}$ is avidin (for example, streptavidin); $R_{4c}$ is

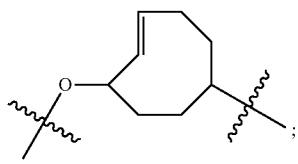 [SMILES: *OC1/C=C/CCC(*)CC1]

the seventh agent comprises compound M1. Preferably, the first, second, third, fourth, fifth and sixth agents are the same agents, and comprise complex of palladium or a complex of ruthenium.

In some preferred embodiments, $R_{3a}$, $R_{3b}$, $R_{3c}$ and $R_{3d}$ are —$CH_2$—$N_3$; $R_{4a}$ and $R_{4b}$ are

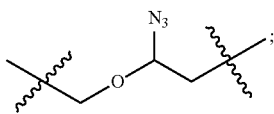

the first, second, third, fourth, fifth and sixth agents comprise a phosphonide such as carboxyphosphine or hydroxyphosphine such as $P(CH_2CH_2COOH)_3$ or $P(CH_2CH_2OH)_3$; $R_{5a}$ is biotin; $R_{5b}$ is an avidin (such as streptavidin); $R_6$ is

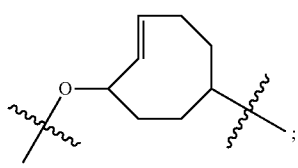 [SMILES: *OC1/C=C/CCC(*)CC1]

the seventh agent comprises compound M1. Preferably, the first, second, third, fourth, fifth and sixth agents are the same agents, and comprise a phosphine such as carboxyphosphine or hydroxyphosphine, for example, $P(CH_2CH_2COOH)_3$ or $P(CH_2CH_2OH)_3$.

In some preferred embodiments, $R_{3a}$, $R_{3b}$, $R_{3c}$, and $R_{3d}$ are —$CH_2$—$N_3$; $R_{4a}$ and $R_{4b}$ are

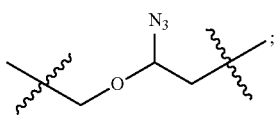 [SMILES: *COC(C*)N=[N+]=[N-]]

the first, second, third, fourth, fifth and sixth agents comprise a phosphonide such as carboxyphosphine or hydroxyphosphine such as $P(CH_2CH_2COOH)_3$ or $P(CH_2CH_2OH)_3$; $R_{5a}$ is biotin; $R_{5b}$ is avidin (for example, streptavidin); $R_6$ is

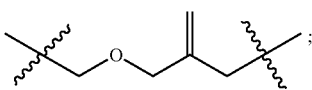 [SMILES: *COCC(=C)C*]

the seventh agent comprises compound M2 and complex of ruthenium. Preferably, the first, second, third, fourth, fifth and sixth agents are the same agents, and comprise a phosphine such as carboxyphosphine or hydroxyphosphine, for example $P(CH_2CH_2COOH)_3$ or $P(CH_2CH_2OH)_3$.

In some preferred embodiments, $R_{3a}$, $R_{3b}$, $R_{3c}$ and $R_{3d}$ are —$CH_2CH=CH_2$; $R_{4a}$, and $R_{4b}$ are

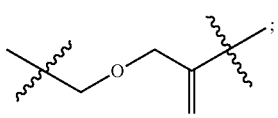 [SMILES: *COCC(*)=C]

the first, second, third, fourth, fifth and sixth agents comprise a complex of palladium or a complex of ruthenium; $R_{5a}$ is biotin; $R_{5b}$ is avidin (for example, streptavidin); $R_6$ is

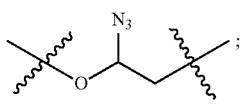 [SMILES: *CC(N=[N+]=[N-])O*]

the seventh comprises compound M3. Preferably, the first, second, third, fourth, fifth and sixth agents are the same agents, and comprise a complex of palladium or a complex of ruthenium.

In some preferred embodiments, $R_{3a}$, $R_{3b}$, $R_{3c}$ and $R_{3d}$ are

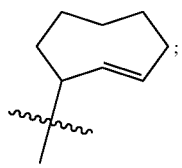 [SMILES: *C1/C=C/CCCCC1]

$R_{4a}$ and $R_{4b}$ are

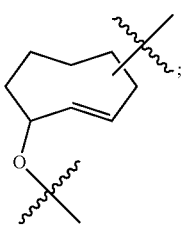

the first, second, third, fourth, fifth and sixth agents comprise Compound Q (for example, the compound Q as defined above); $R_{5a}$ is biotin; $R_{5b}$ is avidin (for example, streptavidin); $R_6$ is

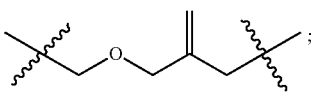 [SMILES: *COCC(=C)C*]

the seventh agent comprises compound M2 and complex of ruthenium. Preferably, the first, second, third, fourth, fifth and sixth agent are the same agents, and comprise Compound Q (e.g., the compound Q as defined above).

In some preferred embodiments, $R_{3a}$, $R_{3b}$, $R_{3c}$ and $R_{3d}$ are

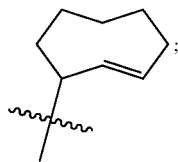 [SMILES: *C1/C=C/CCCCC1]

$R_{4a}$ and $R_{4b}$ are

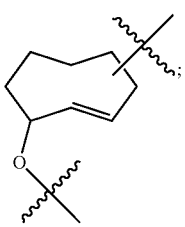

the first, second, third, fourth, fifth and sixth agents comprise Compound Q (for example, the compound Q as defined above); $R_{5a}$ is biotin; $R_{5b}$ is avidin (for example, streptavidin); $R_6$ is

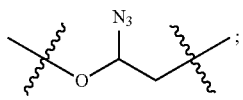 [SMILES: *CC(N=[N+]=[N-])O* ; ";"]

the seventh agent comprises compound M3. Preferably, the first, second, third, fourth, fifth and sixth agent are the same agents, and comprise Compound Q (e.g., the compound Q as defined above).

In some preferred embodiments, Dye in the third compound is Cy3 or AF532.

In some preferred embodiments, $R_{6a}$ in the fourth compound is $Dye_1$. In some preferred embodiments, $Dye_1$ is Cy3 or AF532.

In some preferred embodiments, Dye in the third compound is AF532 and $R_{6a}$ in the fourth compound is AF532.

In some exemplary embodiments, the fourth compound itself does not carry a fluorophore and $R_{6a}$ is a reactive group capable of performing a second bioorthogonal ligation reaction. In some preferred embodiments, $R_{6a}$ is selected from the group consisting of:

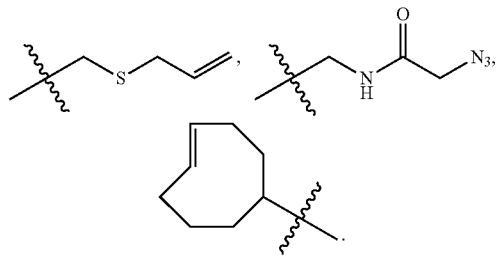

In some exemplary embodiments, compound N capable of performing a second bioorthogonal ligation reaction with $R_{7a}$ is selected from the group consisting of compounds N1, N2, N3.

In some exemplary embodiments, the fourth compound does not carry a fluorophore and $R_{7a}$ is one member of the second binding pair. In some preferred embodiments, the second binding pair is selected from the group consisting of: antigen (e.g., small molecule antigen)-antibody, hapten-antibody, hormone-receptor, ligand-receptor, nucleic acid strand-complementary nucleic acid strand, substrate-enzyme, substrate analog-enzyme, inhibitor-enzyme, sugar-plant lectin, biotin-avidin (for example, avidin and streptavidin), digoxin and digoxin antibody, and 5-position bromodeoxyguanosine and its antibody. In some preferred embodiments, the two members of the binding pair are selected from the group consisting of: (a) biotin and avidin (e.g., streptavidin), (b) desthiobiotin and avidin (for example, streptavidin) and (c) digoxin and digoxin antibody.

In some preferred embodiments, $R_{3a}$, $R_{3b}$, $R_{3c}$ and $R_{3d}$ are —$CH_2$—$N_3$; $R_{4a}$, $R_{4b}$ and $R_{4c}$ are

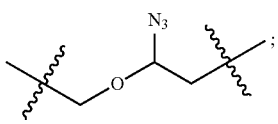 [SMILES: *COC(C*)N=[N+]=[N-] ; ";"]

$R_{5a}$ is biotin; $R_{5b}$ is avidin (e.g., streptavidin); $R_{6a}$ is AF532, $R_8$ is

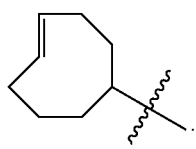

The eighth agent comprises compound N, and the compound N is 1, 2, 4, 5-tetrazine BHQ2.

In some preferred embodiments, the first compound has the structure shown in formula (Ic):

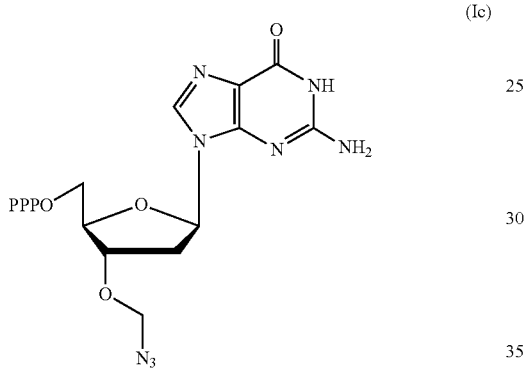

(Ic)

In some preferred embodiments, the second compound has the structure shown in formula (IIc):

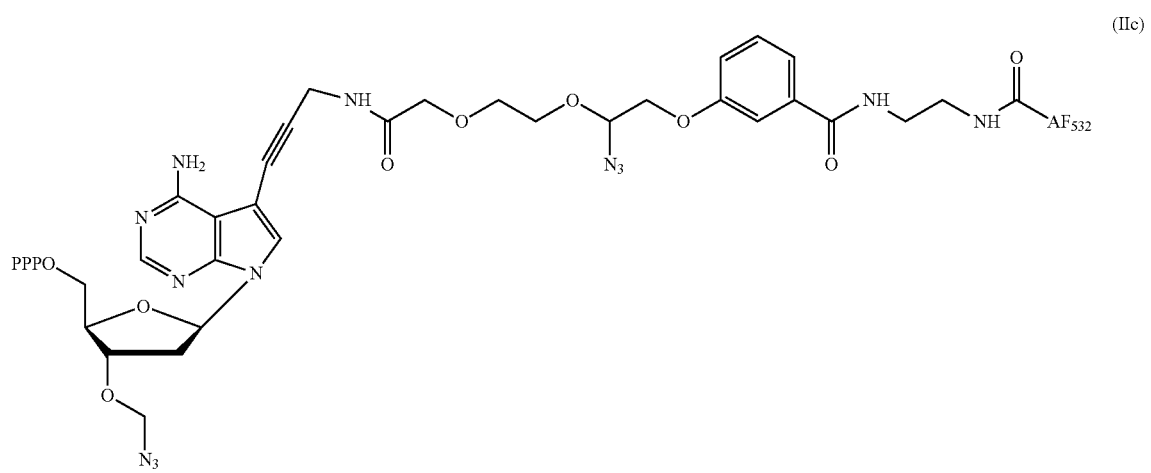

(IIc)

In some preferred embodiments, the third compound has the structure shown in formula (IIIc):

(IIIc)

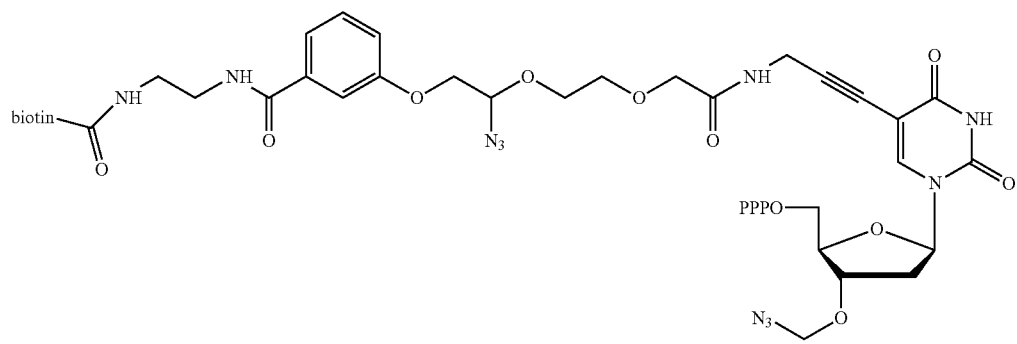

In some preferred embodiments, the fourth compound has the structure shown in formula (IIc):

(IVc)

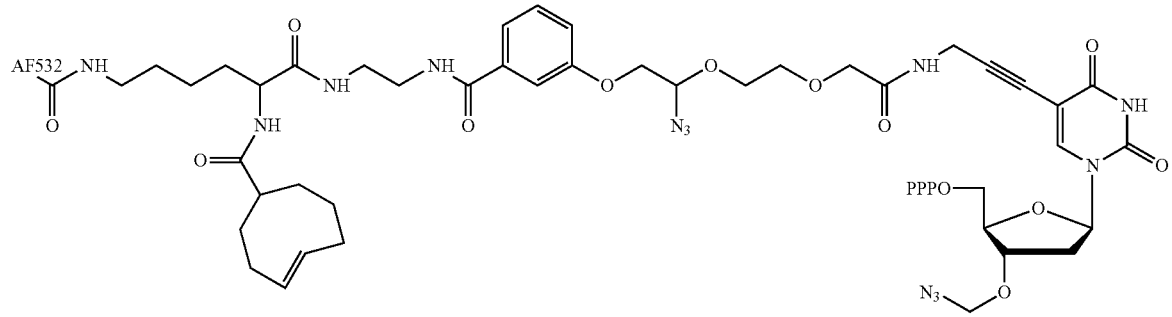

Additionally, as described above, in the method of the present invention, the washing step can be added as needed. The washing step can be added at any desired stage, and optionally, the washing step can be performed one or more times.

For example, in the step (5), after removing the solution phase of the reaction system, one or more washings may be performed to sufficiently remove the residual solution phase. Such a washing step may be advantageous, which can be used to sufficiently remove free compounds (i.e., not incorporated into the growing nucleic acid strand) carrying fluorophore (e.g., compounds of formula (II) and compounds of formula (IV)), thereby reducing the non-specific fluorescent signals as much as possible.

Similarly, in step (7), after removing the solution phase of the reaction system, one or more washings may be performed to sufficiently remove the residual solution phase. Such a washing step may be advantageous, which can be used to sufficiently remove agent carrying the fluorescence used in step (6), thereby reducing non-specific fluorescent signals as much as possible.

Similarly, in step (9), after removing the solution phase of the reaction system, one or more washings may be performed to sufficiently remove the residual solution phase. Such a washing step may be advantageous, which can be used to sufficiently remove the agents used in step (8) as well as the products produced (which may carry fluorescence), thereby reducing non-specific fluorescent signals as much as possible and avoiding adverse effect on subsequent polymerization reaction.

The washing step can be carried out with various suitable washing solutions. Examples of such washing solutions include, but are not limited to, phosphate buffer, citrate buffer, Tris-HCl buffer, acetate buffer, carbonate buffer, and the like. It is within the ability of those skilled in the art to select a suitable washing solution (including suitable ingredients, concentrations, ionic strength, pH, etc.) according to the actual needs.

Exemplary Embodiment 5

In some exemplary embodiments, the ability of the four compounds to emit fluorescent signals can be controlled (for example, maintained or changed) in step (6) by using a binding pair (containing two members that can be interacted with each other by specific non-covalent interaction); and preferably, the removal of the protecting group and the fluorescent signal can be achieved in step (8) by using a reactive group capable of performing a bioorthogonal cleavage reaction. For example, in some exemplary embodiments, the first, second, third, and fourth compounds may have the structures of formulas (I), (II), (III), and (IV), respectively:

(I)

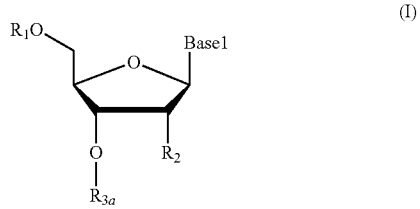

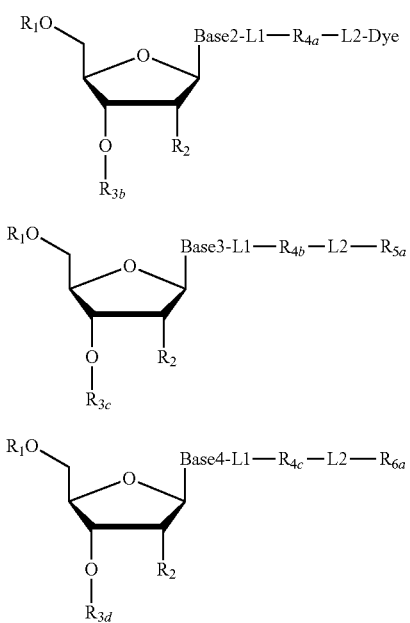

Wherein, Base1, Base2, Base3 and Base4 represent 4 different bases, and are selected from A, (T/U), C and G;

$R_1$ is independently selected from —H, monophosphate group (—PO$_3$H$_2$), diphosphate group (—PO$_3$H—PO$_3$H$_2$), triphosphate group (—PO$_3$H—PO$_3$H—PO$_3$H$_2$) and tetraphosphate group (—PO$_3$H—PO$_3$H—PO$_3$H—PO$_3$H$_2$);

$R_2$ is independently selected from —H and —OH;

$R_{3a}$, $R_{3b}$, $R_{3c}$, $R_{3d}$, $R_{4a}$, $R_{4b}$, and $R_{4c}$ are each independently a reactive group capable of performing a bioorthogonal cleavage reaction;

$R_{5a}$ is one member of the first binding pair;

$R_{6a}$ is one member of the second binding pair, optionally, $R_{6a}$ is Dye$_1$, or is linked with -L3-Dye$_1$;

L1 is independently a linking group or absent;
L2 is independently a linking group or absent;
L3 is a linking group or absent;

Dye and Dye$_1$ represent a fluorophore capable of emitting a fluorescent signal; and, both of them have the same structure, or have different structures but have the same or substantially the same emission spectrum;

optionally, a reactive group $R_8$ capable of performing the bioorthogonal ligation reaction is present between $R_{4c}$ and $R_{6a}$.

In such exemplary embodiment, the fourth compound itself may carry a fluorophore capable of emitting the same fluorescent signal as the second compound, or may not carry a fluorophore, but specifically interacts with/binds to the agent (for example, the other member of the second binding pair, represented by "$R_{6b}$-L4-Dye$_2$" herein) carrying a fluorophore (for example, a fluorophore having the same structure as the second compound, or a fluorophore having the same or substantially the same emission spectrum as the fluorophore of the second compound) in step (5), thereby the fluorophore is introduced into the fourth compound, and is capable of emitting the same fluorescent signal as the second compound.

Further, the third compound can be enabled to carry a fluorophore by specific interaction/binding between $R_{5a}$ and the other member (represented as "$R_{5b}$-L5-Dye$_3$" herein, wherein $R_{5b}$ is the other member of the first binding pair, L5 is a linking group or absent; Dye$_3$ represents a fluorophore that is capable of emitting a fluorescent signal, it is preferably a fluorophore which is the same as the second compound (or a fluorophore which has a different structure but the same or substantially the same emission spectrum) of the first binding pair carrying the fluorophore. In addition, furthermore, (i) $R_{6b}$ can be enabled to specifically interact with/bind to the other member $R_6$ of the third binding pair, to dissociate the conjugate of $R_{6b}$ and $R_{6a}$, thereby making the fourth compound to lose the fluorophore, or (ii) $R_8$ in the fourth compound can be enabled to perform bioorthogonal ligation reaction with the compound carrying the quenching group to quench the fluorescent signal emitted by the fluorophore Dye$_1$ or Dye$_2$ in the fourth compound. In such exemplary embodiments, $R_{6b}$ can be one member of two binding pairs ($R_{6a}$ and $R_{6b}$ of the second binding pair, $R_{6b}$ and $R_6$ of the third binding pair). Particularly preferably, the two members of the first binding pair ($R_{5a}$ and $R_{5b}$) do not interact with the two members of the third binding pair ($R_{6b}$ and $R_{6c}$). Furthermore, it is particularly preferred that $R_{5a}$ and $R_{5b}$ do not influence the specific interaction between $R_{6b}$ and $R_{6c}$, and that $R_{6b}$ and $R_{6c}$ do not influence the specific interaction between $R_{5a}$ and $R_{5b}$.

Therefore, in some preferred embodiments, in step (6), the duplex or the growing nucleic acid strand is subjected to a treatment which has no effect on the first compound and the second compound, but enables $R_{5a}$ to specifically interact with/bind to the other member ($R_{5b}$-L5-Dye$_3$) of the first binding pair carrying the fluorophore (thereby the fluorophore is introduced into the third compound to such that it carries the fluorophore and emits the fluorescent signal), and $R_{6b}$ can be enabled to specifically interact with/bind to the other member ($R_{6c}$) of the third binding pair, thereby making the fourth compound to lose the fluorophore, or $R_8$ in the fourth compound is enabled to perform bioorthogonal ligation reaction with the compound carrying the quencher, thereby quenching the fluorescent signal emitted by fluorophore in the fourth compound. In such exemplary embodiments, prior to the treatment of step (6), the first compound and the third compound, if present, do not fluoresce, and the second compound and the fourth compound, if present, fluoresce; also, after the treatment of step (6), the first compound (if present) still does not fluoresce, the second compound (if present) still fluoresces, the third compound (if present) changes to fluoresce, and the fourth compound, if present, changes to not fluoresce. Therefore, the type of compound incorporated into the 3' end of the growing nucleic acid strand can be determined by the results of two fluorescent signal detections.

Further, in such exemplary embodiments, the protecting group at 3' position of the ribose or deoxyribose in the compound incorporated into the 3' end of the growing nucleic acid strand, and the fluorophore (if present) on the duplex or the growing nucleic acid strand can be removed by subjecting $R_{3a}$, $R_{3b}$, $R_{3c}$, $R_{3d}$, $R_{4a}$, $R_{4b}$, $R_{4c}$ to a bioorthogonal cleavage reaction. Therefore, in some preferred embodiments, the duplex or the growing nucleic acid strand is subjected to a treatment in step (8), and such treatment enables $R_{3a}$, $R_{3b}$, $R_{3c}$, $R_{3d}$, $R_{4a}$, $R_{4b}$, $R_{4c}$ to perform the bioorthogonal cleavage reaction. In such exemplary embodiments, after the treatment of step (8), the growing nucleic acid strand will not have any fluorophore, and its 3'-end nucleotide will have free hydroxyl at 3' position of the ribose or deoxyribose, and the free hydroxyl can be used for initiating next round of polymerization reaction.

Therefore, in some preferred embodiments, the method of the invention comprises the steps of:

(1) providing a nucleic acid molecule to be sequenced on the support or attaching the nucleic acid molecule to be sequenced to the support;

(2) adding primers for initiating nucleotide polymerization, polymerases for performing nucleotide polymerization, and the first, second, third and fourth compounds of formula (I), formula (II), formula (III) and formula (IV), respectively, thereby forming reaction system containing solution phase and solid phase:

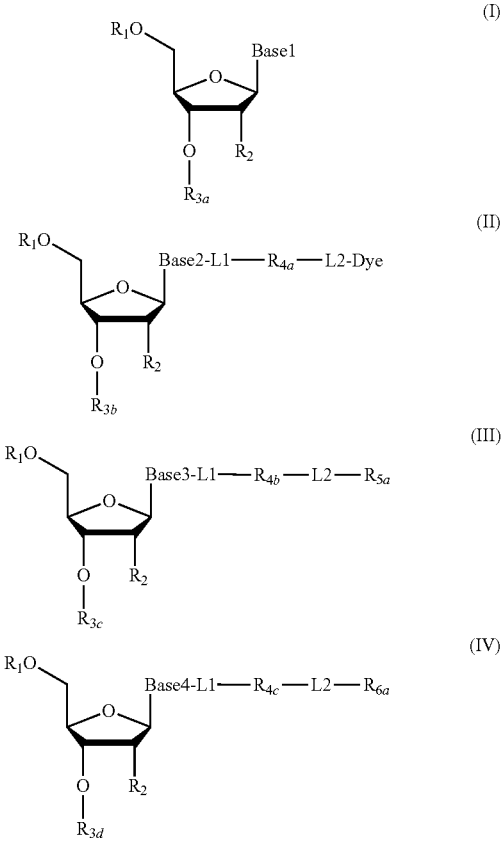

Wherein, Base1, Base2, Base3, and Base4 represent 4 different bases, and are selected from A, (T/U), C, and G;

$R_1$ is each independently selected from —H, monophosphate group (—$PO_3H_2$), diphosphate group (—$PO_3H$—$PO_3H_2$), triphosphate group (—$PO_3H$—$PO_3H$—$PO_3H_2$) and tetraphosphate group (—$PO_3H$—$PO_3H$—$PO_3H$—$PO_3H_2$);

$R_2$ is each independently selected from —H and —OH;

$R_{3a}$, $R_{3b}$, $R_{3c}$, $R_{3d}$, $R_{4a}$, $R_{4b}$, and $R_{4c}$ are each independently a reactive group capable of performing a bioorthogonal cleavage reaction;

$R_{5a}$ is one member of the first binding pair;

$R_{6a}$ is one member of the second binding pair, optionally, $R_{6a}$ is $Dye_1$ or is also linked onto -L3-$Dye_1$;

L1 is independently a linking group or absent;
L2 is independently a linking group or absent;
L3 is a linking group or absent;

Dye and $Dye_1$ represent fluorophore capable of emitting a fluorescent signal; and, they both have the same structure, or have different structures but the same or substantially the same emission spectrum;

optionally, there is a reactive group $R_8$ capable of performing a bioorthogonal ligation reaction between $R_{4c}$ and $R_{6a}$;

(3) annealing the primer to the nucleic acid molecule to be sequenced, and the primer serves as an initial growing nucleic acid strand, and forms a duplex attached to the support together with the nucleic acid molecule to be sequenced;

(4) performing a nucleotide polymerization reaction with polymerase under a condition allowing the polymerase to perform nucleotide polymerization, thereby incorporating one of the four compounds into the 3' end of the growing nucleic acid strand;

(5) (i) the fourth compound cannot emit a fluorescent signal, and then the duplex or the growing nucleic acid strand is subjected to a treatment in a reaction system containing a solution phase and a solid phase, the treatment does not have effect on the first compound, the second compound and the third compound, but enables $R_{6a}$ in the fourth compound to specifically interact with/bind to agent carrying the fluorophore (for example, a fluorophore having the same structure as the second compound, or a fluorophore having the same or substantially the same emission spectrum as the fluorophore of the second compound); thereafter, removing the solution phase of the reaction system in the previous step, retaining the duplex attached on the support and detecting whether the duplex or the growing nucleic acid strand emits the fluorescent signal;

the other member of the second binding pair carrying the fluorophore has the structure: $R_{6b}$-L4-$Dye_2$; wherein, $R_{6b}$ is the other member of the second binding pair, and L4 is independently a linking group or absent; $Dye_2$ represents a fluorophore capable of emitting a fluorescent signal and has the same structure as Dye, or has a different structure but the same or substantially the same emission spectrum; meanwhile, $R_{6b}$ is one member of the third binding pair;

(ii) the fourth compound is capable of emitting the same fluorescent signal as the second compound, then removing the solution phase of the reaction system in the previous step, retaining the duplex attached on the support, and detecting whether the duplex or the growing nucleic acid strand emits the fluorescent signal;

(6) subjecting the duplex or the growing nucleic acid strand to a treatment in a reaction system comprising a solution phase and a solid phase, wherein the treatment does not have influence on the first compound and the second compound, but enables $R_{5a}$ in the third compound to specifically bind to the other member of the first binding pair, thereby introducing the fluorophore into the third compound to enable it to emit a fluorescent signal; and (i) enable the other member $R_{6b}$ to specifically interact with/bind to the other member $R_{6c}$ of the third binding pair to dissociate the conjugate of $R_{6b}$ and $R_{6a}$, thereby making the fourth compound to lose the fluorophore, or (ii) enable $R_8$ in the fourth compound to perform bioorthogonal ligation reaction with compound carrying quenching group, thereby quenching the fluorescent signal emitted by the fluorophore $Dye_1$ or $Dye_2$ in the fourth compound; wherein, the other member of the first binding pair carrying a fluorophore has the following structure: $R_{5b}$-L5-$Dye_3$; wherein $R_{5b}$ is the other member of the first binding pair, and L5 is independently a linking group or absent; $Dye_3$ denotes a fluorophore capable of emitting a fluorescent signal, and has the same structure as the fluorophore in the second compound, or a different structure but the same or substantially the same emission spectrum;

(7) removing the solution phase of the reaction system in the previous step, retaining the duplex attached to the support, and detecting whether the duplex or the growing nucleic acid strand emits the fluorescent signal.

In some preferred embodiments, the method further comprises the steps of:

(8) subjecting the duplex or the growing nucleic acid strand in the previous step to a treatment in a reaction system containing a solution phase and a solid phase, which enables $R_{3a}$, $R_{3b}$, $R_{3c}$, $R_{3d}$, $R_{4a}$, $R_{4b}$ and $R_{4c}$ to perform bioorthogonal cleavage reaction such that the compound incorporated at the 3' end of the growing nucleic acid strand has a free hydroxyl group at the 3' position of the ribose or deoxyribose (in other words, converting —$OR_{3a}$, —$OR_{3b}$, —$OR_{3c}$ or —$OR_{3d}$ (if present) into free hydroxy group) and removing the fluorophore on the duplex or growing nucleic acid strand (in other words, removing the fluorophore attached to $R_{4a}$, $R_{4b}$ or $R_{4c}$), if present;

(9) removing the solution phase of the reaction system in the previous step;

(10) adding a polymerase for performing nucleotide polymerization, and the first compound, the second compound, the third compound, and the fourth compound, thereby forming a reaction system containing a solution phase and a solid phase, and then performing the steps (4)-(7).

In some preferred embodiments, the method further comprises the steps of:

(11) repeating steps (8)-(10) one or more times.

In some exemplary embodiments, if, in step (4), the compound of formula (I) is incorporated into the 3' end of the growing nucleic acid strand, then since the compound of formula (I) does not carry a fluorophore, and it does not react in step (6), no fluorescent signal will be detected in steps (5) and (7). In other words, if no fluorescent signal is detected in both of steps (5) and (7), it can be determined that the compound incorporated at the 3' end of the growing nucleic acid strand is the compound of formula (I).

If, in step (4), the compound of formula (II) is incorporated into the 3' end of the growing nucleic acid strand, since the compound of formula (II) itself carries a fluorophore and does not perform any reaction in step (6), a fluorescent signal will be detected in both steps (5) and (7). In other words, if a fluorescent signal is detected in both of steps (5) and (7), it can be determined that the compound incorporated at the 3' end of the growing nucleic acid strand is the compound of formula (II).

If, in step (4), the compound of formula (II) is incorporated at the 3' end of the growing nucleic acid strand, then (i) since the compound of formula (III) does not carry a fluorophore, no fluorescent signal will be detected in step (5); and (ii) since the compound of formula (III) specifically binds to the other member ($R_{5b}$-L-$Dye_3$) in the first binding pair carrying a fluorophore, introducing the fluorophore into the growing nucleic acid strand, therefore, a fluorescent signal will be detected in step (7). In other words, if a fluorescent signal is not detected in step (5) but is detected in step (7), it can be determined that the compound incorporated at the 3' end of the growing nucleic acid strand is the compound of formula (III).

If, in step (4), the compound of formula (IV) is incorporated at the 3' end of the growing nucleic acid strand, then (i) since the compound of formula (IV) itself carries a fluorophore or is treated in step (5) to carry a fluorophore, therefore, a fluorescent signal will be detected in step (5); and (ii) since the compound of formula (IV) loses fluorophore in step (6) due to dissociation of conjugate of $R_{6a}$ and $R_{6b}$, or performs bioorthogonal ligation reaction, introducing the quenching group into the growing nucleic acid strand, quenching the fluorescent signal emitted by the fluorophore, and therefore, no fluorescent signal will be detected in step (7). In other words, if a fluorescent signal is detected in step (5) and not detected in step (7), it can be determined that the compound incorporated at the 3' end of the growing nucleic acid strand is a compound of the formula (IV).

Therefore, in some preferred embodiments, the method of the present invention further comprises: after step (7), determining the type of the compound incorporated into 3' end of the growing nucleic acid strand in step (4) according to the detection results in steps (5) and (7), wherein, when both of the detection results of steps (5) and (7) are that the duplex or the growing nucleic acid strand does not emit the fluorescent signal, it is determined that the compound incorporated into 3' end of the growing nucleic acid strand in step (4) is the compound of formula (I);

when both of the detection results of steps (5) and (7) are that the duplex or the growing nucleic acid strand emits the fluorescent signal, it is determined that the compound incorporated into 3' end of the growing nucleic acid strand in step (4) is the compound of formula (II);

when the detection result of step (5) is that the duplex or the growing nucleic acid strand does not emit the fluorescent signal, and the detection result of step (7) is that the duplex or the growing nucleic acid strand emits the fluorescent signal, it is determined that the compound incorporated into 3' end of the growing nucleic acid strand in step (4) is the compound of formula (III); and, when the detection result of step (5) is that the duplex or the growing nucleic acid strand emits the fluorescent signal, and the detection result of step (7) is that the duplex or the growing nucleic acid strand does not emit the fluorescent signal, it is determined that the compound incorporated into 3' end of the growing nucleic acid strand in step (4) is the compound of formula (IV).

In some preferred embodiments, the method of the present invention further comprises that, after step (7), based on the base complementary pairing principle, the type of base at the corresponding position in the nucleic acid molecule to be sequenced is determined according to the type of the compound incorporated at the 3' end of the growing nucleic acid strand in step (4).

In some preferred embodiments, the compound of formula (I), the compound of formula (II), the compound of formula (III) and the compound of formula (IV) do not react with each other during the nucleotide polymerization reaction.

In some preferred embodiments, Base1 and Base2 are purine bases, and Base3 and Base4 are pyrimidine bases. In some preferred embodiments, Base1 is base G, Base2 is base A, Base3 is base C, and Base4 is base T or U. In some preferred embodiments, Base1 is base G, Base2 is base A, Base3 is base T or U, and Base4 is base C. In some preferred embodiments, Base1 is base A, Base2 is base G, Base3 is base C, and Base4 is base T or U. In some preferred embodiments, Base1 is base A, Base2 is base G, Base3 is base T or U, and Base4 is base C.

In some preferred embodiments, Base1 and Base2 are pyrimidine bases, and Base3 and Base4 are purine bases. In some preferred embodiments, Base1 is base C, Base2 is base T or U, Base3 is base G, and Base4 is base A. In some preferred embodiments, Base1 is base C, Base2 is base T or U, Base3 is base A, and Base4 is base G. In some preferred embodiments, Base1 is base T or U, Base2 is base C, Base3 is base G, and Base4 is base A. In some preferred embodiments, Base1 is base T or U, Base2 is base C, Base3 is base A, and Base4 is base G.

In some preferred embodiments, the compound of formula (I), the compound of formula (II), the compound of formula (III) and the compound of formula (IV) have the same $R_1$. In some preferred embodiments, $R_1$ is independently —H. In some preferred embodiments, $R_1$ is independently monophosphate group (—$PO_3H_2$). In some preferred embodiments, $R_1$ is independently diphosphate group (—$PO_3H$—$PO_3H_2$). In some preferred embodiments, $R_1$ is independently triphosphate group (—$PO_3H$—$PO_3H$—$PO_3H_2$). In some preferred embodiments, $R_1$ is independently tetraphosphate group (—$PO_3H$—$PO_3H$—$PO_3H$—$PO_3H_2$).

In some preferred embodiments, the compound of formula (I), the compound of formula (II), the compound of formula (III) and the compound of formula (IV) have the same $R_2$. In some preferred embodiments, $R_2$ is independently —H. In some preferred embodiments, $R_2$ is independently —OH.

In some preferred embodiments, $R_{3a}$, $R_{3b}$, $R_{3c}$, $R_{3d}$, $R_{4a}$, $R_{4b}$, $R_{4c}$ are each independently capable of performing a bioorthogonal cleavage reaction. As used herein, the expression "each capable of independently performing a bioorthogonal cleavage reaction" means that the reactive groups, agents, or molecules, etc. mentioned are each capable of performing a bioorthogonal cleavage reaction, while do not interfere with or influence each other. For example, the expression "$R_{3a}$ and $R_{3b}$ are each independently capable of performing a bioorthogonal cleavage reaction" means that both $R_{3a}$ and $R_{3b}$ are capable of performing a bioorthogonal cleavage reaction, and $R_{3a}$ does not influence the progress of the bioorthogonal cleavage reaction of $R_{3b}$, and $R_{3b}$ does not influence the progress of the bioorthogonal cleavage reaction of $R_{3a}$.

In some exemplary embodiments, $R_{3a}$ is the first reactive group capable of performing the bioorthogonal cleavage reaction in the presence of a first agent; $R_{3b}$ is the second reactive group capable of performing the bioorthogonal cleavage reaction in the presence of a second agent; $R_{3c}$ is the third reactive group capable of performing the bioorthogonal cleavage reaction in the presence of a third agent; $R_{3d}$ is the fourth reactive group capable of performing the bioorthogonal cleavage reaction in the presence of a fourth agent; $R_{4a}$ is the fifth reactive group capable of performing the bioorthogonal cleavage reaction in the presence of a fifth agent; $R_{4b}$ is the sixth reactive group capable of performing the bioorthogonal cleavage reaction in the presence of a sixth agent; $R_{4c}$ is the seventh reactive group capable of performing the bioorthogonal cleavage reaction in the presence of a seventh agent;

Preferably, in such embodiments, a first agent, a second agent, a third agent, a fourth agent, a fifth agent, a sixth agent, and a seventh agent can be added in step (8), thereby enabling $R_{3a}$, $R_{3b}$, $R_{3c}$, $R_{3d}$, $R_{4a}$, $R_{4b}$ and $R_{4c}$ (if present) each to perform the bioorthogonal cleavage reaction. Thus, $R_{3a}$, $R_{3b}$, $R_{3c}$, $R_{3d}$ (if present) will be removed from 3' position of ribose or deoxyribose (in other words, —$OR_{3a}$, —$OR_{3b}$, —$OR_{3c}$ or —$OR_{3d}$ (if present) will be converted into a free hydroxy group), and $R_{4a}$ and the fluorophore (if present) attached thereto, $R_{4b}$ and the fl (if present) attached thereto, and $R_{4c}$ and a fluorophore (if present) attached thereto will also be removed. Thus, after step (8), the growing nucleic acid strand will not carry the fluorophore and have free hydroxyl group at the 3' end, which can be used for the next round of polymerization. Therefore, in some preferred embodiments, in step (8), the first agent, the second agent, the third agent, the fourth agent, the fifth agent, the sixth agent, and the seventh agent are added to form a reaction system containing a solution phase and a solid phase, and the duplex is incubated with the first agent, the second agent, the third agent, the fourth agent, the fifth agent, the sixth agent, and the seventh agent under a condition allowing $R_{3a}$, $R_{3b}$, $R_{3c}$, $R_{3d}$, $R_{4a}$, $R_{4b}$ and $R_{4c}$ each to perform the bioorthogonal cleavage reaction.

In some preferred embodiments, $R_{3a}$, $R_{3b}$, $R_{3c}$ and $R_{3d}$ is capable of performing a bioorthogonal cleavage reaction in the presence of the same agent. In this case, preferably, in step (8), the first agent, the second agent, the third agent, and the fourth agent are the same agents.

In some preferred embodiments, $R_{3a}$, $R_{3b}$, $R_{3c}$ and $R_{3d}$ are the same reactive groups. In this case, preferably, in step (8), the first agent, the second agent, the third agent, and the fourth agent are the same agents. In other words, in step (8), the same $R_{3a}$, $R_{3b}$, $R_{3c}$ and $R_{3d}$ (if present) will each perform the bioorthogonal cleavage reaction in the presence of the same agent (i.e., the first agent), and be excised from the growing nucleic acid strand.

In some preferred embodiments, $R_{4a}$, $R_{4b}$ and $R_{4c}$ is capable of performing the bioorthogonal cleavage reaction in the presence of the same agent. Preferably, in step (8), the fifth agent, the sixth agent, and the seventh agent are the same agents.

In some preferred embodiments, $R_{4a}$, $R_{4b}$ and $R_{4c}$ are the same reactive groups. In this case, preferably, in step (8), the fifth agent, the sixth agent, and the seventh agent are the same agents. In other words, in step (8), the same $R_{4a}$, $R_{4b}$ and $R_{4c}$ (if present) will each perform the bioorthogonal cleavage reaction in the presence of the same agent (i.e., the fifth agent), and be excised from the growing nucleic acid strand.

In some preferred embodiments, $R_{3a}$, $R_{3b}$, $R_{3c}$, $R_{3d}$, $R_{4a}$, $R_{4b}$ and $R_{4c}$ is capable of performing the bioorthogonal cleavage reaction in the presence of the same agent. In this case, preferably, in step (8), the first agent, the second agent, the third agent, the fourth agent, the fifth agent, the sixth agent, and the seventh agent are the same agents. In other words, in step (8), it is only necessary to add the same agent (i.e., the first agent), and $R_{3a}$, $R_{3b}$, $R_{3c}$, $R_{3d}$, $R_{4a}$, $R_{4b}$ and $R_{4c}$ (if present) will each perform the bioorthogonal cleavage reaction in the presence of the same agent (i.e., the first agent), and be excised from the growing nucleic acid strand.

In some exemplary embodiments, it is particularly preferred that the two members ($R_{5a}$ and $R_{5b}$) of the first binding pair do not interact with the two members ($R_{6b}$ and $R_{6c}$) of the third binding pair. Furthermore, it is particularly preferred that $R_{5a}$ and $R_{5b}$ do not influence the specific interaction between $R_{6b}$ and $R_{6c}$, and that $R_{6b}$ and $R_{6c}$ do not influence the specific interaction between $R_{5a}$ and $R_{5b}$. In such embodiments, preferably, in step (6), $R_{5b}$-L5-Dye$_3$ and $R_{6c}$ may be added such that $R_{5a}$ (if present) in the compound of formula (III) specifically binds to $R_{5b}$ in $R_{5b}$-L5-Dye$_3$, and the conjugate of $R_{6a}$ (if present) and $R_{6b}$ in the compound of formula (IV) dissociates. Thus, the fluorophore Dye3 linked onto $R_{5b}$ is introduced into the compound of formula (III) through the specific interaction between the two members ($R_{5a}$ and $R_{5b}$) of the first binding pair, such that the compound of formula (III) emits the fluorescent signal. At the same time, the conjugate of $R_{6a}$ and $R_{6b}$ dissociates through the specific interaction between the two members ($R_{6b}$ and $R_{6c}$) of the third binding pair, such that the compound of formula (IV) loses the fluorophore, and the compound of formula (IV) no longer fluoresces. In such embodiments, it is also particularly preferred that, in step (6), $R_{5b}$-L5-Dye$_3$ does not react with the first compound and the second compound, and further preferably, $R_{6c}$ does not react with the first compound and the second compound. Thus, in some preferred embodiments, in step (6), $R_{5b}$-L5-$Dye_3$ and $R_{6c}$ can be added to form a reaction system containing a solution phase and a solid phase, wherein $R_{5b}$ is the other member of the first binding pair, L5 is a linking group or absent; $Dye_3$ represents a fluorophore capable of emitting a fluorescent signal, and $R_{6c}$ is the other member of a third binding pair; then, the duplex is incubated with $R_{5b}$-L5-$Dye_3$ and $R_{6c}$-L6-Que under a condition allowing $R_{5a}$ and $R_{5b}$ to specifically bind to each other and allowing $R_{6a}$ and $R_{6b}$ to specifically bind to each other.

In some exemplary embodiments, the fourth compound does not carry a fluorophore and $R_{6a}$ is one member of the second binding pair. In such embodiments, step (5) comprises adding a ninth agent such that $R_{6a}$ (if present) in the compound of formula (IV) specifically interacts with and/or binds to the other member of the second binding pair. For example, the ninth agent can comprise the other member carrying a fluorophore of a second binding pair having the structure $R_{6b}$-L4-$Dye_2$, wherein, $R_{6b}$ is the other member of the second binding pair, and L4 is independently a linking group or absent; $Dye_2$ represents a fluorophore capable of emitting a fluorescent signal and has the same structure as Dye, or is structurally different but has the same emission spectrum. In such embodiments, step (6) comprises adding a tenth agent such that the conjugate of $R_{6a}$ (if present) and $R_{6b}$ in the compound of formula (IV) dissociates. For example, the tenth agent can comprise the other member $R_{6c}$ of the third binding pair that is capable of specifically binding to $R_{6b}$ to replace $R_{6a}$, such that the conjugate formed by $R_{6a}$ and $R_{6b}$ dissociates.

Preferably, in such embodiments, in step (6), an eighth agent and a ninth agent may be added such that $R_{5a}$ (if present) in the compound of formula (III) specifically interacts with and/or binds to the other member of the first binding pair, and the conjugate formed by $R_{6a}$ and $R_{6b}$ in the compound of formula (IV) dissociates. For example, the eighth agent can comprise the other member of the first binding pair, the other member of the first binding pair carries the same fluorophore (or the structure is different but the emission spectrum is the same or substantially the same) as the second compound and the fourth compound, and the other member of the first binding pair is capable of specifically binding to $R_{5a}$ and thereby introducing the carried fluorophore into the compound of formula (III). Furthermore, the ninth agent comprises the other member of the third binding pair and is capable of specifically interacting with and/or specifically binding to $R_{6b}$ such that the conjugate formed by $R_{6a}$ and $R_{6b}$ in the compound of formula (IV) dissociates and this results in the loss of fluorophores in the compound of formula (IV). In such embodiments, it is also particularly preferred that, in step (6), the eighth agent does not react with the first compound and the second compound, and further preferably, the ninth agent does not react with the first compound and the second compound. Therefore, in some preferred embodiments, in step (6), an eighth agent and a ninth agent may be added to form a reaction system containing a solution phase and a solid phase, wherein the eighth agent comprises the other member of the first binding pair, the other member of the first binding pair can carry the same fluorophore (or a fluorophore having a different structure but the same or substantially the same emission spectrum) as the second compound and the fourth compound, and said the other member of the first binding pair is capable of specifically interacting with and/or binding to $R_{5a}$ to introduce the carried fluorophore into the third compound; the ninth agent comprises the other member of the third binding pair, and the other member of the third binding pair is capable of specifically interacting with and/or binding to $R_{6b}$ such that the conjugate formed by $R_{6a}$ and $R_{6b}$ in the compound of formula (IV) dissociates; then, the duplex is incubated with the seventh agent and the ninth agent under a condition allowing $R_{5a}$ to specifically interact with and/or bind to the other member of the first binding pair and allowing $R_{6b}$ to specifically interact with and/or bind to the other member of the third binding pair.

In some exemplary embodiments, a reactive group $R_8$ capable of performing the third bioorthogonal ligation reaction is present between $R_{5b}$ and $R_{7a}$ of the fourth compound. In some preferred embodiments, $R_{3a}$, $R_{3b}$, $R_{3c}$, $R_{3d}$, $R_{4a}$, $R_{4b}$, $R_{5a}$ and $R_8$ can each perform the bioorthogonal cleavage reaction or bioorthogonal ligation reaction. In some exemplary embodiments, $R_{8a}$ is capable of performing a bioorthogonal ligation reaction in the presence of a tenth agent.

In some preferred embodiments, $R_{3a}$, $R_{3b}$, $R_{3c}$, and $R_{3d}$ are each independently selected from the group consisting of —$CH_2CH$=$CH_2$, —$CH_2N_3$, $C_{3-8}$ cycloalkenyl (e.g., $C_3$ cycloalkenyl, $C_4$ cycloalkenyl, $C_5$ membered cycloalkenyl, $C_6$ cycloalkenyl, $C_7$ cycloalkenyl or $C_8$ cycloalkenyl). In some preferred embodiments, the $C_{3-8}$ cycloalkenyl is selected from the group consisting of $C_3$ cycloalkenyl and $C_8$ cycloalkenyl. In some preferred embodiments, the $C_{3-8}$ cycloalkenyl group is

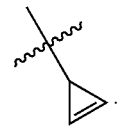

In some preferred embodiments, the $C_{3-8}$ cycloalkenyl group is

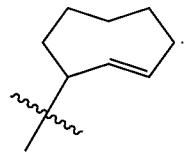

In some preferred embodiments, $R_{3a}$, $R_{3b}$, $R_{3c}$, and $R_{3d}$ are the same reactive groups and are selected from the group consisting of —$CH_2CH$=$CH_2$, —$CH_2N_3$, $C_{3-8}$ cycloalkenyl (e.g., $C_3$ cycloalkenene group, $C_4$ cycloalkenyl group, $C_5$ membered cycloalkenyl group, $C_6$ cycloalkenyl group, $C_7$ cycloalkenyl group or $C_8$ cycloalkenyl group). In some preferred embodiments, the $C_{3-8}$ cycloalkenyl is selected from the group consisting of $C_3$ cycloalkenyl and $C_8$ cycloalkenyl. In some preferred embodiments, the $C_{3-8}$ cycloalkenyl group is

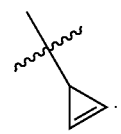

In some preferred embodiments, the $C_{3-8}$ cycloalkenyl group is

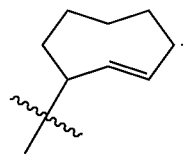

In some preferred embodiments, $R_{3a}$, $R_{3b}$, $R_{3c}$, and $R_{3d}$ are the same reactive groups and are all —$CH_2N_3$.

In some preferred embodiments, $R_{4a}$, $R_{4b}$ and $R_{4c}$ are each independently selected from the group consisting of:

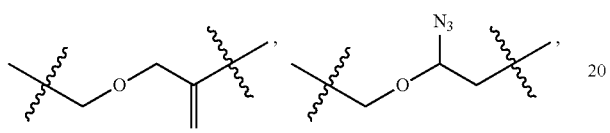

—O—$C_3$-8 cycloalkenylene. In some preferred embodiments, the "—O—$C_{3-8}$ cycloalkenylene subunit" is selected from the group consisting of —O—$C_3$ cycloalkenylene subunit, —O—$C_4$ cycloalkenylene subunit, —O—$C_5$ cycloalkenylene subunit, —O—$C_6$ cycloalkenylene subunit, —O—$C_7$ cycloalkenylene subunit, and —O—$C_8$ cycloalkenylene subunit. In some preferred embodiments, the "—O—$C_{3-8}$ cycloalkenylene subunit" is

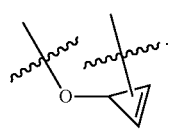

In some preferred embodiments, the "—O—$C_{3-8}$ cycloalkenylene subunit" is

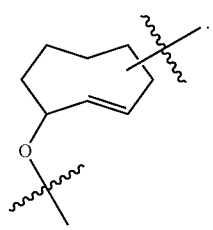

In some preferred embodiments, $R_{4a}$, $R_{4b}$ and $R_{4c}$ are the same reactive groups and are selected from the group consisting of:

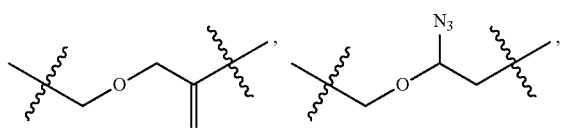

—O—$C_{3-8}$ cycloalkenylene. In some preferred embodiments, the "—O—$C_{3-8}$ cycloalkenylene subunit" is selected from the group consisting of —O—$C_3$ cycloalkenylene subunit, —O—$C_4$ cycloalkenylene subunit, —O—$C_5$ cycloalkenylene subunit, —O—$C_6$ cycloalkenylene subunit, —O—$C_7$ cycloalkenylene subunit, and —O—$C_8$ cycloalkenylene subunit. In some preferred embodiments, the "—O—$C_{3-8}$ cycloalkenylene subunit" is

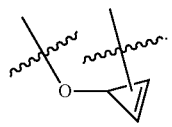

In some preferred embodiments, the "—O—$C_{3-8}$ cycloalkenylene subunit" is

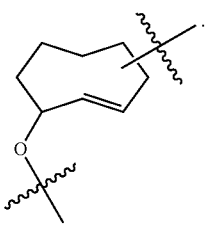

In some preferred embodiments, both $R_{4a}$, $R_{4b}$ and $R_{4c}$ are

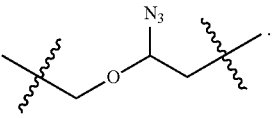

In some preferred embodiments, the first agent, the second agent, the third agent, the fourth agent, the fifth agent, the sixth agent and the seventh agent each independently comprise materials selected from the group consisting of:

a complex of palladium (for example, a complex of palladium with four triphenylphosphine 3,3',3"-trisulfonic acids);

a complex of ruthenium (for example, a complex of ruthenium with quinoline carboxylate (or a derivative thereof), allyl or cyclopentadiene);

a phosphide (e.g., a carboxyphosphine or hydroxyphosphine such as $P(CH_2CH_2COOH)_3$ or $P(CH_2CH_2OH)_3$); and Compound Q having the structural formula

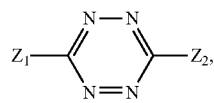

wherein $Z_1$ and $Z_2$ are each independently selected from a modified or unmodified alkyl (e.g., a $C_1$-$C_6$ alkyl such as $C_1$ alkyl, $C_2$ alkyl, $C_3$ alkyl, $C_4$ alkyl, $C_5$ alkyl or $C_6$ alkyl) and modified or unmodified aryl (for example, 6-10 membered aryl such as 6-membered aryl, 7-membered aryl, 8-membered aryl, 9-membered aryl or 10-membered aryl such as phenyl or pyridyl).

In some preferred embodiments, $R_{3a}$, $R_{3b}$, $R_{3c}$ and $R_{3d}$ are —$CH_2CH=CH_2$. In this case, preferably, $R_{4a}$, $R_{4b}$ and $R_{4c}$ are

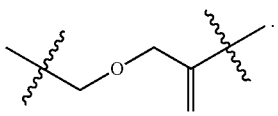

Further preferably, the first agent, the second agent, the third agent, the fourth agent, the fifth agent, the sixth agent and the seventh agent comprise a complex of palladium or a complex of ruthenium. Preferably, the first agent, the second agent, the third agent, the fourth agent, the fifth agent, the sixth agent and the seventh agent are the same agents, and comprise a complex of palladium or a complex of ruthenium.

In some preferred embodiments, $R_{3a}$, $R_{3b}$, $R_{3c}$, and $R_{3d}$ are —$CH_2$—$N_3$. In this case, preferably, $R_{4a}$, $R_{4b}$ and $R_{4c}$ are

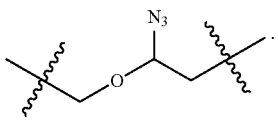

Further preferably, the first agent, the second agent, the third agent, the fourth agent, the fifth agent, the sixth agent and the seventh agent comprise phosphonate such as carboxyl phosphonate or hydroxyl phosphonate such as $P(CH_2CH_2COOH)_3$ or $P(CH_2CH_2OH)_3$. Preferably, the first agent, the second agent, the third agent, the fourth agent, the fifth agent, the sixth agent and the seventh agent are the same agents, and they comprise phosphonate such as carboxyl phosphonate or hydroxyl phosphonate such as $P(CH_2CH_2COOH)_3$ or $P(CH_2CH_2OH)_3$.

In some preferred embodiments, $R_{3a}$, $R_{3b}$, $R_{3c}$, and $R_{3d}$ are

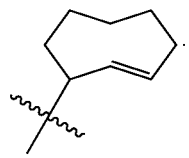 [SMILES: *C1/C=C/CCCCC1 ; "."]

In this case, preferably, $R_{4a}$, $R_{4b}$ and $R_{4c}$ are

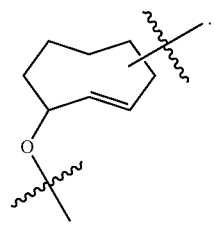

Further preferably, the first agent, the second agent, the third agents, the fourth agent, the fifth agent, the sixth agent and the seventh agent comprise the compound Q as defined above. Further preferably, in compound Q, $Z_1$ is a methyl group; and $Z_2$ is a modified or unmodified pyridyl group. More preferably, compound Q is

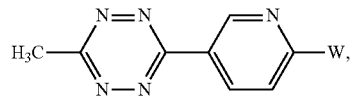

wherein, W is hydrogen or a modifying group. Preferably, the first agent, the second agent, the third agent, the fourth agent, the fifth agent, the sixth agent and the seventh agent are the same agents and comprise the compound Q as defined above.

In some preferred embodiments, the linking groups L1, L2 and L3 in the first compound, the second compound, the third compound, and the fourth compound, and linking groups L4, L5 and L6 in $R_{6b}$-L4-Dye$_2$, $R_{5b}$-L5-Dye$_3$ and $R_{6c}$-L6-Que are each independent and are not particularly limited. A person skilled in the art can select suitable linking groups L1, L2, L3, L4, L5 and L6 according to the bases (Base1, Base2, Base3 and Base4) and the reactive groups ($R_{4a}$, $R_{4b}$ and $R_{4c}$) used in the compounds and members ($R_{5a}$, $R_{5b}$, $R_{6a}$ and $R_{6b}$) of the first binding pair and the second binding pair.

In some exemplary embodiments, the linking groups L1, L2, L3, L4, L5 and L6 are each independently selected from the group consisting of:

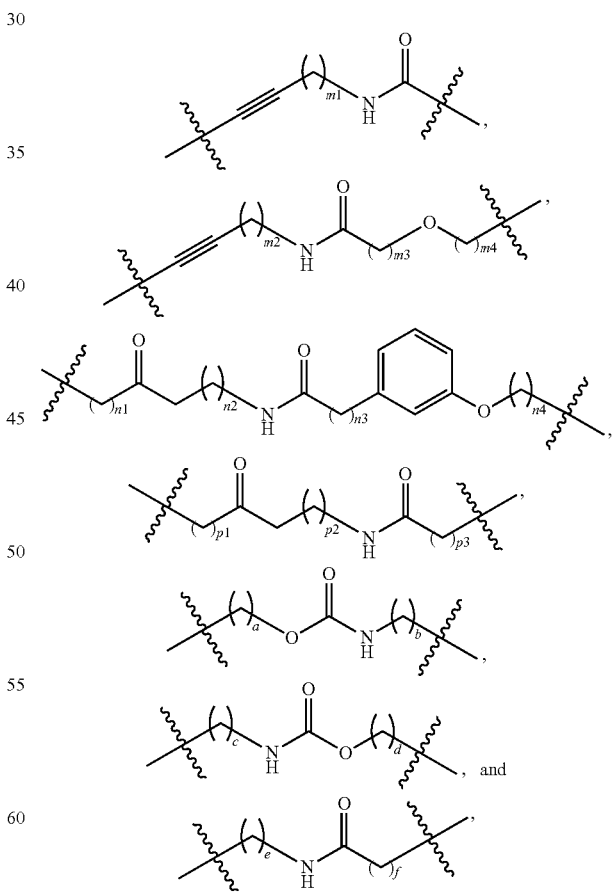

wherein m1, m2, m3, m4, n1, n2, n3, n4, p1, p2, p3, a, b, c, d, e and f are each independently selected from 0, 1, 2, 3, 4, 5 or 6.

In some exemplary embodiments, L1 in the first compound, the second compound, the third compound, and the fourth compound are each independently selected from the group consisting of:

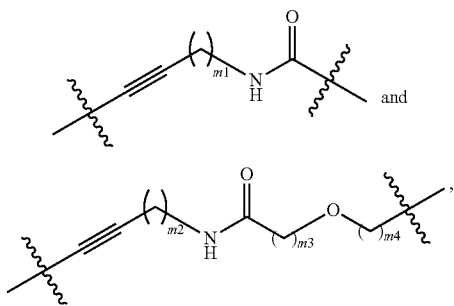

wherein m1, m2, m3, and m4 are each independently selected from 0, 1, 2, 3, 4, 5 or 6.

In some preferred embodiments, L1 in the first compound, the second compound, the third compound, and the fourth compound are each independently selected from the group consisting of:

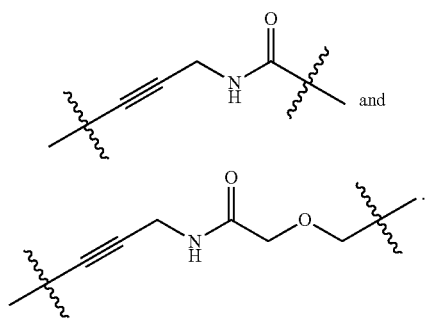

In some preferred embodiments, L2 in the first compound, the second compound, the third compound, and the fourth compound are each independently selected from the group consisting of:

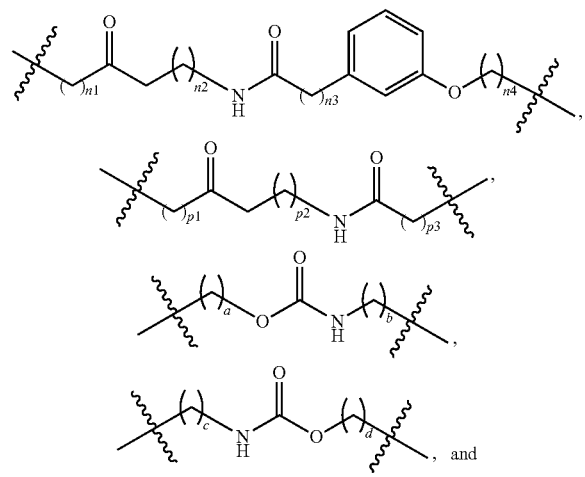

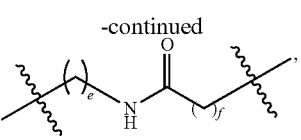

wherein n1, n2, n3, n4, p1, p2, p3, a, b, c, d, e, and f are each independently selected from 0, 1, 2, 3, 4, 5, or 6.

In some preferred embodiments, L2 in the first compound, the second compound, the third compound, and the fourth compound are each independently selected from the group consisting of:

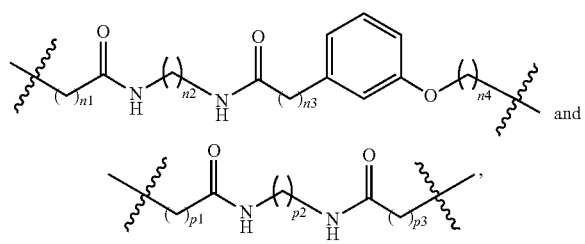

wherein n1, n2, n3, n4, p1, p2, p3 are each independently selected from 0, 1, 2, 3, 4, 5 or 6.

In some preferred embodiments, L2 in the first compound, the second compound, the third compound, and the fourth compound are each independently selected from the group consisting of:

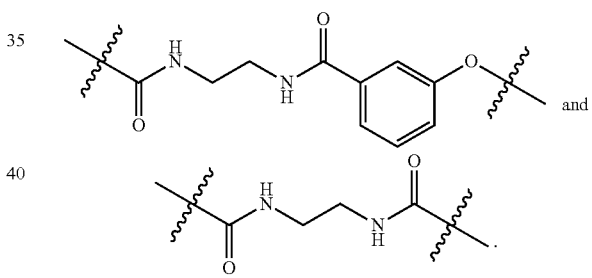

In some preferred embodiments, $R_{5a}$ and $R_{5b}$ are two members of the first binding pair, $R_{6a}$ and $R_{6b}$ are two members of the second binding pair, and $R_{6b}$ and $R_{6c}$ are two members of the third binding pair. In some preferred embodiments, the first binding pair and the second binding pair are each independently selected from the group consisting of: an antigen (e.g., a small molecule antigen)-antibody, a hapten-antibody, a hormone-receptor, a ligand-receptor, nucleic acid strand-complementary nucleic acid strand, substrate-enzyme, substrate analog-enzyme, inhibitor-enzyme, sugar-plant lectin, biotin-avidin (for example, avidin and streptavidin), digoxin and digoxin antibody, and 5-position bromodeoxyguanosine and its antibody.

In some preferred embodiments, the two members of the first binding pair are selected from the group consisting of: (a) biotin and avidin (for example, streptavidin), (b) digoxin and digoxin antibody; and (c) desthiobiotin and streptavidin.

In some preferred embodiments, the two members of the second binding pair are selected from the group consisting of: (a) biotin and avidin (for example, streptavidin); (b) digoxin and digoxin antibody; (c) desthiobiotin and streptavidin.

In some preferred embodiments, the two members of the third binding pair are selected from the group consisting of: (a) biotin and avidin (for example, streptavidin), (b) digoxin and digoxin antibody; (c) desthiobiotin and streptavidin.

It is particularly preferred that the two members of the first binding pair ($R_{5a}$ and $R_{5b}$) do not interact with the two members of the third binding pair ($R_{6a}$ and $R_{6c}$). Furthermore, it is particularly preferred that $R_{5a}$ and $R_{5b}$ do not influence the specific interaction between $R_{6b}$ and $R_{6c}$, and that $R_{6b}$ and $R_{6c}$ do not influence the specific interaction between $R_{5a}$ and $R_{5b}$. Thus, in some preferred embodiments, the two members of the first binding pair are digoxin and digoxin antibody, and the two members of the third binding pair are streptavidin and biotin, respectively. In some preferred embodiments, the two members of the second binding pair are desthiobiotin and streptavidin, respectively.

In some preferred embodiments, $R_{3a}$, $R_{3b}$, $R_{3c}$, and $R_{3d}$ are —$CH_2CH$=$CH_2$; $R_{4a}$, $R_{4b}$ and $R_{4c}$ are

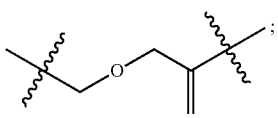 [SMILES: ";" ; *COCC(*)=C]

the first, second, third, fourth, fifth, sixth and seventh agent comprise a complex of palladium or a complex of ruthenium; $R_{5a}$ is biotin; $R_{5b}$ is avidin (for example, streptavidin); $R_{6a}$ is digoxin; $R_{6b}$ is digoxin antibody. Preferably, the first, second, third, fourth, fifth, sixth and seventh agents are the same agents, and comprise a complex of palladium or a complex of ruthenium.

In some preferred embodiments, $R_{3a}$, $R_{3b}$, $R_{3c}$, and $R_{3d}$ are —$CH_2$—$N_3$; $R_{4a}$, $R_{4b}$ and $R_{4c}$ are

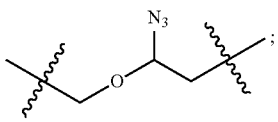 [SMILES: *COC(C*)N=[N+]=[N-] ; ";"]

the first, second, third, fourth, fifth, sixth and seventh agent comprise a phosphide such as a carboxyl phosphide or a hydroxyl phosphide such as $P(CH_2CH_2COOH)_3$ or $P(CH_2CH_2OH)_3$; $R_{5a}$ is biotin; $R_{5b}$ is avidin (for example, streptavidin); $R_{6a}$ is digoxin; $R_{6b}$ is digoxin antibody. Preferably, the first, second, third, fourth, fifth, sixth and seventh agents are the same agents and comprise a phosphide such as a carboxyl phosphide or a hydroxyl phosphide such as $P(CH_2CH_2COOH)_3$ or $P(CH_2CH_2OH)_3$.

In some preferred embodiments, $R_{3a}$, $R_{3b}$, $R_{3c}$, and $R_{3d}$ are —$CH_2$—$N_3$; $R_{4a}$, $R_{4b}$ and $R_{4c}$ are

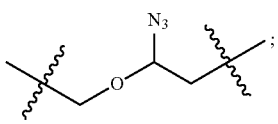 [SMILES: *COC(C*)N=[N+]=[N-] ; ";"]

the first, second, third, fourth, fifth, sixth and seventh agents comprise a phosphide such as a carboxyl phosphide or a hydroxyl phosphide, such as $P(CH_2CH_2COOH)_3$ or $P(CH_2CH_2OH)_3$; $R_{5a}$ is digoxin; $R_{5b}$ is digoxin antibody; $R_{6a}$ is biotin; $R_{6b}$ is avidin (for example, streptavidin).

Preferably, the first, second, third, fourth, fifth, sixth and seventh agents are the same agents and comprise a phosphide such as a carboxyl phosphide or a hydroxyl phosphide such as $P(CH_2CH_2COOH)_3$ or $P(CH_2CH_2OH)_3$.

In some preferred embodiments, $R_{3a}$, $R_{3b}$, $R_{3c}$, and $R_{3d}$ are —$CH_2CH$=$CH_2$; $R_{4a}$, $R_{4b}$ and $R_{4c}$ are

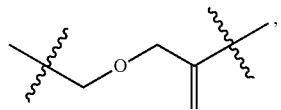 [SMILES: "," ; *COCC(*)=C]

the first, second, third, fourth, fifth, sixth and seventh agents comprise a complex of palladium or a complex of ruthenium; $R_{5a}$ is digoxin; $R_{5b}$ is digoxin antibody; $R_{6a}$ is biotin; $R_{6b}$ is avidin (for example, streptavidin). Preferably, the first, second, third, fourth, fifth, sixth and seventh agents are the same agents are the same agents, and comprise a complex of palladium or a complex of ruthenium.

In some preferred embodiments, $R_{3a}$, $R_{3b}$, $R_{3c}$, and $R_{3d}$ are

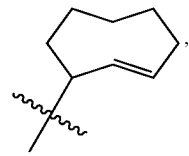

$R_{4a}$, $R_{4b}$ and $R_{4c}$ are

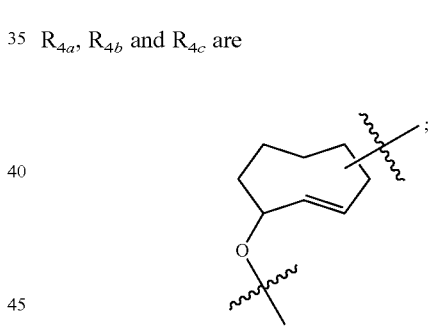

the first, second, third, fourth, fifth, sixth and seventh agent comprises Compound Q (for example, the compound Q as defined above); $R_{5a}$ is biotin; $R_{5b}$ is avidin (for example, streptavidin); $R_{6a}$ is digoxin; $R_{6b}$ is digoxin antibody. Preferably, the first, second, third, fourth, fifth, sixth and seventh agent are the same agents, and comprise Compound Q (e.g., the compound Q as defined above).

In some preferred embodiments, $R_{3a}$, $R_{3b}$, $R_{3c}$, and $R_{3d}$ are

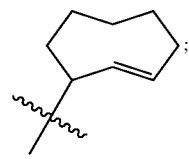

$R_{4a}$, $R_{4b}$ and $R_{4c}$ are

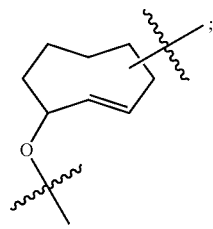

the first, second, third, fourth, fifth, sixth and seventh agent comprises Compound Q (for example, the compound Q as defined above); $R_{5a}$ is digoxin; $R_{5b}$ is digoxin antibody; $R_{6a}$ is biotin; $R_{6b}$ is avidin (for example, streptavidin). Preferably, the first, second, third, fourth, fifth, sixth and seventh agent are the same agents, and comprise Compound Q (e.g., the compound Q as defined above).

In some preferred embodiments, $R_{3a}$, $R_{3b}$, $R_{3c}$, and $R_{3d}$ are —CH$_2$CH=CH$_2$; $R_{4a}$, $R_{4b}$ and $R_{4c}$ are

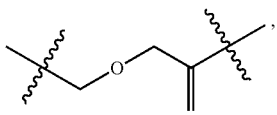 [SMILES: "," ; *COCC(*)=C]

the first, second, third, fourth, fifth, sixth and seventh agents comprise a complex of palladium or a complex of ruthenium; $R_{5a}$ is biotin; $R_{5b}$ is avidin (for example, streptavidin); $R_{6a}$ is Cy3; $R_{6b}$ is Cy3 antibody. Preferably, the first, second, third, fourth, fifth, sixth and seventh agents are the same agents, and comprise a complex of palladium or a complex of ruthenium.

In some preferred embodiments, $R_{3a}$, $R_{3b}$, $R_{3c}$, and $R_{3d}$ are

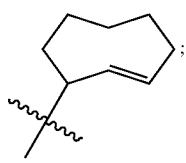

$R_{4a}$, $R_{4b}$ and $R_{4c}$ are

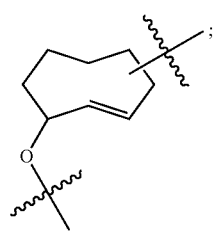

the first, second, third, fourth, fifth, sixth and seventh agent comprises Compound Q (for example, the compound Q as defined above); $R_{5a}$ is biotin; $R_{5b}$ is avidin (for example, streptavidin); $R_{6a}$ is Cy3; $R_{6b}$ is Cy3 antibody. Preferably, the first, second, third, fourth, fifth, sixth and seventh agent are the same agents, and comprise Compound Q (e.g., the compound Q as defined above).

In some preferred embodiments, $R_{3a}$, $R_{3b}$, $R_{3c}$, and $R_{3d}$ are

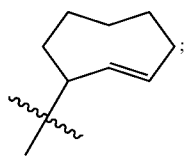

$R_{4a}$, $R_{4b}$ and $R_{4c}$ are

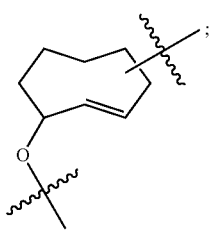

the first, second, third, fourth, fifth, sixth and seventh agent comprises Compound Q (for example, the compound Q as defined above); $R_{5a}$ is biotin; $R_{5b}$ is avidin (for example, streptavidin); $R_{6a}$ is Cy3; $R_{6b}$ is Cy3 antibody. Preferably, the first, second, third, fourth, fifth, sixth and seventh agent are the same agents, and comprise compound Q (e.g., the compound Q as defined above).

In some preferred embodiments, $R_{3a}$, $R_{3b}$, $R_{3c}$, and $R_{3d}$ are —CH$_2$—N$_3$; $R_{4a}$, $R_{4b}$ and $R_{4c}$ are

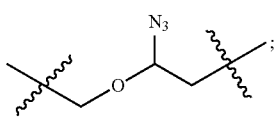 [SMILES: *COC(C*)N=[N+]=[N-]]

$R_{5a}$ is digoxin; $R_{5b}$ is digoxin antibody; $R_{6a}$ is desthiobiotin; $R_{6b}$ is streptavidin avidin (for example, streptavidin); $R_{6c}$ is biotin.

In some preferred embodiments, the first compound has the structure shown in formula (Id):

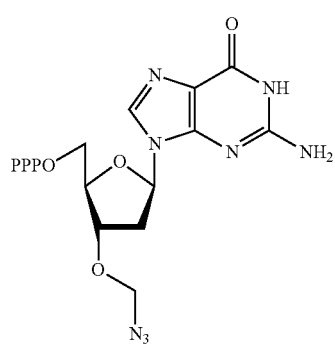

(Id)

In some preferred embodiments, the second compound has the structure shown in formula (IId):

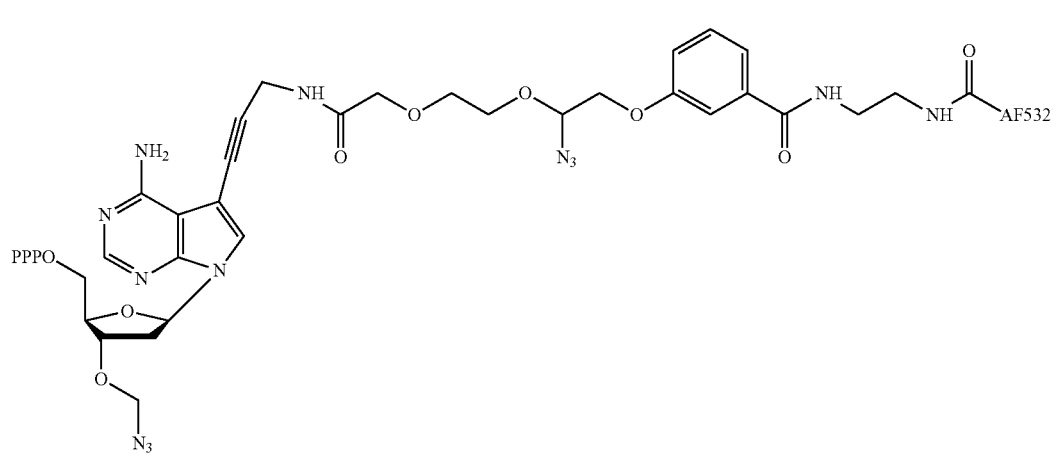

(IId)

In some preferred embodiments, the third compound has the structure shown in formula (IIId):

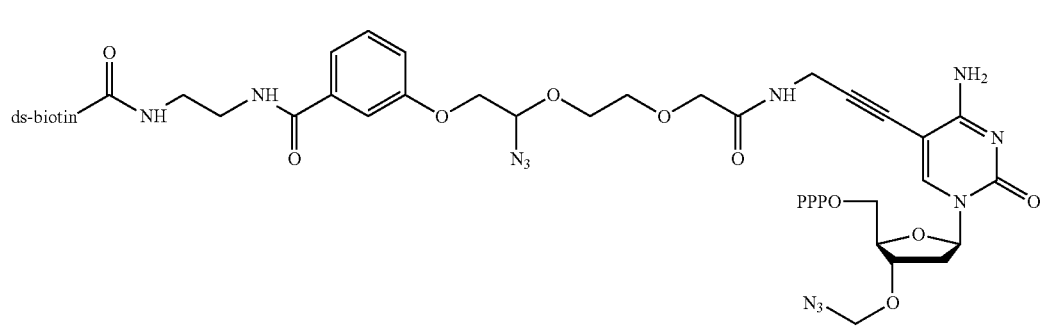

(IIId)

In some preferred embodiments, the fourth compound has the structure shown in formula (IVd):

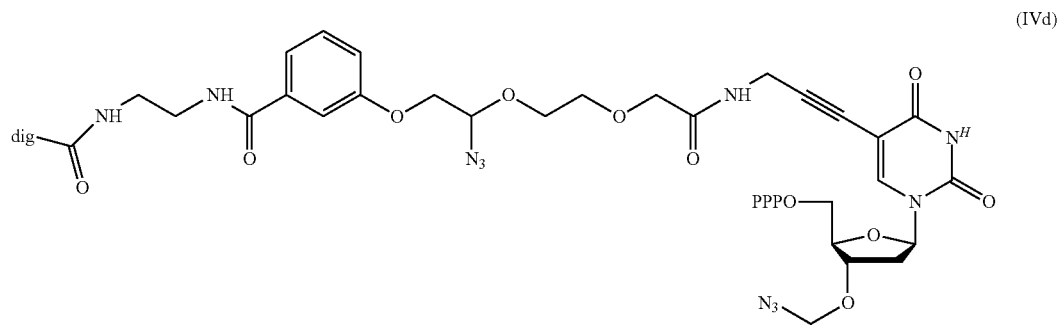

(IVd)

Additionally, as described above, washing steps can be added as needed in the method according to the present invention. The washing step can be added at any desired stage, and optionally, the washing step can be performed one or more times.

For example, one or more washings may be performed to sufficiently remove the residual solution phase in step (5) after removing the solution phase of the reaction system. Such washing step may be advantageous in that it can be used to substantially remove free (i.e., not incorporated into the growing nucleic acid strands) fluorophore-containing compounds (e.g., compound of formula (II) or compound of formula (IV)) to minimize non-specific fluorescent signals.

Similarly, one or more washings may be performed to sufficiently remove the residual solution phase in step (7), after removing the solution phase of the reaction system, such a washing step may be advantageous in that it can be used to sufficiently remove the agent carrying fluorescence used in step (6) to minimize non-specific fluorescent signals.

Similarly, one or more washings may be performed to sufficiently remove the residual solution phase in step (9) after removing the solution phase of the reaction system. Such a washing step may be advantageous, and it can be used to sufficiently remove the agents used in step (8) as well as the products produced (which may carry fluorescence), thereby reducing non-specific fluorescent signals and avoiding adverse effect on the subsequent polymerization reaction as much as possible.

Various suitable washing solution can be used for washing step. Examples of such washing solution comprise, but not limited to, phosphate buffer, citrate buffer, Tris-HCl buffer, acetate buffer, carbonate buffer, and the like. It is within the ability of those skilled in the art to select a suitable washing solution (including suitable ingredients, concentration, ionic strength, pH value, etc.) for washing step according to the actual needs.

Exemplary Embodiment 6

In some exemplary embodiments, the ability of the four compounds to emit fluorescent signals can be controlled (for example, maintained or changed) in step (6) by using a binding pair (containing two members that can be interacted with each other by specific non-covalent function); and preferably, the removal of the protecting group and the fluorescent signal can be achieved in step (8) by using a reactive group capable of performing a bioorthogonal cleavage reaction. For example, in some exemplary embodiments, the first, second, third, and fourth compounds may have the structures of formulas (I), (II), (III), and (IV), respectively:

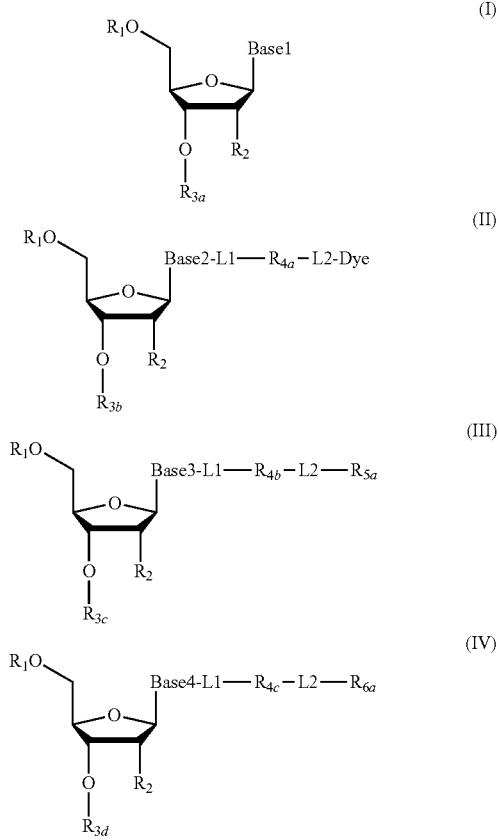

Wherein, Base1, Base2, Base3 and Base4 represent 4 different bases, and are selected from A, (T/U), C and G;

$R_1$ is independently selected from —H, monophosphate group (—PO$_3$H$_2$), diphosphate group (—PO$_3$H—PO$_3$H$_2$), triphosphate group (—PO$_3$H—PO$_3$H—PO$_3$H$_2$) and tetraphosphate group (—PO$_3$H—PO$_3$H—PO$_3$H—PO$_3$H$_2$);

$R_2$ is independently selected from —H and —OH;

$R_{3a}$, $R_{3b}$, $R_{3c}$, $R_{3d}$, $R_{4a}$, $R_{4b}$, and $R_{4c}$ are each independently a reactive group capable of performing a bioorthogonal cleavage reaction;

$R_{5a}$ is a reactive group capable of performing the first bioorthogonal ligation reaction;

$R_{6a}$ is one member of the first binding pair, optionally, $R_{6a}$ is Dye$_1$, or is linked with -L3-Dye$_1$;

L1 is independently a linking group or absent;
L2 is independently a linking group or absent;
L3 is a linking group or absent;

Dye and Dye$_1$ represent a fluorophore capable of emitting a fluorescent signal; and, both of them have the same structure, or have different structures but the same or substantially the same emission spectrum;

optionally, a reactive group $R_8$ capable of performing the bioorthogonal ligation reaction is present between $R_{4c}$ and $R_{6a}$.

In such exemplary embodiment, the fourth compound itself may carry a fluorophore capable of emitting the same fluorescent signal as the second compound, or may not carry a fluorophore, but specifically interacts with/binds to the agent (for example, the other member of the first binding pair, represented by "$R_{6b}$-L4-Dye$_2$" herein) carrying a fluorophore (for example, a fluorophore having the same structure as the second compound, or a fluorophore having the same or substantially the same emission spectrum as the fluorophore of the second compound) in step (5), thereby the fluorophore is introduced into the fourth compound, and is capable of emitting the same fluorescent signal as the second compound.

Further, $R_{5a}$ can be enabled to perform the bioorthogonal ligation reaction with the compound carrying the fluorophore (represented as M herein) such that the third compound can be enabled to carry a fluorophore. In addition, furthermore, (i) $R_{6b}$ can be enabled to specifically interact with/bind to the other member $R_{6c}$ of the second binding pair, to dissociate the conjugate of $R_{6b}$ and $R_{6a}$, thereby making the fourth compound to lose the fluorophore, or (ii) $R_8$ in the fourth compound can be enabled to perform bioorthogonal ligation reaction with the compound carrying the quenching group to quench the fluorescent signal emitted by the fluorophore Dye$_1$ or Dye$_2$ in the fourth compound. In such exemplary embodiments, $R_{6b}$ can be one member of two binding pairs ($R_{6a}$ and $R_{6b}$ of the first binding pair, $R_{6b}$ and $R_{6c}$ of the second binding pair). Particularly preferably, the two members of the first binding pair ($R_{5a}$ and $R_{5b}$) do not interact with the two members of the third binding pair ($R_{6b}$ and $R_{6c}$). Furthermore, it is particularly preferred that M do not influence the specific interaction between $R_{6b}$ and $R_{6c}$, and that $R_{6b}$ and $R_{6c}$ do not influence the bioorthogonal ligation reaction between $R_{5a}$ and M.

Therefore, in some preferred embodiments, in step (6), the duplex or the growing nucleic acid strand is subjected to a treatment which has no influence on the first compound and the second compound, but enables $R_{5a}$ to perform the bioorthogonal ligation reaction with M (thereby the fluorophore is introduced into the third compound to enable it to carry the fluorophore, and emit the fluorescent signal), and, the treatment enables $R_{6b}$ to specifically interact with/bind to the other member ($R_6$) of the second binding pair (thereby making the fourth compound to lose the fluorophore), or $R_8$ in the fourth compound is enabled to perform bioorthogonal ligation reaction with the compound carrying the quencher, thereby quenching the fluorescent signal emitted by fluorophore in the fourth compound. In such exemplary embodiments, prior to the treatment of step (6), the first compound and the third compound, if present, do not fluoresce, and the second compound and the fourth compound, if present, fluoresce; also, after the treatment of step (6), the first compound (if present) still does not fluoresce, the second compound (if present) still fluoresces, the third compound (if present) changes to fluoresce, and the fourth compound, if present, changes to not fluoresce. Therefore, the type of compound incorporated into the 3' end of the growing nucleic acid strand can be determined by the results of two fluorescent signal detections.

Further, in such exemplary embodiments, the protecting group at 3' position of the ribose or deoxyribose in the compound incorporated into the 3' end of the growing nucleic acid strand, and the fluorophore (if present) on the duplex or the growing nucleic acid strand can be removed by subjecting $R_{3a}$, $R_{3b}$, $R_{3c}$, $R_{3d}$, $R_{4a}$, $R_{4b}$, $R_{4c}$ to a bioorthogonal cleavage reaction. Therefore, in some preferred embodiments, the duplex or the growing nucleic acid strand is subjected to a treatment in step (8), and such treatment enables $R_{3a}$, $R_{3b}$, $R_{3c}$, $R_{3d}$, $R_{4a}$, $R_{4b}$, $R_{4c}$ to perform the bioorthogonal cleavage reaction. In such exemplary embodiments, after the treatment of step (8), the growing nucleic acid strand will not have any fluorophore, and its 3'-end nucleotide will have free hydroxyl at 3' position of the ribose or deoxyribose, and the free hydroxyl can be used for initiating next round of polymerization reaction.

Therefore, in some preferred embodiments, the method of the invention comprises the steps of:

(1) providing a nucleic acid molecule to be sequenced on the support or attaching the nucleic acid molecule to be sequenced to the support;

(2) adding primers for initiating nucleotide polymerization, polymerases for performing nucleotide polymerization, and the first, second, third and fourth compounds of formula (I), formula (II), formula (III) and formula (IV), respectively, thereby forming reaction system containing solution phase and solid phase:

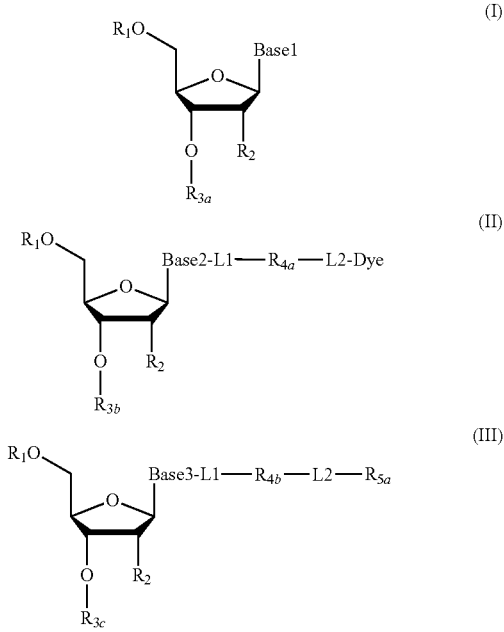

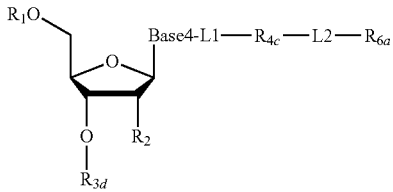

wherein, Base1, Base2, Base3, and Base4 represent 4 different bases, and are selected from A, (T/U), C, and G;

$R_1$ is each independently selected from —H, monophosphate group (—PO$_3$H$_2$), diphosphate group (—PO$_3$H—PO$_3$H$_2$), triphosphate group (—PO$_3$H—PO$_3$H—PO$_3$H$_2$) and tetraphosphate group (—PO$_3$H—PO$_3$H—PO$_3$H—PO$_3$H$_2$);

$R_2$ is each independently selected from —H and —OH;

$R_{3a}$, $R_{3b}$, $R_{3c}$, $R_{3d}$, $R_{4a}$, $R_{4b}$ and $R_{4c}$ are each independently a reactive group capable of performing a bioorthogonal cleavage reaction;

$R_{5a}$ is a reactive group capable of performing the first bioorthogonal ligation reaction;

$R_{6a}$ is one member of the first binding pair, optionally, $R_{6a}$ is Dye$_1$ or is also linked onto -L3-Dye$_1$;

L1 is independently a linking group or absent;
L2 is independently a linking group or absent;
L3 is a linking group or absent;

Dye and Dye, represent fluorophore capable of emitting a fluorescent signal; and, they both have the same structure, or have different structures but the same or substantially the same emission spectrum;

optionally, there is a reactive group $R_8$ capable of performing a bioorthogonal ligation reaction between $R_{4c}$ and $R_{6a}$;

(3) annealing the primer to the nucleic acid molecule to be sequenced, and the primer serves as an initial growing nucleic acid strand, and forms a duplex attached to the support together with the nucleic acid molecule to be sequenced;

(4) performing a nucleotide polymerization reaction with polymerase under a condition allowing the polymerase to perform nucleotide polymerization, thereby incorporating one of the four compounds into the 3' end of the growing nucleic acid strand;

(5) (i) the fourth compound cannot emit a fluorescent signal, and then the duplex or the growing nucleic acid strand is subjected to a treatment in a reaction system containing a solution phase and a solid phase, the treatment does not have influence on the first compound, the second compound and the third compound, but enables $R_{6a}$ in the fourth compound to specifically interact with/bind to agent carrying the fluorophore (for example, a fluorophore having the same structure as the second compound, or a fluorophore having the same or substantially the same emission spectrum as the fluorophore of the second compound); thereafter, removing the solution phase of the reaction system of the previous step, retaining the duplex attached on the support and detecting whether the duplex or the growing nucleic acid strand emits the fluorescent signal;

the other member of the first binding pair carrying the fluorophore has the structure: $R_{6b}$-L4-Dye$_2$; wherein, $R_{6b}$ is the other member of the first binding pair, and L4 is independently a linking group or absent; Dye$_2$ represents a fluorophore capable of emitting a fluorescent signal and has the same structure as Dye, or has a different structure but the same or substantially the same emission spectrum; meanwhile, $R_{6b}$ is one member of the second binding pair;

(ii) the fourth compound is capable of emitting the same fluorescent signal as the second compound, then removing the solution phase of the reaction system in the previous step, retaining the duplex attached on the support, and detecting whether the duplex or the growing nucleic acid strand emits the fluorescent signal;

(6) subjecting the duplex or the growing nucleic acid strand to a treatment in a reaction system comprising a solution phase and a solid phase, wherein the treatment does not have influence on the first compound and the second compound, but enables $R_{5a}$ in the third compound to perform the first bioorthogonal ligation reaction with agent carrying the fluorophore (for example, the same fluorophore as the second compound, or the fluorophore having the same or substantially the same emission spectrum as the fluorophore of the second compound), thereby introducing the fluorophore in said agent into the third compound to enable it to emit a fluorescent signal; and (i) enable the other member $R_{6b}$ to specifically interact with/bind to the other member $R_{6c}$ of the second binding pair to dissociate the conjugate of $R_{6b}$ and $R_{6a}$, thereby making the fourth compound to lose the fluorophore, or (ii) enable $R_8$ in the fourth compound to perform bioorthogonal ligation reaction with compound carrying the quenching group, thereby quenching the fluorescent signal emitted by the fluorophore $Dye_1$ or $Dye_2$ in the fourth compound. Wherein, the other member of the second binding pair carrying the quenching group has the following structure: $R_{6c}$-L'-Que; wherein $R_{6c}$ is the other member of the second binding pair, and L' is independently a linking group or absent; Que represents a quenching group capable of quenching the fluorescent signal emitted by $Dye_1$ or $Dye_2$; and (7) removing the solution phase of the reaction system in the previous step, retaining the duplex attached to the support, and detecting whether the duplex or the growing nucleic acid strand emits the fluorescent signal.

In some preferred embodiments, the method further comprises the steps of:

(8) subjecting the duplex or the growing nucleic acid strand in the previous step to a treatment in a reaction system containing a solution phase and a solid phase, which enables $R_{3a}$, $R_{3b}$, $R_{3c}$, $R_{3d}$, $R_{4a}$, $R_{4b}$ and $R_{4c}$ to perform bioorthogonal cleavage reaction such that the compound incorporated at the 3'end of the growing nucleic acid strand has a free hydroxyl group at the 3' position of the ribose or deoxyribose (in other words, converting $-OR_{3a}$, $-OR_{3b}$, $-OR_{3c}$ or $-OR_{3d}$ (if present) into free hydroxy group) and removing the fluorophore on the duplex or growing nucleic acid strand (in other words, removing the fluorophore attached to $R_{4a}$, $R_{4b}$ or $R_{4c}$), if present;

(9) removing the solution phase of the reaction system in the previous step;

(10) adding a polymerase for performing nucleotide polymerization, and the first compound, the second compound, the third compound, and the fourth compound, thereby forming a reaction system containing a solution phase and a solid phase, and then performing the steps (4)-(7).

In some preferred embodiments, the method further comprises the step of:

(11) repeating steps (8)-(10) one or more times.

In some exemplary embodiments, in step (4), if the compound of formula (I) is incorporated into the 3' end of the growing nucleic acid strand, then since the compound of formula (I) does not carry a fluorophore, and it does not react in step (6), and therefore, no fluorescent signal will be detected in steps (5) and (7). In other words, if no fluorescent signal is detected in both of steps (5) and (7), it can be determined that the compound incorporated at the 3' end of the growing nucleic acid strand is the compound of formula (I).

If, in step (4), the compound of formula (II) is incorporated into the 3' end of the growing nucleic acid strand, then since the compound of formula (II) itself carries a fluorophore and it does not perform any reaction in step (6). Therefore, the fluorescent signal will be detected in both steps (5) and (7). In other words, if a fluorescent signal is detected in both of steps (5) and (7), it can be determined that the compound incorporated at the 3' end of the growing nucleic acid strand is the compound of formula (II).

If, in step (4), the compound of formula (III) is incorporated at the 3' end of the growing nucleic acid strand, then (i) since the compound of formula (III) does not carry a fluorophore, therefore, no fluorescent signal will be detected in step (5); and (ii) since the compound of formula (III) performs the bioorthogonal ligation reaction with compound M carrying the fluorophore in step (6), thereby the fluorophore is introduced into the growing nucleic acid strand, therefore, a fluorescent signal will be detected in step (7). In other words, if no fluorescent signal is detected in step (5) and a fluorescent signal is detected in step (7), it can be determined that the compound incorporated at the 3' end of the growing nucleic acid strand is the compound of formula (III).

If in step (4), the compound of formula (IV) is incorporated at the 3' end of the growing nucleic acid strand, then (i) since the compound of formula (IV) itself carries a fluorophore or is treated in step (5) to carry a fluorophore, therefore, a fluorescent signal will be detected in step (5); and (ii) since the compound of formula (IV) loses fluorophore in step (6) due to dissociation of conjugate of $R_{6a}$ and $R_{6b}$, or performs bioorthogonal ligation reaction, introducing the quenching group into the growing nucleic acid strand, quenching the fluorescent signal emitted by the fluorophore, therefore, no fluorescent signal will be detected in step (7). In other words, if a fluorescent signal is detected in step (5) and not detected in step (7), it can be determined that the compound incorporated at the 3' end of the growing nucleic acid strand is a compound of the formula (IV).

Therefore, in some preferred embodiments, the method of the present invention further comprises: after step (7), determining the type of the compound incorporated into 3' end of the growing nucleic acid strand in step (4) according to the detection results in steps (5) and (7), wherein, when both of the detection results of steps (5) and (7) are that the duplex or the growing nucleic acid strand does not emit the fluorescent signal, it is determined that the compound incorporated into 3' end of the growing nucleic acid strand in step (4) is the compound of formula (I);

when both of the detection results of steps (5) and (7) are that the duplex or the growing nucleic acid strand emits the fluorescent signal, it is determined that the compound incorporated into 3' end of the growing nucleic acid strand in step (4) is the compound of formula (II);

when the detection result of step (5) is that the duplex or the growing nucleic acid strand does not emit the fluorescent signal, and the detection result of step (7) is that the duplex or the growing nucleic acid strand emits the fluorescent signal, it is determined that the compound incorporated into 3' end of the growing nucleic acid strand in step (4) is the compound of formula (III); and, when the detection result of step (5) is that the duplex or the growing nucleic acid strand emits the fluorescent signal, and the detection result of step (7) is that the duplex or the growing nucleic acid strand does not emit the fluorescent signal, it is determined that the compound incorporated into 3' end of the growing nucleic acid strand in step (4) is the compound of formula (IV).

In some preferred embodiments, the method of the present invention further comprises that, after step (7), based on the base complementary pairing principle, the type of base at the corresponding position in the nucleic acid molecule to be sequenced is determined according to the type of the compound incorporated at the 3' end of the growing nucleic acid strand in step (4).

In some preferred embodiments, the compound of formula (I), the compound of formula (II), the compound of formula (III) and the compound of formula (IV) do not react with each other during the nucleotide polymerization reaction.

In some preferred embodiments, Base1 and Base2 are purine bases, and Base3 and Base4 are pyrimidine bases. In some preferred embodiments, Base1 is base G, Base2 is base A, Base3 is base C, and Base4 is base T or U. In some preferred embodiments, Base1 is base G, Base2 is base A, Base3 is base T or U, and Base4 is base C. In some preferred embodiments, Base1 is base A, Base2 is base G, Base3 is base C, and Base4 is base T or U. In some preferred embodiments, Base1 is base A, Base2 is base G, Base3 is base T or U, and Base4 is base C.

In some preferred embodiments, Base1 and Base2 are pyrimidine bases, and Base3 and Base4 are purine bases. In some preferred embodiments, Base1 is base C, Base2 is base T or U, Base3 is base G, and Base4 is base A. In some preferred embodiments, Base1 is base C, Base2 is base T or U, Base3 is base A, and Base4 is base G. In some preferred embodiments, Base1 is base T or U, Base2 is base C, Base3 is base G, and Base4 is base A. In some preferred embodiments, Base1 is base T or U, Base2 is base C, Base3 is base A, and Base4 is base G.

In some preferred embodiments, the compound of formula (I), the compound of formula (II), the compound of formula (III) and the compound of formula (IV) have the same $R_1$. In some preferred embodiments, $R_1$ is independently —H. In some preferred embodiments, $R_1$ is independently monophosphate group (—PO$_3$H$_2$). In some preferred embodiments, $R_1$ is independently diphosphate group (—PO$_3$H—PO$_3$H$_2$). In some preferred embodiments, $R_1$ is independently triphosphate group (—PO$_3$H—PO$_3$H—PO$_3$H$_2$). In some preferred embodiments, $R_1$ is independently tetraphosphate group (—PO$_3$H—PO$_3$H—PO$_3$H—PO$_3$H$_2$).

In some preferred embodiments, the compound of formula (I), the compound of formula (II), the compound of formula (III) and the compound of formula (IV) have the same $R_2$. In some preferred embodiments, $R_2$ is independently —H. In some preferred embodiments, $R_2$ is independently —OH.

In some preferred embodiments, $R_{3a}$, $R_{3b}$, $R_{3c}$, $R_{3d}$, $R_{4a}$, $R_{4b}$, $R_{4c}$ are each independently capable of performing a bioorthogonal cleavage reaction. As used herein, the expression "each capable of independently performing a bioorthogonal cleavage reaction" means that the reactive groups, agents, or molecules, etc. mentioned are each capable of performing a bioorthogonal cleavage reaction, while do not interfere with or influence each other. For example, the expression "$R_{3a}$ and $R_{3b}$ are each independently capable of performing a bioorthogonal cleavage reaction" means that both $R_{3a}$ and $R_{3b}$ are capable of performing a bioorthogonal cleavage reaction, and $R_{3a}$ does not influence the progress of the bioorthogonal cleavage reaction of $R_{3b}$, and $R_{3b}$ does not influence the progress of the bioorthogonal cleavage reaction of $R_{3a}$.

In some exemplary embodiments, $R_{3a}$ is the first reactive group capable of performing the bioorthogonal cleavage reaction in the presence of a first agent; $R_{3b}$ is the second reactive group capable of performing the bioorthogonal cleavage reaction in the presence of a second agent; $R_{3c}$ is the third reactive group capable of performing the bioorthogonal cleavage reaction in the presence of a third agent; $R_{3d}$ is the fourth reactive group capable of performing the bioorthogonal cleavage reaction in the presence of a fourth agent; $R_{4a}$ is the fifth reactive group capable of performing the bioorthogonal cleavage reaction in the presence of a fifth agent; $R_{4b}$ is the sixth reactive group capable of performing the bioorthogonal cleavage reaction in the presence of a sixth agent; and, $R_{4c}$ is the seventh reactive group capable of performing the bioorthogonal cleavage reaction in the presence of a seventh agent;

Preferably, in such embodiments, a first agent, a second agent, a third agent, a fourth agent, a fifth agent, a sixth agent, and a seventh agent can be added in step (8), thereby enabling $R_{3a}$, $R_{3b}$, $R_{3c}$, $R_{3d}$, $R_{4a}$, $R_{4b}$ and $R_{4c}$ (if present) each to perform the bioorthogonal cleavage reaction. Thus, $R_{3a}$, $R_{3b}$, $R_{3c}$, $R_{3d}$ (if present) will be removed from 3' position of ribose or deoxyribose (in other words, —OR$_{3a}$, —OR$_{3b}$, —OR$_{3c}$ or —OR$_{3d}$ (if present) will be converted into a free hydroxy group), and $R_{4a}$ and the fluorophore (if present) attached thereto, $R_{4b}$ and the fluorophore (if present) attached thereto, and $R_{4c}$ and the fluorophore (if present) attached thereto will also be removed. Thus, after step (8), the growing nucleic acid strand will not carry the fluorophore and have free hydroxyl group at the 3' end, which can be used for the next round of polymerization. Therefore, in some preferred embodiments, in step (8), the first agent, the second agent, the third agent, the fourth agent, the fifth agent, the sixth agent, and the seventh agent are added to form a reaction system containing a solution phase and a solid phase, and the duplex is incubated with the first agent, the second agent, the third agent, the fourth agent, the fifth agent, the sixth agent, and the seventh agent under a condition allowing $R_{3a}$, $R_{3b}$, $R_{3c}$, $R_{3d}$, $R_{4a}$, $R_{4b}$ and $R_{4c}$ each to perform the bioorthogonal cleavage reaction.

In some preferred embodiments, $R_{3a}$, $R_{3b}$, $R_{3c}$ and $R_{3d}$ is capable of performing a bioorthogonal cleavage reaction in the presence of the same agent. In this case, preferably, in step (8), the first agent, the second agent, the third agent, and the fourth agent are the same agents.

In some preferred embodiments, $R_{3a}$, $R_{3b}$, $R_{3c}$ and $R_{3d}$ are the same reactive groups. In this case, preferably, in step (8), the first agent, the second agent, the third agent, and the fourth agent are the same agents. In other words, in step (8), the same $R_{3a}$, $R_{3b}$, $R_{3c}$ and $R_{3d}$ (if present) will each perform the bioorthogonal cleavage reaction in the presence of the same agent (i.e., the first agent), and be excised from the growing nucleic acid strand.

In some preferred embodiments, $R_{4a}$, $R_{4b}$ and $R_{4c}$ is capable of performing the bioorthogonal cleavage reaction in the presence of the same agent. Preferably, in step (8), the fifth agent, the sixth agent, and the seventh agent are the same agents.

In some preferred embodiments, $R_{4a}$, $R_{4b}$ and $R_{4c}$ are the same reactive groups. In this case, preferably, in step (8), the fifth agent, the sixth agent, and the seventh agent are the same agents. In other words, in step (8), the same $R_{4a}$, $R_{4b}$ and $R_{4c}$ (if present) will each perform the bioorthogonal cleavage reaction in the presence of the same agent (i.e., the fifth agent), and be excised from the growing nucleic acid strand.

In some preferred embodiments, $R_{3a}$, $R_{3b}$, $R_{3c}$, $R_{3d}$, $R_{4a}$, $R_{4b}$ and $R_{4c}$ is capable of performing the bioorthogonal cleavage reaction in the presence of the same agent. In this case, preferably, in step (8), the first agent, the second agent, the third agent, the fourth agent, the fifth agent, the sixth agent, and the seventh agent are the same agents. In other words, in step (8), it is only necessary to add the same agent (i.e., the first agent), and $R_{3a}$, $R_{3b}$, $R_{3c}$, $R_{3d}$, $R_{4a}$, $R_{4b}$ and $R_{4c}$ (if present) will each perform the bioorthogonal cleavage reaction in the presence of the same agent (i.e., the first agent), and be excised from the growing nucleic acid strand.

In some exemplary embodiments, it is particularly preferred that the two members $R_{5a}$ do not interact with the two members ($R_{6b}$ and $R_{6c}$) of the second binding pair. Furthermore, it is particularly preferred that $R_{5a}$ does not influence the specific interaction between $R_{6b}$ and $R_{6c}$, and that $R_{6b}$ and $R_{6c}$ do not influence the bioorthogonal ligation reaction between $R_{5a}$ and M. In such embodiments, preferably, in step (6), M and $R_{6c}$ may be added, and the compound M carries the same fluorophore (or fluorophore which has different structure but the same or substantially the same emission spectrum) as the second compound and the fourth compound such that $R_{5a}$ (if present) in the compound of formula (III) performs bioorthogonal ligation reaction with M, and the conjugate of $R_{6a}$ (if present) and $R_{6b}$ in the compound of formula (IV) dissociates. Thus, the fluorophore Dye3 is introduced into the compound of formula (III) through the bioorthogonal ligation reaction between $R_{5a}$ in the compound and M, such that the compound of formula (III) emits the fluorescent signal. At the same time, the conjugate of $R_{6a}$ and $R_{6b}$ dissociates through the specific interaction between the two members ($R_{6b}$ and $R_{6c}$) of the second binding pair, such that the compound of formula (IV) loses the fluorophore, and the compound of formula (IV) no longer fluoresces. In such embodiments, it is also particularly preferred that, in step (6), M does not react with the first compound and the second compound, and further preferably, $R_{6c}$ does not react with the first compound and the second compound. Thus, in some preferred embodiments, M and $R_{6c}$ can be added to in step (6) form a reaction system containing a solution phase and a solid phase; and then, the duplex is incubated with $R_{6c}$-L6-Que under conditions that allow $R_{5a}$ to specifically bind to $R_{5b}$ and allow $R_{6b}$ to specifically bind to $R_{6c}$.

In some exemplary embodiments, the fourth compound does not carry a fluorophore and $R_{6a}$ is one member of the first binding pair. In such embodiments, step (5) comprises adding a ninth agent such that $R_{6a}$ (if present) in the compound of formula (IV) specifically interacts with and/or binds to the other member of the first binding pair. For example, the ninth agent can comprise the other member carrying a fluorophore of a first binding pair having the structure $R_{6b}$-L4-Dye$_2$, wherein, $R_{6b}$ is the other member of the first binding pair, and L4 is independently a linking group or absent; Dye$_2$ represents a fluorophore capable of emitting a fluorescent signal and has the same structure as Dye, or is structurally different but has the same emission spectrum. In such embodiments, step (6) comprises adding a tenth agent such that the conjugate of $R_{6a}$ (if present) and $R_{6b}$ in the compound of formula (IV) dissociates. For example, the tenth agent can comprise the other member $R_{6c}$ of the second binding pair that is capable of specifically binding to $R_{6b}$ to replace $R_{6a}$, such that the conjugate formed by $R_{6a}$ and $R_{6b}$ dissociates.

Preferably, in such embodiments, in step (6), an eighth agent and a ninth agent may be added to make $R_{5a}$ (if present) in the compound of formula (III) to perform the bioorthogonal ligation reaction with M, and to dissociate the conjugate formed by $R_{6a}$ in compound of formula (IV) with $R_{6b}$. For example, the eighth agent may comprise compound M, which carries the same fluorophore (or a fluorophore that has a different structure but the same or substantially the same emission spectrum) as the second compound and the fourth compound, and, M is capable of performing bioorthogonal ligation reaction with $R_{5a}$, thereby introducing the fluorophore into the third compound; and, the ninth agent comprises the other member of the second binding pair and is capable of specifically interacting with and/or binding to $R_{6b}$, thereby dissociating the conjugate formed by $R_{6a}$ in compound of formula (IV) with $R_{6b}$ and making the compound of formula (IV) to lose its fluorophore. In such embodiments, it is particularly preferred that, in step (6), the eighth agent does not react with the first compound or with the second compound, and further preferably, the ninth agent does not react with the first compound or with the second compound. Therefore, in some preferred embodiments, in step (6), the eighth agent and the ninth agent may be added to form a reaction system comprising a solution phase and a solid phase, wherein the eighth agent comprises compound M, and the compound M carries the same fluorophore (or a fluorophore having a different structure but the same or substantially the same emission spectrum) as the second compound and the fourth compound, and the compound M is capable of performing a bioorthogonal ligation reaction with $R_{5a}$, thereby introducing a fluorophore in compound M into the third compound; the ninth agent comprises the other member of the second binding pair, and the other member of the second binding pair is capable of specifically interacting with and/or binding to $R_{6b}$ to make the conjugate formed by $R_{6a}$ in the compound of formula (IV) and $R_{6b}$ to dissociate; then, the duplex is incubated with the eighth agent and the ninth agent under a condition that allows $R_{5a}$ to perform bioorthogonal ligation reaction with M and allows $R_{6b}$ to specifically interact with/bind to the other member of the second binding pair.

In some exemplary embodiments, a reactive group $R_8$ capable of performing the third bioorthogonal ligation reaction is present between $R_{5b}$ and $R_{7a}$ of the fourth compound. In some preferred embodiments, $R_{3a}$, $R_{3b}$, $R_{3c}$, $R_{3d}$, $R_{4a}$, $R_{4b}$, $R_{5a}$ and $R_8$ can each perform the bioorthogonal cleavage reaction or bioorthogonal ligation reaction. In some exemplary embodiments, $R_{8a}$ is capable of performing a bioorthogonal ligation reaction in the presence of a tenth agent.

In some preferred embodiments, $R_{3a}$, $R_{3b}$, $R_{3c}$, and $R_{3d}$ are each independently selected from the group consisting of —CH$_2$CH=CH$_2$, —CH$_2$N$_3$, $C_{3-8}$ cycloalkenyl (e.g., $C_3$ cycloalkenyl, $C_4$ cycloalkenyl, $C_5$ membered cycloalkenyl, $C_6$ cycloalkenyl, $C_7$ cycloalkenyl or $C_8$ cycloalkenyl). In some preferred embodiments, the $C_{3-8}$ cycloalkenyl is selected from the group consisting of $C_3$ cycloalkenyl and $C_8$ cycloalkenyl. In some preferred embodiments, the $C_{3-8}$ cycloalkenyl group is

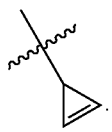

In some preferred embodiments, the $C_3$-8 cycloalkenyl group is

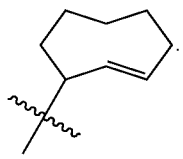

In some preferred embodiments, $R_{3a}$, $R_{3b}$, $R_{3c}$, and $R_{3d}$ are the same reactive groups and are selected from the group consisting of —$CH_2CH=CH_2$, —$CH_2N_3$, $C_{3-8}$ cycloalkenyl (e.g., $C_3$ cycloalkenene group, $C_4$ cycloalkenyl group, $C_5$ membered cycloalkenyl group, $C_6$ cycloalkenyl group, $C_7$ cycloalkenyl group or $C_8$ cycloalkenyl group). In some preferred embodiments, the $C_{3-8}$ cycloalkenyl is selected from the group consisting of $C_3$ cycloalkenyl and $C_8$ cycloalkenyl. In some preferred embodiments, the $C_{3-8}$ cycloalkenyl group is

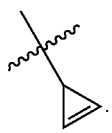 [SMILES: *C1C=C1]

In some preferred embodiments, the $C_{3-8}$ cycloalkenyl group is

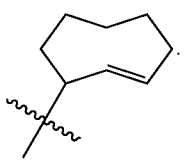 [SMILES: *C1/C=C/CCCCC1]

In some preferred embodiments, $R_{3a}$, $R_{3b}$, $R_{3c}$, and $R_{3d}$ are the same reactive groups and are all —$CH_2N_3$.

In some preferred embodiments, $R_{4a}$, $R_{4b}$ and $R_{4c}$ are each independently selected from the group consisting of:

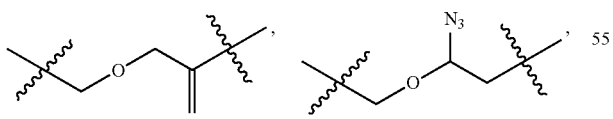

—O—$C_{3-8}$ cycloalkenylene. In some preferred embodiments, the "—O—$C_{3-8}$ cycloalkenylene subunit" is selected from the group consisting of —O—$C_3$ cycloalkenylene subunit, —O—$C_4$ cycloalkenylene subunit, —O—$C_5$ cycloalkenylene subunit, —O—$C_6$ cycloalkenylene subunit, —O—$C_7$ cycloalkenylene subunit, and —O—$C_8$ cycloalkenylene subunit. In some preferred embodiments, the "—O—$C_{3-8}$ cycloalkenylene subunit" is

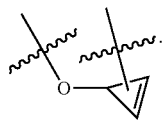

In some preferred embodiments, the "—O—$C_{3-8}$ cycloalkenylene subunit" is

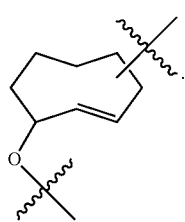

In some preferred embodiments, $R_{4a}$, $R_{4b}$ and $R_{4c}$ are the same reactive groups and are selected from the group consisting of:

—O—$C_{3-8}$ cycloalkenylene. In some preferred embodiments, the "—O—$C_{3-8}$ cycloalkenylene subunit" is selected from the group consisting of —O—$C_3$ cycloalkenylene subunit, —O—$C_4$ cycloalkenylene subunit, —O—$C_5$ cycloalkenylene subunit, —O—$C_6$ cycloalkenylene subunit, —O—$C_7$ cycloalkenylene subunit, and —O—$C_8$ cycloalkenylene subunit. In some preferred embodiments, the "—O—$C_{3-8}$ cycloalkenylene subunit" is

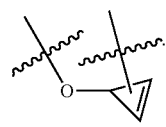

In some preferred embodiments, the "—O—$C_{3-8}$ cycloalkenylene subunit" is

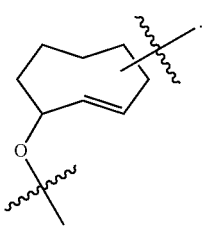

In some preferred embodiments, both $R_{4a}$, $R_{4b}$ and $R_{4c}$ are

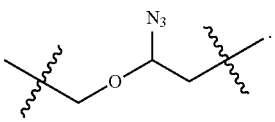

In some preferred embodiments, the first agent, the second agent, the third agent, the fourth agent, the fifth agent, the sixth agent and the seventh agent each independently comprise materials selected from the group consisting of:

a complex of palladium (for example, a complex of palladium with four triphenylphosphine 3,3',3"-trisulfonic acids);

a complex of ruthenium (for example, a complex of ruthenium with quinoline carboxylate (or a derivative thereof), allyl or cyclopentadiene);

a phosphide (e.g., a carboxyphosphine or hydroxyphosphine such as $P(CH_2CH_2COOH)_3$ or $P(CH_2CH_2OH)_3$); and Compound Q having the structural formula

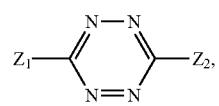

wherein $Z_1$ and $Z_2$ are each independently selected from a modified or unmodified alkyl (e.g., a $C_1$-$C_{06}$ alkyl such as a $C_1$ alkyl, $C_2$ alkyl, $C_3$ alkyl, $C_4$ alkyl, $C_5$ alkyl or $C_6$ alkyl) and a modified or unmodified aryl (for example, 6-10 membered aryl such as 6-membered aryl, 7-membered aryl, 8-membered aryl, 9-membered aryl or 10-membered aryl such as phenyl or pyridyl).

In some preferred embodiments, $R_{3a}$, $R_{3b}$, $R_{3c}$ and $R_{3d}$ are —$CH_2CH$=$CH_2$. In this case, preferably, $R_{4a}$, $R_{4b}$ and $R_{4c}$ are

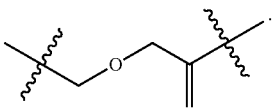 [SMILES: *COCC(*)=C]

Further preferably, the first agent, the second agent, the third agent, the fourth agent, the fifth agent, the sixth agent and the seventh agent comprise a complex of palladium or a complex of ruthenium. Preferably, the first agent, the second agent, the third agent, the fourth agent, the fifth agent, the sixth agent and the seventh agent are the same agents, and comprise a complex of palladium or a complex of ruthenium.

In some preferred embodiments, $R_{3a}$, $R_{3b}$, $R_{3c}$, and $R_{3d}$ are —$CH_2$—$N_3$. In this case, preferably, $R_{4a}$, $R_{4b}$ and $R_{4c}$ are

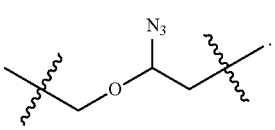 [SMILES: *COC(C*)N=[N+]=[N-]]

Further preferably, the first agent, the second agent, the third agent, the fourth agent, the fifth agent, the sixth agent and the seventh agent comprise phosphonate such as carboxyl phosphonate or hydroxyl phosphonate such as $P(CH_2CH_2COOH)_3$ or $P(CH_2CH_2OH)_3$. Preferably, the first agent, the second agent, the third agent, the fourth agent, the fifth agent, the sixth agent and the seventh agent are the same agents, and they comprise phosphonate such as carboxyl phosphonate or hydroxyl phosphonate such as $P(CH_2CH_2COOH)_3$ or $P(CH_2CH_2OH)_3$.

In some preferred embodiments, $R_{3a}$, $R_{3b}$, $R_{3c}$, and $R_{3d}$ are

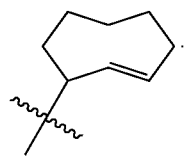

In this case, preferably, $R_{4a}$, $R_{4b}$ and $R_{4c}$ are

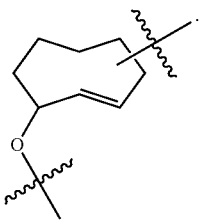

Further preferably, the first agent, the second agent, the third agents, the fourth agent, the fifth agent, the sixth agent and the seventh agent comprise the compound Q as defined above. Further preferably, in compound Q, $Z_1$ is a methyl group; and $Z_2$ is a modified or unmodified pyridyl group. More preferably, compound Q is

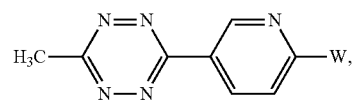

wherein, W is hydrogen or a modifying group.

Preferably, the first agent, the second agent, the third agent, the fourth agent, the fifth agent, the sixth agent and the seventh agent are the same agents and comprise the compound Q as defined above.

In some preferred embodiments, the linking groups L1, L2 and L3 in the first compound, the second compound, the third compound, and the fourth compound, and linking groups L4 and L6 in $R_{6b}$-L4-$Dye_2$ and $R_{6c}$-L6-Que are each independent and are not particularly limited. A person skilled in the art can select suitable linking groups L1, L2, L3, L4 and L6 according to the bases (Base1, Base2, Base3 and Base4) and the reactive groups ($R_{4a}$, $R_{4b}$ and $R_{4c}$) used in the compounds and members ($R_{5a}$, $R_{5b}$, $R_{6a}$ and $R_{6b}$) of the first binding pair and the second binding pair.

In some exemplary embodiments, the linking groups L1, L2, L3, L4 and L6 are each independently selected from the group consisting of:

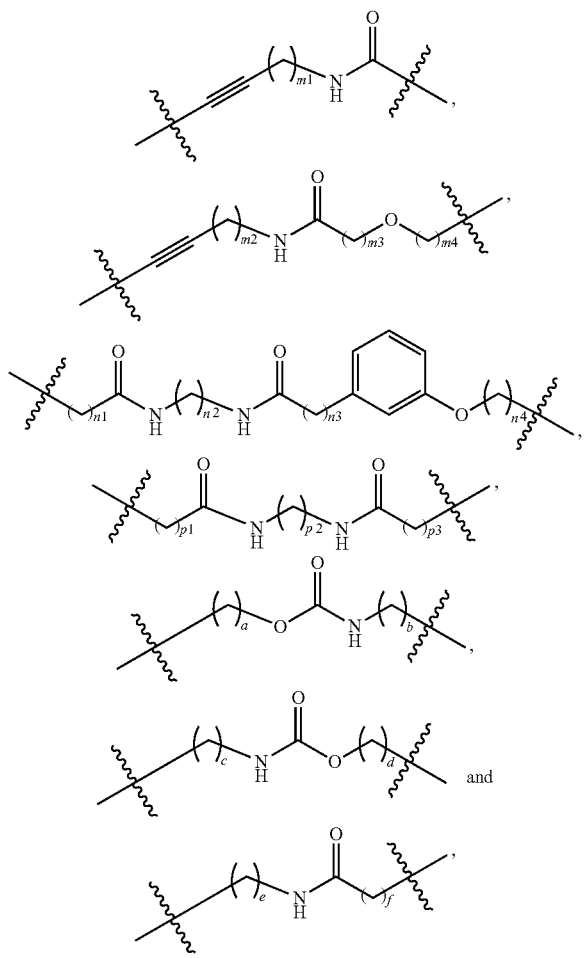

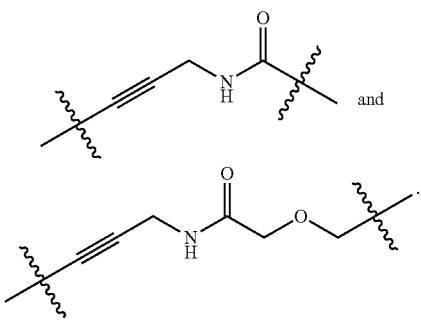 [SMILES: *C#CCNC(*)=O ; *C#CCNC(=O)COC*]

In some preferred embodiments, L2 in the first compound, the second compound, the third compound, and the fourth compound are each independently selected from the group consisting of:

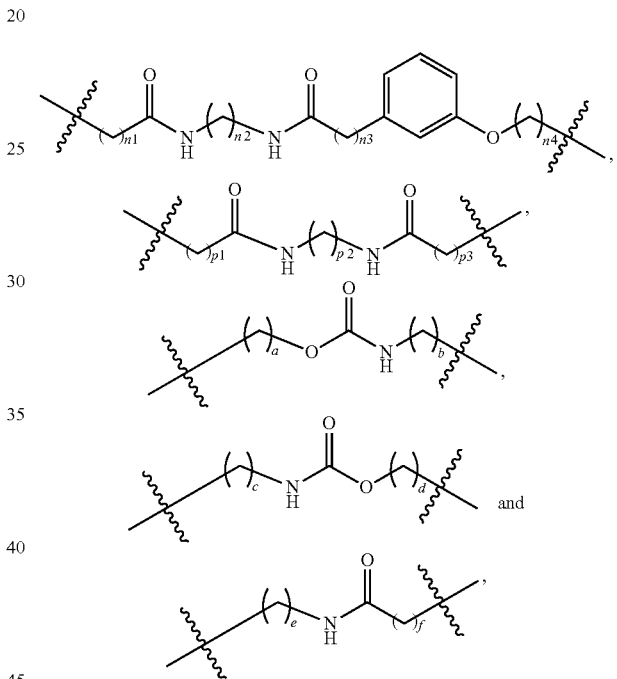

wherein n1, n2, n3, n4, p1, p2, p3, a, b, c, d, e, and f are each independently selected from 0, 1, 2, 3, 4, 5, or 6.

In some preferred embodiments, L2 in the first compound, the second compound, the third compound, and the fourth compound are each independently selected from the group consisting of:

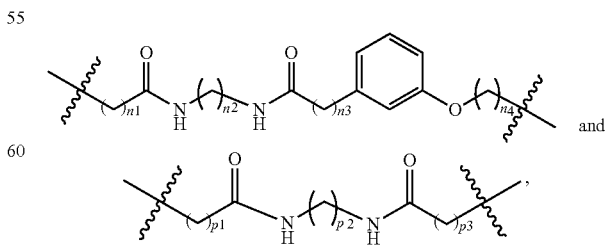

wherein n1, n2, n3, n4, p1, p2, p3 are each independently selected from 0, 1, 2, 3, 4, 5 or 6.

wherein m1, m2, m3, m4, n1, n2, n3, n4, p1, p2, p3, a, b, c, d, e and f are each independently selected from 0, 1, 2, 3, 4, 5 or 6.

In some exemplary embodiments, L1 in the first compound, the second compound, the third compound, and the fourth compound are each independently selected from the group consisting of:

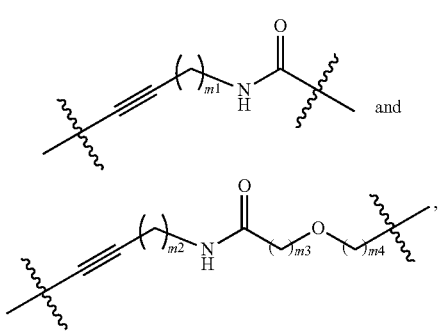

wherein m1, m2, m3, and m4 are each independently selected from 0, 1, 2, 3, 4, 5 or 6.

In some preferred embodiments, L1 in the first compound, the second compound, the third compound, and the fourth compound are each independently selected from the group consisting of:

In some preferred embodiments, L2 in the first compound, the second compound, the third compound, and the fourth compound are independently selected from the group consisting of:

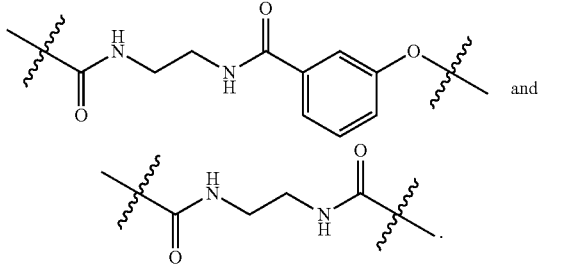

and

In some preferred embodiments, $R_{6a}$ and $R_{6b}$ are two members of the first binding pair, $R_{6b}$ and $R_{6c}$ are two members of the second binding pair. In some preferred embodiments, the first binding pair and the second binding pair are independently selected from the group consisting of: an antigen (e.g., a small molecule antigen)-antibody, a hapten-antibody, a hormone-receptor, a ligand-receptor, nucleic acid strand-complementary nucleic acid strand, substrate-enzyme, substrate analog-enzyme, inhibitor-enzyme, sugar-plant lectin, biotin-avidin (for example, avidin and streptavidin), digoxin and digoxin antibody, and 5-position bromodeoxyguanosine and its antibody.

In some preferred embodiments, the two members of the first binding pair are selected from the group consisting of: (a) biotin and avidin (for example, streptavidin), (b) digoxin and digoxin antibody; and (c) desthiobiotin and streptavidin.

In some preferred embodiments, the two members of the second binding pair are selected from the group consisting of: (a) biotin and avidin (for example, streptavidin); (b) digoxin and digoxin antibody; (c) desthiobiotin and streptavidin.

It is particularly preferred that $R_{5a}$ does not interact with the two members of the second binding pair ($R_{6b}$ and $R_{6c}$). Furthermore, it is particularly preferred that $R_{5a}$ does not influence the specific interaction between $R_{6b}$ and $R_{6c}$, and that $R_{6b}$ and $R_{6c}$ do not influence the bioorthogonal ligation reaction between $R_{5a}$ and M.

In some preferred embodiments, $R_{3a}$, $R_{3b}$, $R_{3c}$, and $R_{3d}$ are —CH$_2$CH=CH$_2$; $R_{4a}$, $R_{4b}$ and $R_{4c}$ are

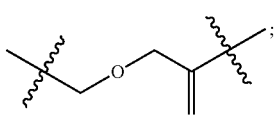 [SMILES: *COCC(*)=C]

the first, second, third, fourth, fifth, sixth and seventh agent comprise a complex of palladium or a complex of ruthenium; $R_{5a}$ is biotin; $R_{5b}$ is avidin (for example, streptavidin); $R_{6a}$ is digoxin; $R_{6b}$ is digoxin antibody. Preferably, the first, second, third, fourth, fifth, sixth and seventh agents are the same agents, and comprise a complex of palladium or a complex of ruthenium.

In some preferred embodiments, $R_{3a}$, $R_{3b}$, $R_{3c}$, and $R_{3d}$ are —CH$_2$—N$_3$; $R_{4a}$, $R_{4b}$ and $R_{4c}$ are

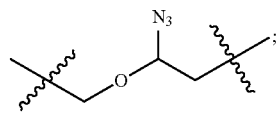 [SMILES: *COC(C*)N=[N+]=[N-]]

the first, second, third, fourth, fifth, sixth and seventh agent comprise a phosphide such as a carboxyl phosphide or a hydroxyl phosphide such as P(CH$_2$CH$_2$COOH)$_3$ or P(CH$_2$CH$_2$OH)$_3$; $R_{5a}$ is biotin; $R_{5b}$ is avidin (for example, streptavidin); $R_{6a}$ is digoxin; $R_{6b}$ is digoxin antibody. Preferably, the first, second, third, fourth, fifth, sixth and seventh agents are the same agents and comprise a phosphide such as a carboxyl phosphide or a hydroxyl phosphide such as P(CH$_2$CH$_2$COOH)$_3$ or P(CH$_2$CH$_2$OH)$_3$.

In some preferred embodiments, $R_{3a}$, $R_{3b}$, $R_{3c}$, and $R_{3d}$ are —CH$_2$—N$_3$; $R_{4a}$, $R_{4b}$ and $R_{4c}$ are

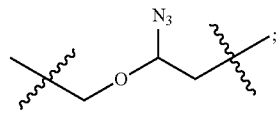 [SMILES: *COC(C*)N=[N+]=[N-]]

the first, second, third, fourth, fifth, sixth and seventh agents comprise a phosphide such as a carboxyl phosphide or a hydroxyl phosphide, such as P(CH$_2$CH$_2$COOH)$_3$ or P(CH$_2$CH$_2$OH)$_3$; $R_{5a}$ is digoxin; $R_{5b}$ is digoxin antibody; $R_{6a}$ is biotin; $R_{6b}$ is avidin (for example, streptavidin). Preferably, the first, second, third, fourth, fifth, sixth and seventh agents are the same agents and comprise a phosphide such as a carboxyl phosphide or a hydroxyl phosphide such as P(CH$_2$CH$_2$COOH)$_3$ or P(CH$_2$CH$_2$OH)$_3$.

In some preferred embodiments, $R_{3a}$, $R_{3b}$, $R_{3c}$, and $R_{3d}$ are —CH$_2$CH=CH$_2$; $R_{4a}$, $R_{4b}$ and $R_{4c}$ are

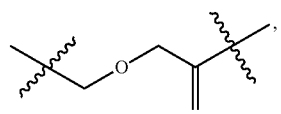 [SMILES: *COCC(*)=C]

the first, second, third, fourth, fifth, sixth and seventh agents comprise a complex of palladium or a complex of ruthenium; $R_{5a}$ is digoxin; $R_{5b}$ is digoxin antibody; $R_{6a}$ is biotin; $R_{6b}$ is avidin (for example, streptavidin). Preferably, the first, second, third, fourth, fifth, sixth and seventh agents are the same agents are the same agents, and comprise a complex of palladium or a complex of ruthenium.

In some preferred embodiments, $R_{3a}$, $R_{3b}$, $R_{3c}$, and $R_{3d}$ are

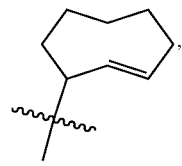 [SMILES: *C1/C=C/CCCCC1]

$R_{4a}$, $R_{4b}$ and $R_{4c}$ are

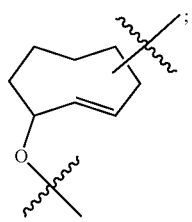

the first, second, third, fourth, fifth, sixth and seventh agent comprises Compound Q (for example, the compound Q as defined above); $R_{5a}$ is biotin; $R_{5b}$ is avidin (for example, streptavidin); $R_{6a}$ is digoxin; $R_{6b}$ is digoxin antibody. Preferably, the first, second, third, fourth, fifth, sixth and seventh agent are the same agents, and comprise Compound Q (e.g., the compound Q as defined above).

In some preferred embodiments, $R_{3a}$, $R_{3b}$, $R_{3c}$, and $R_{3d}$ are

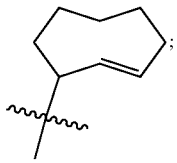 [SMILES: *C1/C=C/CCCCC1]

$R_{4a}$, $R_{4b}$ and $R_{4c}$ are

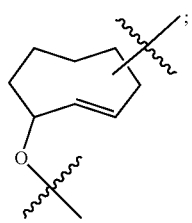

the first, second, third, fourth, fifth, sixth and seventh agent comprises Compound Q (for example, the compound Q as defined above); $R_{5a}$ is digoxin; $R_{5b}$ is digoxin antibody; $R_{6a}$ is biotin; $R_{6b}$ is avidin (for example, streptavidin). Preferably, the first, second, third, fourth, fifth, sixth and seventh agent are the same agents, and comprise Compound Q (e.g., the compound Q as defined above).

In some preferred embodiments, $R_{3a}$, $R_{3b}$, $R_{3c}$, and $R_{3d}$ are —CH$_2$CH=CH$_2$; $R_{4a}$, $R_{4b}$ and $R_{4c}$ are

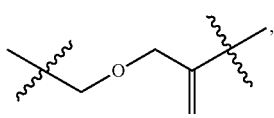 [SMILES: *COCC(*)=C]

the first, second, third, fourth, fifth, sixth and seventh agents comprise a complex of palladium or a complex of ruthenium; $R_{5a}$ is biotin; $R_{5b}$ is avidin (for example, streptavidin); $R_{6a}$ is Cy3; $R_{6b}$ is Cy3 antibody. Preferably, the first, second, third, fourth, fifth, sixth and seventh agents are the same agents, and comprise a complex of palladium or a complex of ruthenium.

In some preferred embodiments, $R_{3a}$, $R_{3b}$, $R_{3c}$, and $R_{3d}$ are

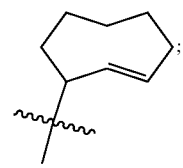 [SMILES: *C1/C=C/CCCCC1]

$R_{4a}$, $R_{4b}$ and $R_{4c}$ are

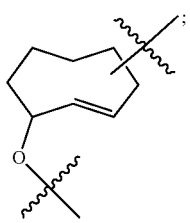

the first, second, third, fourth, fifth, sixth and seventh agent comprises Compound Q (for example, the compound Q as defined above); $R_{5a}$ is biotin; $R_{5b}$ is avidin (for example, streptavidin); $R_{6a}$ is Cy3; $R_{6b}$ is Cy3 antibody. Preferably, the first, second, third, fourth, fifth, sixth and seventh agent are the same agents, and comprise Compound Q (e.g., the compound Q as defined above).

In some preferred embodiments, $R_{3a}$, $R_{3b}$, $R_{3c}$, and $R_{3d}$ are

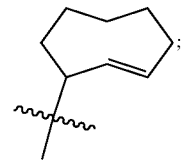 [SMILES: *C1/C=C/CCCCC1]

$R_{4a}$, $R_{4b}$ and $R_{4c}$ are

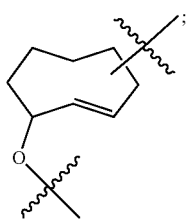

the first, second, third, fourth, fifth, sixth and seventh agent comprises Compound Q (for example, the compound Q as defined above); $R_{5a}$ is biotin; $R_{5b}$ is avidin (for example, streptavidin); $R_{6a}$ is Cy3; $R_{6b}$ is Cy3 antibody. Preferably, the first, second, third, fourth, fifth, sixth and seventh agent are the same agents, and comprise Compound Q (e.g., the compound Q as defined above).

In some embodiments, compound M is selected from the following compounds:

compound M1, which has the structural formula

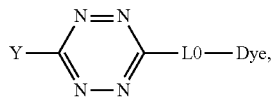

wherein, Y is selected from alkyl (for example, $C_1$-$C_6$ alkyl such as $C_1$ alkyl, $C_2$ alkyl, $C_3$ alkyl, $C_4$ alkyl, $C_5$ alkyl or $C_6$ alkyl) and aryl (for example, 6-10 membered aryl such as 6-membered aryl, 7-membered aryl, 8-membered aryl, 9-membered aryl or 10-membered aryl such as a phenyl group), L0 is absent or linking group, Dye is a fluorophore, and the fluorophore is the same as the fluorophore in the second compound and the fourth compound (or the fluorophore has a different structure but the same or substantially the same emission spectrum as that of the second compound and the fourth compound);

compound M2, which has a structural formula

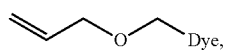

wherein Dye is a fluorophore, and the fluorophore is the same as the fluorophore in the second compound and the fourth compound (or different in structure but the same or substantially the same emission spectrum);

compound M3, which has the formula

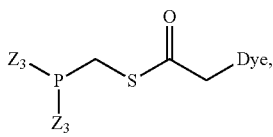

wherein, $Z_3$ is independently selected from alkyl (for example, $C_1$-$C_6$ alkyl, such as $C_1$ alkyl, $C_2$ alkyl, $C_3$ alkyl, $C_4$ alkyl, $C_5$ alkyl or $C_6$ alkyl) and aryl (for example, 6-10 membered aryl such as a 6-membered aryl, 7-membered aryl, 8-membered aryl, 9-membered aryl or 10-membered aryl such as phenyl group), and Dye is a fluorophore. The fluorophore is the same as the fluorophore in the second compound and the fourth compound (or the structures are different but the emission spectra are the same or substantially the same).

In the embodiment of the present invention, the linking group L0 is not particularly limited. A person skilled in the art can select a suitable linking group L0 according to actual needs. For example, in some preferred embodiments, L0 can be

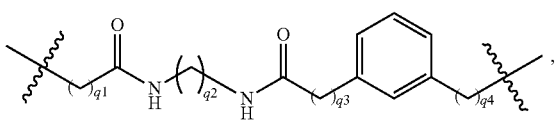

wherein q1, q2, q3, q4 are independently selected from 0, 1, 2, 3, 4, 5 or 6.

Additionally, as described above, in the method of the present invention, the washing step can be added as needed.

The washing step can be added at any desired stage, and optionally, the washing step can be performed one or more times.

For example, in step (5), after removing the solution phase of the reaction system, one or more washings may be performed to sufficiently remove the residual solution phase. Such washing step may be advantageous, which can be used to sufficiently remove free (i.e., not incorporated into the nucleic acid strands) compound carrying the fluorophore (for example, compound of formula (II) and compound of formula (IV)), thereby minimizing non-specific fluorescent signals.

Similarly, in step (7), after removing the solution phase of the reaction system, one or more washings may be performed to sufficiently remove the residual solution phase. Such washing step may be advantageous, which can be used to sufficiently remove the agent carrying the fluorophore used in step (6) to minimize non-specific fluorescent signals.

Similarly, in step (9), after removing the solution phase of the reaction system, one or more washings may be performed to sufficiently remove the residual solution phase. Such washing step may be advantageous, which can be used to sufficiently remove the agents used in step (8) as well as the products produced (which may carry fluorescence), thereby minimizing non-specific fluorescent signals and avoiding adverse effect on the subsequent polymerization reaction.

The washing step can be carried out with a variety of suitable washing solutions. Examples of such washing solutions include, but are not limited to, phosphate buffer, citrate buffer, Tris-HCl buffer, acetate buffer, carbonate buffer, and the like. It is within the ability of those skilled in the art to select a suitable washing solution (including suitable components, concentrations, ionic strength, pH, etc.) according to the actual needs.

II. Kit

In one aspect, the invention provides a kit for sequencing a nucleic acid molecule, comprising four compounds as defined above. In some preferred embodiments, the kit of the invention comprises four compounds (i.e., the first, second, third, and fourth compounds), wherein:

the four compounds are derivatives of nucleotides A, (T/U), C and G, respectively, and have a base complementary pairing ability; and, the hydroxyl group (—OH) at the 3' position of the ribose or deoxyribose of the four compounds is protected by a protecting group; and, the protecting group can be removed;

the first compound and the third compound are incapable of emitting a fluorescent signal (e.g., carrying no fluorophore), the second compound is capable of emitting a fluorescent signal (e.g., carrying a fluorophore), the fourth compound is capable of emitting a fluorescent signal, or is capable of emitting the same fluorescent signal as the second compound (e.g., carrying a fluorophore which is the same as the fluorophore in the second compound, or has a different structure but the same or substantially the same emission spectrum as that of the second compound); and, the third compound is capable of emitting the same fluorescent signal as the second compound after a treatment (e.g., carrying the same fluorophore as that in the second compound, or carrying a fluorophore that has a different structure but the same or substantially the same emission spectrum as that of the second compound), and (i) the fourth compound itself is capable of emitting the same fluorescent signal as the second compound, and can remove its fluorescent signal after treatment (e.g., removing its fluorophore, or quenching the fluorescent signal emitted by its fluorophore), or (ii) the fourth compound itself does not emit a fluorescent signal, and is capable of emitting the same fluorescent signal as the second compound after the first treatment (for example, carrying a fluorophore the same as that in the second compound, or carrying a fluorophore that has a different structure but the same or substantially the same emission spectrum as that of the second compound), and it can remove its fluorescent signal after the second treatment (for example, removing its fluorophore, or quenching the fluorescent signal emitted by its fluorophore).

In some preferred embodiments, the protecting group at the 3' position of the ribose or deoxyribose of the four compounds can be removed by a bioorthogonal cleavage reaction. For example, the protecting group is a reactive group capable of performing a bioorthogonal cleavage reaction. Thus, the protecting group can be removed by subjecting the four compounds to the bioorthogonal cleavage reaction.

In some preferred embodiments, the third compound comprises a reactive group which is capable of performing a bioorthogonal ligation reaction. Thus, a fluorophore can be introduced into the third compound by subjecting the reactive group to the bioorthogonal ligation reaction such that the compound has the ability to emit a fluorescent signal. Thus, in such embodiments, the third compound can be subjected to a bioorthogonal ligation reaction to enable it to emit the same fluorescent signal as the second compound.

In some preferred embodiments, the third compound comprises one member of the binding pair. Thus, a fluorophore can be introduced into the third compound by the specific interaction between the member and the other member of the binding pair (which carries a fluorophore), to enable the compound to have the ability to emit a fluorescent signal. Thus, in such embodiments, a fluorophore can be introduced into the third compound by contacting the third compound with the other member of the binding pair carrying the fluorophore to enable it to emit the same fluorescent signal as the second compound.

In some preferred embodiments, the fourth compound comprises a reactive group which is capable of performing a bioorthogonal cleavage reaction. Thus, the fluorophore in the fourth compound can be cleaved by subjecting the reactive group to a bioorthogonal cleavage reaction, rendering the compound unable to emit the fluorescent signal. Thus, in such embodiments, the fluorophore in the fourth compound can be removed by subjecting the fourth compound to a bioorthogonal cleavage reaction such that the fourth compound no longer emits a fluorescent signal.

In some preferred embodiments, the fourth compound comprises one member of the binding pair. Thereby, a quenching group capable of quenching fluorescence can be introduced into the fourth compound by a specific interaction between the member and the other member of the binding pair (which carries a quenching group), rendering the compound to loss the ability to emit the fluorescent signal. Thus, in such embodiments, a quenching group can be introduced into the fourth compound by contacting the fourth compound with the other member of the binding pair carrying the quenching group, enabling the fourth compound no longer to emit the fluorescent signal.

In some preferred embodiments, the fourth compound comprises a reactive group capable of performing a bioorthogonal ligation reaction. Thus, a quenching group capable of quenching fluorescence can be introduced into the fourth compound by subjecting the reactive group to the bioorthogonal ligation reaction, rendering the compound to loss the ability to emit a fluorescent signal. Thus, in such embodiments, the quenching group can be introduced into the fourth compound by subjecting the fourth compound to a bioorthogonal ligation reaction, enabling the fourth compound no longer to emit the fluorescent signal.

In some preferred embodiments, the fourth compound does not carry a fluorophore, but it comprises a reactive group capable of performing a bioorthogonal ligation reaction. Thus, a fluorophore can be introduced into the fourth compound by subjecting the reactive group to a bioorthogonal ligation reaction to enable it to have the ability to emit the fluorescent signal. Thus, in such embodiments, the fourth compound can be subjected to a bioorthogonal ligation reaction such that it emits the same fluorescent signal as the second compound.

In some preferred embodiments, the fourth compound does not carry a fluorophore, but it comprises one member of the binding pair. Thus, a fluorophore can be introduced into the fourth compound by the specific interaction between the member and the other member of the binding pair (which carries a fluorophore), to enable it to have ability to emit a fluorescent signal. Thus, in such embodiments, a fluorophore can be introduced into the fourth compound by contacting the fourth compound with the other member of the binding pair carrying the fluorophore, enabling the fourth compound to emit the same fluorescent signal as the second compound.

In some preferred embodiments, the fourth compound comprises one member of the first binding pair, and the other member of the first binding pair is simultaneously one member of the second binding pair. Thus, a fluorophore can be introduced into the fourth compound by the specific interaction between one member of the first binding pair and the other member of the first binding pair (which carries a fluorophore) to enable the compound to have an ability to emit the fluorescent signal; and, the conjugate of the first binding pair is dissociated by the specific interaction between the member of the second binding pair and the other member of the second binding pair, thereby making the fourth compound to lose the fluorophore, and to lose the ability to emit the fluorescent signal.

In some exemplary embodiments, the first, second, third, and fourth compounds have the structures of Formula (I), Formula (II), Formula (III), and Formula (IV), respectively:

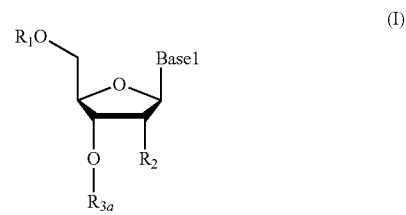

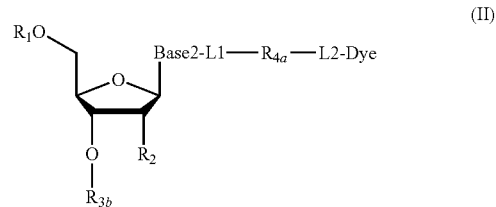

-continued

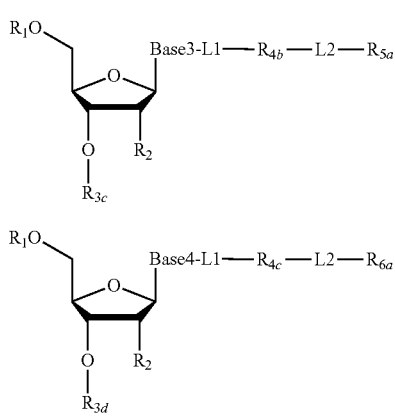

(III)

(IV)

wherein, Base1, Base2, Base3, and Base4 represent 4 different bases, and are selected from A, (T/U), C, and G;

$R_1$ is each independently selected from —H, a monophosphate group (—$PO_3H_2$), a diphosphate group (—$PO_3H$—$PO_3H_2$), a triphosphate group (—$PO_3H$—$PO_3H$—$PO_3H_2$) and a tetraphosphate group (—$PO_3H$—$PO_3H$—$PO_3H$—$PO_3H_2$);

$R_2$ is each independently selected from —H and —OH;

$R_{3a}$, $R_{3b}$, $R_{3c}$, $R_{3d}$, $R_{4a}$, $R_{4b}$, and $R_{5b}$ are independently a reactive group capable of performing a bioorthogonal cleavage reaction;

$R_{5a}$ is a reactive group capable of performing a first bioorthogonal ligation reaction;

L1 is independently a linking group or absent;

L2 is independently a linking group or absent;

Dye represents a fluorophore capable of emitting a fluorescent signal;

$R_{7a}$ is a fluorophore capable of emitting a fluorescent signal ($Dye_1$), or a reactive group capable of performing a second bioorthogonal ligation reaction, or one member of a binding pair;

also, Dye and $Dye_1$ have the same structure, or have different structures but have the same or substantially the same emission spectrum;

optionally, a reactive group $R_8$ capable of performing a third bioorthogonal ligation reaction is present between $R_{5b}$ and $R_{7a}$.

In some preferred embodiments, the four compounds are as defined in Exemplary Embodiment 1 above. In some preferred embodiments, the kit further comprises an agent that carries a fluorophore (e.g., the same fluorophore as the second compound, or a fluorophore that differs in structure but emits the same or substantially the same spectrum), it is capable of performing a first bioorthogonal ligation reaction with $R_{5a}$ in the third compound to introduce the fluorophore into the third compound to make the third compound to emit a fluorescent signal.

In some preferred embodiments, the kit further comprises an agent capable of subjecting $R_{5b}$ in the fourth compound to a bioorthogonal cleavage reaction to remove the fluorophore in the fourth compound.

In some preferred embodiments, the kit further comprises an agent that carries a fluorophore (e.g., the same fluorophore as the second compound, or a fluorophore that differs in structure but emits the same or substantially the same spectrum), it is capable of performing a second bioorthogonal ligation reaction with $R_{7a}$ in the fourth compound, or is capable of specifically binding to $R_{7a}$, thereby introducing the fluorophore into the fourth compound to make the fourth compound to emit the fluorescent signal.

In some preferred embodiments, the kit further comprises a quencher-carrying agent capable of performing a third bioorthogonal ligation reaction with $R_8$ in the fourth compound to quench the fluorescence emitted by the fourth compound signal.

In some preferred embodiments, the kit further comprises any one or more of the agents described in Exemplary Embodiment 1, other than the four compounds described.

In some exemplary embodiments, the first, second, third, and fourth compounds have the structures of Formula (I), Formula (II), Formula (III), and Formula (IV), respectively:

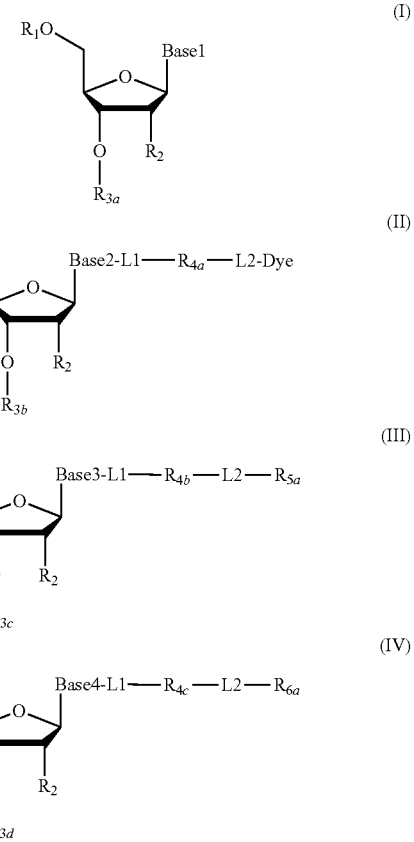

wherein, Base1, Base2, Base3, and Base4 represent 4 different bases, and are selected from A, (T/U), C, and G;

$R_1$ is each independently selected from —H, a monophosphate group (—$PO_3H_2$), a diphosphate group (—$PO_3H$—$PO_3H_2$), a triphosphate group (—$PO_3H$—$PO_3H$—$PO_3H_2$) and a tetraphosphate group (—$PO_3H$—$PO_3H$—$PO_3H$—$PO_3H_2$);

$R_2$ is each independently selected from —H and —OH;

$R_{3a}$, $R_{3b}$, $R_{3c}$, $R_{3d}$, $R_{4a}$, $R_{4b}$, and $R_{4c}$ are each independently a reactive group capable of performing a bioorthogonal cleavage reaction;

$R_{5a}$ is one member of the first binding pair;

$R_{6a}$ is (i) one member of the second binding pair, and is one member of the third binding pair; or is (ii) just one member of the third binding pair; and, $R_{6a}$ is $Dye_1$, or $R_{6a}$ is linked with -L3-$Dye_1$;

L1 is independently a linking group or absent;

L2 is independently a linking group or absent;

L3 is a linking group or absent;

Dye and Dye₁ represent a fluorophore capable of emitting a fluorescent signal; and, both of them have the same structure, or have different structures but have the same or substantially the same emission spectrum;

optionally, a reactive group $R_8$ capable of performing the bioorthogonal ligation reaction is present between $R_{4c}$ and $R_{6a}$.

In some preferred embodiments, the four compounds are as defined in Exemplary Embodiment 2 above.

In some preferred embodiments, the kit further comprises $R_{6b}$-L4-Dye₂; wherein $R_{6b}$ is the other member of the second binding pair, L4 is independently a linking group or absent; Dye₂ represents fluorophore capable of emitting fluorescent signal, and it has the same structure as Dye, or a different structure but with the same or substantially the same emission spectrum. The $R_{6b}$ in the $R_{6b}$-L4-Dye₂ is capable of specifically interacting with/binding to $R_{6a}$ in the fourth compound, thereby introducing the fluorophore (Dye₂) into the fourth compound to make the fourth compound to emit a fluorescent signal.

In some preferred embodiments, the kit further comprises $R_{5b}$-L5-Dye₃, wherein $R_{5b}$ is the other member of the first binding pair, L5 is a linking group or absent; Dye₃ represents fluorophore which is capable of emitting a fluorescent signal, which is preferably the same fluorophore as the second compound (or a fluorophore that has a different structure from that of the second compound but their emission spectrum is the same or substantially the same). $R_{5b}$ in the $R_{5b}$-L5-Dye₃ is capable of specifically interacting with/binding to $R_{5a}$ in the third compound, thereby introducing the fluorophore (Dye) into the third compound to make the third compound to emit a fluorescent signal.

In some preferred embodiments, the kit further comprises $R_{6b}$-L6-Que, wherein $R_{6b}$ is the other member of the second binding pair, $L_6$ is a linking group or absent; Que represents a quenching group which is capable of quenching the fluorescent signal emitted by Dye. $R_{6b}$ in the $R_{6b}$-L6-Que is capable of specifically interacting with/bind to $R_{6a}$ in the fourth compound, thereby introducing the quenching group (Que) into the fourth compound and quenching fluorescent signal emitted by the fluorescent signal (Dye) in the fourth compound.

In some preferred embodiments, the kit further comprises an agent carrying a quencher, which is capable of performing a third bioorthogonal ligation reaction with $R_8$ in the fourth compound to quench the fluorescent signal emitted by the fourth compound.

In some preferred embodiments, the kit further comprises any one or more of the agents described in Exemplary Embodiment 2 in addition to the four compounds described.

In some exemplary embodiments, the first, second, third, and fourth compounds have the structures of Formula (I), Formula (II), Formula (III), and Formula (IV), respectively:

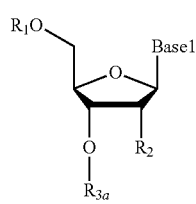
(I)

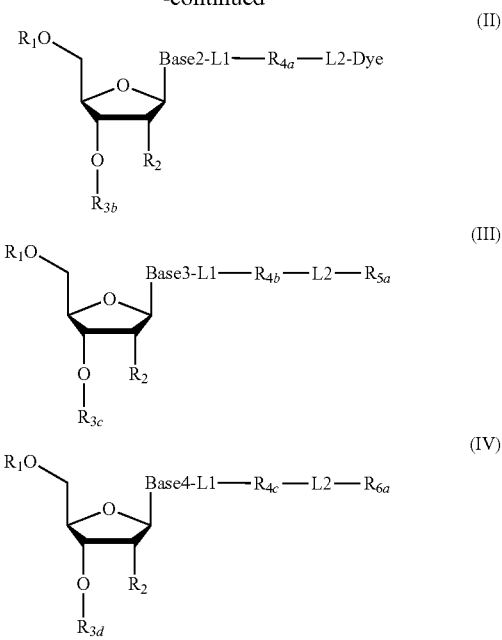

wherein, Base1, Base2, Base3, and Base4 represent 4 different bases, and are selected from A, (T/U), C, and G;

$R_1$ is each independently selected from —H, a monophosphate group (—PO₃H₂), a diphosphate group (—PO₃H—PO₃H₂), a triphosphate group (—PO₃H—PO₃H—PO₃H₂) and a tetraphosphate group (—PO₃H—PO₃H—PO₃H—PO₃H₂);

$R_2$ is each independently selected from —H and —OH;

$R_{3a}$, $R_{3b}$, $R_{3c}$, $R_{3d}$, $R_{4a}$, $R_{4b}$, and $R_{4c}$ are each independently a reactive group capable of performing a bioorthogonal cleavage reaction;

$R_{5a}$ is a reactive group which is capable of performing a first bioorthogonal ligation reaction;

$R_{6a}$ is (i) one member of the first binding pair and is one member of the second binding pair; or is (ii) only one member of the second binding pair, and $R_{6a}$ is Dye₁, or $R_{6a}$ is also linked with -L3-Dye₁;

L1 is independently a linking group or absent;

L2 is independently a linking group or absent;

L3 is a linking group or absent;

Dye represents a fluorophore capable of emitting a fluorescent signal; Dye and Dye₁ have the same structure, or have different structures but the same or substantially the same emission spectrum;

optionally, a reactive group $R_8$ capable of performing a second bioorthogonal ligation reaction is present between $R_{4c}$ and $R_{6a}$.

In some preferred embodiments, the four compounds are as defined in Exemplary Embodiment 3 above.

In some preferred embodiments, the kit further comprises $R_{6b}$-L4-Dye₂; wherein $R_{6b}$ is the other member of the first binding pair, L4 is independently a linking group or absent; Dye₂ represents the fluorophore which is capable of emitting the fluorescent signal, and it has the same structure as Dye, or a different structure but the same or substantially the same emission spectrum. The $R_{6b}$ in $R_{6b}$-L4-Dye₂ is capable of specifically interacting with/binding to $R_{6a}$ in the fourth compound, thereby introducing the fluorophore (Dye₂) into the fourth compound to make the fourth compound to emit a fluorescent signal.

In some preferred embodiments, the kit further comprises an agent carrying a fluorophore (for example, a fluorophore which is the same as the fluorophore of the second compound, or has the same or substantially the same emission spectrum as that of the second compound), which is capable of performing the bioorthogonal ligation reaction with $R_{5a}$ in the third compound, thereby introducing the fluorophore into the third compound to make the third compound to emit a fluorescent signal.

In some preferred embodiments, the kit further comprises $R_{6c}$-L'-Que, wherein $R_{6c}$ is the other member of the second binding pair, L' is a linking group or absent; Que represents a quenching group which is capable of quenching the fluorescent signal emitted by Dye. $R_{6c}$ in $R_{6c}$-L'-Que is capable of specifically interacting with/binding to $R_{6a}$ in the fourth compound, thereby introducing the quenching group (Que) into the fourth compound and quenching the fluorescent signal emitted by a fluorophore (Dye) in the fourth compound.

In some preferred embodiments, the kit further comprises an agent carrying a quencher which is capable of performing the third bioorthogonal ligation reaction with $R_8$ in the fourth compound to quench the fluorescent signal emitted by the fourth compound.

In some preferred embodiments, the kit further comprises any one or more of the agents described in Exemplary Embodiment 3 besides the four compounds described.

In some exemplary embodiments, the first, second, third, and fourth compounds have the structures of Formula (I), Formula (II), Formula (III), and Formula (IV), respectively:

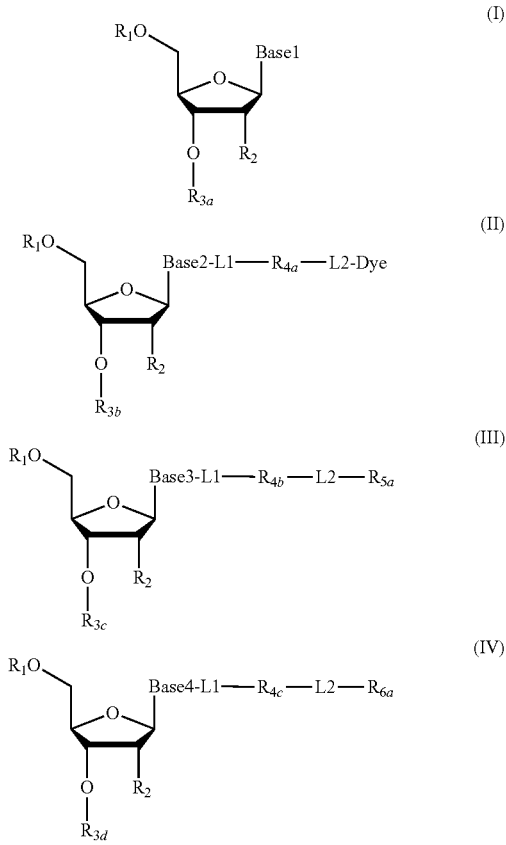

wherein, Base1, Base2, Base3, and Base4 represent 4 different bases, and are selected from A, (T/U), C, and G;

$R_1$ is independently selected from —H, monophosphate group (—PO$_3$H$_2$), diphosphate group (—PO$_3$H—PO$_3$H$_2$), triphosphate group (—PO$_3$H—PO$_3$H—PO$_3$H$_2$) and tetraphosphate group (—PO$_3$H—PO$_3$H—PO$_3$H—PO$_3$H$_2$);

$R_2$ is independently selected from —H and —OH;

$R_{3a}$, $R_{3b}$, $R_{3c}$, $R_{3d}$, $R_{4a}$, $R_{4b}$, and $R_6$ are independently a reactive group capable of performing a bioorthogonal cleavage reaction;

$R_{5a}$ is one member of the first binding pair;

$R_{6a}$ is a fluorophore which is capable of emitting a fluorescent signal (Dye$_1$), a reactive group which is capable of performing a first bioorthogonal ligation reaction, and/or one member of the second binding pair;

L1 is independently a linking group or absent;

L2 is independently a linking group or absent;

Dye and Dye$_1$ represent fluorophores capable of emitting a fluorescent signal; and, Dye and Dye$_1$ have the same structure, or have different structures but have the same or substantially the same emission spectrum.

Optionally, there is a reactive group $R_8$ capable of performing a second bioorthogonal ligation reaction between $R_{4c}$ and $R_{6a}$;

in some preferred embodiments, the four compounds are as defined in Exemplary Embodiment 4 above.

In some preferred embodiments, the kit further comprises $R_{6b}$-L-Dye$_1$; wherein $R_{6b}$ is the other member of the second binding pair, L is independently a linking group or is absent; Dye$_1$ represents the fluorophore which is capable of emitting the fluorescent signal, and it has the same structure as Dye, or a different structure but the same or substantially the same emission spectrum. $R_{6b}$ in $R_{6b}$-L-Dye$_1$ is capable of specifically interacting with/binding to $R_{6a}$ in the fourth compound, thereby introducing the fluorophore (Dye$_1$) into the fourth compound to make the fourth compound to emit a fluorescent signal.

In some preferred embodiments, the kit further comprises an agent carrying a fluorophore (for example, a fluorophore which is the same to the fluorophore as the second compound, or a fluorophore which has the same or substantially the same emission spectrum as the fluorophore of the second compound), which is capable of performing the first bioorthogonal ligation reaction with $R_{6a}$ in the fourth compound to introduce the fluorophore into the third compound to make the third compound to emit a fluorescent signal.

In some preferred embodiments, the kit further comprises $R_{5b}$-L-Dye$_2$, wherein $R_{5b}$ is the other member of the first binding pair, L is a linking group or is absent; Dye$_2$ represents the fluorophore which is capable of emitting the fluorescent signal, which is preferably the same fluorophore as the second compound, or a fluorophore which has the same or substantially the same emission spectrum as the fluorophore of the second compound. $R_{5b}$ in said $R_{5b}$-L-Dye$_2$ is capable of specifically interacting with/binding to $R_{5a}$ in the third compound, thereby introducing the fluorophore (Dye$_2$) into the third compound to make the third compound to emit a fluorescent signal.

In some preferred embodiments, the kit further comprises an agent carrying a quencher, which is capable of performing a second bioorthogonal ligation reaction with $R_8$ in the fourth compound to quench the fluorescent signal emitted by the fourth compound.

In some preferred embodiments, the kit further comprises an agent which enables $R_{4c}$ in the fourth compound to perform the bioorthogonal cleavage reaction to remove the fluorophore in the fourth compound.

In some preferred embodiments, the kit further comprises any one or more of the agents described in Exemplary Embodiment 4 in addition to the four compounds described.

In some exemplary embodiments, the first, second, third, and fourth compounds have the structures of Formula (I), Formula (II), Formula (III), and Formula (IV), respectively:

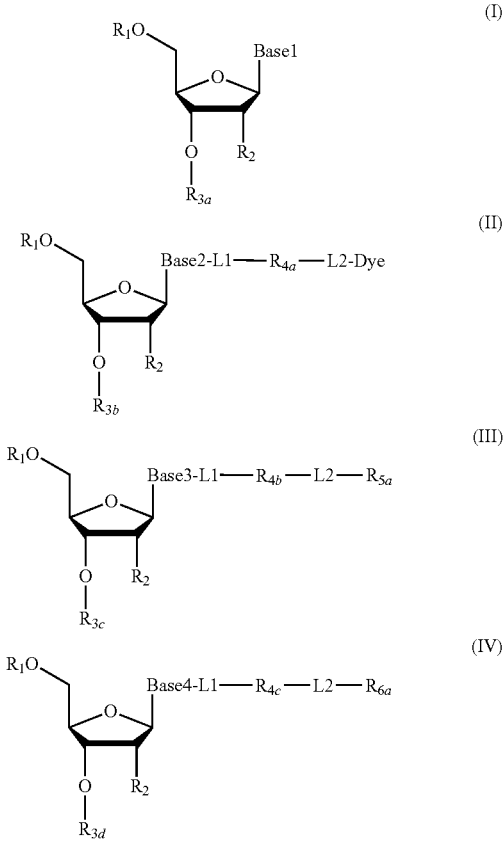

wherein, Base1, Base2, Base3, and Base4 represent 4 different bases, and are selected from A, (T/U), C, and G;

$R_1$ is independently selected from —H, monophosphate group (—$PO_3H_2$), diphosphate group (—$PO_3H$—$PO_3H_2$), triphosphate group (—$PO_3H$—$PO_3H$—$PO_3H_2$) and tetraphosphate group (—$PO_3H$—$PO_3H$—$PO_3H$—$PO_3H_2$);

$R_2$ is independently selected from —H and —OH;

$R_{3a}$, $R_{3b}$, $R_{3c}$, $R_{3d}$, $R_{4a}$, $R_{4b}$, and $R_{4c}$ are independently a reactive group capable of performing a bioorthogonal cleavage reaction;

$R_{5a}$ is one member of the first binding pair;

$R_{6a}$ is one member of the second binding pair, optionally, $R_{6a}$ is $Dye_1$ or is also linked onto -L3-$Dye_1$;

L1 is independently a linking group or absent;

L2 is independently a linking group or absent;

L3 is a linking group or absent;

Dye and $Dye_1$ represent fluorophore capable of emitting a fluorescent signal; and, both have the same structure, or have different structures but the same or substantially the same emission spectrum;

optionally, a reactive group $R_8$ which is capable of performing a bioorthogonal ligation reaction is present between $R_{4c}$ and $R_{6a}$.

In some preferred embodiments, said four compounds are as defined in Exemplary Embodiment 5 above.

In some preferred embodiments, the kit further comprises $R_{6b}$-L4-$Dye_2$; wherein $R_{6b}$ is the other member of the second binding pair, L4 is independently a linking group or absent; $Dye_2$ represents the fluorophore which is capable of emitting the fluorescent signal, and it has the same structure as Dye, or different structure but the same or substantially the same emission spectrum. $R_{6b}$ in the $R_{6b}$-L4-$Dye_2$ is capable of specifically interacting with/binding to $R_{6a}$ in the fourth compound, thereby introducing the fluorophore ($Dye_1$) into the fourth compound to make the fourth compound to emit a fluorescent signal.

In some preferred embodiments, the kit further comprises the other member of the second binding pair, which is capable of specifically interacting with/binding to $R_{6b}$ to dissociate the conjugate formed by $R_{6a}$ and $R_{6b}$, thereby making the fourth compound to lose the fluorophore.

In some preferred embodiments, the kit further comprises $R_{5b}$-L5-$Dye_3$, wherein $R_{5b}$ is the other member of the first binding pair, L5 is a linking group or absent; $Dye_3$ represents the fluorophore which is capable of emitting the fluorescent signal, which is preferably the same fluorophore as the second compound, or a fluorophore which has the same or substantially the same emission spectrum as the fluorophore of the second compound. $R_{5b}$ in said $R_{5b}$-L5-$Dye_3$ is capable of specifically interacting with/binding to $R_{5a}$ in the third compound, thereby introducing the fluorophore ($Dye_3$) into the third compound to make the third compound to emit a fluorescent signal.

In some preferred embodiments, the kit further comprises an agent carrying a quencher which is capable of performing a second bioorthogonal ligation reaction with $R_8$ in the fourth compound to quench the fluorescent signal emitted by the fourth compound.

In some preferred embodiments, the kit further comprises an agent which enables $R_{4c}$ in the fourth compound to perform the bioorthogonal cleavage reaction to remove the fluorophore in the fourth compound.

In some preferred embodiments, the kit further comprises any one or more of the agents described in Exemplary Embodiment 5 in addition to the four compounds described.

In some exemplary embodiments, the first, second, third, and fourth compounds have the structures of Formula (I), Formula (II), Formula (III), and Formula (IV), respectively:

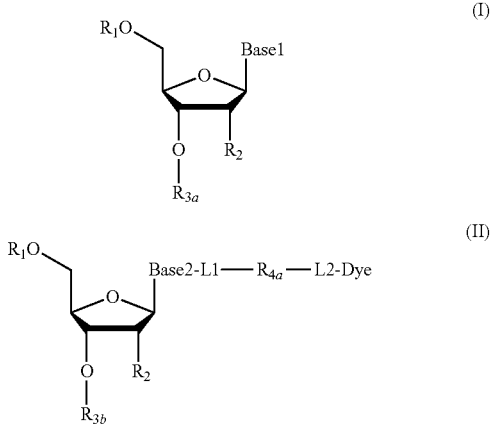

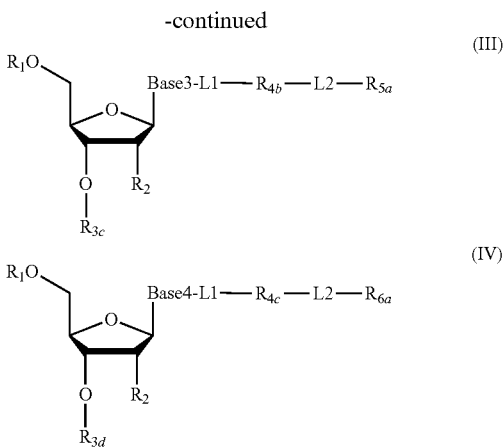

wherein, Base1, Base2, Base3, and Base4 represent 4 different bases, and are selected from A, (T/U), C, and G;

$R_1$ is independently selected from —H, monophosphate group (—PO$_3$H$_2$), diphosphate group (—PO$_3$H—PO$_3$H$_2$), triphosphate group (—PO$_3$H—PO$_3$H—PO$_3$H$_2$) and tetraphosphate group (—PO$_3$H—PO$_3$H—PO$_3$H—PO$_3$H$_2$);

$R_2$ is independently selected from —H and —OH;

$R_{3a}$, $R_{3b}$, $R_{3c}$, $R_{3d}$, $R_{4a}$, $R_{4b}$, and $R_{4c}$ are independently a reactive group capable of performing a bioorthogonal cleavage reaction;

$R_{5a}$ is a reactive group capable of performing a first bioorthogonal ligation reaction;

$R_{6a}$ is one member of the first binding pair, optionally, $R_{6a}$ is Dye$_1$ or is also linked onto -L3-Dye$_1$;

L1 is independently a linking group or absent;
L2 is independently a linking group or absent;
L3 is a linking group or absent;

Dye represents a fluorophore capable of emitting a fluorescent signal; Dye and Dye$_1$ have the same structure, or have different structures but the same or substantially the same emission spectrum;

optionally, a reactive group $R_8$ capable of performing a second bioorthogonal ligation reaction is present between $R_{4c}$ and $R_{6a}$.

In some preferred embodiments, the four compounds are as defined in Exemplary Embodiment 6 above.

In some preferred embodiments, the kit further comprises $R_{6b}$-L4-Dye$_2$; wherein $R_{6b}$ is the other member of the first binding pair, L4 is independently a linking group or absent; Dye$_2$ represents a fluorophore capable of emitting a fluorescent signal and has the same structure as Dye, or is structurally different but has the same or substantially the same emission spectrum. $R_{6b}$ in the $R_{6b}$-L4-Dye$_2$ is capable of specifically interacting with/binding to $R_{6a}$ in the fourth compound, thereby introducing the fluorophore (Dye$_1$) into the fourth compound to make the fourth compound to emit a fluorescent signal.

In some preferred embodiments, the kit further comprises the other member of the second binding pair, which is capable of specifically interacting with/binding to $R_{6b}$ to dissociate the conjugate formed by $R_{6a}$ and $R_{6b}$, making the fourth compound to loss the fluorophore.

In some preferred embodiments, the kit further comprises an agent carrying a fluorophore (for example, a fluorophore as the second compound, or a fluorophore which has the same fluorophore as the second compound, or the same or substantially the same emission spectrum as the fluorophore of the second compound), which is capable of performing the bioorthogonal ligation reaction with $R_{5a}$ in the third compound, thereby introducing the fluorophore into the third compound to make the third compound to emit a fluorescent signal.

In some preferred embodiments, the kit further comprises an agent carrying a quencher which is capable of performing a second bioorthogonal ligation reaction with $R_8$ in the fourth compound to quench the fluorescent signal emitted by the fourth compound.

In some preferred embodiments, the kit further comprises an agent capable of subjecting $R_{4c}$ in the fourth compound to a bioorthogonal cleavage reaction to remove the fluorophore in the fourth compound.

In some preferred embodiments, the kit further comprises any one or more of the agents described in Exemplary Embodiment 6, in addition to the four compounds described.

In some preferred embodiments, the kit of the present invention further comprises: agents and/or devices for extracting nucleic acid molecules from the sample; agents for pretreating the nucleic acid molecules; a support for attaching a nucleic acid molecule to be sequenced; agent for attaching the nucleic acid molecule to be sequenced to the support (for example, covalent or non-covalent attaching); a primer for initiating nucleotide polymerization; polymerases for performing a nucleotide polymerization reaction; one or more buffer solutions; one or more washing solutions; or any combination thereof.

In some preferred embodiments, the kit of the invention further comprises agents and/or devices for extracting nucleic acid molecules from the sample.

Methods for extracting nucleic acid molecules from a sample are well known in the art. Therefore, various agents and/or devices for extracting nucleic acid molecules, such as agents for disrupting cells, agents for precipitating DNA, agents for washing DNA, agents for dissolving DNA, agents for precipitating RNA, agents for washing RNA, agents for dissolving RNA, agents for removing protein, and agents for removing DNA (for example, when the nucleic acid molecule of interest is RNA), agents for removing RNA (for example, when the nucleic acid molecule of interest is DNA), and any combination thereof, can be configured as needed.

In some preferred embodiments, the kit of the invention further comprises an agent for pretreating the nucleic acid molecule. In the kit of the present invention, the agent for pretreating the nucleic acid molecule is not limited, and may be selected according to actual needs. The agent for pretreating a nucleic acid molecule includes, for example, an agent for fragmentation of a nucleic acid molecule (for example, DNase I), an agent for complementing the end of a nucleic acid molecule (for example, DNA polymerase such as T4 DNA polymerase, Pfu DNA polymerase, Klenow DNA polymerase), an adapter molecule, a tag molecule, an agent for linking an adapter molecule to a nucleic acid molecule of interest (e.g., a ligase, such as T4 DNA ligase), an agent for repairing a nucleic acid nick (e.g., a DNA polymerase losing 3'-5' exonuclease activity but showing 5'-3' exonuclease activity), agents for amplifying nucleic acid molecules (e.g., DNA polymerase, primers, dNTPs), agents for separating and purifying the nucleic acid molecules (e.g., a chromatography column), and any combination thereof.

In some preferred embodiments, the kit of the invention further comprises a support for linking the nucleic acid molecule to be sequenced. The support may have any technical feature described in detail above for the support and any combination thereof.

For example, in the present invention, the support may be made of various suitable materials. Such materials include, for example, inorganics, natural polymers, synthetic polymers, and any combination thereof. Specific examples include, but are not limited to, cellulose, cellulose derivatives (such as nitrocellulose), acrylic resins, glass, silica gel, polystyrene, gelatin, polyvinylpyrrolidone, copolymers of vinyl and acrylamide, and polystyrene crosslinked with divinylbenzene, etc (see, for example, Merrifield Biochemistry 1964, 3, 1385-1390), polyacrylamide, latex, dextran, rubber, silicon, plastic, natural sponge, metal plastic, crosslinked dextran (e.g., Sephadex™), agarose gel (Sepharose™), and other supports known to those skilled in the art.

In some preferred embodiments, the support for linking the nucleic acid molecule to be sequenced may be a solid support comprising an inert substrate or matrix (e.g., slides, polymer beads, etc.), said inert substrate or matrix has been functionalized, for example, by the use of intermediate materials containing reactive groups that allow covalent linking of biomolecules such as polynucleotides. Examples of such supports include, but are not limited to, polyacrylamide hydrogels supported on an inert substrate such as glass, in particular polyacrylamide hydrogels as described in WO 2005/065814 and US 2008/0280773, wherein, the content of the patent application is hereby incorporated by reference in its entirety. In such embodiments, the biomolecule (e.g., a polynucleotide) can be directly covalently linked onto the intermediate material (e.g., a hydrogel), while the intermediate material itself can be non-covalently linked onto the substrate or matrix (for example, a glass substrate). In some preferred embodiments, the support is a glass slide or wafer having a surface modified with a layer of avidin, chemical groups of amino, acrylamide silane or aldehyde groups.

In the present invention, the support or solid support is not limited by its size, shape and configuration. In some embodiments, the support or solid support is a planar structure, such as a slide, chip, microchip, and/or array. The surface of such support may be in the form of a planar layer. In some embodiments, the support or surface thereof is non-planar, such as the inner or outer surface of a tube or container. In some embodiments, the support or solid support comprises microspheres or beads. In some preferred embodiments, the support for linking the nucleic acid molecule to be sequenced is an array of beads or wells.

In some preferred embodiments, the kit of the invention further comprise agents for linking (e.g., covalently or non-covalently linking) a nucleic acid molecule to be sequenced to a support. Such agents include, for example, agents that activate or modify a nucleic acid molecule (e.g., at its 5' end), for example, phosphoric acid, thiol, amine, carboxylic acid or aldehyde; agents that activates or modifies the surface of the support, for example, amino-alkoxysilane (for example, aminopropyltrimethoxysilane, aminopropyltriethoxysilane, 4-aminobutyltriethoxysilane, etc.); crosslinking agent, for example, succinic anhydride, phenyl diisothiocyanates (Guo et al., 1994), maleic anhydride (Yang et al., 1998), 1-ethyl-3-(3-dimethylaminopropyl)-carbodiimide hydrochloride (EDC), m-maleimidobenzoic acid-N-hydroxysuccinimide (MBS), N-succinimidyl [4-iodoacetyl] aminobenzoic acid (SIAB), succinimidyl 4-(N-maleimidomethyl)cyclohexane-1-carboxylate (SMCC), N-γ-maleimidobutyryloxy-succinimideester (GMBS), 4-(p-maleimidophenyl)butyric acid succinimide (SMPB); and any combination thereof.

In some preferred embodiments, the kits of the invention further comprise primers for initiating nucleotide polymerization. In the present invention, the primers are not subject to any additional limitation as long as it is capable of specifically annealing to a region of the target nucleic acid molecule. In some exemplary embodiments, the primers may be 5-50 bp in length, such as 5-10, 10-15, 15-20, 20-25, 25-30, 30-35, 35-40, 40-45, 45-50 bp. In some exemplary embodiments, the primers may comprise naturally occurring or non-naturally occurring nucleotides. In some exemplary embodiments, the primer comprises or consists of a naturally occurring nucleotide. In some exemplary embodiments, the primer comprises a modified nucleotide, such as a locked nucleic acid (LNA). In some preferred embodiments, the primer comprises a universal primer sequence.

In some preferred embodiments, the kit of the invention further comprises a polymerase for performing a nucleotide polymerization reaction. In the present invention, various suitable polymerases can be used. In some exemplary embodiments, the polymerase (e.g., DNA polymerase) can synthesize new DNA strand using DNA as a template. In some exemplary embodiments, the polymerase (e.g., a reverse transcriptase) can synthesize new DNA strand using RNA as a template. In some exemplary embodiments, the polymerase can synthesize new RNA strand (e.g., RNA polymerase) using DNA or RNA as a template. Accordingly, in some preferred embodiments, the polymerase is selected from the group consisting of DNA polymerase, RNA polymerase, and reverse transcriptase.

In some preferred embodiments, the kit of the invention further comprises one or more buffer solutions. Such buffers include, but are not limited to, buffer solutions for DNase I, buffer solutions for DNA polymerases, buffer solutions for ligases, buffer solutions for eluting nucleic acid molecules, and buffer solutions for performing a nucleotide polymerization reaction (for example, PCR) and buffer solutions for performing a ligation reaction. The kit of the present invention may comprise any one or more of the above buffer solutions.

In some preferred embodiments, the kit of the invention further comprises one or more washing solutions. Examples of such washing solutions include, but are not limited to, phosphate buffer, citrate buffer, Tris-HCl buffer, acetate buffer, carbonate buffer, and the like. The kit of the present invention may comprise any one or more of the above washing solutions.

Advantageous Effects of the Invention

Compared with the prior art, the technical solutions of the present invention have the following beneficial effects:

(1) The method of the invention uses only one fluorescent dye or two fluorescent dyes which is capable of emitting the same fluorescent signal. Therefore, the sequencing device used in the sequencing method of the present invention only needs to be equipped with one exciting light source and one camera. On the one hand, the cost of the sequencing device is greatly reduced, which will conduce to the promotion and apply of the sequencing device and sequencing device method; on the other hand, the volume of the sequencing device is significantly reduced, which will make the sequencing device more portable and easy to carry.

(2) The method of the invention distinguishes bases by the presence or absence of fluorescence. The method of the present invention has higher sensitivity and higher accuracy than a method for distinguishing bases by the wavelength of fluorescence.

The embodiments of the present invention will be detailed with drawings and examples. However, it will be understood by those skilled in the art that the following drawings and examples are provided for illustration purpose only and not as a limitation on the scope of the invention. In accordance with the drawings and the following detailed description of the preferred embodiments, the objects and advantages of the invention will become apparent to those skilled in the art.

DETAILED DESCRIPTION OF THE INVENTION

The invention is described with reference to the following examples which are intended to illustrate, but not limit the invention. It will be understood by those skilled in the art that the following examples are provided for illustration purpose only and not as a limitation on the scope of the invention.

Detailed Embodiment 1

Preparation Example 1. Preparation of Derivative of dGTP dGTP derivative is synthesized by ACME BIOPHARMA Co., LTD, and the synthetic method is proceeded by reference to the document (US20130189743A1). The compound is purified by analytical HPLC to give a product with a purity greater than 95%. MALDI-TOF: molecular formula $C_{11}H_{17}N_8O_{13}P3[M]$ (obtained by calculation), molecular weight: 562.01 (calc), 561.00 [M–H]– (found). The structure of the compound is shown in Formula 1.

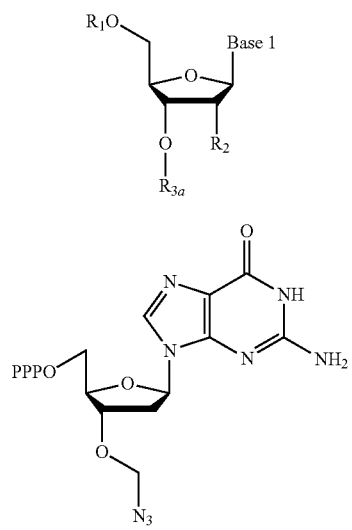

Synthetic Route:

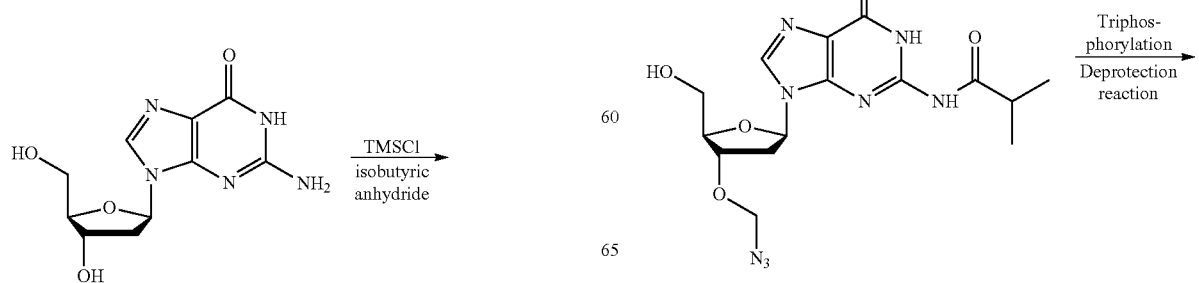

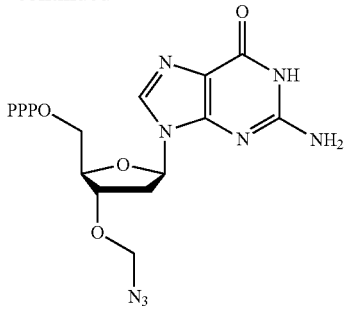

Preparation Example 2. Preparation of Derivative of dATP

The dATP derivative is synthesized by ACME BIO-PHARMA Co., LTD, the synthetic method is proceeded by reference to (US20130189743A1), and the compound is purified by analytical HPLC to obtain a product having a purity of more than 95%. MALDI-TOF: molecular formula $C_{60}H_{68}N_{15}O_{25}P_3S_2[M]$ (obtained by calculation), molecular weight 1555.31 (calc), 1554.25 [M−H]− (found).

The structure of the compound is shown in Formula 2.

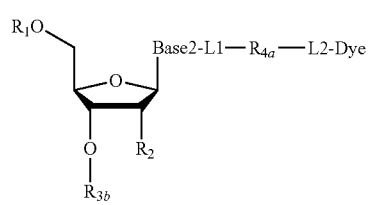

The synthetic route includes the following stages 1 and 2:

Stage 1:

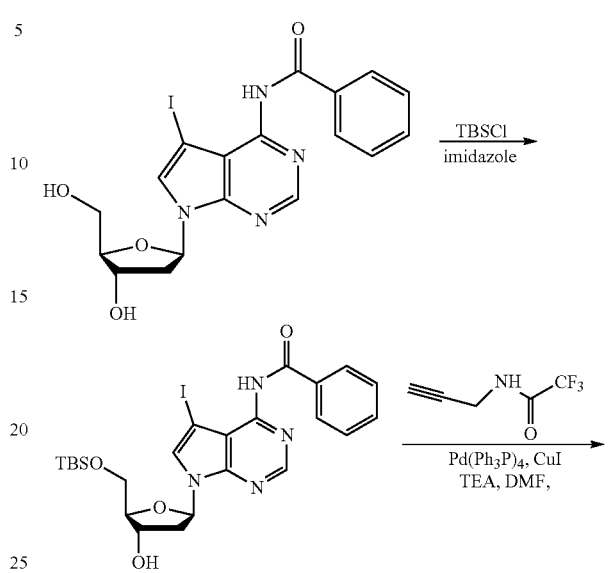

(II)

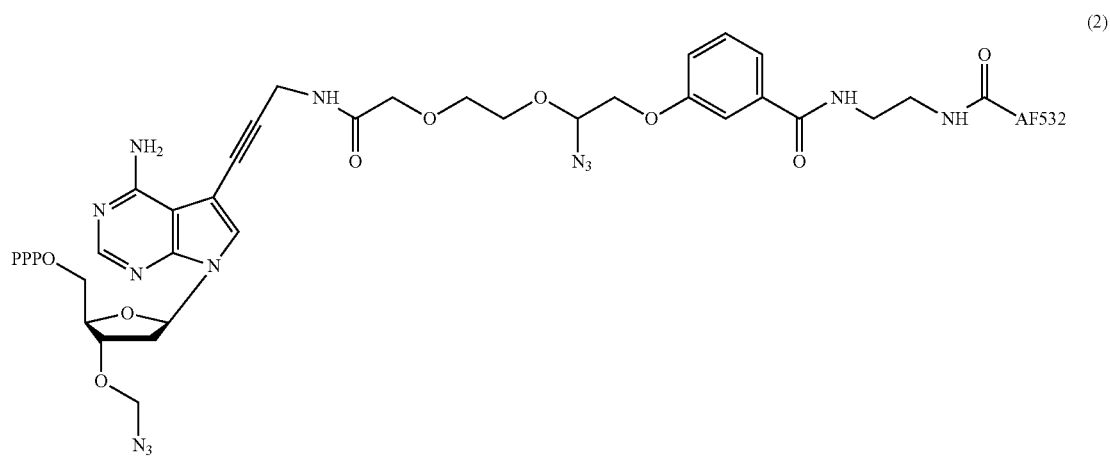

(2)

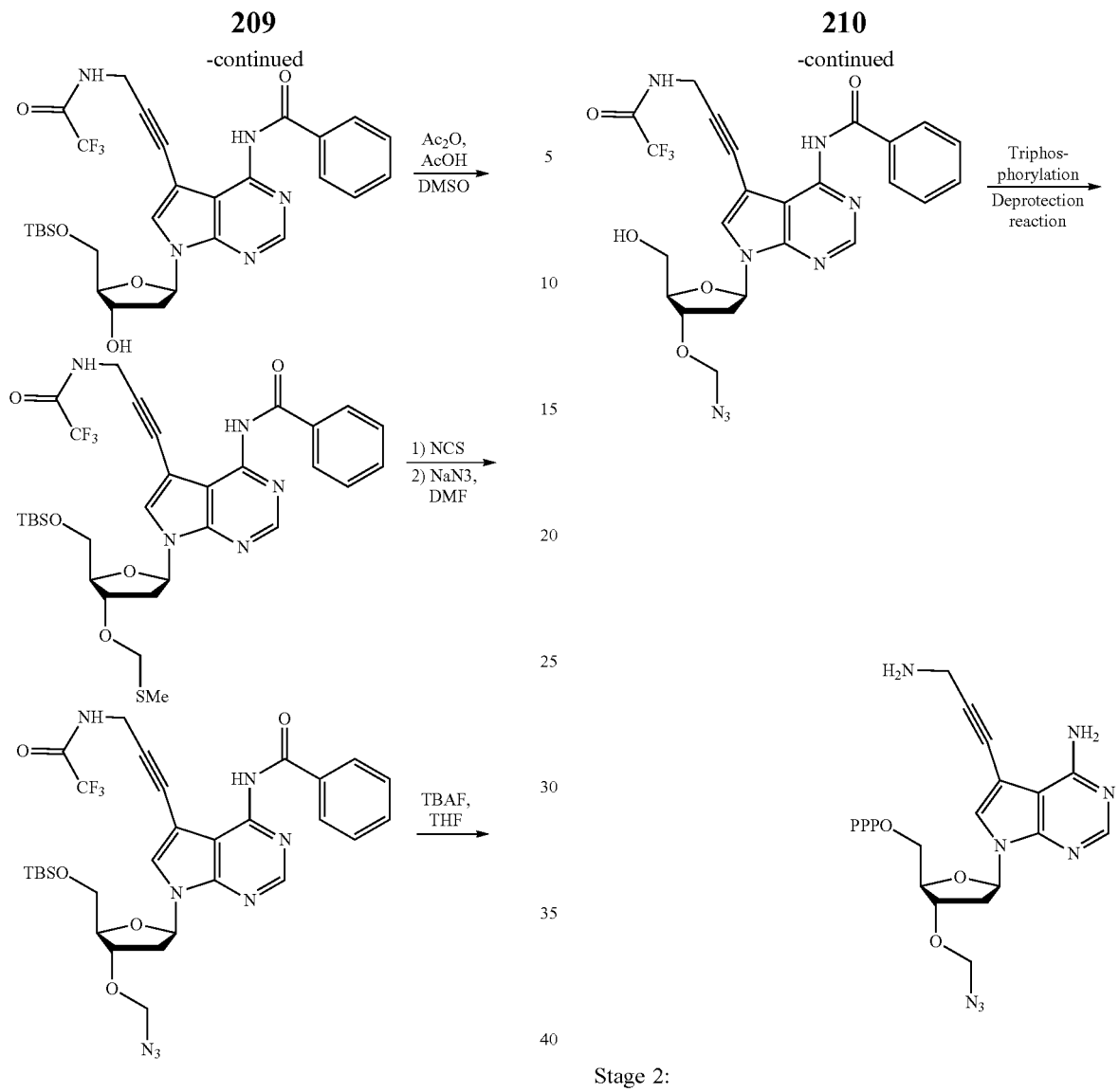
Stage 2:
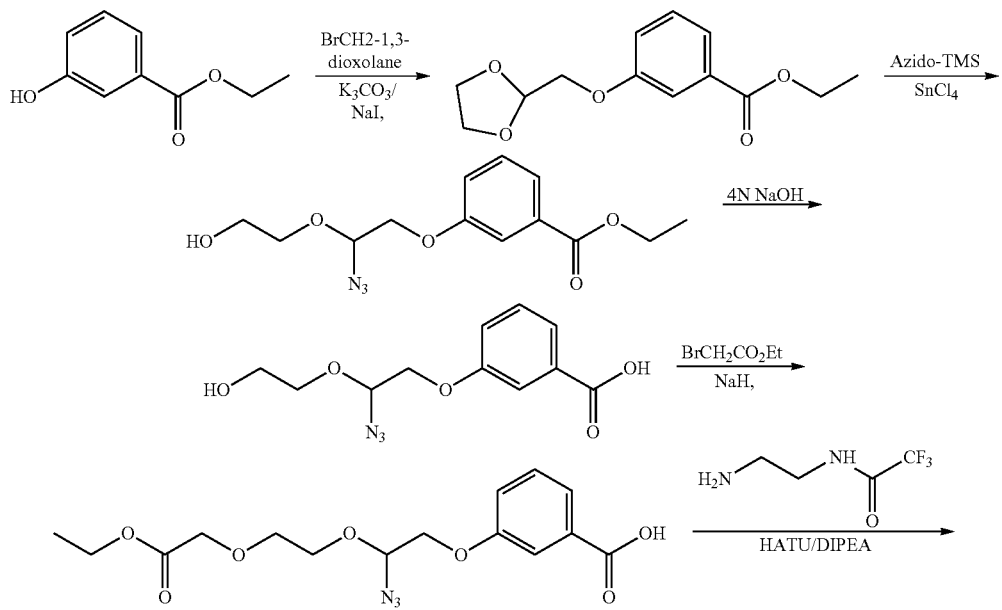

-continued

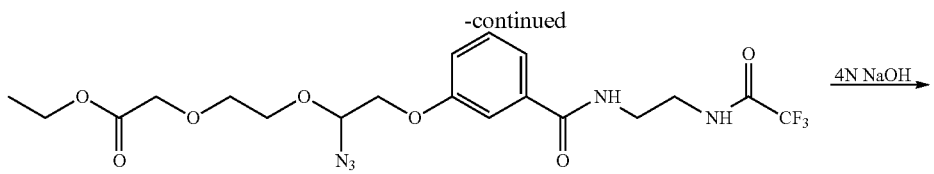

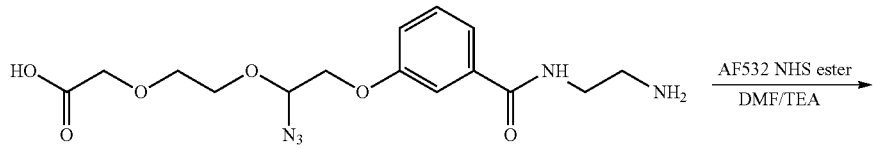

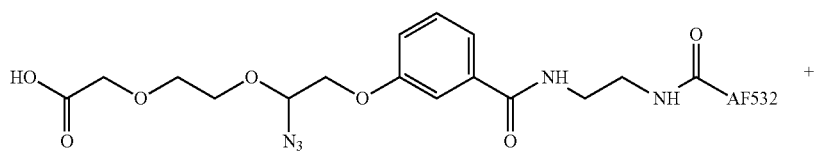

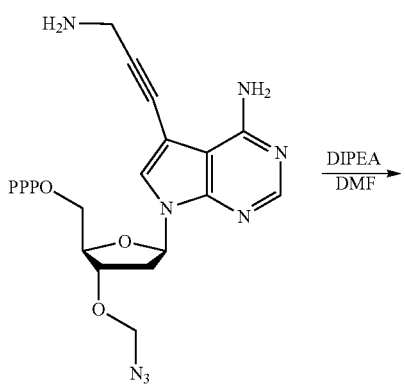

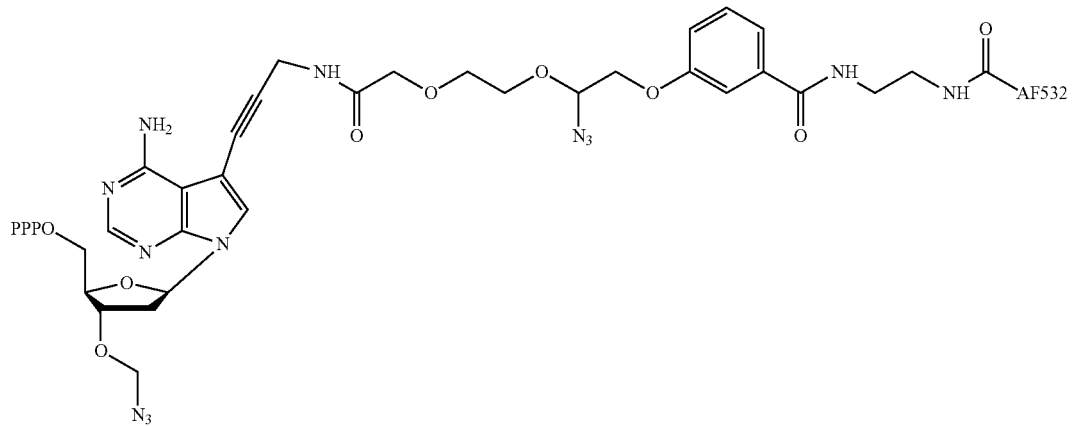

Preparation Example 3. Preparation of the Derivative of dTTP

The dTTP derivative is synthesized by ACME BIO-PHARMA Co., LTD, and the synthetic method is proceeded by reference to US20130189743A1 and Bioconjugate Chem. 2014, 25, 1730-1738. The compound is purified by analytical HPLC to give a product with a purity greater than 95%. MALDI-TOF: molecular formula $C_{37}H_{50}N_{11}O_{20}P_3$ [M](obtained by calculation), molecular weight 1061.25 (calc), 1060.11 [M–H]– (found). The structure of the compound is shown in the formula (3).

213 214
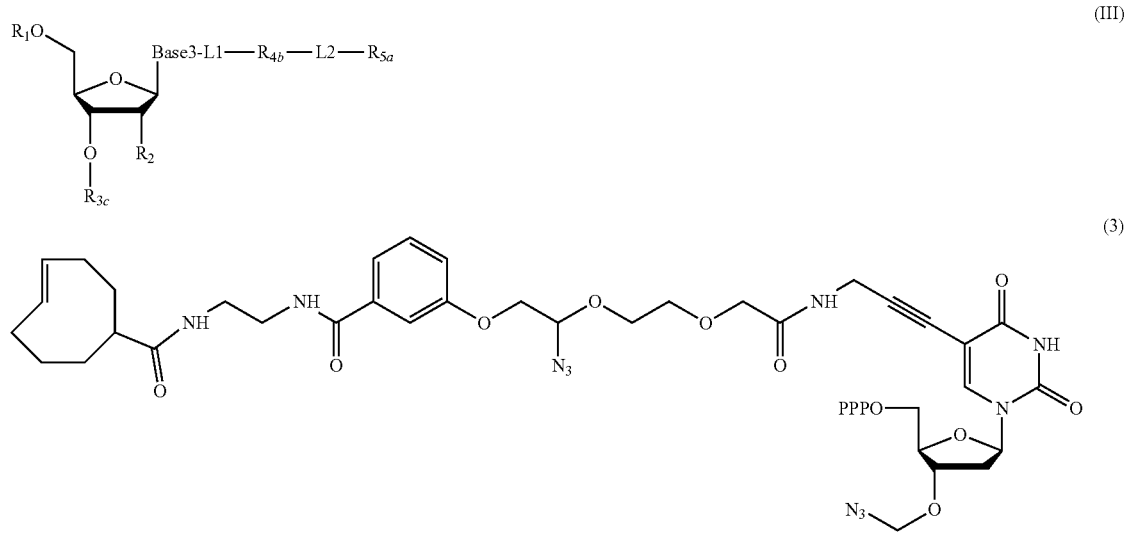
Synthetic Route:
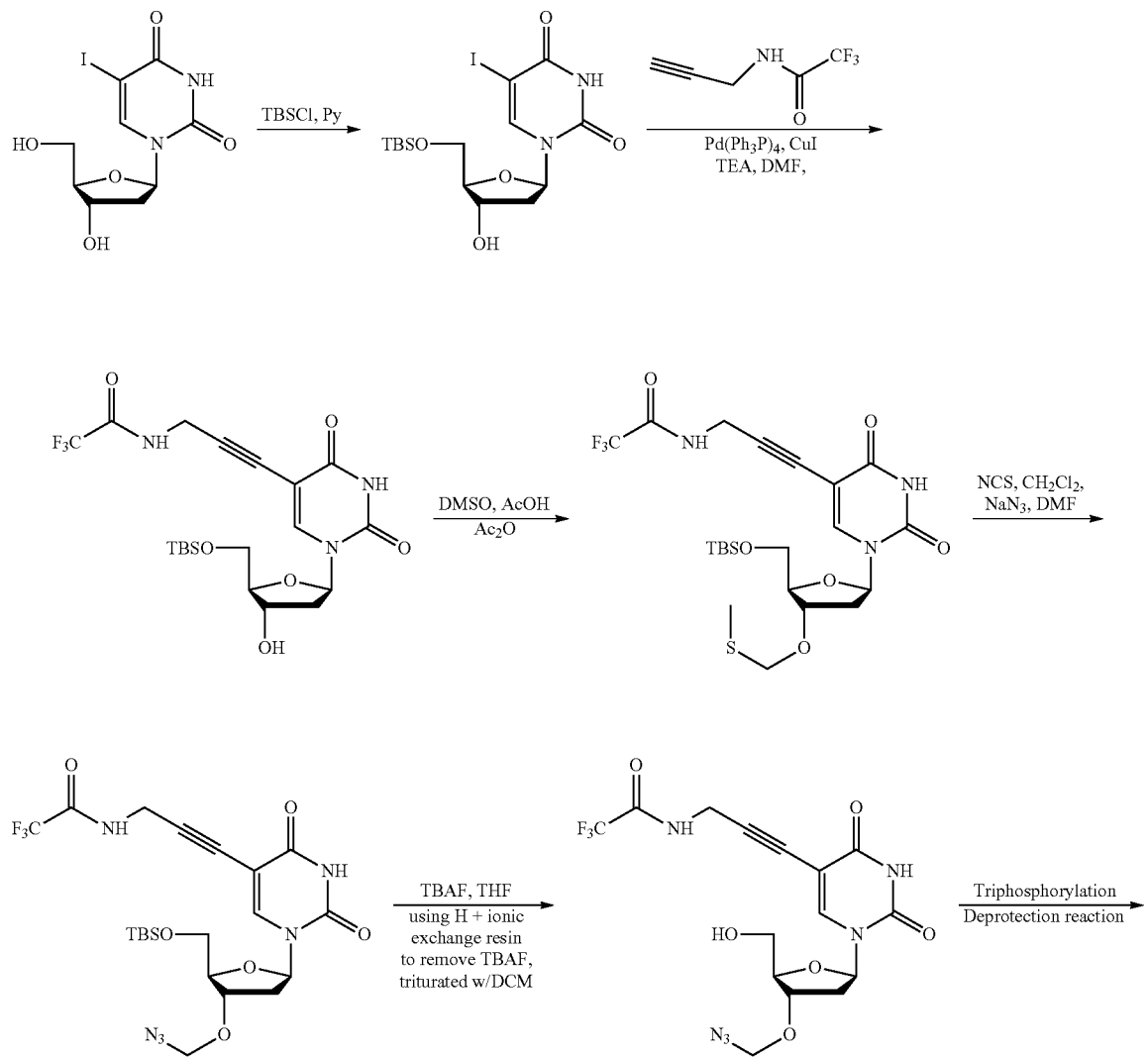

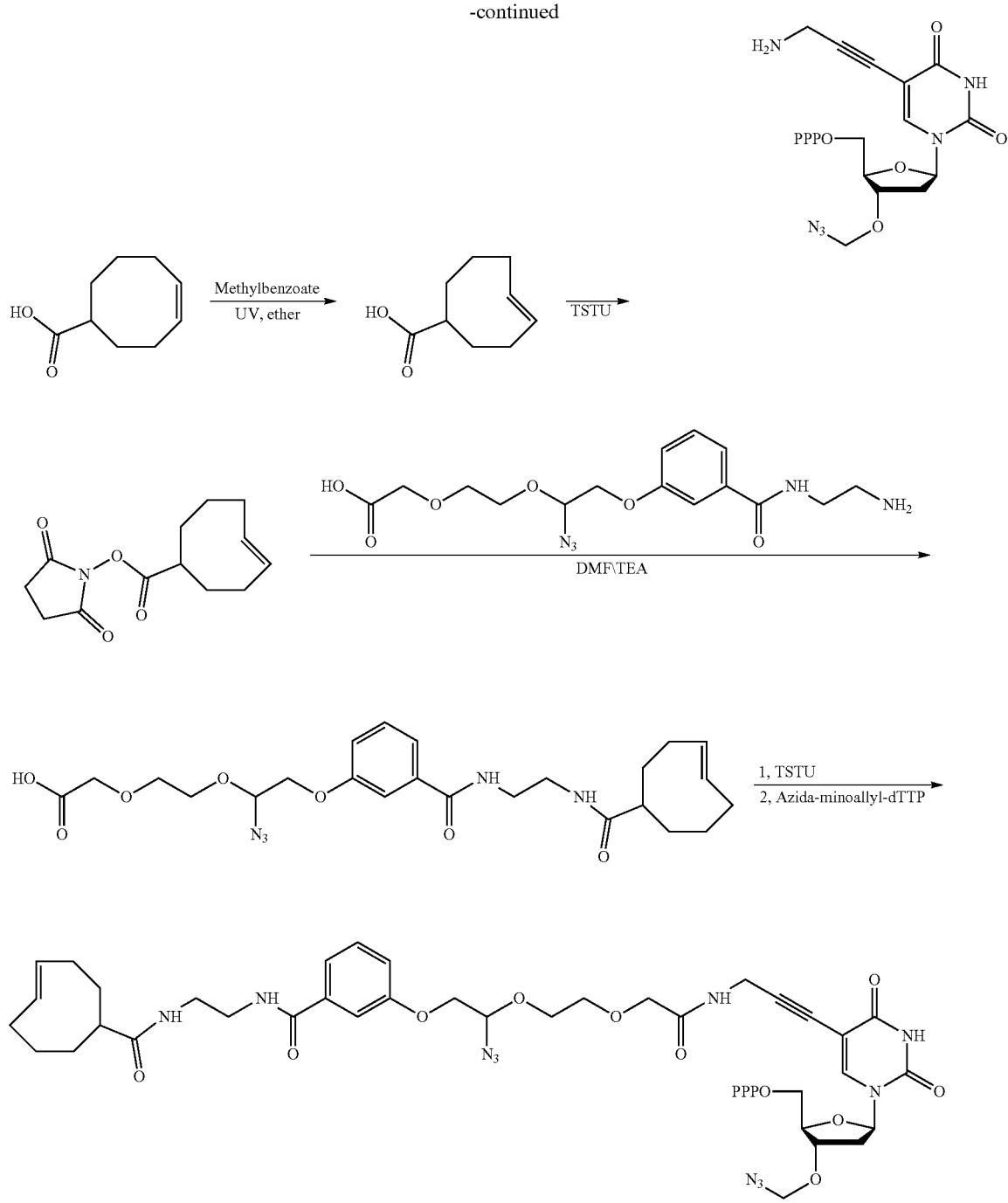

Preparation Example 4. Preparation of the Derivative of dCTP

The dCTP derivative is synthesized by ACME BIO-PHARMA Co., LTD, and the synthetic method is proceeded by reference to US20130189743A1 and Bioconjugate Chem. 2016; 27(7): 1697-16706. The compound is purified by analytical HPLC to give a product with a purity greater than 95%. MALDI-TOF: molecular formula $C_{54}H_{64}N_{11}O_{24}P_3S_2$[M] (obtained by calculation), molecular weight 1406.27 (calc), 1405.26 [M–H]– (found). The structure of the compound is shown in the formula 4.

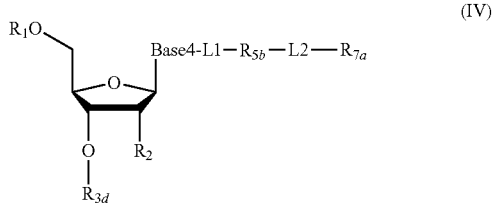

(IV)

217
-continued
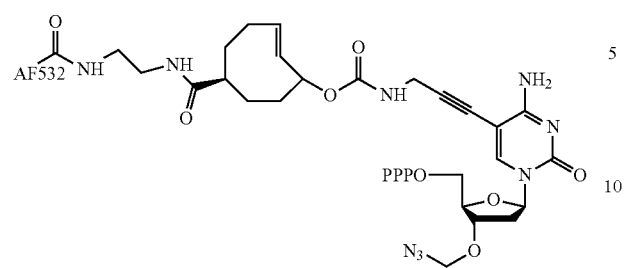
(4)
Synthetic Route:
218
-continued
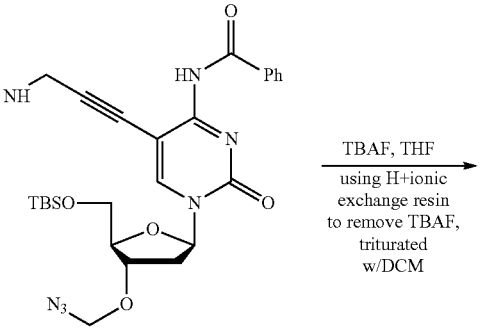
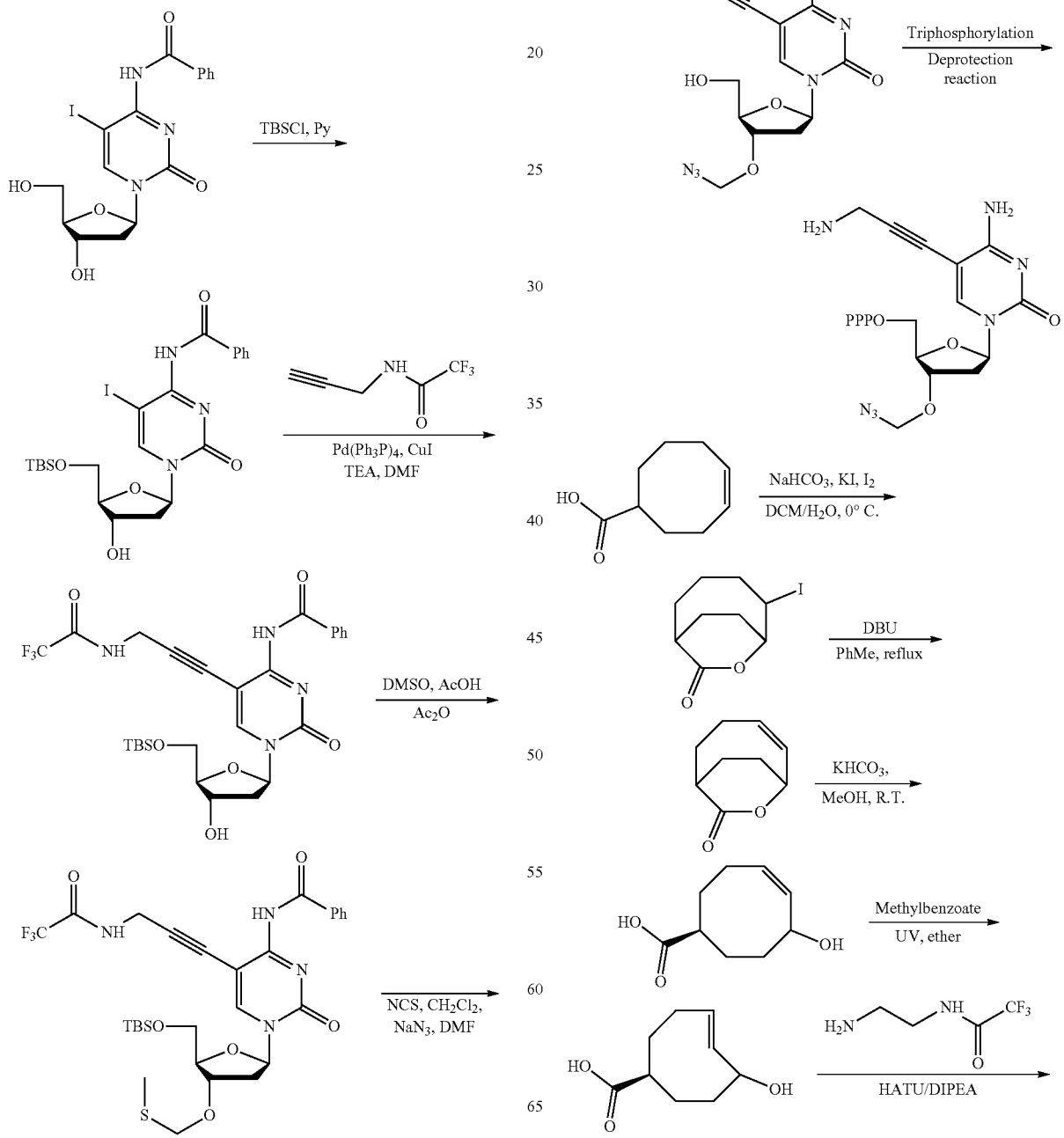

-continued

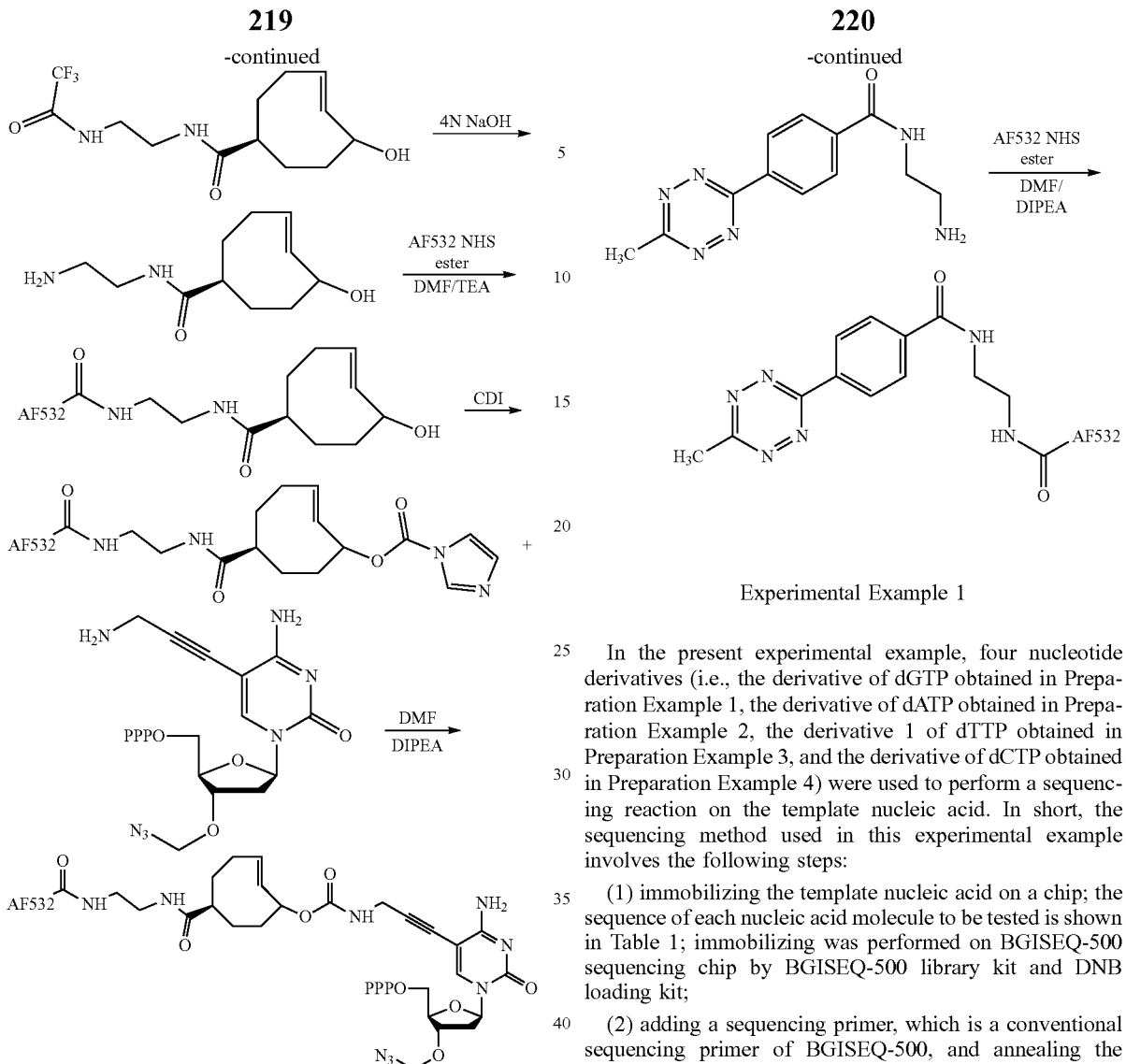

Preparation Example 5. Synthesis of 1,2,4,5-Tetrazine Derivative

The compound 1,2,4,5-tetrazine derivative for bioorthogonal reaction is synthesized by ACME BIO-PHARMA Co., LTD., and the method is proceeded by reference Bioconjugate Chem. 2014, 25, 1730-1738, to obtain a red solid.

ESI: molecular formula $C_{42}H_{42}N_8O_9S_2[M]$ (obtained by calculation), molecular weight 866.25 (calc), 865.24 [M–H]– (found).

Synthetic Route:

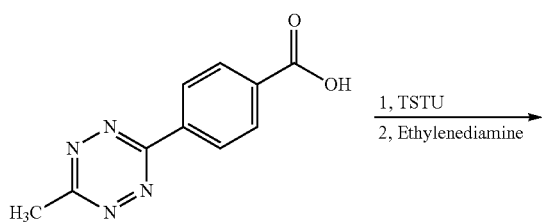

Experimental Example 1

In the present experimental example, four nucleotide derivatives (i.e., the derivative of dGTP obtained in Preparation Example 1, the derivative of dATP obtained in Preparation Example 2, the derivative 1 of dTTP obtained in Preparation Example 3, and the derivative of dCTP obtained in Preparation Example 4) were used to perform a sequencing reaction on the template nucleic acid. In short, the sequencing method used in this experimental example involves the following steps:

(1) immobilizing the template nucleic acid on a chip; the sequence of each nucleic acid molecule to be tested is shown in Table 1; immobilizing was performed on BGISEQ-500 sequencing chip by BGISEQ-500 library kit and DNB loading kit;

(2) adding a sequencing primer, which is a conventional sequencing primer of BGISEQ-500, and annealing the primer to the template nucleic acid molecule to form a duplex linked onto the chip together with the template nucleic acid molecule;

(3) performing a polymerization with polymerase under a condition allowing the polymerase to perform nucleotide polymerization, thereby incorporating one of the four compounds into the 3' end of the growing nucleic acid strand; the DNA polymerase and buffer solution used were identical to the BGISEQ-500 sequencing agents, in which the nucleotides used were replaced with the four nucleotides synthesized in this embodiment, and the agents in this experiment remained the same as the BGISEQ-500 agents except for the cleavage agent;

(4) removing the solution phase of the reaction system in the previous step, retaining the duplex attached onto the support, adding a scanning buffer, and then detecting whether the duplex or the growing nucleic acid strand emits the fluorescent signal, taking a photo, and storing the photo (i.e., experimental photograph 1);

(5) removing the solution phase, washing, adding a solution comprising a bioorthogonal reaction agent, thereby allowing the duplex or the growing nucleic acid strand subjected to a treatment in a reaction system containing a solution phase and a solid phase, wherein the treatment has no effect on the G and A bases, but enables

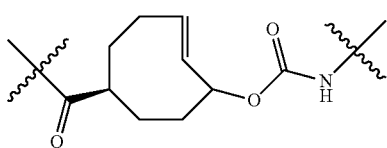

of the C base to perform a bioorthogonal cleavage reaction with the agent

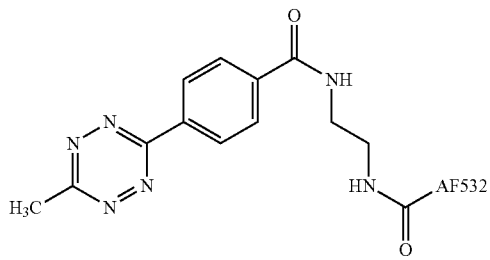

carrying AF532, thereby removing the fluorophore in C base, and enables

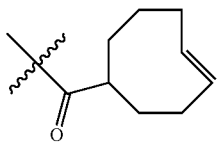 [SMILES: *C(=O)C1CC/C=C/CCC1]

in T base to perform a bioorthogonal ligation reaction, thereby introducing a fluorophore in the agent into the T base to make the T base to emit a fluorescent signal;

wherein the solution comprising a bioorthogonal reaction agent used is a 1× phosphate buffer solution containing 1 mM of 1,2,4,5,-tetrazine derivative, the reaction temperature is 35° C. and the reaction time is 1-5 minutes;

(6) removing the solution phase of the reaction system in the previous step, retaining the duplex attached onto the support, adding BGISEQ-500 scanning buffer, and then detecting whether the duplex or the growing nucleic acid strand emits the fluorescent signal, taking a photo, and storing the photo (i.e., experiment photograph 2);

(7) removing the solution phase, washing, and subjecting the chip to a treatment to remove the protecting groups in derivatives of the four nucleotides, In other words, including performing bioorthogonal cleavage reactions of azidomethylene and azidomethylidyne, thereby allowing the compound incorporated at the 3' end of the growing nucleic acid strand to have a free hydroxyl group at the 3' position of the deoxyribose (in other words, converting —$OCH_2N_3$ (if present) into a free hydroxyl group), and removing the fluorophore AF532, if present, from the duplex or the growing nucleic acid strand;

the reaction agent for cleaving azidomethylene and azidomethylidyne comprises: 1 M sodium chloride, 0.1 M tris, pH=9, 10 mM thpp.

(8) removing the solution phase of the reaction system in the previous step;

(9) adding a polymerase for performing nucleotide polymerization, and the first compound, the second compound, the third compound, and the fourth compound, thereby forming a reaction system containing a solution phase and a solid phase, and then performing steps (3)-(6).

In some preferred embodiments, the method further comprises the step of:

(10) repeating steps (7)-(9) one or more times.

After taking the two photographs (i.e., experimental photographs 1 and 2), the signals at the same position are compared. FIG. 1 shows the comparison results of experimental photographs 1 and 2, wherein:

the triangular region indicates that the position (nucleic acid molecule) has no fluorescent signal in both photographs 1 and 2; correspondingly, according to the structure of the derivatives of the four nucleotides used, it can be determined that base G is incorporated into the primer, thus it can be determined that the base at the corresponding position of the nucleic acid molecule is C.

The elliptical region indicates that the position (nucleic acid molecule) has a fluorescent signal in photograph 1, but has no fluorescent signal in photograph 2; correspondingly, according to the structure of the derivatives of the four nucleotides used, it can be determined that base C is incorporation into the primer, therefore, it can be determined that the base at the corresponding position of the nucleic acid molecule is G.

The square region indicates that the position (nucleic acid molecule) has fluorescent signals in both photographs 1 and 2; correspondingly, according to the structure of the derivatives of the four nucleotides used, it can be determined that base A is incorporated into the primer, thus it can be determined that the base at the corresponding position of the nucleic acid molecule is T.

The circular region indicates that the position (nucleic acid molecule) has no fluorescent signal in photograph 1, but has a fluorescent signal in photograph 2; correspondingly, it can be determined that base T is incorporated into the primer according to the structures of the derivatives of the four nucleotides used, and thus, it can be determined that the base at the corresponding position of the nucleic acid molecule is A.

Using the above method for 10 cycles of sequencing, wherein the test sample was a mixture of 36 different sequences, comparing with the 36 sequences after sequencing, and the ratio of achieving full match and allowing one error is 94.65%.

The results indicate that the method of the present embodiment enables accurate sequencing of the template nucleic acid using only one fluorophore.

TABLE 1

| Number (SEQ ID NO:) | Sequence | ratio (%)* | Number (SEQ ID NO:) | Sequence | ratio (%)* |
|---|---|---|---|---|---|
| 1 | TAGGTCCGAT | 3.76 | 19 | TGTCTGCGAA | 2.19 |
| 2 | GGACGGAATC | 1.91 | 20 | ATTGGTACAA | 2.94 |
| 3 | CTTACTGCCG | 2.15 | 21 | CGATTGTGGT | 1.78 |
| 4 | ACCTAATTGA | 3.22 | 22 | ACAGACTTCC | 2.31 |
| 5 | TTCGTATCCG | 2.22 | 23 | TCCACACTCT | 2.83 |
| 6 | GGTAACGAGC | 4.62 | 24 | CACCACAAGC | 2.18 |
| 7 | CAACGTATAA | 3.25 | 25 | TAGAGGACAA | 4.00 |
| 8 | ACGTCGCGTT | 1.89 | 26 | CCTAGCGAAT | 2.14 |

TABLE 1-continued

| Number (SEQ ID NO:) | Sequence | ratio (%)* | Number (SEQ ID NO:) | Sequence | ratio (%)* |
|---|---|---|---|---|---|
| 9 | TTCTGCTAGC | 2.64 | 27 | GTAGTCATCG | 1.68 |
| 10 | AGGAAGATAG | 2.27 | 28 | GCTGAGCTGT | 2.65 |
| 11 | GCTCTTGCTT | 2.56 | 29 | AACCTAGATA | 4.31 |
| 12 | CAAGCACGCA | 2.05 | 30 | TTGCCATCTC | 2.82 |
| 13 | CGGCAATCCG | 2.65 | 31 | AGATCTTGCG | 1.44 |
| 14 | ATCAGGATTC | 2.55 | 32 | CGCTATCGGC | 2.29 |
| 15 | TCATTCCAGA | 2.64 | 33 | GCAACGATGG | 4.10 |
| 16 | GATGCTGGAT | 2.22 | 34 | TAATCGTTCA | 2.39 |
| 17 | GTGAGTGATG | 2.35 | 35 | GTTCGCTCTA | 2.17 |
| 18 | GAGTCAGCTG | 1.83 | 36 | TCTCACACAT | 3.64 |

*The ratio of the amount of samples that can match the specific numbered sequence (including full match and allowing one error) to the amount of all samples Detailed Embodiment 2

Preparation Example 1. Preparation of the Derivative of dGTP

The dGTP derivative is synthesized by ACME BIO-PHARMA Co., LTD., and the synthetic method is proceeded by reference to US20130189743A1. The compound is purified by analytical HPLC to give a product with a purity greater than 95%. MALDI-TOF: molecular formula $C_{11}H_{17}N_8O_{13}P_3[M]$ (obtained by calculation), molecular weight: 562.01 (calc), 561.00 [M–H]– (found). The structure of the compound is shown in Formula 1.

Synthetic Route:

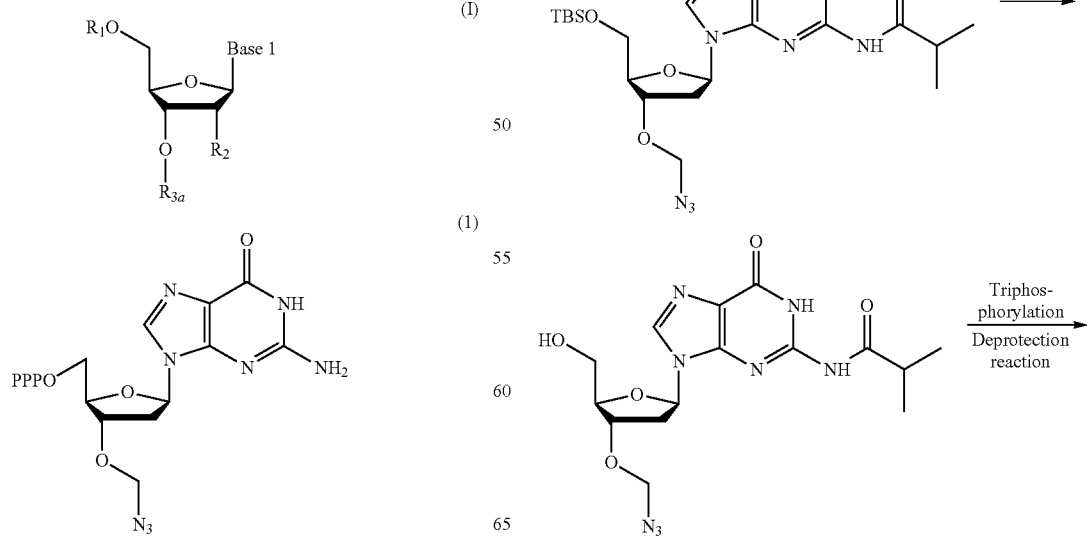

225

-continued

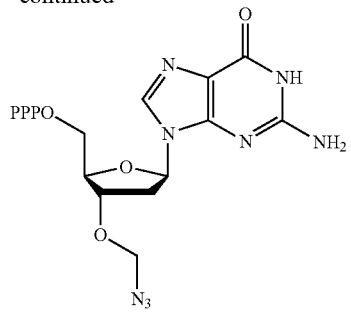

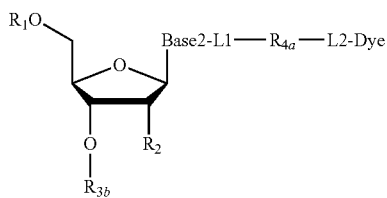

226

Preparation Example 2. Preparation of the Derivative of dATP

The dATP derivative is synthesized by ACME BIO-PHARMA Co., LTD., the synthetic method is proceeded by reference US20130189743A1, and the compound is purified by analytical HPLC to obtain a product having a purity greater than 95%. MALDI-TOF: molecular formula $C_{60}H_{68}N_{15}O_{25}P_3S_2$[M] (obtained by calculation), molecular weight 1555.31 (calc), 1554.25 [M–H]– (found). The structure of the compound is shown in Formula 2.

(II)

(2)

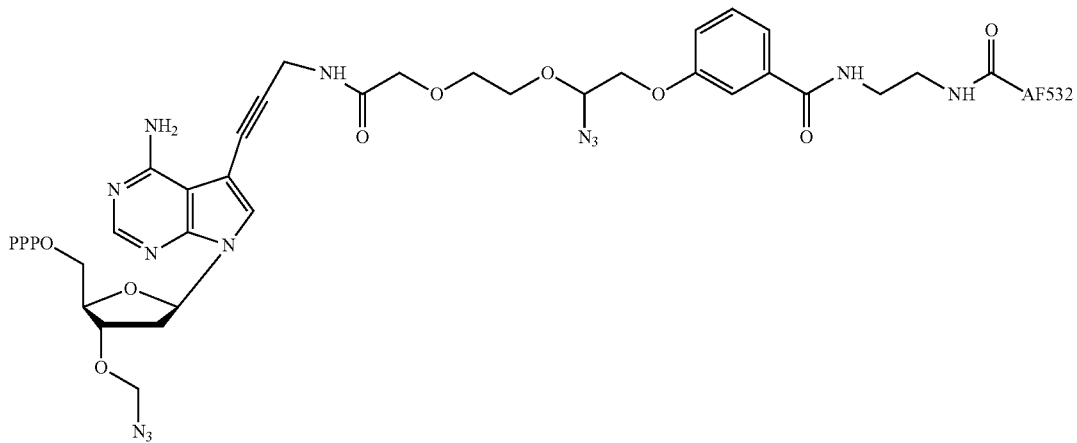

Synthetic Route:

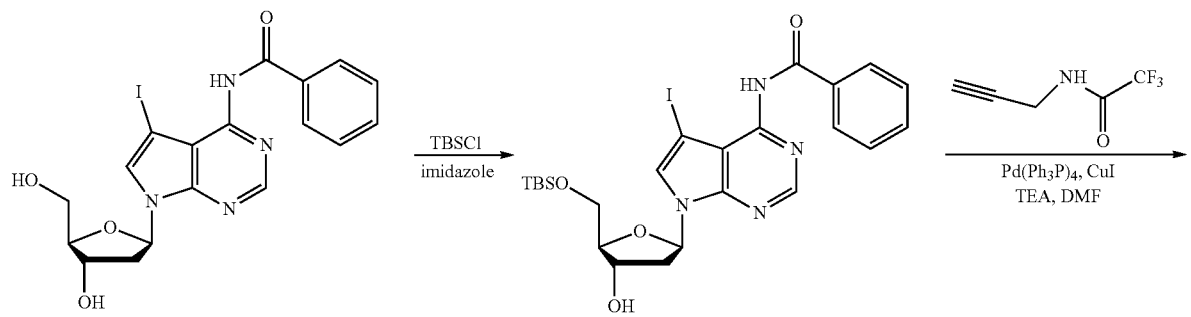

227 228
-continued
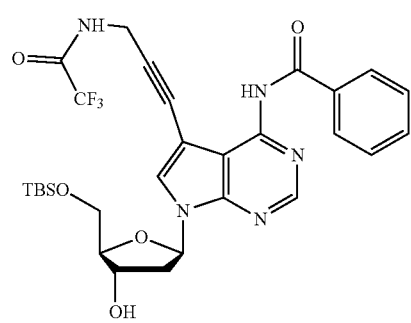
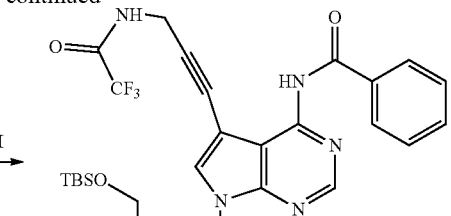
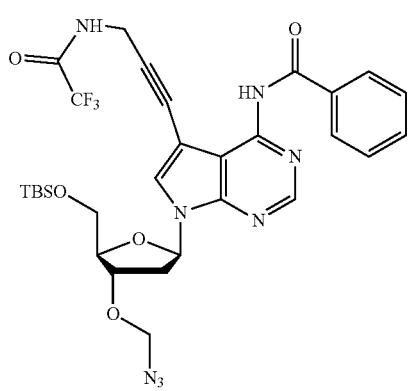
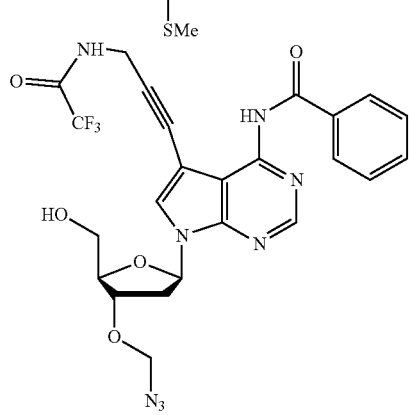
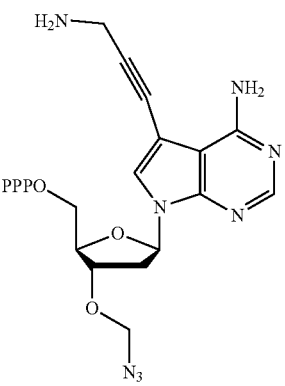
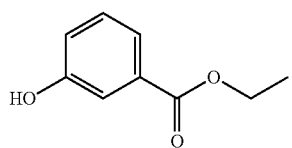
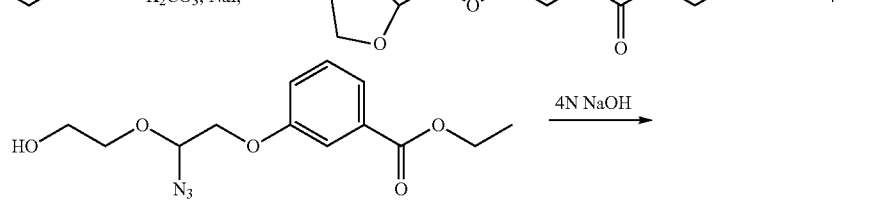
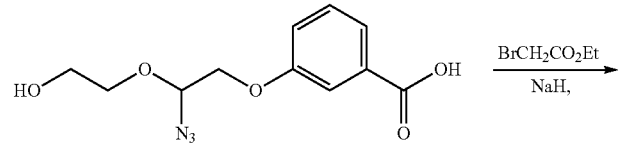
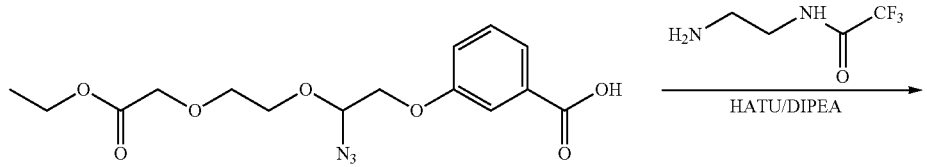

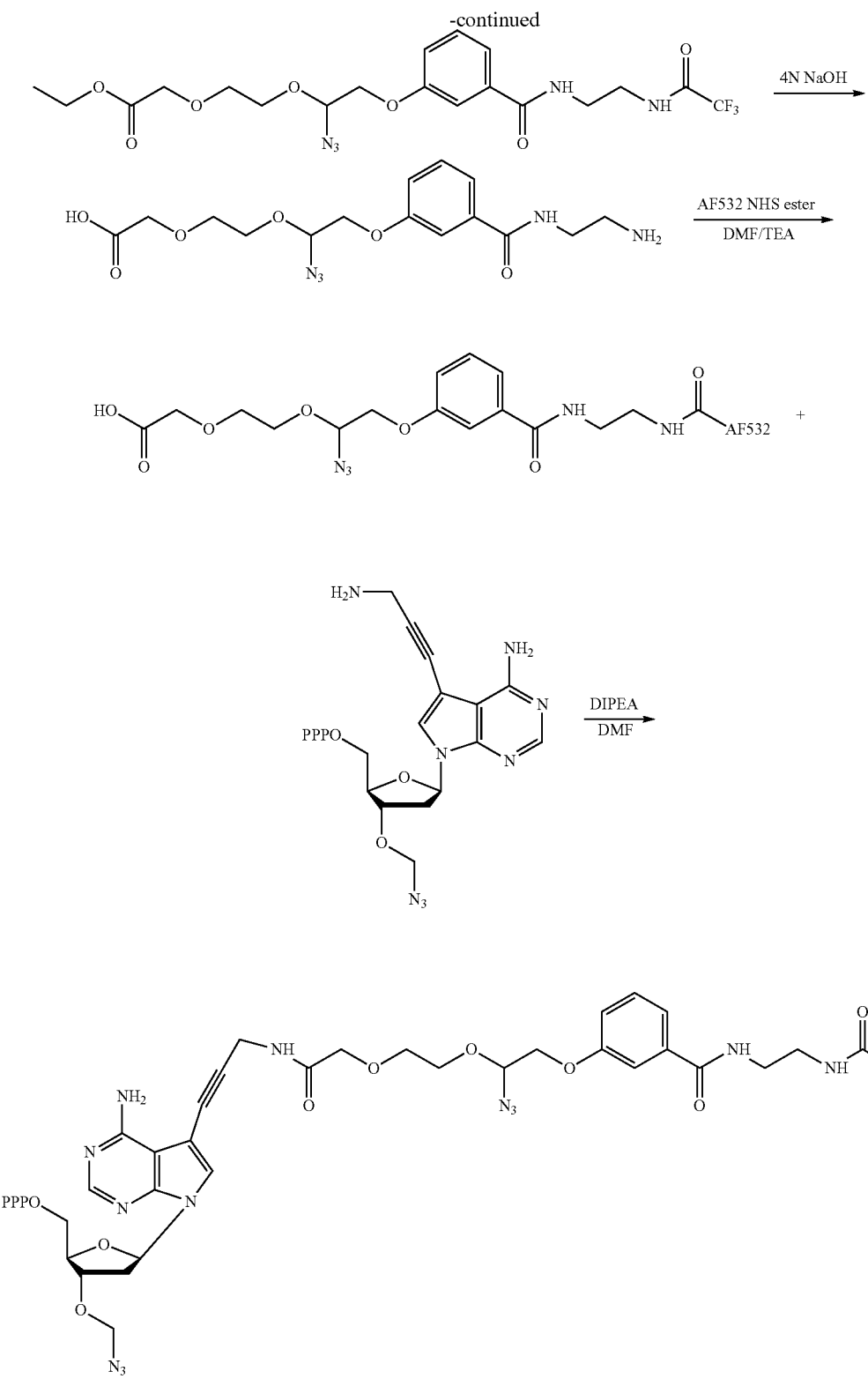

Preparation Example 3. Preparation of the Derivative of dTTP

The dTTP derivative is synthesized by ACME BIO-PHARMA Co., LTD., the synthetic method is proceeded by reference to US20130189743A1 and Nucleic Acids Res., 15, 4513-4534, and the compound is purified by analytical HPLC to obtain a product having a purity greater than 95%. MALDI-TOF: molecular formula $C_{37}H_{50}N_{11}O_{20}P_3[M]$ (obtained by calculation), molecular weight 1061.25 (calc), 1060.11 [M−H]− (found). The structure of the compound is shown in the formula (3).

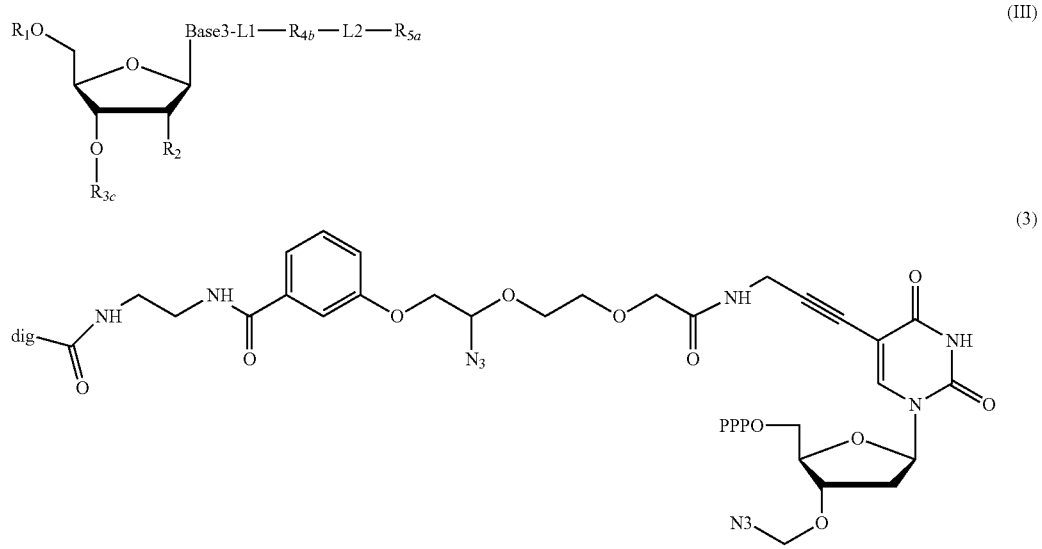
Synthetic Route:
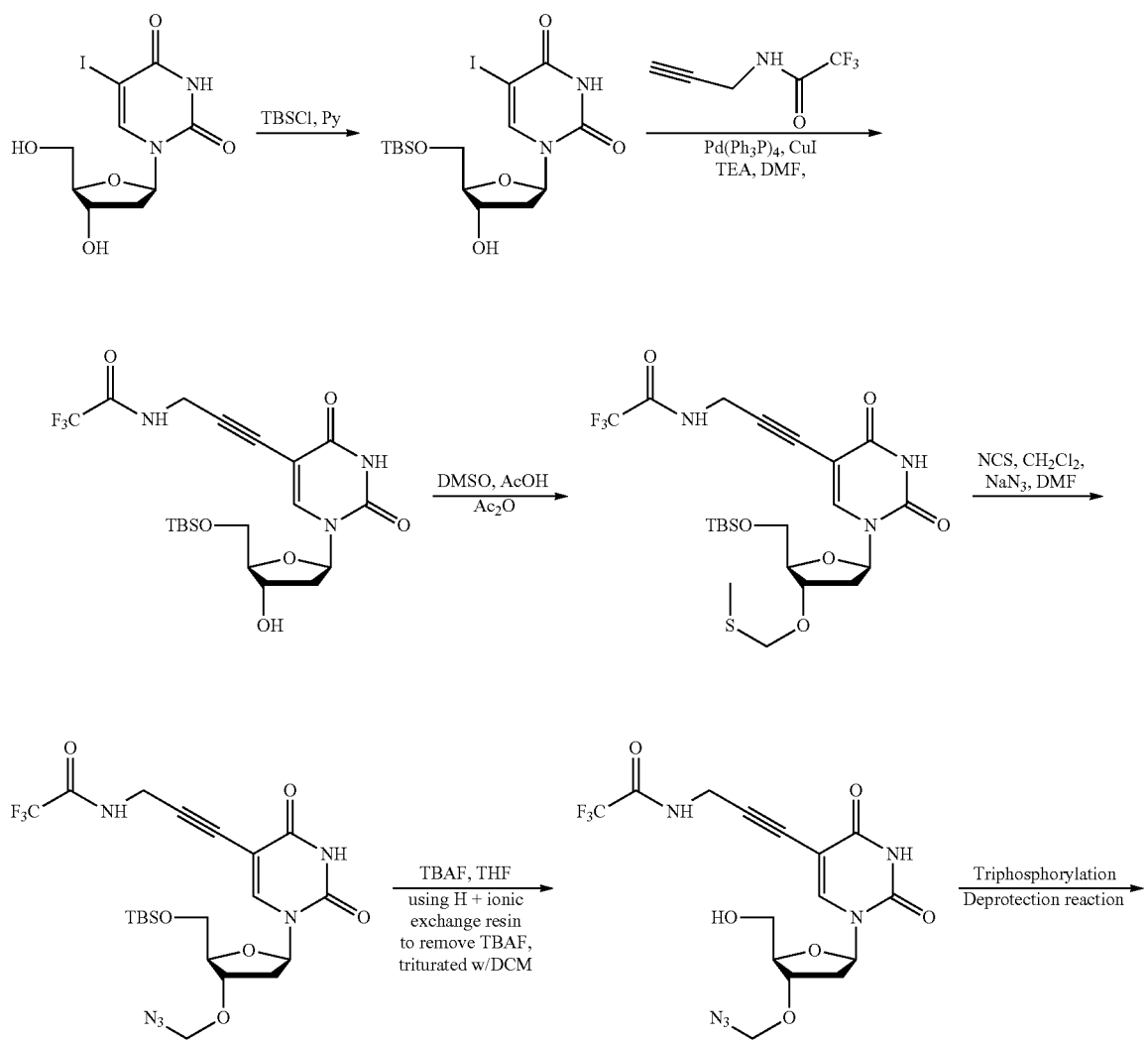

-continued

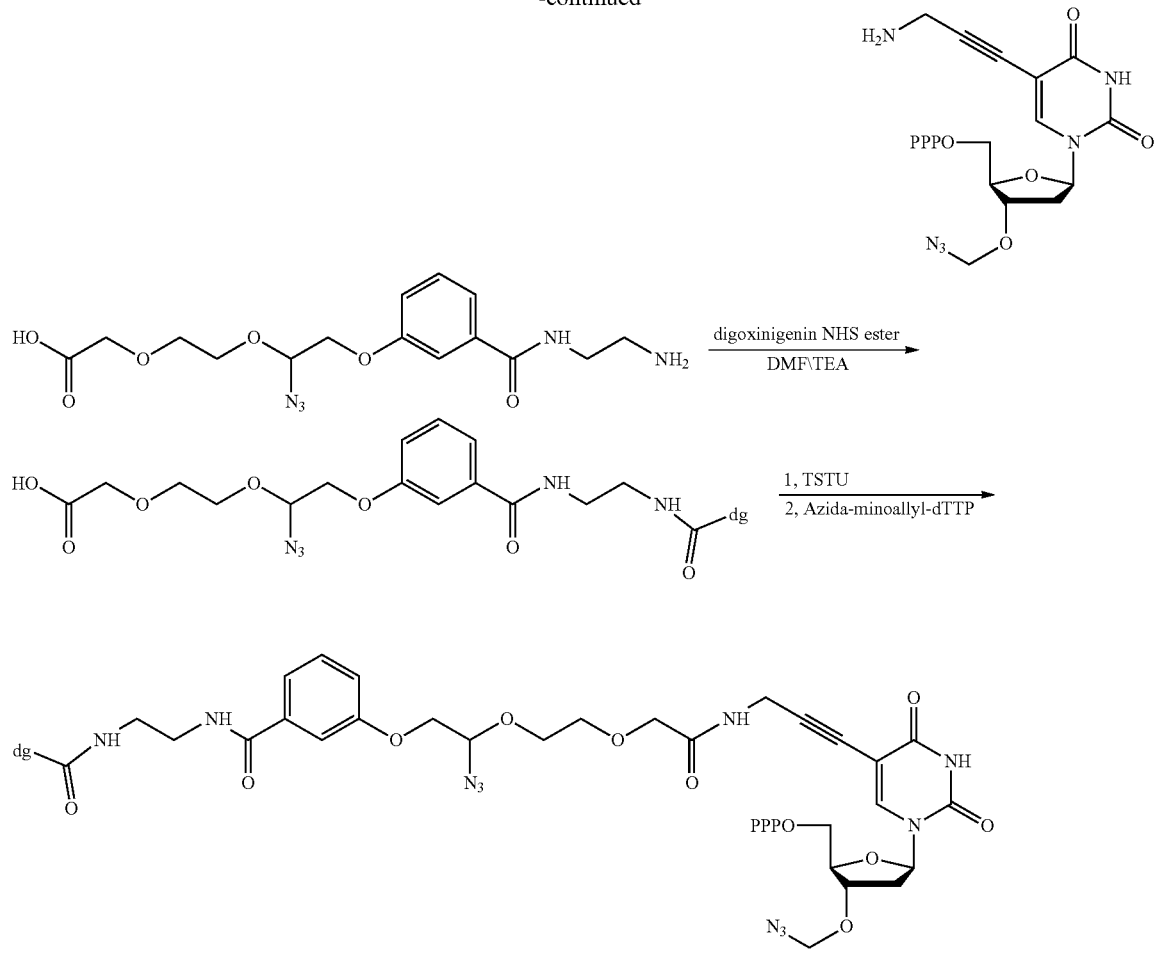

dig:

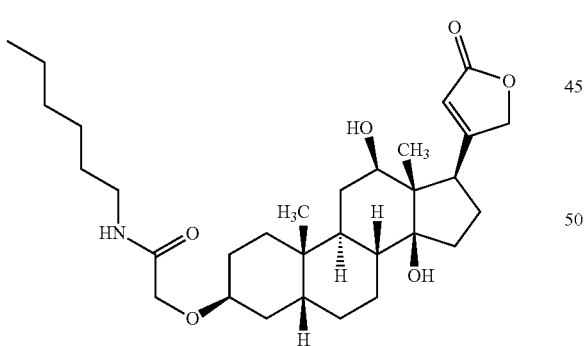

digoxingenin

Preparation Example 4. Preparation of the Derivative of dCTP

The dCTP derivative is synthesized by ACME BIO-PHARMA Co., LTD., (Synthetic Method Reference US20130189743A1 and Nucleic Acids Res., 15, 4513-4534). The compound is purified by analytical HPLC to give a product with a purity greater than 95%. MALDI-TOF: Molecular Formula $C_{38}H_{55}N_{14}O_{20}P_3[M]$ (Obtained by Calculation), Molecular weight 1120.29 (calc), 1119.35 [M-H]- (found). The structure of the compound is shown in the formula (4).

(IV)

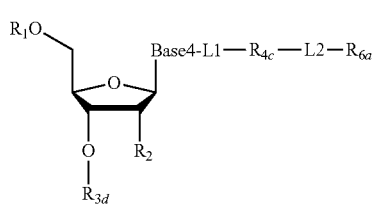

(4)
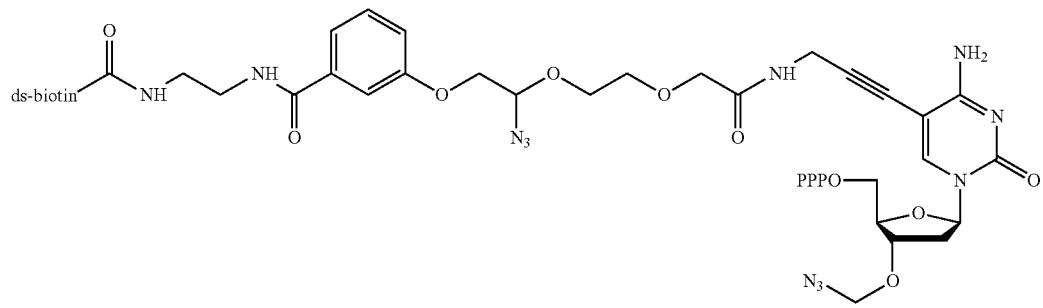
Synthetic Route:
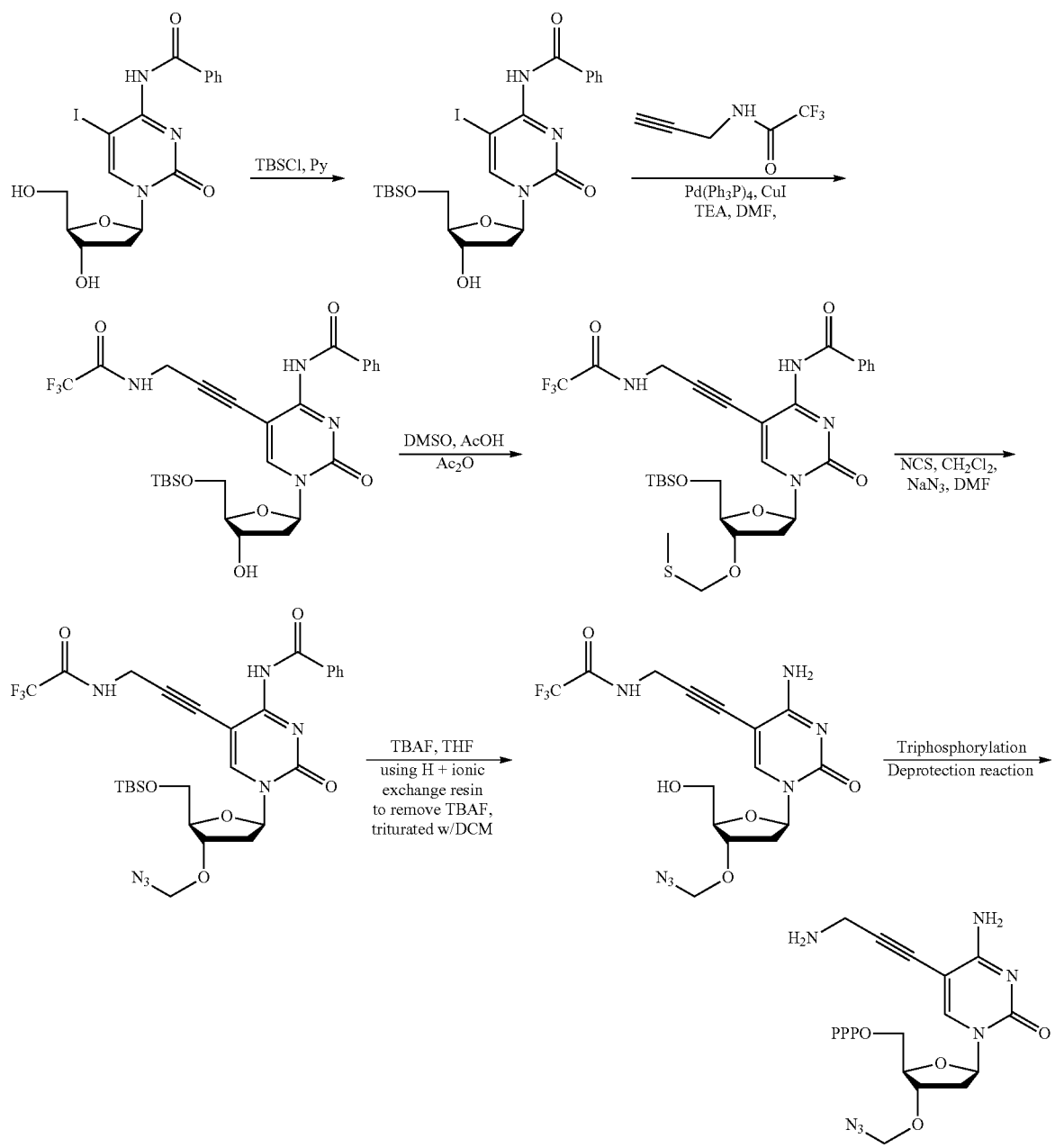

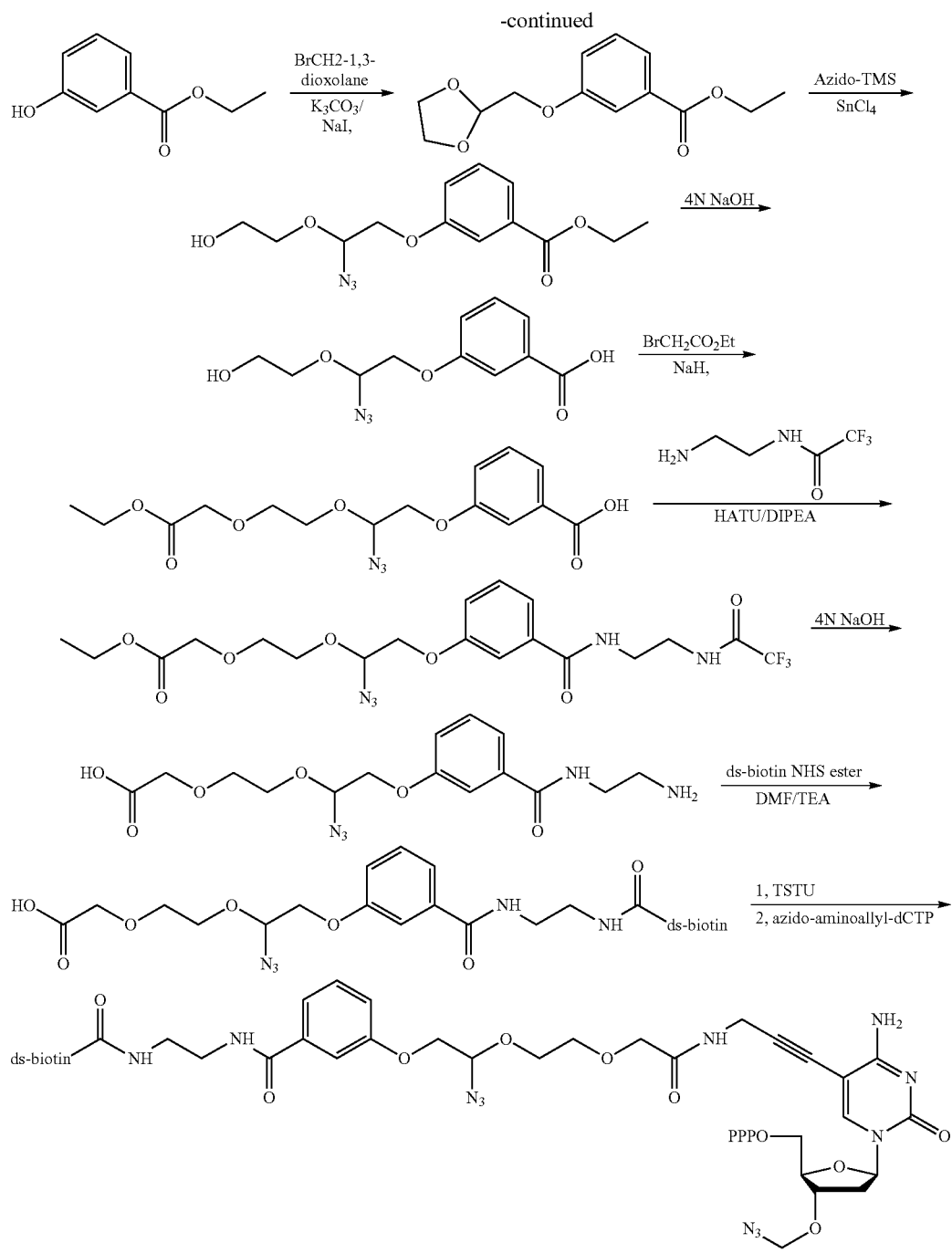

ds-biotin:

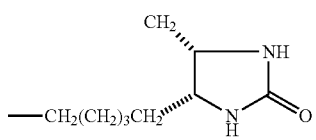

desthiobiotin

The first binding pair: digoxingenin and digoxigenin antibody. The dTTP derivative can be linked with Cy3 by binding digoxingenin on the dTTP derivative to a digoxi- genin antibody modified with Cy3 (digoxigenin antibody-cy3). Digoxingenin and digoxigenin antibody-cy3 are purchased from antibody online (catalogue number: ABIN739187).

The second binding pair: desthiobiotin and streptavidin. The dCTP derivative can be linked with Cy3 by binding desthiobiotin on the dCTP derivative to streptavidin modified with Cy3 (having the same excitation wavelength as AF532). The streptavidin modified with Cy3 was purchased from sigma (catalogue number: S6402-1ML).

The third binding pair: streptavidin and biotin. The desthiobiotin-streptavidin conjugate can be dissociated by specific binding between streptomycin and biotin, thereby making dCTP to lose its fluorophore.

Experimental Example 2

In the present experimental example, four nucleotide derivatives (i.e., the derivative of dGTP obtained in Preparation Example 1, the derivative of dATP obtained in Preparation Example 2, the derivative 1 of dTTP obtained in Preparation Example 3, and the derivative of dCTP obtained in Preparation Example 4) were used to perform a sequencing reaction on the template nucleic acid. In short, the sequencing method used in this experimental example involves the following steps:

(1) immobilizing the template nucleic acid on a chip; the sequence of each nucleic acid molecule to be tested is shown in Table 2; immobilizing was performed on BGISEQ-500 sequencing chip by BGISEQ-500 library kit and DNB loading kit;

(2) adding a sequencing primer, which is a conventional sequencing primer of BGISEQ-500, and annealing the primer to the template nucleic acid molecule to form a duplex linked onto the chip together with the template nucleic acid molecule;

(3) performing a polymerization with polymerase under a condition allowing the polymerase to perform nucleotide polymerization, thereby incorporating one of the four compounds into the 3' end of the growing nucleic acid strand; the DNA polymerase and buffer solution used were identical to the BGISEQ-500 sequencing agents, in which the nucleotides used were replaced with the four nucleotides synthesized in this embodiment, and the agents in this experiment remained the same as the BGISEQ-500 agents except for the cleavage agent;

(4) removing the solution phase of the reaction system in the previous step, retaining the duplex attached onto the support, adding the specific binding agent 1 and carrying out the reaction at 35° C. for 1 minute;

wherein the specific binding agent 1 comprises: 1× phosphate buffer, 1 μg/ml BSA, and 10 ng/ml streptavidin-cy3;

(5) adding a scanning buffer, and then detecting whether the duplex or the growing nucleic acid strand emits the fluorescent signal, taking a photo, and storing the photo (i.e., experimental photograph 1);

(6) removing the solution phase, washing, adding the specific binding agent 2 and carrying out the reaction at 35° C. for 1-5 minute, thereby allowing the duplex or the growing nucleic acid strand subjected to a treatment in a reaction system containing a solution phase and a solid phase, wherein the treatment has no effect on the G and A bases, but the biotin in the agent acts with the desthiobiotin-streptavidin conjugate carried by the C base, thereby replacing desthiobiotin, forming a biotin-streptavidin conjugate, and detaching streptavidin-cy3 from the C base, thereby making the C base to lose the fluorophore; and the digoxigenin antibody-cy3 in the agent is capable of specifically binding to the digoxigenin in T base, thereby introducing the fluorophore Cy3 into the T base to enable the T base to emit a fluorescent signal.

Dyeing agent 2 comprises: 1× phosphate buffer, 1 μg/ml BSA, 10 ng/ml digoxigenin antibody-cy3 and 10 μM biotin.

(7) removing the solution phase of the reaction system in the previous step, retaining the duplex attached onto the support, adding BGISEQ-500 scanning buffer, and then detecting whether the duplex or the growing nucleic acid strand emits the fluorescent signal, taking a photo, and storing the photo (i.e., experiment photograph 2);

(8) removing the solution phase, washing, and subjecting the chip to a treatment to remove the protecting groups in derivatives of the four nucleotides, including performing bioorthogonal cleavage reactions of azidomethylene and azidomethylidyne, thereby allowing the compound incorporated at the 3' end of the growing nucleic acid strand to have a free hydroxyl group at the 3' position of the deoxyribose (in other words, converting —$OCH_2N_3$ (if present) into a free hydroxyl group), and removing the fluorophore AF532, if present, from the duplex or the growing nucleic acid strand; the reaction agent for cleaving azidomethylene and azidomethylidyne comprises: 1 M sodium chloride, 0.1 M tris, pH=9, 10 mM thpp.

(9) removing the solution phase of the reaction system in the previous step;

(10) adding a polymerase for performing nucleotide polymerization, and the first compound, the second compound, the third compound, and the fourth compound, thereby forming a reaction system containing a solution phase and a solid phase, and then performing steps (4)-(7).

In some preferred embodiments, the method further comprises the step of:

(11) repeating steps (8)-(10) one or more times.

Figure 2:
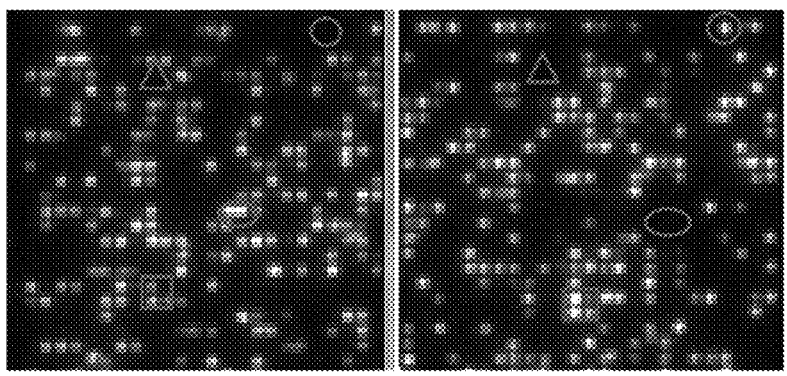
FIG. 2 shows the comparison results of Experimental Photos 1 and 2 obtained in Experimental Example 2.
Figure 3:
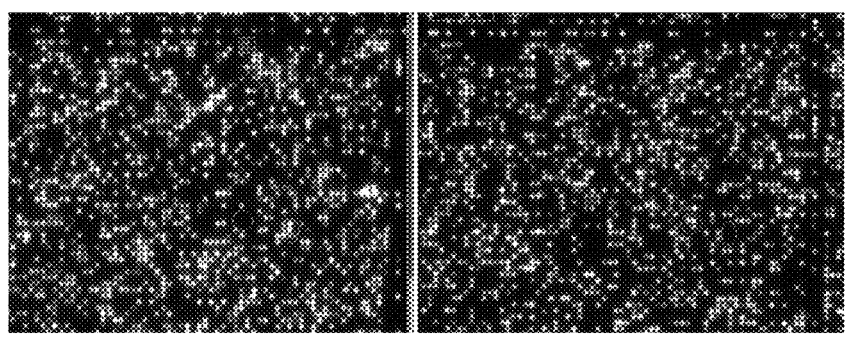
FIG. 3 shows the comparison results of Experimental Photos 1 and 2 obtained in Experimental Example 3.
Figure 4:
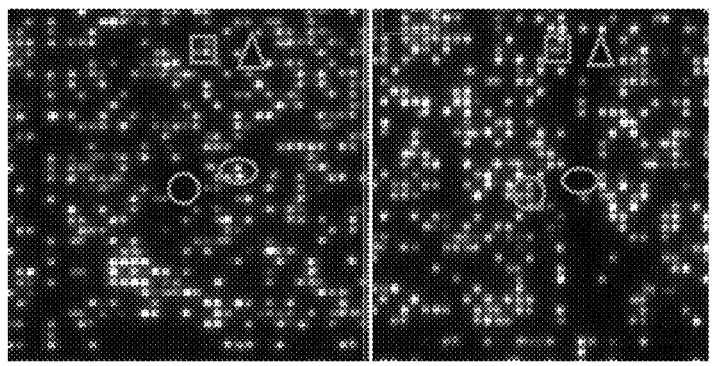
FIG. 4 shows the comparison results of Experimental Photos 1 and 2 obtained in Experimental Example 4.

After taking the two photographs (i.e., experimental photographs 1 and 2), the signals at the same position are compared. FIG. 2 shows the comparison results of experimental photographs 1 and 2, wherein:

the triangular region indicates that the position (nucleic acid molecule) has no fluorescent signal in both photographs 1 and 2; correspondingly, according to the structure of the derivatives of the four nucleotides used, it can be determined that base G is incorporated into the primer, thus it can be determined that the base at the corresponding position of the nucleic acid molecule is C.

The elliptical region indicates that the position (nucleic acid molecule) has a fluorescent signal in photograph 1, but has no fluorescent signal in photograph 2; correspondingly, according to the structure of the derivatives of the four nucleotides used, it can be determined that base C is incorporation into the primer, therefore, it can be determined that the base at the corresponding position of the nucleic acid molecule is G.

The square region indicates that the position (nucleic acid molecule) has fluorescent signals in both photographs 1 and 2; correspondingly, according to the structure of the derivatives of the four nucleotides used, it can be determined that base A is incorporated into the primer, thus it can be determined that the base at the corresponding position of the nucleic acid molecule is T.

The circular region indicates that the position (nucleic acid molecule) has no fluorescent signal in photograph 1, but has a fluorescent signal in photograph 2; correspondingly, it can be determined that base T is incorporated into the primer according to the structures of the derivatives of the four nucleotides used, and thus, it can be determined that the base at the corresponding position of the nucleic acid molecule is A.

Using the above method for 10 cycles of sequencing, wherein the test sample was a mixture of 36 different sequences, comparing with the 36 sequences after sequencing, and the ratio of achieving full match and allowing one error was 92.85%.

The results indicate that the method of the present embodiment enables accurate sequencing of the template nucleic acid using only one fluorophore.

TABLE 2

| Number (SEQ ID NO:) | Sequence | ratio (%)* | Number (SEQ ID NO:) | Sequence | ratio (%)* |
|---|---|---|---|---|---|
| 2 | GGACGGAATC | 2.11 | 20 | ATTGGTACAA | 2.76 |
| 3 | CTTACTGCCG | 2.29 | 21 | CGATTGTGGT | 1.80 |
| 4 | ACCTAATTGA | 3.10 | 22 | ACAGACTTCC | 2.24 |
| 5 | TTCGTATCCG | 2.34 | 23 | TCCACACTCT | 2.67 |
| 6 | GGTAACGAGC | 4.16 | 24 | CACCACAAGC | 2.13 |
| 7 | CAACGTATAA | 3.12 | 25 | TAGAGGACAA | 3.64 |
| 8 | ACGTCGCGTT | 2.09 | 26 | CCTAGCGAAT | 2.10 |
| 9 | TTCTGCTAGC | 2.66 | 27 | GTAGTCATCG | 1.72 |
| 10 | AGGAAGATAG | 2.38 | 28 | GCTGAGCTGT | 2.52 |
| 11 | GCTCTTGCTT | 2.60 | 29 | AACCTAGATA | 3.89 |
| 12 | CAAGCACGCA | 2.21 | 30 | TTGCCATCTC | 2.66 |
| 13 | CGGCAATCCG | 2.67 | 31 | AGATCTTGCG | 1.52 |
| 14 | ATCAGGATTC | 2.59 | 32 | CGCTATCGGC | 2.22 |
| 15 | TCATTCCAGA | 2.66 | 33 | GCAACGATGG | 3.72 |
| 16 | GATGCTGGAT | 2.34 | 34 | TAATCGTTCA | 2.31 |
| 17 | GTGAGTGATG | 2.44 | 35 | GTTCGCTCTA | 2.12 |
| 18 | GAGTCAGCTG | 2.05 | 36 | TCTCACACAT | 3.34 |

*The ratio of the amount of samples that can match the specific numbered sequence (including full match and allowing one error) to the amount of all samples

Detailed Embodiment 3

Preparation Example 1. Synthesis of the Derivative of dGTP

The dGTP derivative is synthesized by ACME BIO-PHARMA Co, LTD., and the synthetic method is referred to in (US20130189743A1). The compound is purified by analytical HPLC to give a product with a purity greater than 95%. MALDI-TOF: molecular formula $C_{11}H_{17}N_8O_{13}P_3[M]$ (obtained by calculation), molecular weight: 562.01 (calc), 561.00 [M–H]– (found). The structure of the compound is shown in the formula (1).

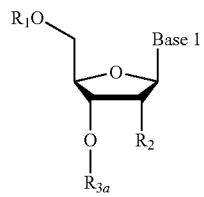

(I)

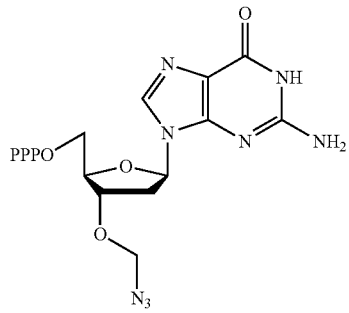

(1)

Synthetic Route:

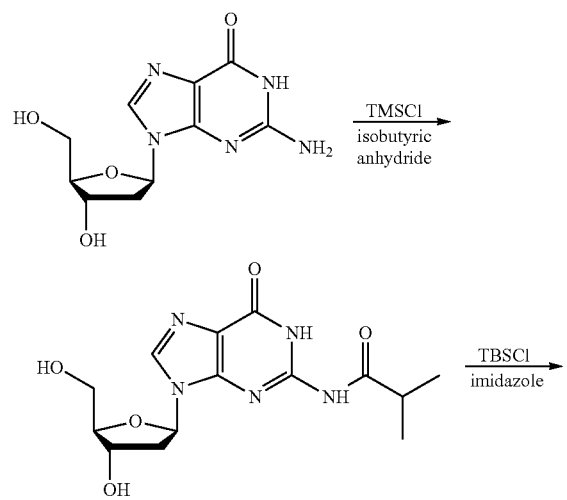

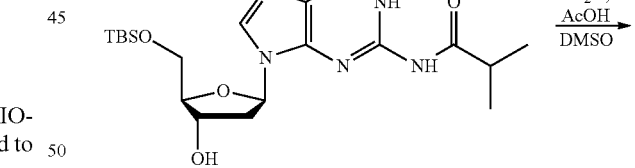

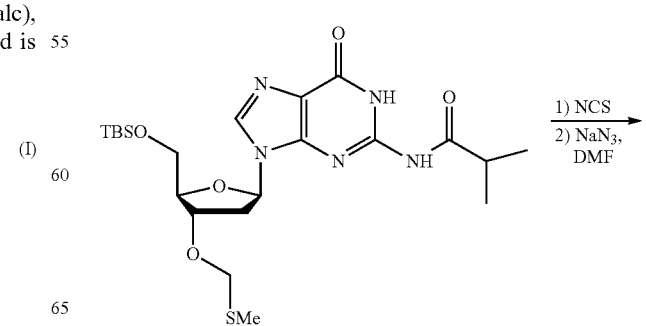

243

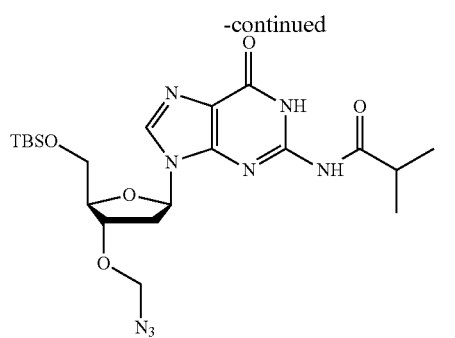

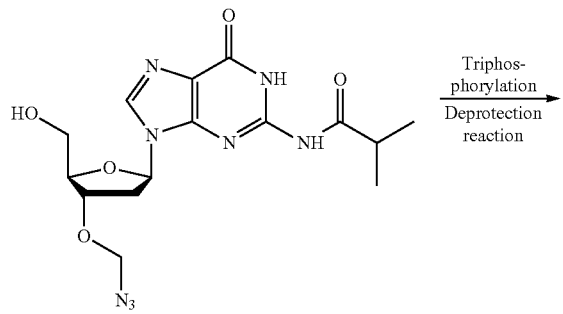

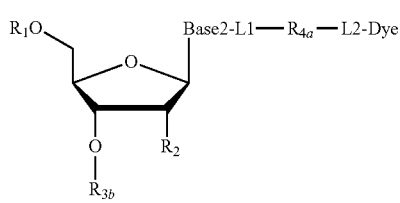

244

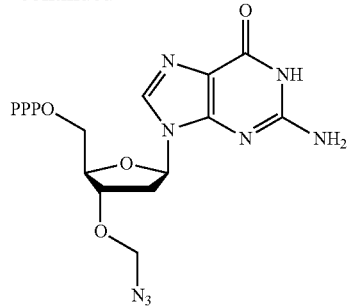

Preparation Example 2. Synthesis of the Derivative of dATP

The dATP derivative is synthesized by ACME BIO-PHARMA Co., LTD., the synthesis method is referred to in (US20130189743A1), and the compound is purified by analytical HPLC to obtain a product having a purity of more than 95%. MALDI-TOF: molecular formula $C_{60}H_{68}N_{15}O_{25}P_3S_2[M]$ (obtained by calculation), molecular weight 1555.31 (calc), 1554.25 [M−H]− (found). The structure of the compound is shown in the formula (2).

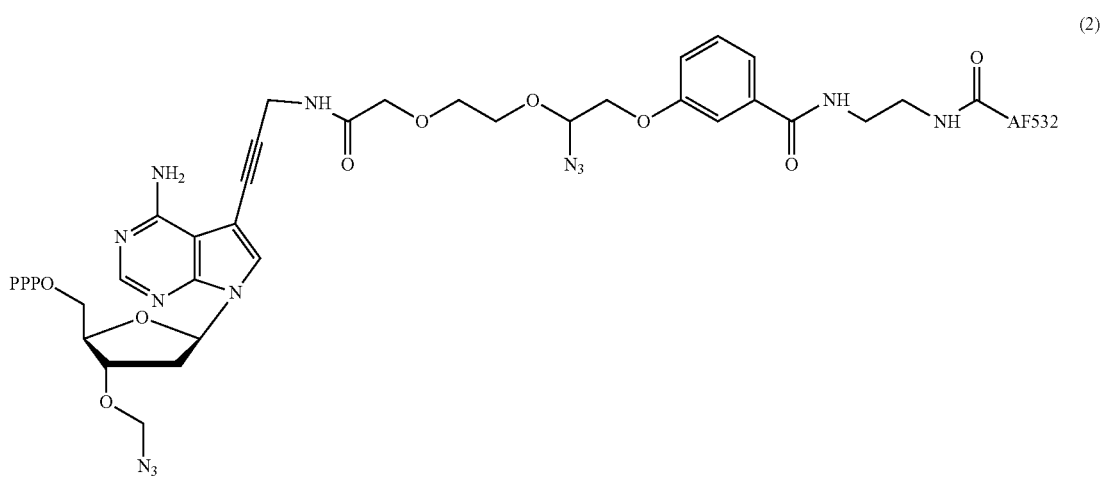

(2)

Synthetic Route:
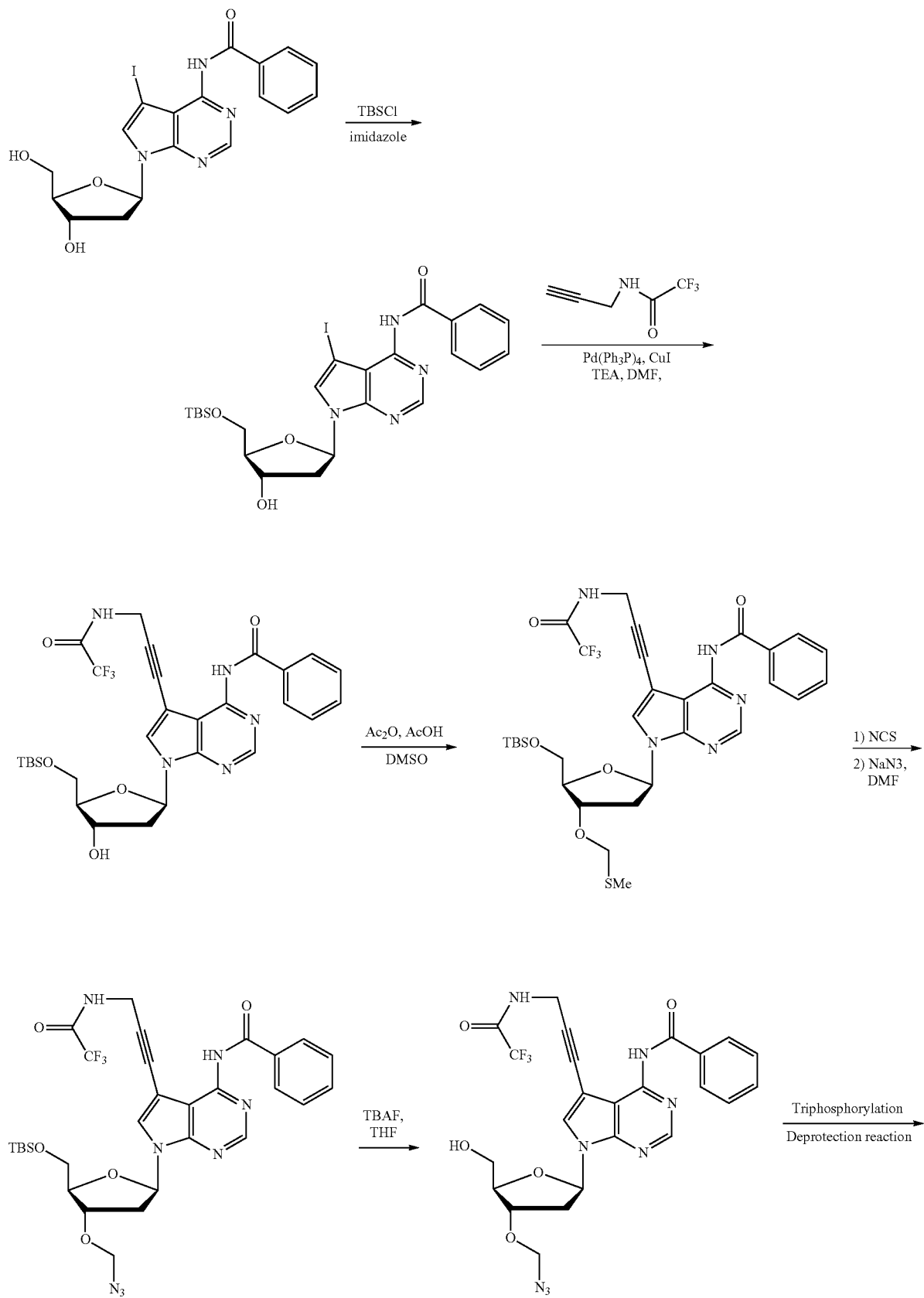

247 248
-continued
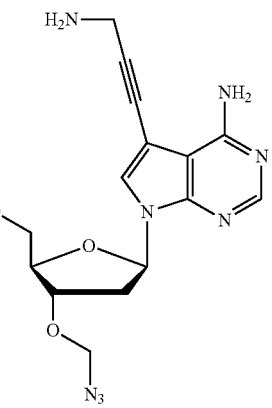
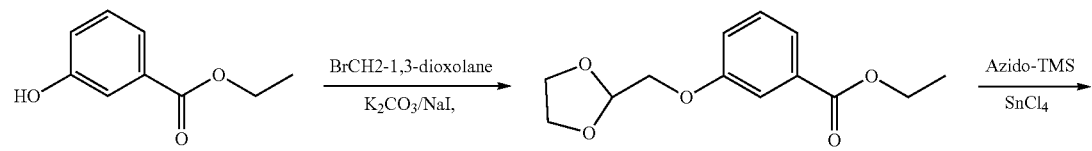
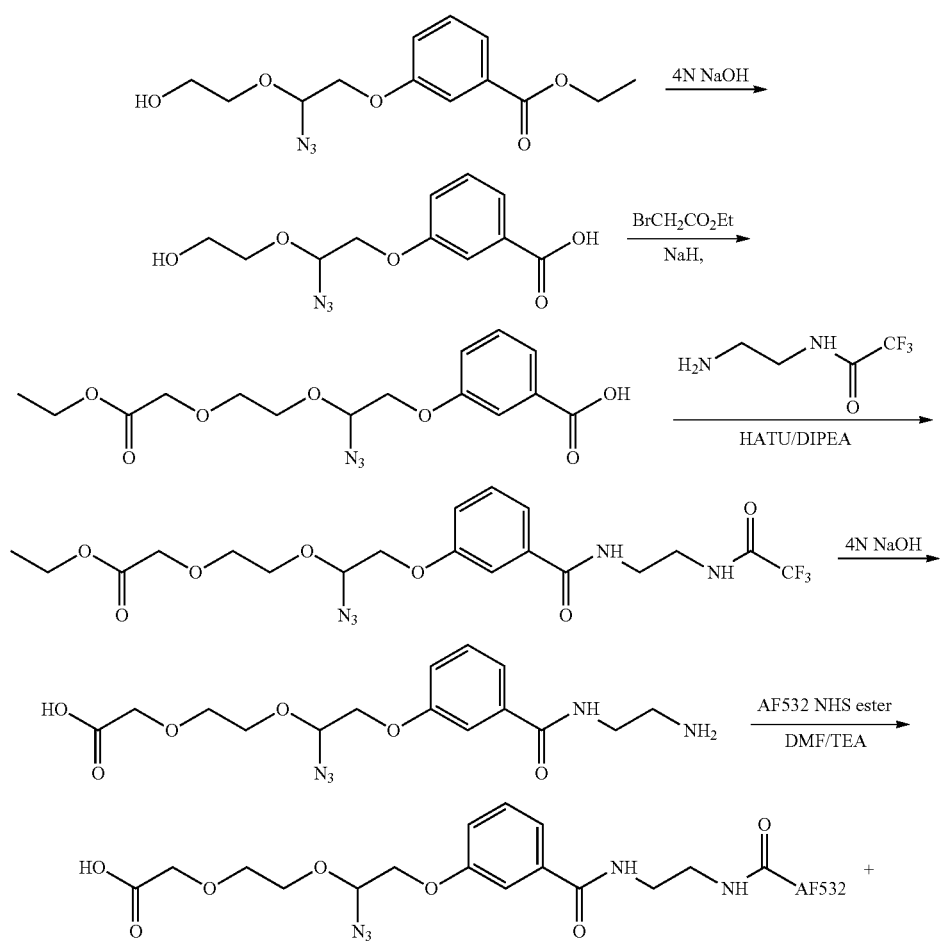

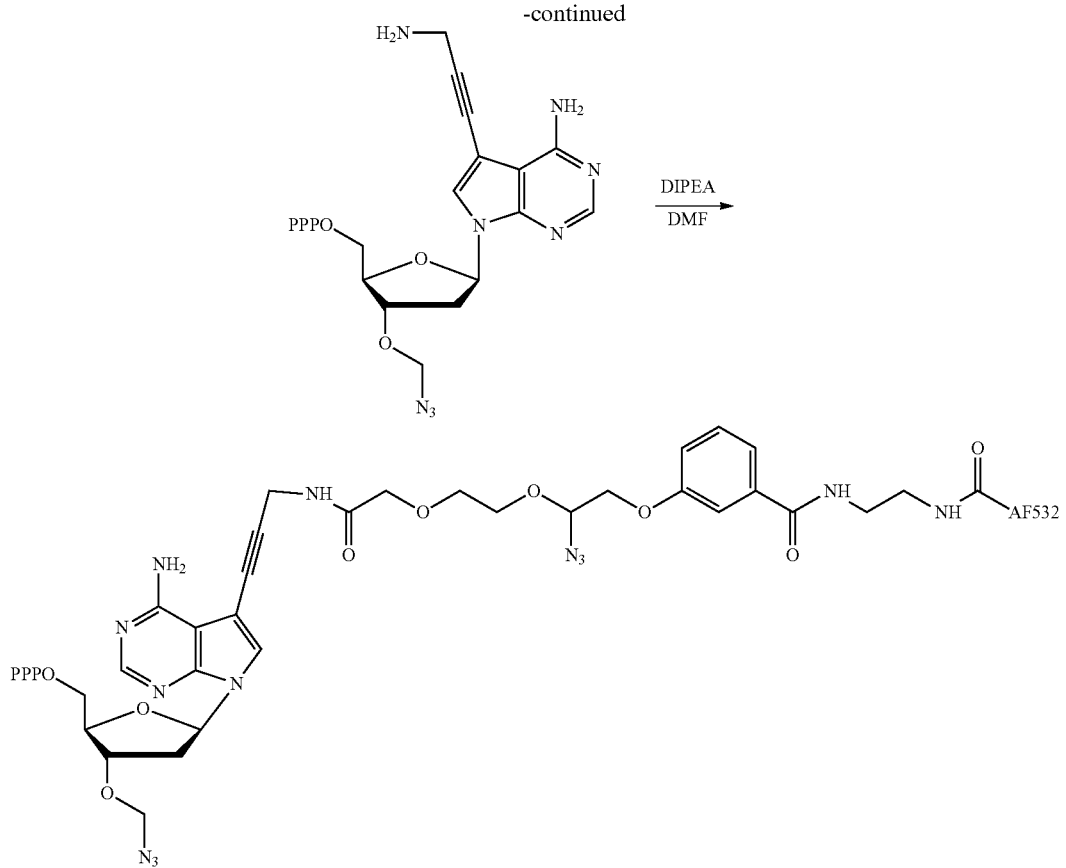

Preparation Example 3 Preparation of the Derivative of dTTP

The dTTP derivative is synthesized by ACME BIO-PHARMA Co., LTD., the synthetic method is referred to in US20130189743A1 and ucleic Acids Res., 15, 4513-4534, and the compound is purified by analytical HPLC to obtain a product having a purity greater than 95%. MALDI-TOF: molecular formula $C_{38}H_{52}N_{13}O_{21}P_3S[M]$ (obtained by calculation), molecular weight: 1151.23 (calc), 1150.21 [M−H]− (found). The structure of the compound is shown in the formula (3).

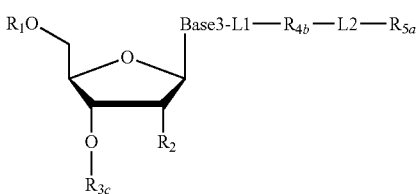

(III)

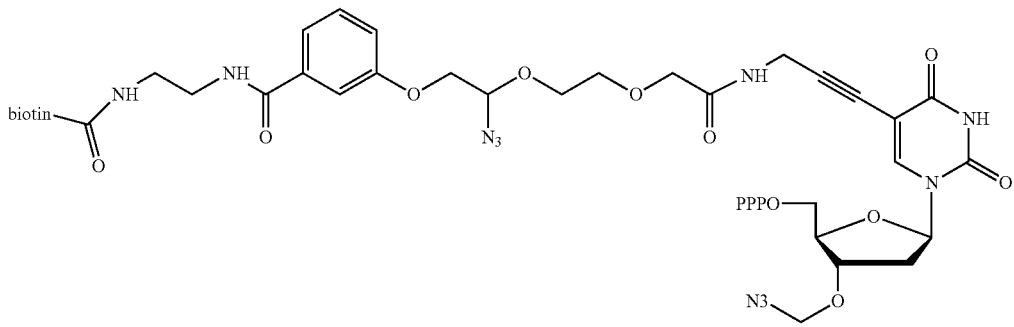

(3)

Synthetic Route:
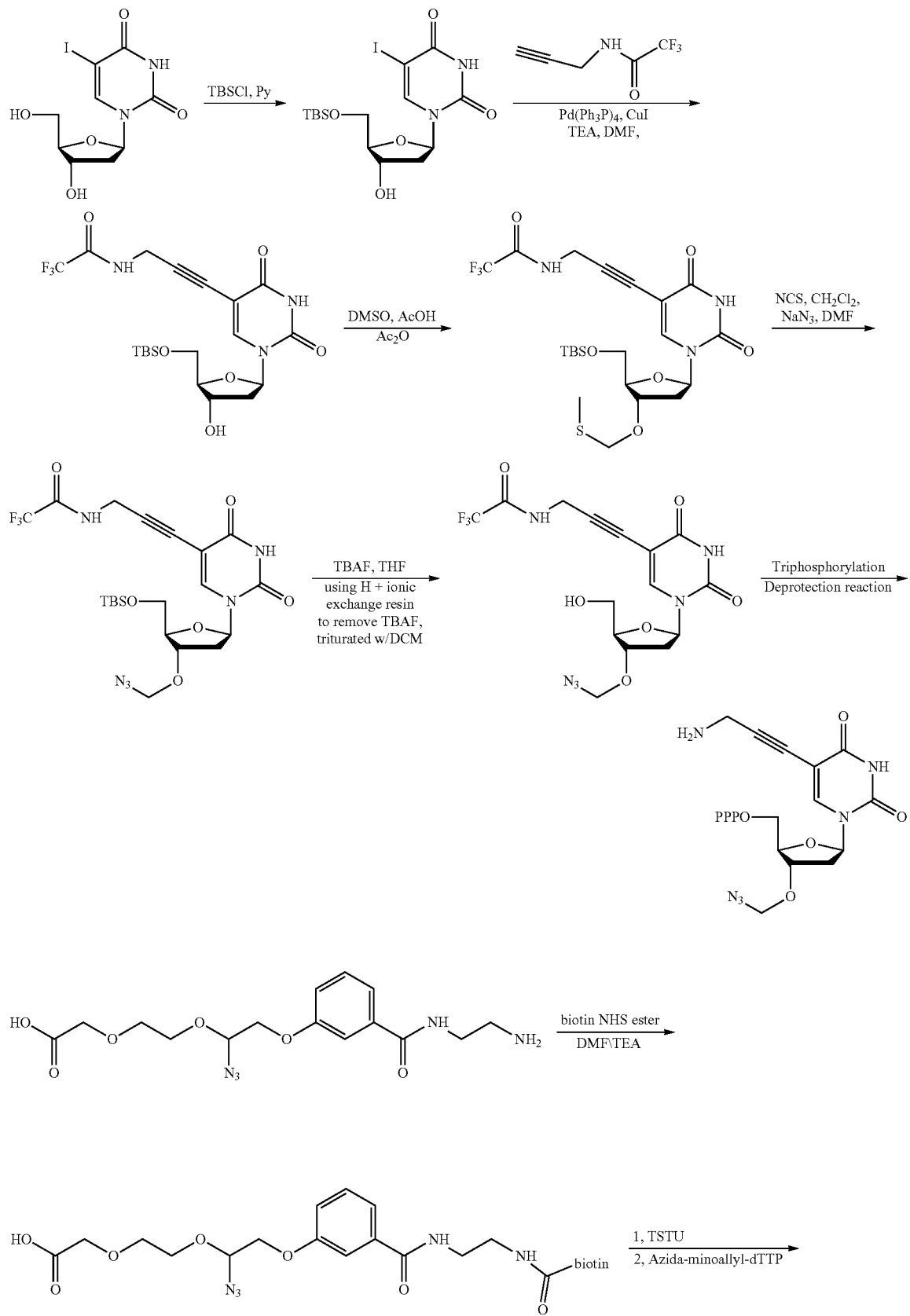

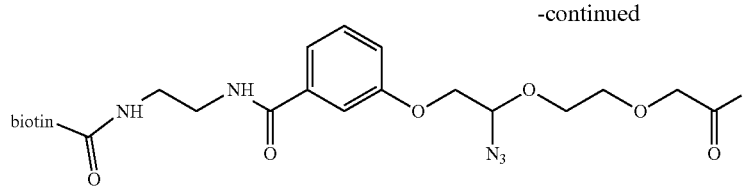

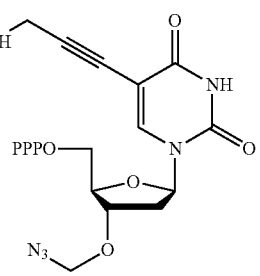

Preparation Example 4. Preparation of the Derivative of dCTP

The dCTP derivative is synthesized by ACME BIO-PHARMA Co., LTD., (the synthetic method is referred to in US20130189743A1 and Nucleic Acids Res., 15, 4513-4534). The compound is purified by analytical HPLC to give a product with a purity greater than 95%. MALDI-TOF: molecular formula $C_{59}H_{76}ClN_{14}O_{19}P_3$ [M] (obtained by calculation), molecular weight 1412.43 (calc.), 1411.33 [M−H]− (found). The structure of the compound is shown in the formula (4).

(IV)

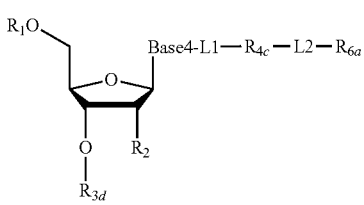

(4)

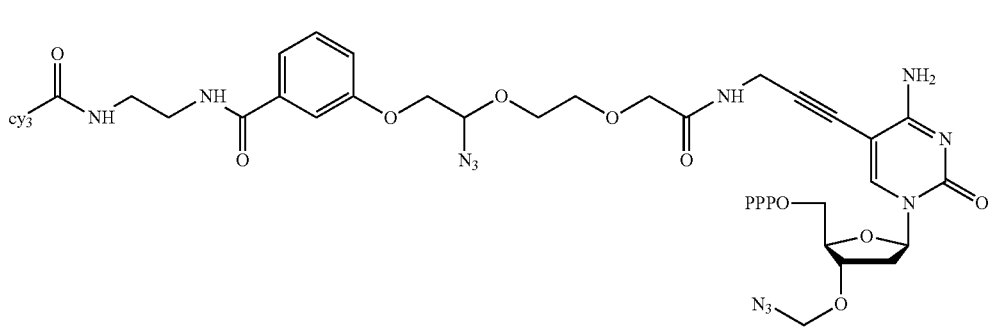

Synthetic Route:

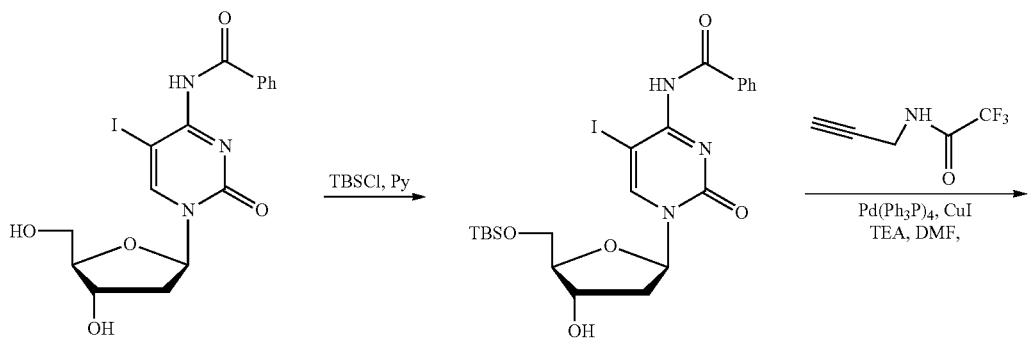

255 256
-continued
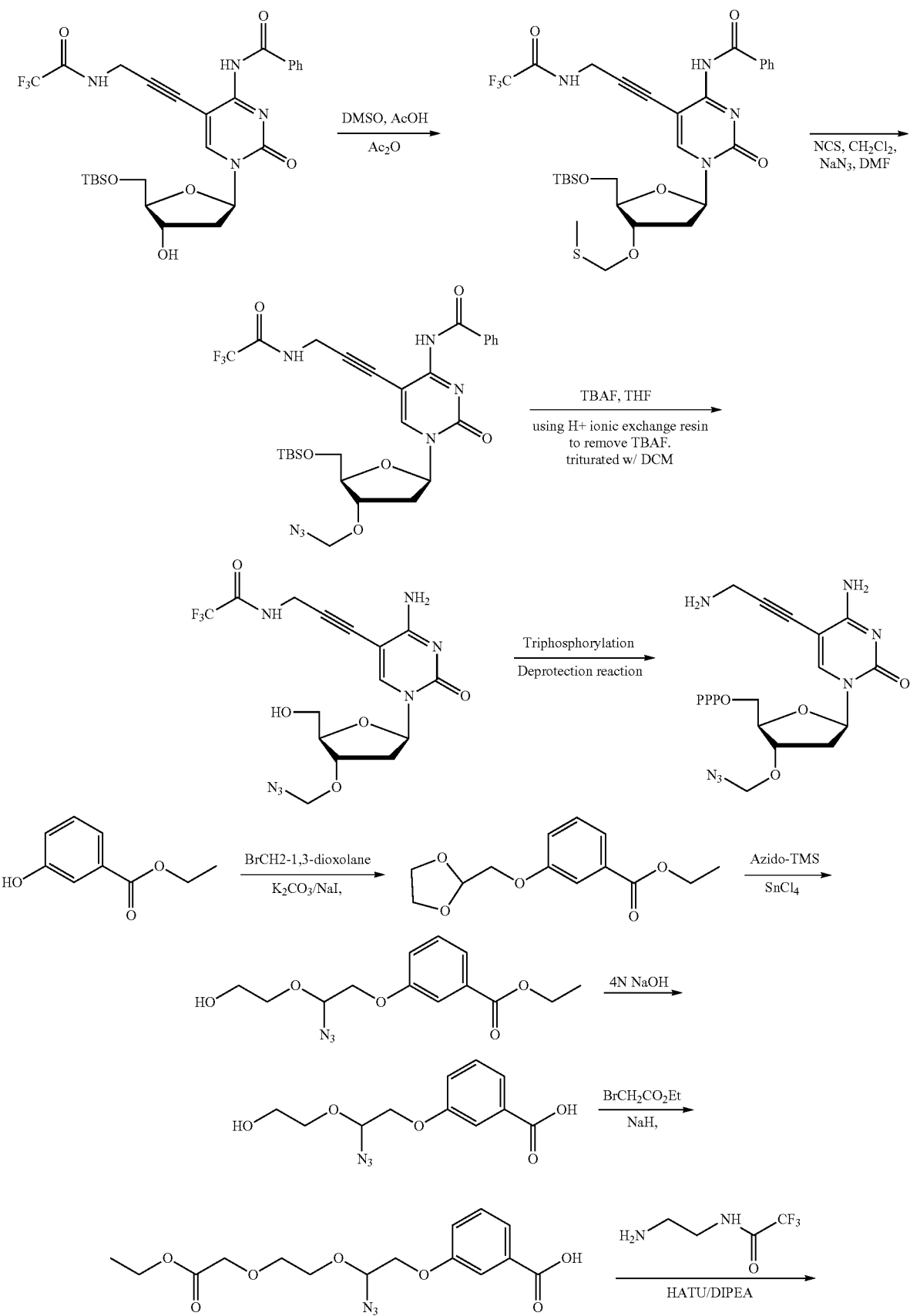

-continued

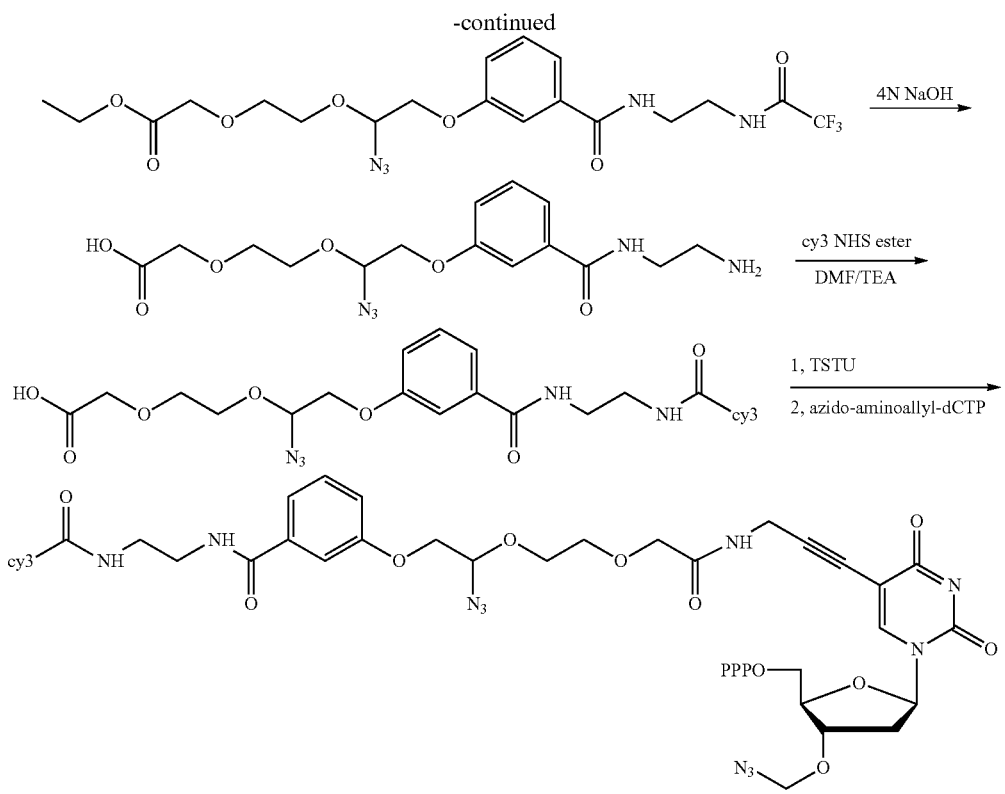

The first binding pair: biotin and streptavidin-AF532 (thermofisher, catalogue number: S11224). The dTTP derivative can be combined with AF532 by binding biotin on the dTTP derivative to streptavidin modified with AF532. Streptavidin-AF532 is purchased by thermofisher, catalogue number: S11224.

The second binding pair: Cy3 and cy3 antibody. Cy3 can be quenched by BHQ2 Quencher by specifically binding Cy3 on the dCTP derivative to the cy3 antibody with the quencher BHQ2 (Cy3 antibody-BHQ2). Cy3 antibody-BHQ2 was purchased from Santa cruz biotech, catalogue number: sc-166894.

Staining agent: 1λPBS buffer, 1 μg/ml BSA, 10 ng/ml streptavidin-AF532 and 10 ng/ml cy3 antibody-BHQ2 (black hole quencher).

Dying time and temperature: 30 seconds, 350° C.

Experimental Example 3

In the present experimental example, four nucleotide derivatives (i.e., the derivative of dGTP obtained in Preparation Example 1, the derivative of dATP obtained in Preparation Example 2, the derivative 1 of dTTP obtained in Preparation Example 3, and the derivative of dCTP obtained in Preparation Example 4) were used to perform a sequencing reaction on the template nucleic acid. In short, the sequencing method used in this experimental example involves the following steps:

(1) immobilizing the template nucleic acid on a chip; the sequence of each nucleic acid molecule to be tested is shown in Table 3; immobilizing was performed on BGISEQ-500 sequencing chip by BGISEQ-500 library kit and DNB loading kit;

(2) adding a sequencing primer, which is a conventional sequencing primer of BGISEQ-500, and annealing the primer to the template nucleic acid molecule to form a duplex linked onto the chip together with the template nucleic acid molecule;

(3) performing a polymerization with polymerase under a condition allowing the polymerase to perform nucleotide polymerization, thereby incorporating one of the four compounds into the 3' end of the growing nucleic acid strand; the DNA polymerase and buffer solution used were identical to the BGISEQ-500 sequencing agents, in which the nucleotides used were replaced with the four nucleotides synthesized in this embodiment, and the agents in this experiment remained the same as the BGISEQ-500 agents except for the cleavage agent;

(4) removing the solution phase of the reaction system in the previous step, retaining the duplex attached onto the support, adding a scanning buffer, and then detecting whether the duplex or the growing nucleic acid strand emits the fluorescent signal, taking a photo, and storing the photo (i.e., experimental photograph 1);

(5) removing the solution phase, washing, and adding the specific binding agent and reacting at 35° C. for 1-5 minutes; allowing the duplex or the growing nucleic acid strand subjected to a treatment in a reaction system containing a solution phase and a solid phase, wherein the treatment has no effect on G and A bases, but cy3 antibody-BHQ2 in the agent enables cy3 dye carried by C base to bind with the cy3 antibody, thereby making the cy3 dye to be specifically quenched by the BHQ2 Quencher, thereby losing the fluorescence; and the streptavidin-AF532 in the agent is capable of specifically binding to the biotin in T base, thereby introducing the fluorophore in the agent into the T base to make the T base to emit a fluorescent signal; the excitation and emission spectra of cy3 are almost the same as those of AF532, and BHQ2 can completely quench the signal of Cy3, therefore, the cy3 antibody linked with BHQ2 can completely quench the signal of cy3, thus, the addition of the cy3 antibody-BHQ2 to the staining agent enables signal conversion from 1 to 0, while AF532 is not affected.

The specific binding agent comprises: 1× phosphate buffer, 1 μg/ml BSA, 10 ng/ml cy3 antibody-BHQ2 and 10 ng/ml streptavidin-AF532.

(6) removing the solution phase of the reaction system in the previous step, retaining the duplex attached onto the support, adding BGISEQ-500 scanning buffer, and then detecting whether the duplex or the growing nucleic acid strand emits the fluorescent signal, taking a photo, and storing the photo (i.e., experiment photograph 2).

(7) removing the solution phase, washing, and subjecting the chip to a treatment to remove the protecting groups in derivatives of the four nucleotides, including performing bioorthogonal cleavage reactions of azidomethylene and azidomethylidyne, thereby allowing the compound incorporated at the 3' end of the growing nucleic acid strand to have a free hydroxyl group at the 3' position of the ribose or deoxyribose (in other words, converting —OCH$_2$N$_3$ (if present) into a free hydroxyl group), and removing the fluorophore (in other words, removing the fluorophore linking with —OCH$_2$N$_3$—R), if present, from the duplex or the growing nucleic acid strand;

the reaction agent for cleaving azidomethylene and azidomethylidyne comprises: 1 M sodium chloride, 0.1 M tris, pH=9, 10 mM thpp.

(8) removing the solution phase of the reaction system in the previous step;

(9) adding a polymerase for performing nucleotide polymerization, and the first compound, the second compound, the third compound, and the fourth compound, thereby forming a reaction system containing a solution phase and a solid phase, and then performing steps (3)-(6).

In some preferred embodiments, the method further comprises the step of:

(10) repeating steps (7)-(9) one or more times.

After taking the two photographs (i.e., experimental photographs 1 and 2), the signals at the same position are compared. FIG. 1 shows the comparison results of experimental photographs 1 and 2, wherein:

the triangular region indicates that the position (nucleic acid molecule) has no fluorescent signal in both photographs 1 and 2; correspondingly, according to the structure of the derivatives of the four nucleotides used, it can be determined that base G is incorporated into the primer, thus it can be determined that the base at the corresponding position of the nucleic acid molecule is C.

The elliptical region indicates that the position (nucleic acid molecule) has a fluorescent signal in photograph 1, but has no fluorescent signal in photograph 2; correspondingly, according to the structure of the derivatives of the four nucleotides used, it can be determined that base C is incorporation into the primer, therefore, it can be determined that the base at the corresponding position of the nucleic acid molecule is G.

The square region indicates that the position (nucleic acid molecule) has fluorescent signals in both photographs 1 and 2; correspondingly, according to the structure of the derivatives of the four nucleotides used, it can be determined that base A is incorporated into the primer, thus it can be determined that the base at the corresponding position of the nucleic acid molecule is T.

The circular region indicates that the position (nucleic acid molecule) has no fluorescent signal in photograph 1, but has a fluorescent signal in photograph 2; correspondingly, it can be determined that base T is incorporated into the primer according to the structures of the derivatives of the four nucleotides used, and thus, it can be determined that the base at the corresponding position of the nucleic acid molecule is A.

Using the above method for 10 cycles of sequencing, wherein the test sample was a mixture of 36 different sequences, comparing with the 36 sequences after sequencing, and the ratio of achieving full match and allowing one error was 97.3%.

The results indicate that the method of the present embodiment enables accurate sequencing of the template nucleic acid using only one fluorophore.

TABLE 3

| Number (SEQ ID NO:) | Sequence | ratio (%)* | Number (SEQ ID NO:) | Sequence | ratio (%)* |
|---|---|---|---|---|---|
| 1 | TAGGTCCGAT | 3.80 | 19 | TGTCTGCGAA | 2.29 |
| 2 | GGACGGAATC | 1.93 | 20 | ATTGGTACAA | 3.07 |
| 3 | CTTACTGCCG | 2.17 | 21 | CGATTGTGGT | 1.86 |
| 4 | ACCTAATTGA | 3.25 | 22 | ACAGACTTCC | 2.42 |
| 5 | TTCGTATCCG | 2.24 | 23 | TCCACACTCT | 2.96 |
| 6 | GGTAACGAGC | 4.66 | 24 | CACCACAAGC | 2.28 |
| 7 | CAACGTATAA | 3.28 | 25 | TAGAGGACAA | 4.19 |
| 8 | ACGTCGCGTT | 1.91 | 26 | CCTAGCGAAT | 2.24 |
| 9 | TTCTGCTAGC | 2.67 | 27 | GTAGTCATCG | 1.75 |
| 10 | AGGAAGATAG | 2.29 | 28 | GCTGAGCTGT | 2.77 |
| 11 | GCTCTTGCTT | 2.59 | 29 | AACCTAGATA | 4.51 |
| 12 | CAAGCACGCA | 2.07 | 30 | TTGCCATCTC | 2.95 |
| 13 | CGGCAATCCG | 2.68 | 31 | AGATCTTGCG | 1.53 |
| 14 | ATCAGGATTC | 2.57 | 32 | CGCTATCGGC | 2.39 |
| 15 | TCATTCCAGA | 2.67 | 33 | GCAACGATGG | 4.28 |
| 16 | GATGCTGGAT | 2.24 | 34 | TAATCGTTCA | 2.50 |
| 17 | GTGAGTGATG | 2.37 | 35 | GTTCGCTCTA | 2.27 |
| 18 | GAGTCAGCTG | 1.85 | 36 | TCTCACACAT | 3.81 |

*The ratio of the amount of samples that can match the specific numbered sequence (including full match and allowing one error) to the amount of all samples Detailed Embodiment 4

Preparation Example 1. Preparation of the Derivative of dGTP

The dGTP derivative is synthesized by ACME BIO-PHARMA Co., LTD., and the synthetic method is referred to in (US20130189743A1). The compound is purified by analytical HPLC to obtain a product having a purity greater than 95%. MALDI-TOF: molecular formula: C$_{11}$H$_{17}$N$_8$O$_{13}$P$_3$[M] (obtained by calculation), molecular weight: 562.01 (calc), 561.00 [M–H]– (found). The structure of the compound is shown in the formula (1).

261

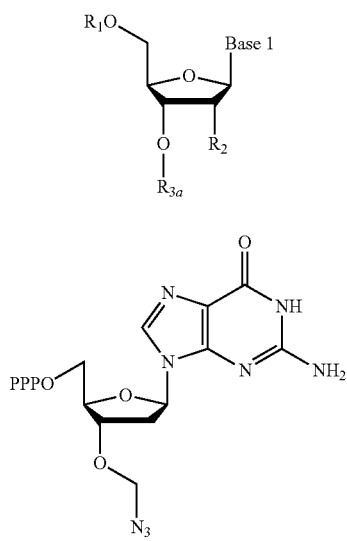

Synthetic Route:

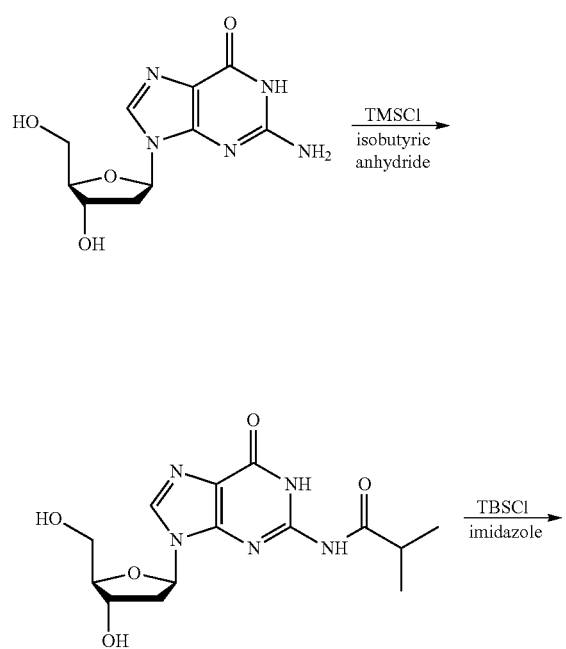

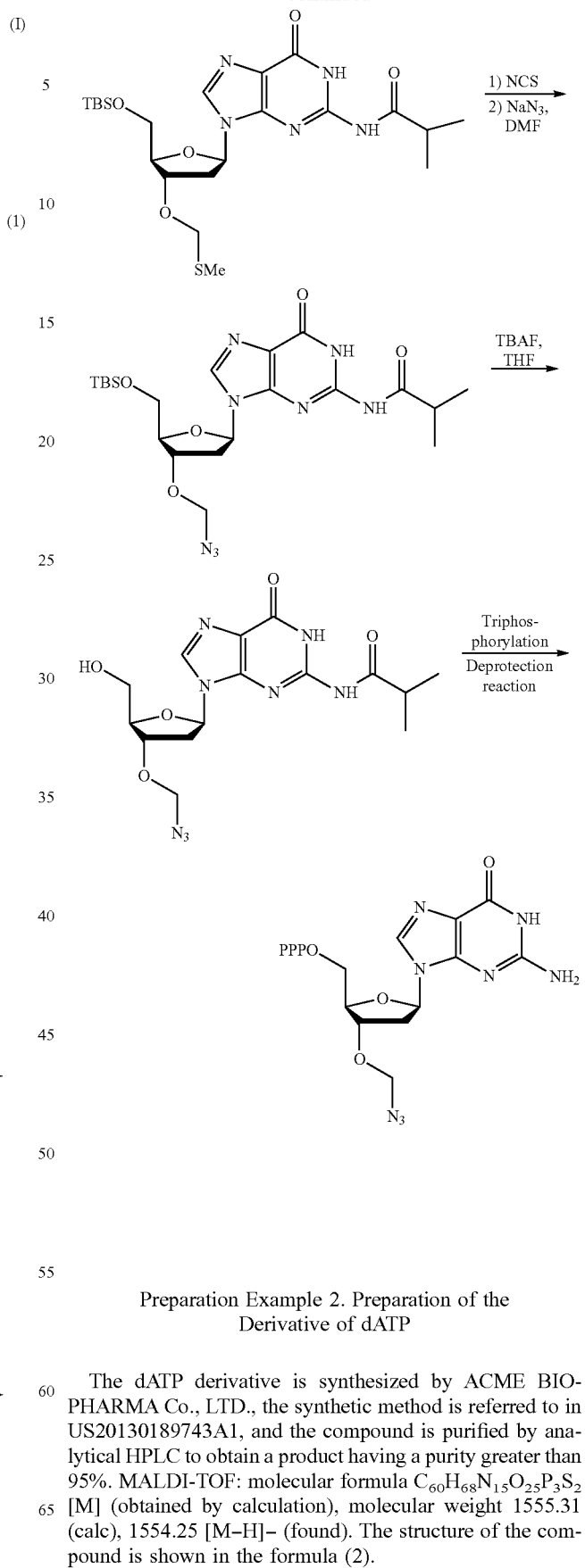

Preparation Example 2. Preparation of the Derivative of dATP

The dATP derivative is synthesized by ACME BIO-PHARMA Co., LTD., the synthetic method is referred to in US20130189743A1, and the compound is purified by analytical HPLC to obtain a product having a purity greater than 95%. MALDI-TOF: molecular formula $C_{60}H_{68}N_{15}O_{25}P_3S_2$ [M] (obtained by calculation), molecular weight 1555.31 (calc), 1554.25 [M–H]– (found). The structure of the compound is shown in the formula (2).

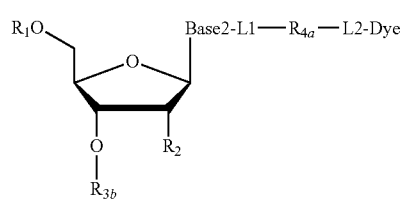
(II)
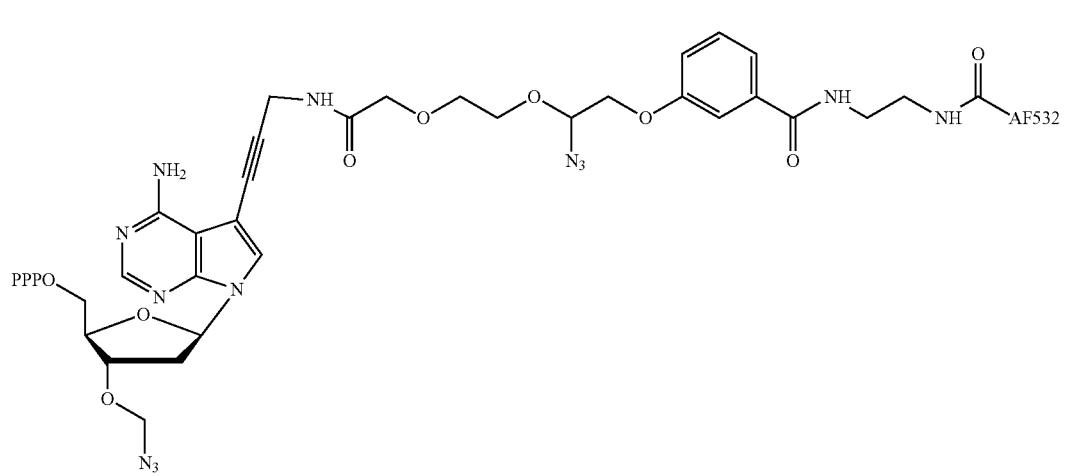
(2)
Synthetic Route:
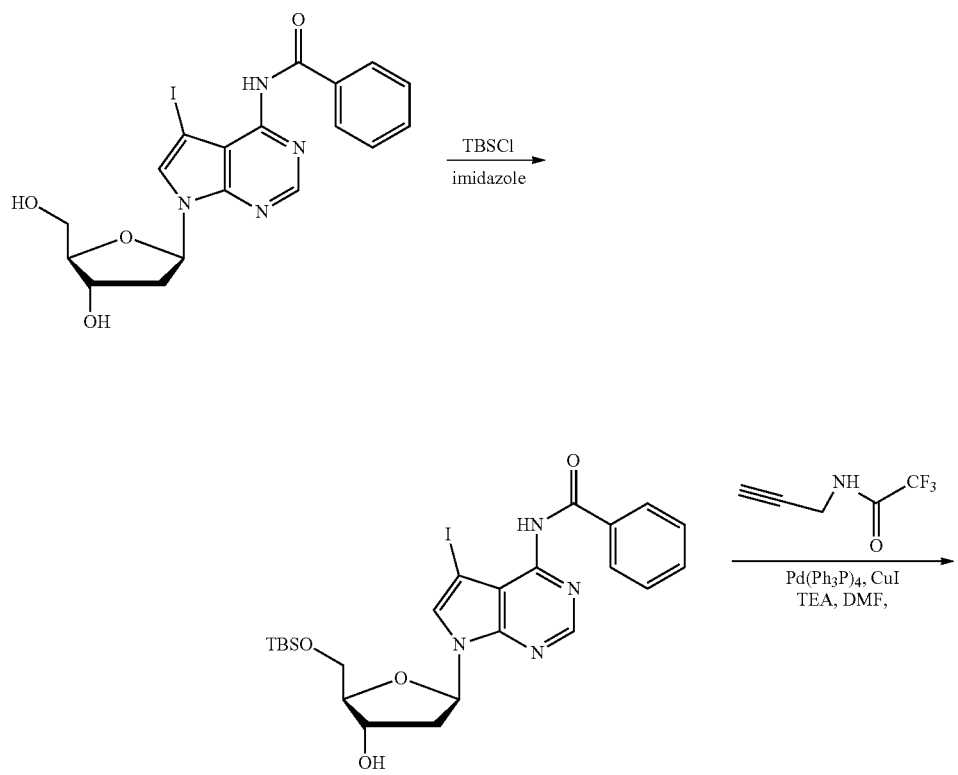

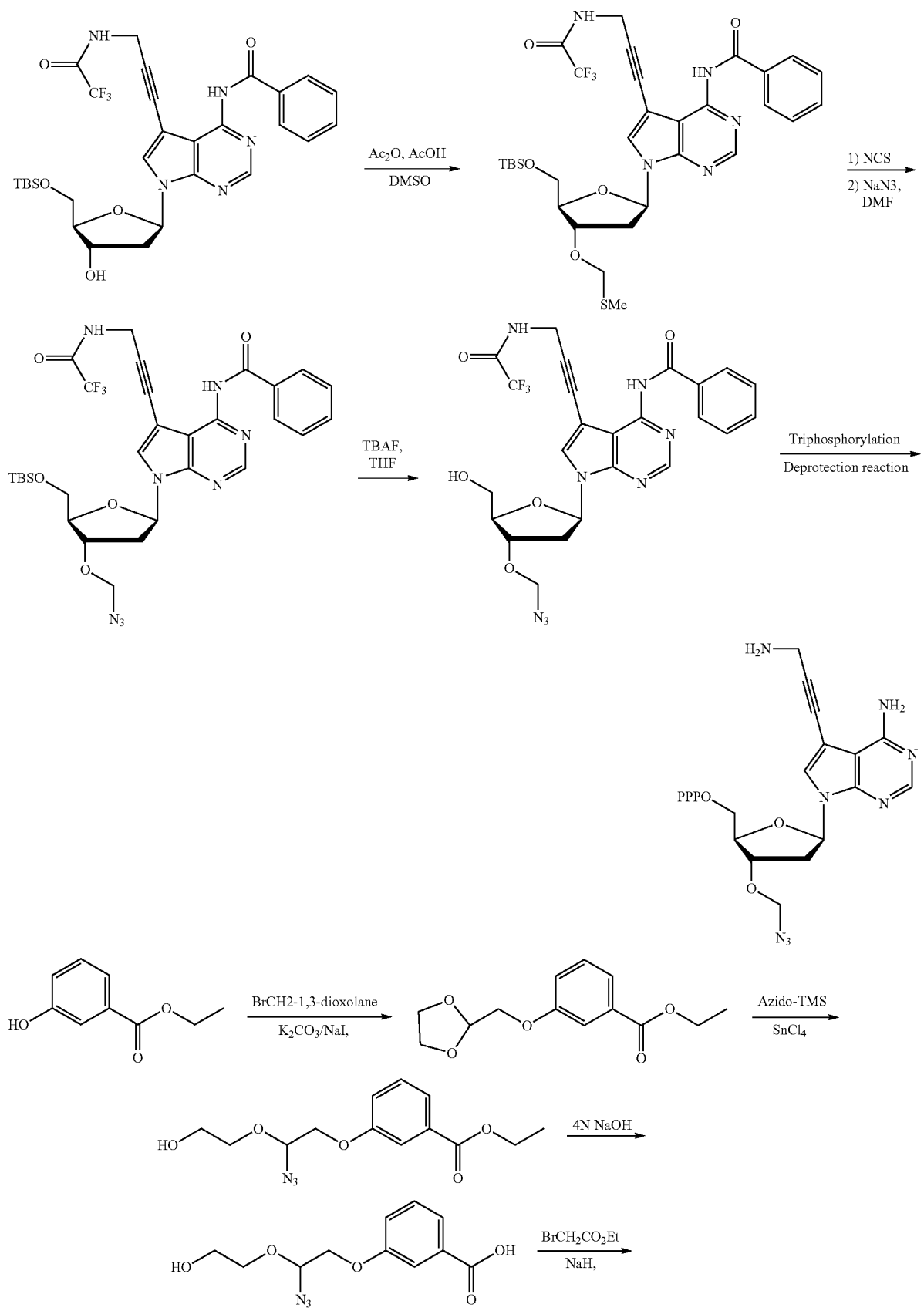

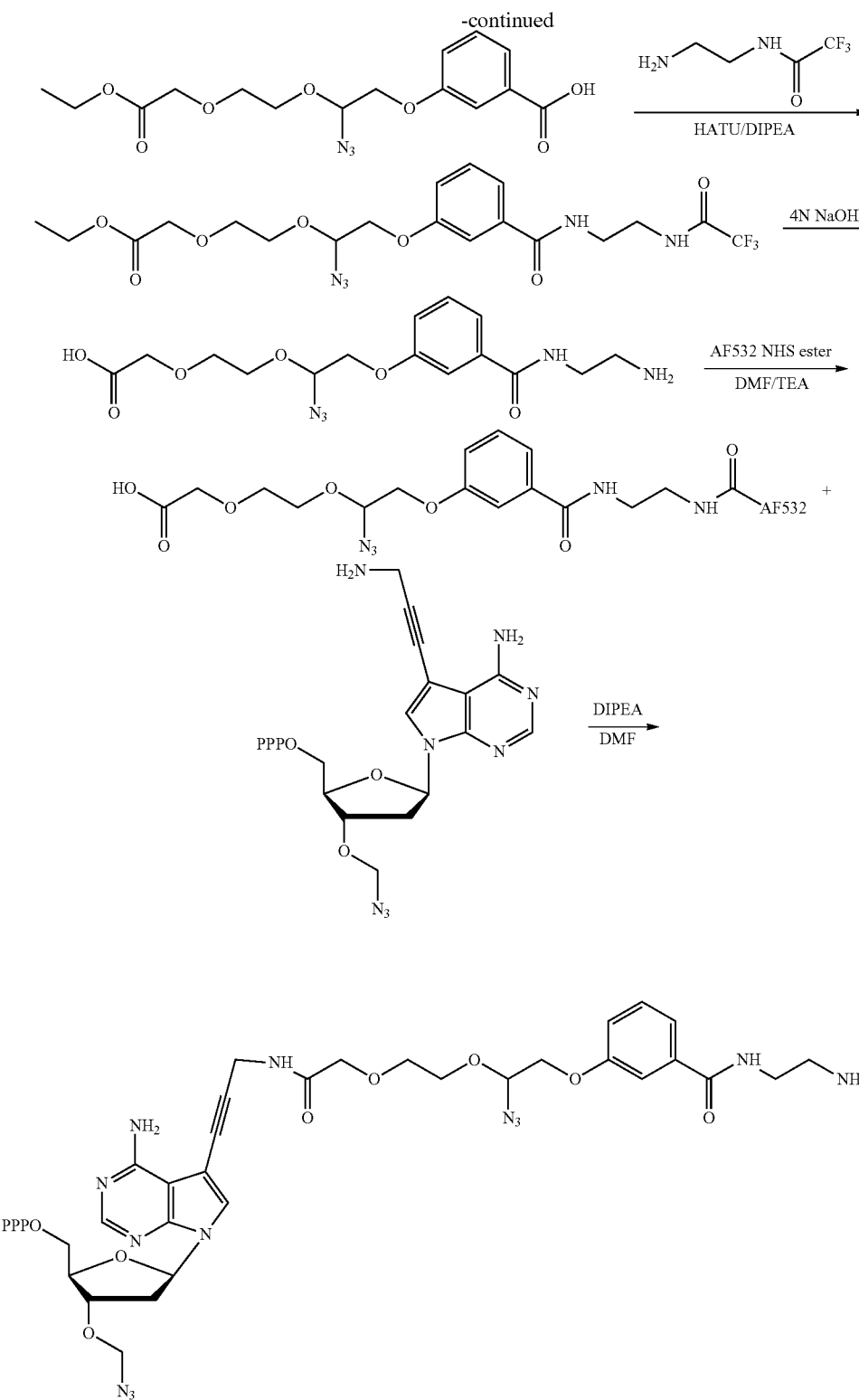

Preparation Example 3. Preparation of the Derivative of dTTP

The dTTP derivative is synthesized by ACME BIO-PHARMA Co., LTD., and the synthetic method is referred to US20130189743A1 and Nucleic Acids Res., 15, 4513-4534. The compound is purified by analytical HPLC to give a product with a purity greater than 95%. MALDI-TOF: molecular formula $C_{38}H_{52}N_{13}O_{21}P_3S[M]$ (obtained by calculation), molecular weight 1151.23 (calc.), 1150.21 [M−H]− (found). The structure of the compound is shown in the formula (3).

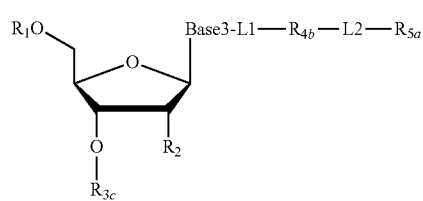
(III)
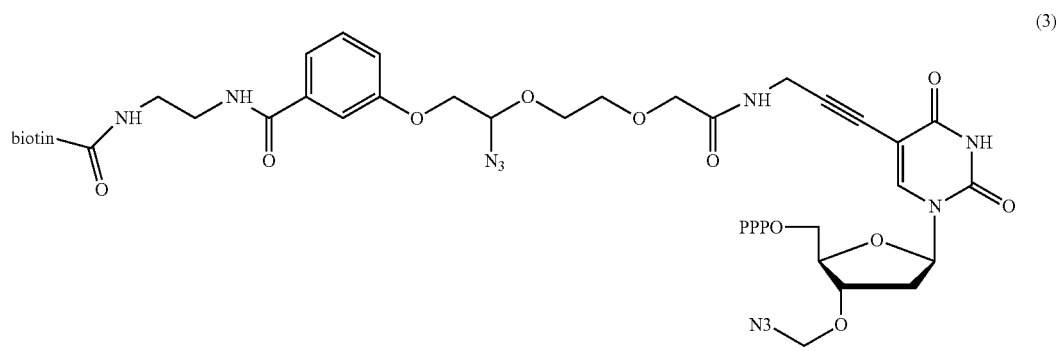
(3)
Synthetic Route:
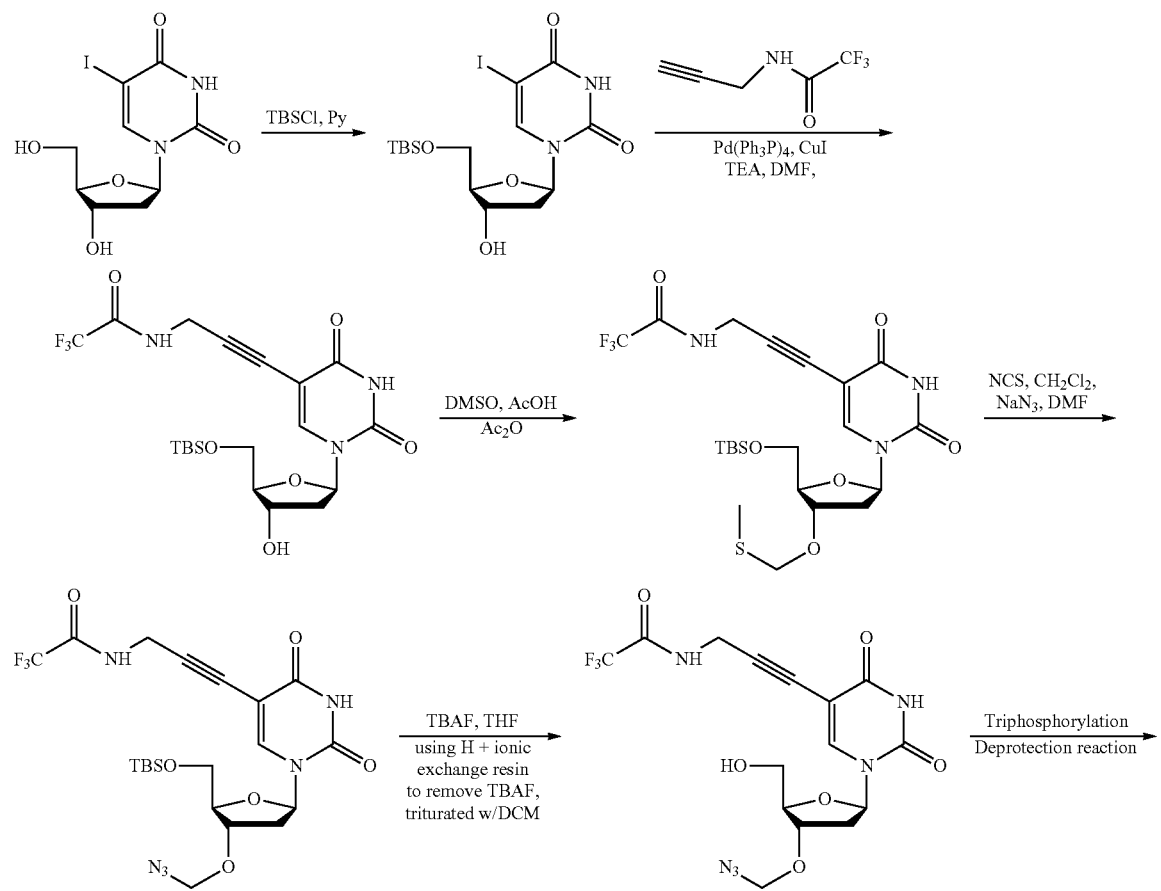

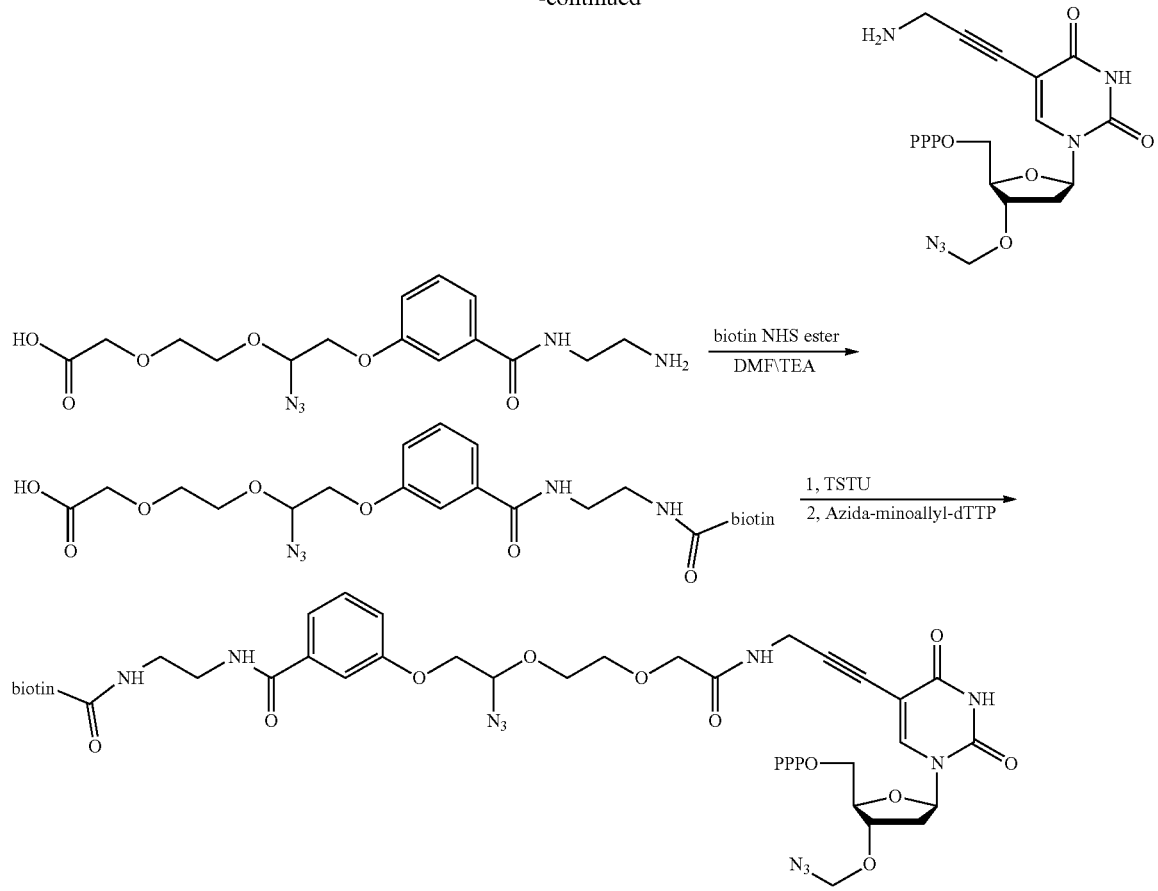

Preparation Example 4. Preparation of the Derivative of dCTP

The dCTP derivative is synthesized by ACME BIO-PHARMA Co., LTD., (the synthetic method is referred to in US20130189743A1, Nucleic Acids Res., 15, 4513-4534 and Bioconjug Chem. 2016; 27(7): 1697-16706)). The compound is purified by analytical HPLC to give a product with a purity greater than 95%. MALDI-TOF: molecular formula $C_{74}H_{93}N_{16}O_{28}P_3S_2[M]$ (obtained by calculation), molecular weight 1810.50 (calc), 1809.43 [M–H]– (found). The structure of the compound is shown in the formula (4).

(IV)

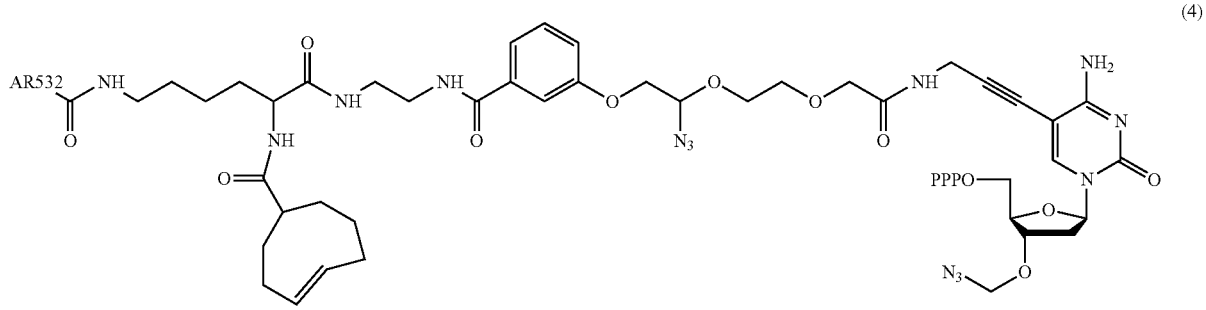

(4)

Synthetic Route:
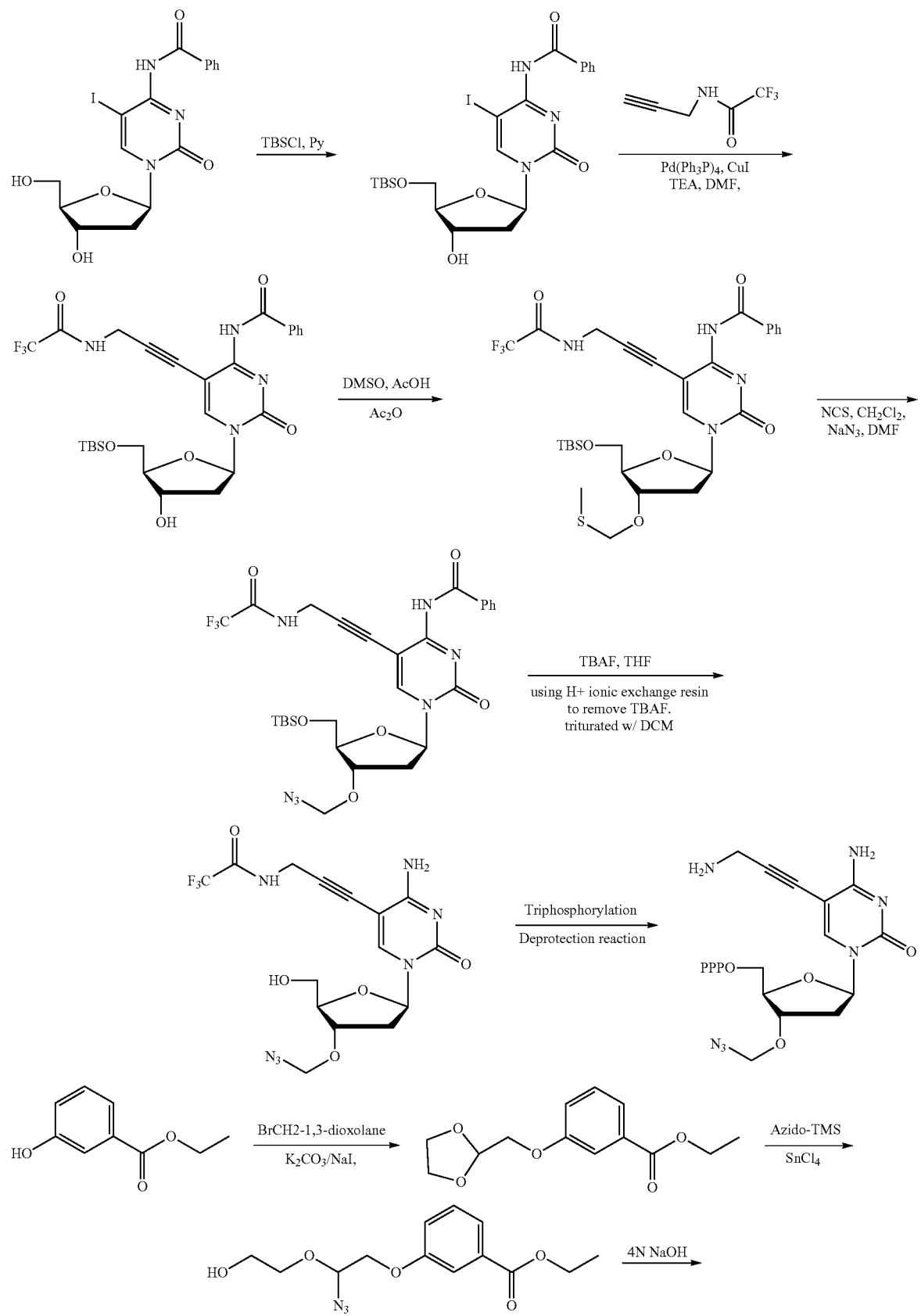

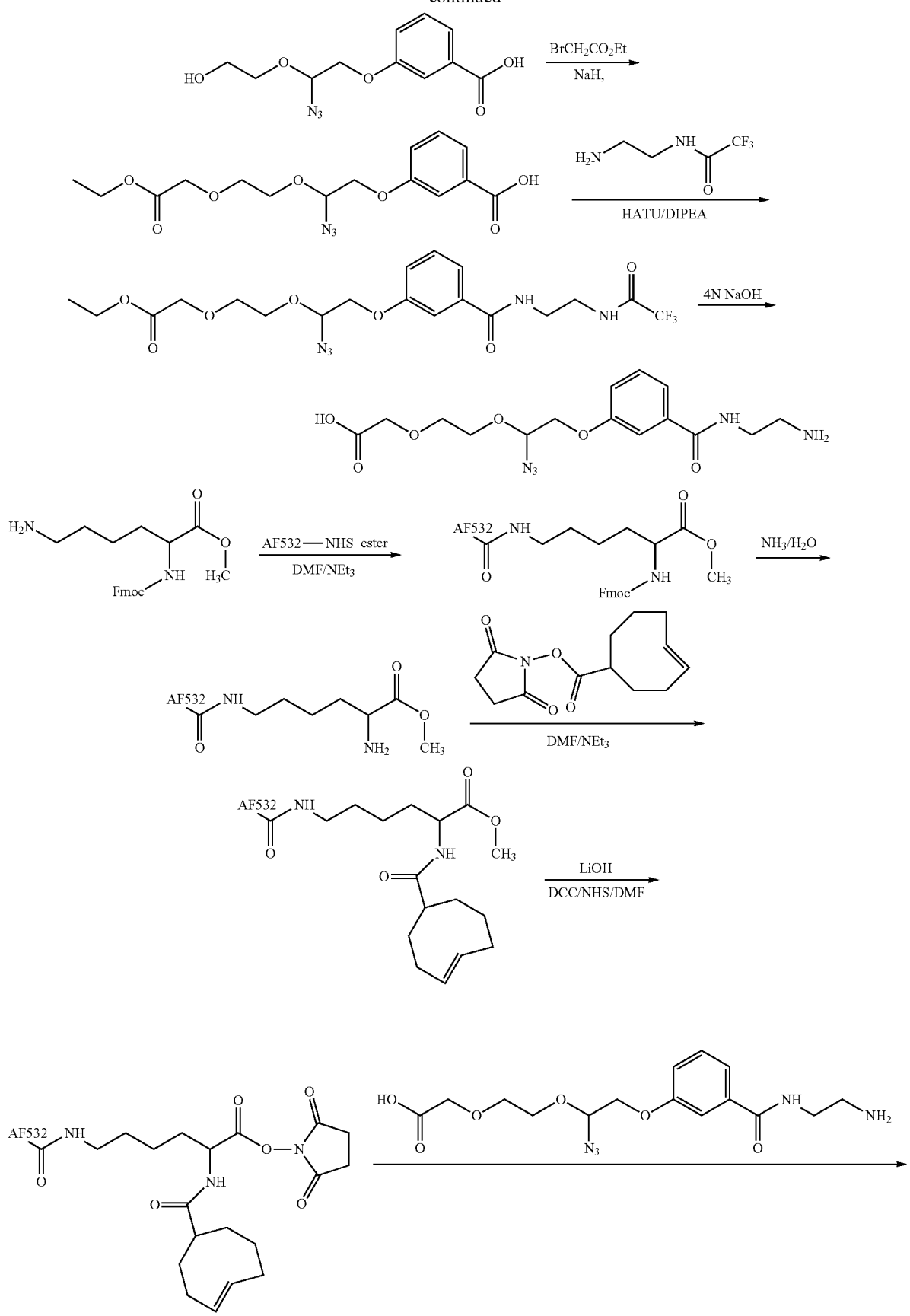

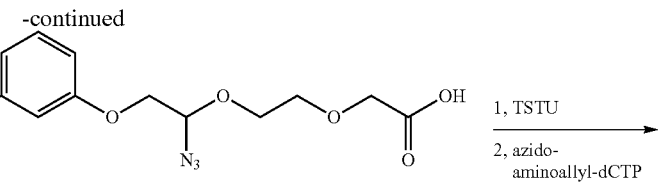
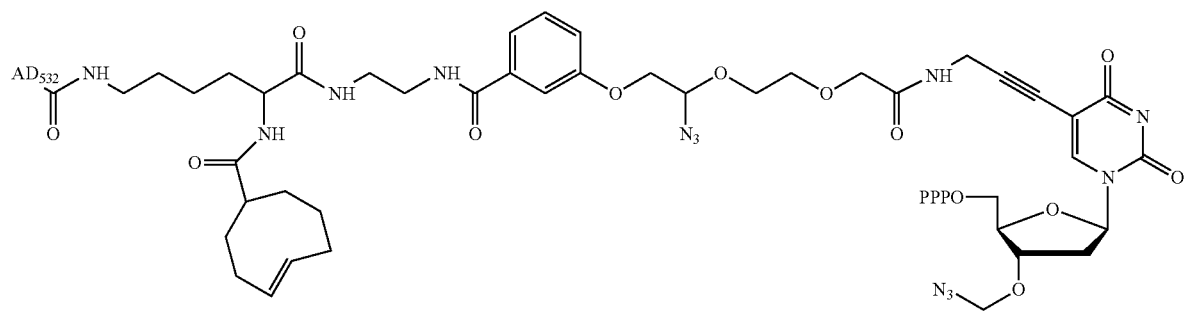
Preparation Example 5: Preparation of 1,2,4,5-tetrazine BHQ2
The compound 1,2,4,5-tetrazine BHQ2 for bioorthogonal reaction is synthesized by Heiya Medical Technology (Shanghai) Co., Ltd., The method is referred to in literature Bioconjugate Chem. 2014, 25, 1730-1738. ESI: molecular formula $C_{37}H_{38}N_{12}O_6$[M](obtained by calculation), molecular weight 746.30 (calc.), 747.29 [M+H]+ (found).
Synthetic Route:
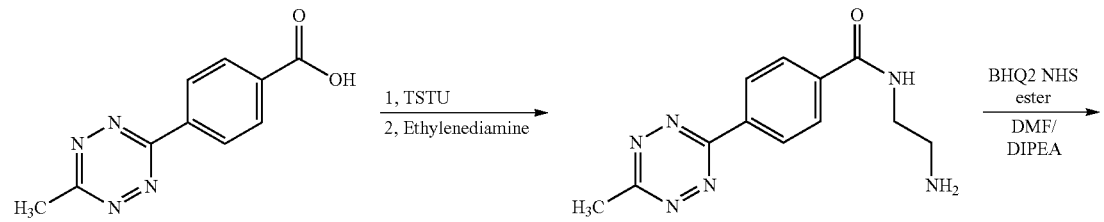
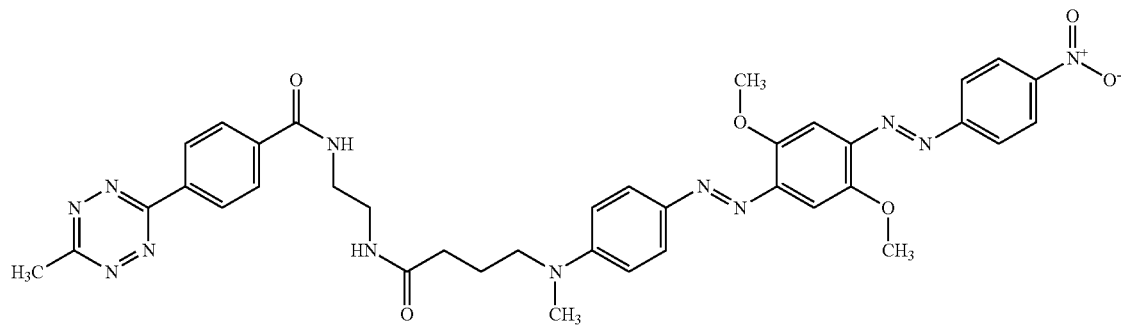

The binding pair: the biotin is capable of specifically binding to streptavidin. The dTTP derivative can be linked with AF532 by binding biotin on the dTTP derivative to streptavidin modified with AF532. Streptavidin modified with AF532 (Streptavidin-AF532) was purchased from thermofisher, catalogue number. S11224).

Experimental Example 4

In the present experimental example, four nucleotide derivatives (i.e., the derivative of dGTP obtained in Preparation Example 1, the derivative of dATP obtained in Preparation Example 2, the derivative of dTTP obtained in Preparation Example 3, and the derivative of dCTP obtained in Preparation Example 4 were used. In short, the sequencing method used in this experimental example involves the following steps:

(1) immobilizing the template nucleic acid on a chip; the sequence of each nucleic acid molecule to be tested is shown in Table 4; immobilizing was performed on BGISEQ-500 sequencing chip by BGISEQ-500 library kit and DNB loading kit;

(2) adding a sequencing primer, which is a conventional sequencing primer of BGISEQ-500, and annealing the primer to the template nucleic acid molecule to form a duplex linked onto the chip together with the template nucleic acid molecule;

(3) performing a polymerization with polymerase under a condition allowing the polymerase to perform nucleotide polymerization, thereby incorporating one of the four compounds into the 3' end of the growing nucleic acid strand; the DNA polymerase and buffer solution used were identical to the BGISEQ-500 sequencing agents, in which the nucleotides used were replaced with the four nucleotides synthesized in this embodiment, and the agents in this experiment remained the same as the BGISEQ-500 agents except for the cleavage agent;

(4) removing the solution phase of the reaction system in the previous step, retaining the duplex attached onto the support, adding a scanning buffer, and then detecting whether the duplex or the growing nucleic acid strand emits the fluorescent signal, taking a photo, and storing the photo (i.e., experimental photograph 1);

(5) removing the solution phase, washing, adding a solution comprising the specific binding agent and reacting at 35° C. for 1-5 minutes, thereby allowing the duplex or the growing nucleic acid strand subjected to a treatment in a reaction system containing a solution phase and a solid phase, wherein the treatment has no effect on the G and A bases, but enables 1,2,4,5-tetrazine BHQ2 in the agent to perform bioorthogonal ligation reaction with the trans-cyclooctene carried by C base, thereby allowing the AF532 dye specifically quenched by BHQ2 Quencher, and making the C base to lose the fluorescent signal; and streptavidin-AF532 in the agent is capable of specifically binding to biotin in T base, thereby introducing the fluorophore in the agent into T base to make the T base to emit a fluorescent signal.

Since the excitation and emission spectra of cy3 are almost the same as those of AF532, and BHQ2 can completely quench the signal of cy3, therefore, cy3 antibody-BHQ2 can completely quench the signal of cy3, thus, the addition of cy3 antibody-BHQ2 to the staining agent enables signal conversion from 1 to 0, while AF532 is not influenced.

The specific binding agent comprises: 1× phosphate buffer, 1 µg/ml BSA, 1 Um 1,2,4,5 tetrazine-BHQ 2 and 10 ng/ml streptavidin-AF532.

(6) removing the solution phase of the reaction system in the previous step, retaining the duplex attached onto the support, adding BGISEQ-500 scanning buffer, and then detecting whether the duplex or the growing nucleic acid strand emits the fluorescent signal, taking a photo, and storing the photo (i.e., experiment photograph 2).

(7) removing the solution phase, washing, and subjecting the chip to a treatment to remove the protecting groups in derivatives of the four nucleotides, wherein the treatment enables azidomethylene and azidomethylidyne to perform bioorthogonal cleavage reaction, thereby allowing the compound incorporated at the 3' end of the growing nucleic acid strand to have a free hydroxyl group at the 3' position of the deoxyribose (in other words, converting —OCH$_2$N$_3$ (if present) into a free hydroxyl group), and removing the fluorophore, if present, from the duplex or the growing nucleic acid strand (in other words, removing the fluorophore linked with —OCH$_2$N$_3$—R);

the reaction agent for cleaving azidomethylene and azidomethylidyne comprises: 1 M sodium chloride, 0.1 M tris, pH=9, 10 mM thpp.

(8) removing the solution phase of the reaction system in the previous step;

(9) adding a polymerase for performing nucleotide polymerization, and the first compound, the second compound, the third compound, and the fourth compound, thereby forming a reaction system containing a solution phase and a solid phase, and then performing steps (3)-(6).

In some preferred embodiments, the method further comprises the step of:

(10) repeating steps (7)-(9) one or more times.

After taking the two photographs (i.e., experimental photographs 1 and 2), the signals at the same position are compared. FIG. 1 shows the comparison results of experimental photographs 1 and 2, wherein:

the triangular region indicates that the position (nucleic acid molecule) has no fluorescent signal in both photographs 1 and 2; correspondingly, according to the structure of the derivatives of the four nucleotides used, it can be determined that base G is incorporated into the primer, thus it can be determined that the base at the corresponding position of the nucleic acid molecule is C.

The elliptical region indicates that the position (nucleic acid molecule) has a fluorescent signal in photograph 1, but has no fluorescent signal in photograph 2; correspondingly, according to the structure of the derivatives of the four nucleotides used, it can be determined that base C is incorporation into the primer, therefore, it can be determined that the base at the corresponding position of the nucleic acid molecule is G.

The square region indicates that the position (nucleic acid molecule) has fluorescent signals in both photographs 1 and 2; correspondingly, according to the structure of the derivatives of the four nucleotides used, it can be determined that base A is incorporated into the primer, thus it can be determined that the base at the corresponding position of the nucleic acid molecule is T.

The circular region indicates that the position (nucleic acid molecule) has no fluorescent signal in photograph 1, but has a fluorescent signal in photograph 2; correspondingly, it can be determined that base T is incorporated into the primer according to the structures of the derivatives of the four nucleotides used, and thus, it can be determined that the base at the corresponding position of the nucleic acid molecule is A.

Using the above method for 10 cycles of sequencing, wherein the test sample was a mixture of 36 different sequences, comparing with the 36 sequences after sequencing, and the ratio of achieving full match and allowing one error was 94.93%.

The results indicate that the method of the present embodiment enables accurate sequencing of the template nucleic acid using only one fluorophore.

TABLE 4

| Number (SEQ ID NO:) | Sequence | ratio (%)* | Number (SEQ ID NO:) | Sequence | ratio (%)* |
|---|---|---|---|---|---|
| 1 | TAGGTCCGAT | 3.20 | 19 | TGTCTGCGAA | 2.70 |
| 2 | GGACGGAATC | 2.37 | 20 | ATTGGTACAA | 2.54 |
| 3 | CTTACTGCCG | 2.11 | 21 | CGATTGTGGT | 1.91 |
| 4 | ACCTAATTGA | 2.92 | 22 | ACAGACTTCC | 2.59 |
| 5 | TTCGTATCCG | 2.51 | 23 | TCCACACTCT | 2.57 |
| 6 | GGTAACGAGC | 3.70 | 24 | CACCACAAGC | 2.98 |
| 7 | CAACGTATAA | 3.53 | 25 | TAGAGGACAA | 3.63 |
| 8 | ACGTCGCGTT | 2.08 | 26 | CCTAGCGAAT | 2.04 |
| 9 | TTCTGCTAGC | 2.36 | 27 | GTAGTCATCG | 2.01 |
| 10 | AGGAAGATAG | 2.48 | 28 | GCTGAGCTGT | 2.48 |
| 11 | GCTCTTGCTT | 3.23 | 29 | AACCTAGATA | 3.59 |
| 12 | CAAGCACGCA | 2.41 | 30 | TTGCCATCTC | 2.51 |
| 13 | CGGCAATCCG | 2.29 | 31 | AGATCTTGCG | 1.87 |
| 14 | ATCAGGATTC | 2.52 | 32 | CGCTATCGGC | 2.35 |
| 15 | TCATTCCAGA | 3.20 | 33 | GCAACGATGG | 3.49 |
| 16 | GATGCTGGAT | 2.36 | 34 | TAATCGTTCA | 2.31 |
| 17 | GTGAGTGATG | 2.36 | 35 | GTTCGCTCTA | 2.21 |
| 18 | GAGTCAGCTG | 2.57 | 36 | TCTCACACAT | 2.94 |

*The ratio of the amount of samples that can match the specific numbered sequence (including full match and allowing one error) to the amount of all samples Although the specific embodiments of the invention have been described in detail, a person skilled in the art will understand that various modifications and changes can be made on the details of the present invention, and such variations are within the scope of the invention. The full scope of the invention is given by the appended claims and any equivalents thereof.

The invention claimed is:

1. A method of sequencing a nucleic acid molecule, comprising the steps of:
   (1) providing a nucleic acid molecule to be sequenced attached onto a support, or attaching a nucleic acid molecule to be sequenced onto a support;
   (2) adding a primer for initiating a nucleotide polymerization, a polymerase for performing the nucleotide polymerization, and the first, second, third and fourth compounds which have structures of formula (I), formula (II), formula (III), and formula (IV), respectively, to form a reaction system comprising a solution phase and a solid phase:

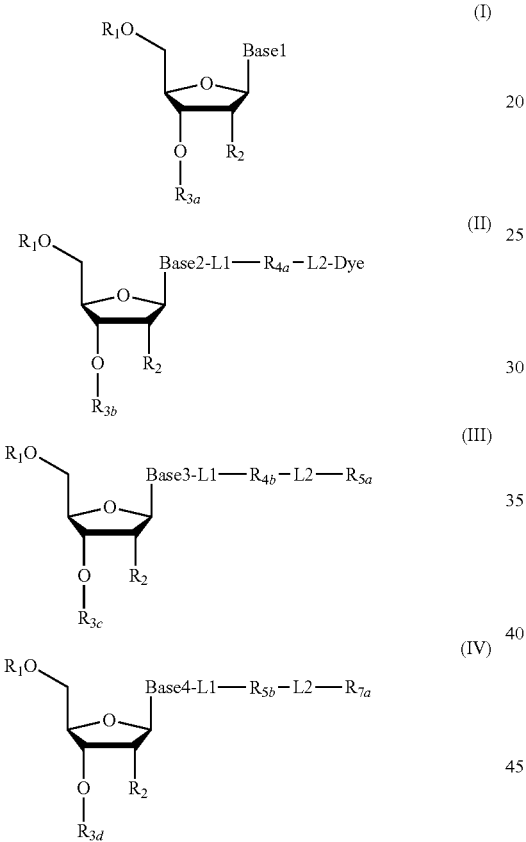

wherein, Base1, Base2, Base3, and Base4 represent 4 different bases, and are selected from A, T/U, C, and G;

$R_1$ is independently selected from —H, —$PO_3H_2$, —$PO_3H$—$PO_3H_2$, —$PO_3H$—$PO_3H$—$PO_3H_2$ and —$PO_3H$—$PO_3H$—$PO_3H$—$PO_3H_2$;

$R_2$ is independently selected from —H and —OH;

$R_{3a}$, $R_{3b}$, $R_{3c}$, and $R_{3d}$ are —$CH_2$—$N_3$;

$R_{4a}$ and $R_{4b}$ are

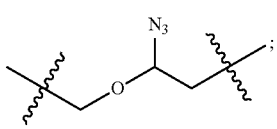

$R_{5a}$ is

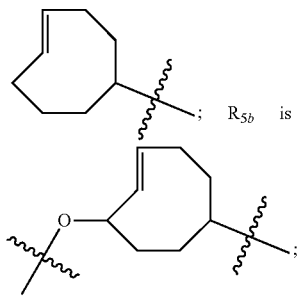

; $R_{5b}$ is

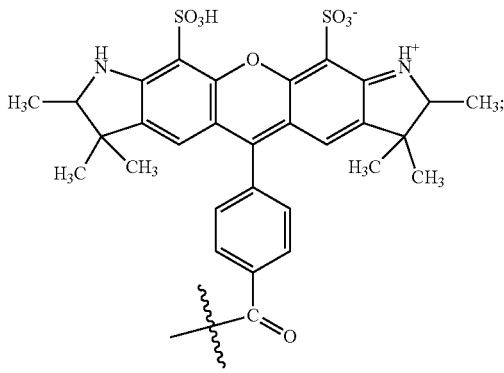

L1 is independently a linking group or absent;
L2 is independently a linking group or absent;
Dye represents a fluorophore capable of emitting a fluorescent signal;
$R_{7a}$ is $Dye_1$, and Dye and $Dye_1$ have the same structure, or have different structures but have the same or substantially the same emission spectrum;
optionally, Dye and $R_{7a}$ are AF532 which has a structure of the following:

(3) annealing the primer to the nucleic acid molecule to be sequenced, wherein the primer serves as an initial growing nucleic acid strand, and forms a duplex attached to the support together with the nucleic acid molecule to be sequenced;
(4) performing a nucleotide polymerization reaction using the polymerase under a condition allowing the polymerase to perform the nucleotide polymerization, thereby incorporating one of the four compounds at the 3' end of the growing nucleic acid strand;
(5) removing the solution phase of the reaction system of the previous step, retaining the duplex attached to the support, and detecting whether the duplex or the growing nucleic acid strand emits the fluorescent signal; or
(6) subjecting the duplex or the growing nucleic acid strand to a treatment in a reaction system containing a solution phase and a solid phase, wherein the treatment has no effect on the first compound and the second compound, and enables $R_{5a}$ in the third compound to perform the first bioorthogonal ligation reaction with an agent carrying a fluorophore, thereby the fluorophore in the agent is introduced into the third compound and make the third compound to emit a fluorescent signal; and said agent enables $R_{5b}$ in the fourth compound to perform the bioorthogonal cleavage reaction, thereby removing the fluorophore in the fourth compound;
optionally, the agent carrying a fluorophore is 1,2,4,5-tetrazine derivative having a structure as the following:

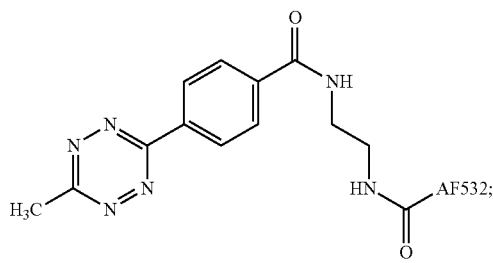

and (7) removing the solution phase of the reaction system in the previous step, retaining the duplex attached to the support, and detecting whether the duplex or the growing nucleic acid strand emits the fluorescent signal;
optionally, the method further comprises the following steps:
(8) subjecting the duplex or the growing nucleic acid strand in the previous step to a treatment in a reaction system containing a solution phase and a solid phase, wherein the treatment enables $R_{3a}$, $R_{3b}$, $R_{3c}$, $R_{3d}$, $R_{4a}$ and $R_{4b}$ to perform the bioorthogonal cleavage reaction, thereby allowing the compound incorporated at the 3' end of the growing nucleic acid strand to have a free hydroxyl group at the 3' position of the ribose or deoxyribose, in other words, converting —$OR_{3a}$, —$OR_{3b}$, —$OR_{3c}$ or —$OR_{3d}$ if present into a free hydroxyl group, and, removing the fluorophore on the duplex or the growing nucleic acid strand in other words, removing the fluorophore attached to $R_{4a}$ or $R_{4b}$, if present;
(9) removing the solution phase of the reaction system in the previous step;
(10) adding a polymerase for performing a nucleotide polymerization, and the first compound, the second compound, the third compound, and the fourth compound, thereby forming a reaction system containing a solution phase and a solid phase, and then performing the steps (4)-(7);
optionally, the method further comprises the step of:
(11) repeating steps (8)-(10) one or more times;
optionally, the first compound has the structure shown in formula (Ia):

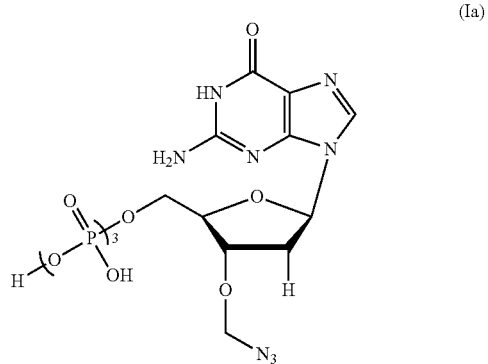

the second compound has the structure shown in formula (IIa):

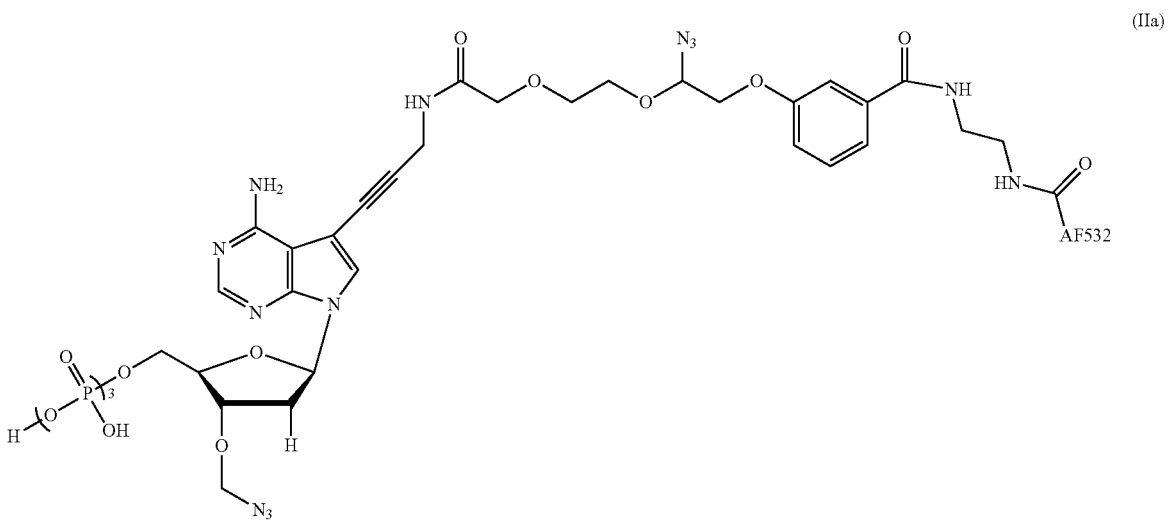

the third compound has the structure shown in formula (IIIa):

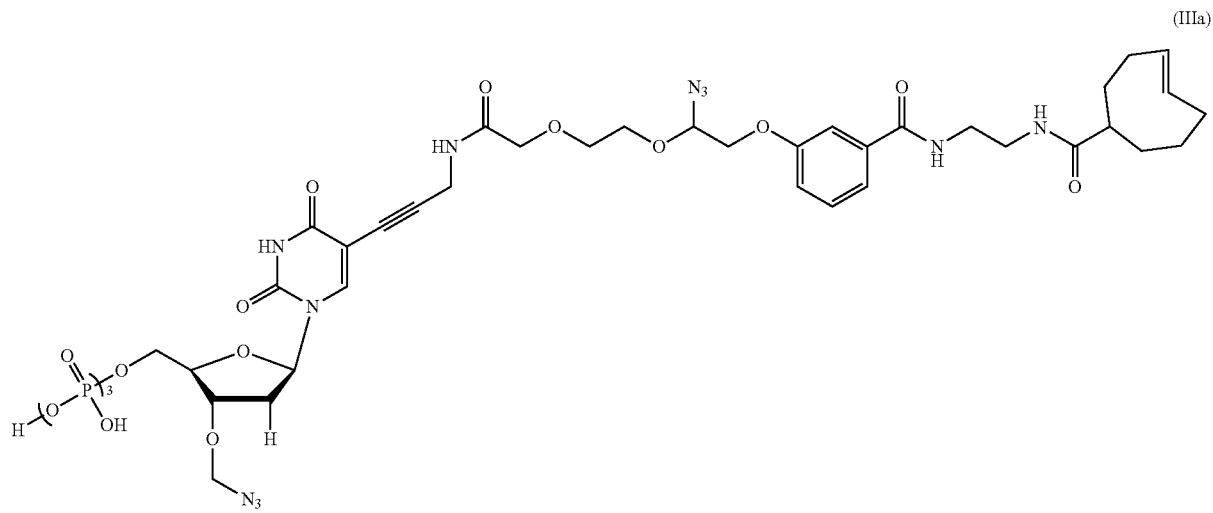

the fourth compound has the structure shown in formula (IVa):

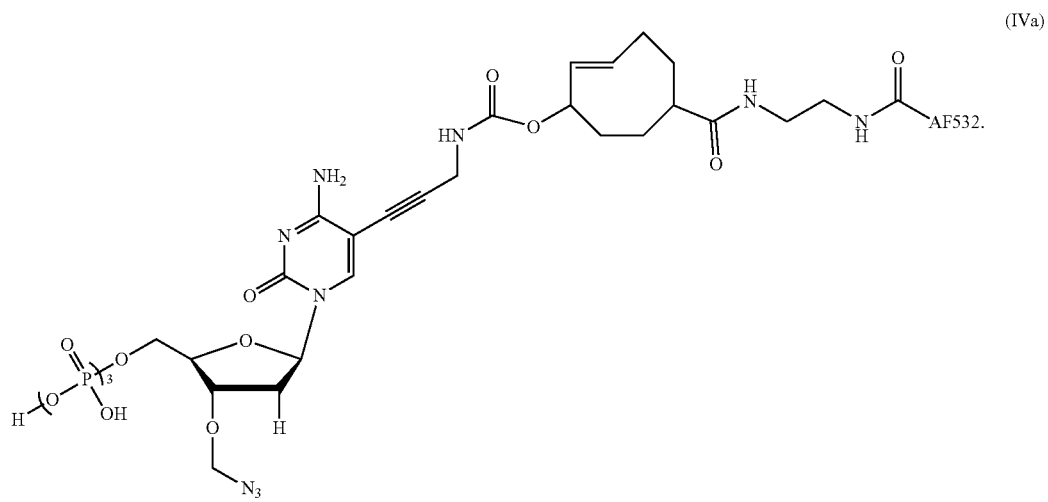

2. A method of sequencing a nucleic acid molecule, comprising the steps of:
(1) providing a nucleic acid molecule to be sequenced attached onto a support, or attaching the nucleic acid molecule to be sequenced onto a support;
(2) adding a primer for initiating a nucleotide polymerization, a polymerase for performing the nucleotide polymerization, and the first, second, third and fourth compounds having structures of formula (I), formula (II), formula (III), and formula (IV), respectively, to form a reaction system comprising a solution phase and a solid phase:

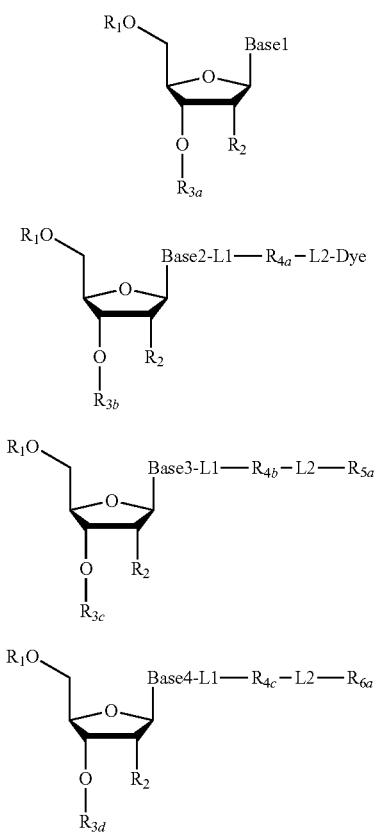

(I)

(II)

(III)

(IV)

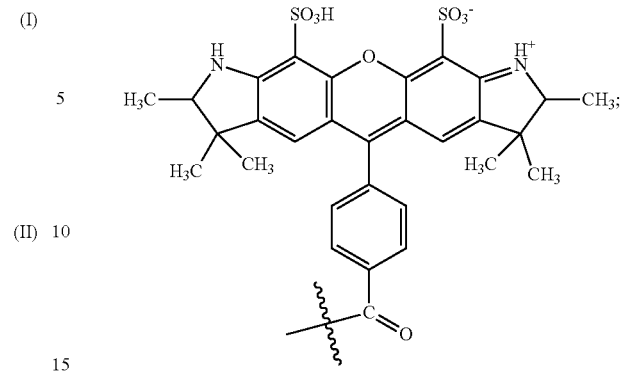

wherein, Base1, Base2, Base3, and Base4 represent 4 different bases, and are selected from A, T/U, C, and G;

$R_1$ is independently selected from —H, —PO$_3$H$_2$, —PO$_3$H—PO$_3$H$_2$, —PO$_3$H—PO$_3$H—PO$_3$H$_2$ and —PO$_3$H—PO$_3$H—PO$_3$H—PO$_3$H$_2$;

$R_2$ is independently selected from —H and —OH;

$R_{3a}$, $R_{3b}$, $R_{3c}$, and $R_{3d}$ are —CH$_2$—N$_3$;

$R_{4a}$, $R_{4b}$ and $R_{4c}$ are

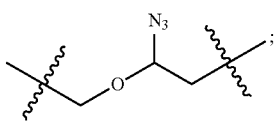

$R_{5a}$ is one member of the first binding pair, and optionally is biotin;

$R_{6a}$ is one member of the third binding pair and is Dye$_1$; optionally, $R_{6a}$ is Cy3;

L1 is independently a linking group or absent;

L2 is independently a linking group or absent;

L3 is a linking group or absent;

Dye and Dye$_1$ represent fluorophore capable of emitting a fluorescent signal; and, both of them have the same structure, or have different structures but have the same or substantially the same emission spectrum;

optionally, Dye represents AF532 which has a structure as the following:

(3) annealing the primer to the nucleic acid molecule to be sequenced, wherein the primer serves as an initial growing nucleic acid strand, and forms a duplex attached to the support together with the nucleic acid molecule to be sequenced;

(4) performing a nucleotide polymerization reaction using the polymerase under a condition allowing the polymerase to perform the nucleotide polymerization, thereby incorporating one of the four compounds at the 3' end of the growing nucleic acid strand;

(5) removing the solution phase of the reaction system in the previous step, retaining the duplex attached to the support, and detecting whether the duplex or the growing nucleic acid strand emits the fluorescent signal;

(6) subjecting the duplex or the growing nucleic acid strand to a treatment in a reaction system containing a solution phase and a solid phase, wherein the treatment has no effect on the first compound and the second compound, and enables $R_{5a}$ in the third compound specifically bind to the other member of the first binding pair carrying a fluorophore, introducing the fluorophore into the third compound to make the third compound to emit a fluorescent signal; and said treatment makes $R_{6a}$ in the fourth compound specifically bind to the other member of the third binding pair carrying a quenching group to quench the fluorescent signal emitted by the fluorophore Cy3 in the fourth compound, the other member of the first binding pair carrying a fluorophore has the structure: $R_{5b}$-L5-Dye$_3$; wherein $R_{5b}$ is streptavidin, and L5 is independently a linking group or absent; Dye$_3$ represents AF532, which has a structure as the following:

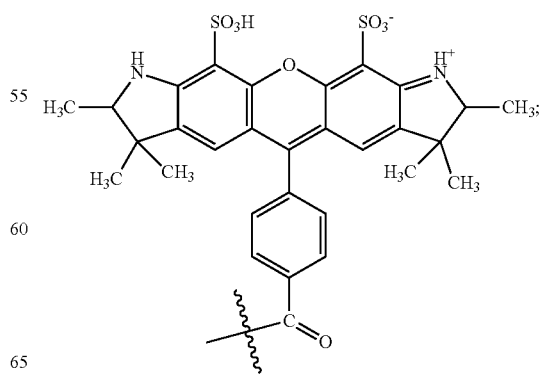

and, the other member of the third binding pair carrying the quenching group has the structure: $R_{6c}$-L6-Que; wherein $R_{6c}$ is Cy3 antibody, and L6 is independently a linking group or absent; Que represents BHQ2 which has a structure of the following:

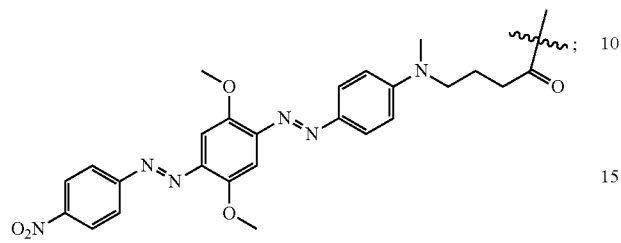

and (7) removing the solution phase of the reaction system in the previous step, retaining the duplex attached to the support, and detecting whether the duplex or the growing nucleic acid strand emits the fluorescent signal;

optionally, the method further comprises the steps of:

(8) subjecting the duplex or the growing nucleic acid strand in the previous step to a treatment in a reaction system containing a solution phase and a solid phase, wherein the treatment enables $R_{3a}$, $R_{3b}$, $R_{3c}$, $R_{3d}$, $R_{4a}$, $R_{4b}$, or $R_{4c}$ to perform the bioorthogonal cleavage reaction, making the compound incorporated at the 3' end of the growing nucleic acid strand has a free hydroxyl group at the 3' position of the ribose or deoxyribose, in other words, converting —$OR_{3a}$, —$OR_{3b}$, —$OR_{3c}$ or —$OR_{3d}$ if present into free hydroxyl group and removing the fluorophore on the duplex or the growing nucleic acid strand, in other words, removing the fluorophore attached to $R_{4a}$, $R_{4b}$ or $R_{4c}$, if present;

(9) removing the solution phase of the reaction system in the previous step;

(10) adding a polymerase for performing a nucleotide polymerization, and the first compound, the second compound, the third compound, and the fourth compound, thereby forming a reaction system containing a solution phase and a solid phase, and then performing the steps (4)-(7);

optionally, the method further comprises the step of:

(11) repeating steps (8)-(10) one or more times;

wherein, the first compound has the structure shown in formula (Ib):

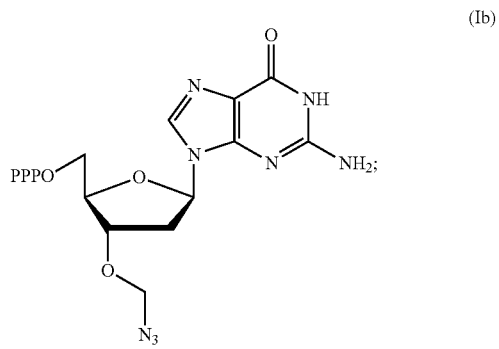

the second compound has the structure shown in formula (IIb):

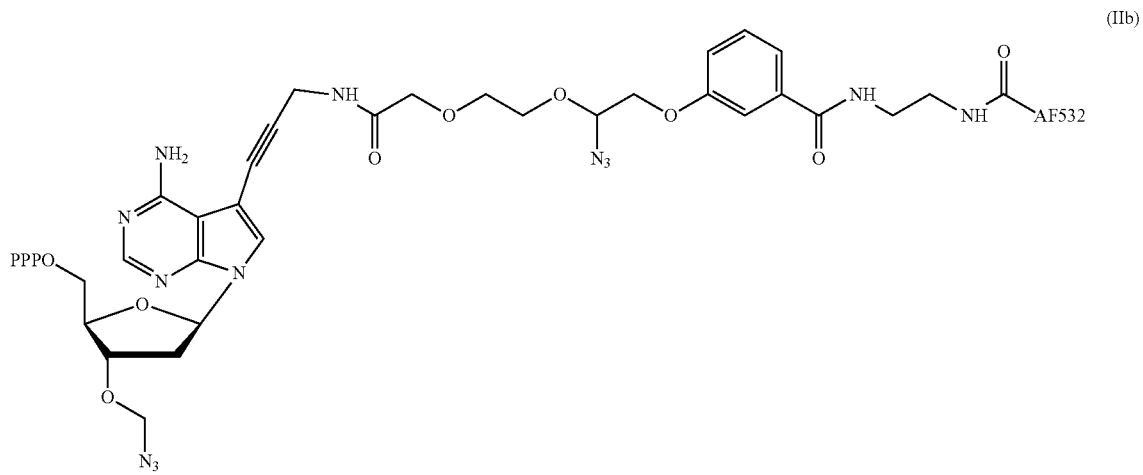

the third compound has the structure shown in formula (IIIb):

(IIIb)

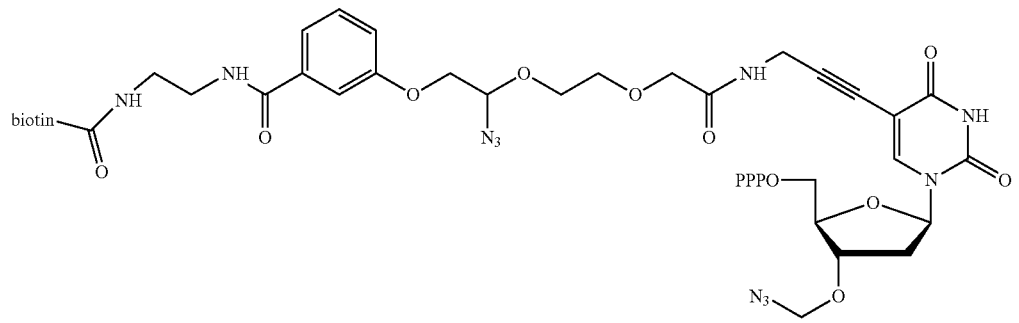

the fourth compound has the structure shown in formula (IVb):

(IVb)

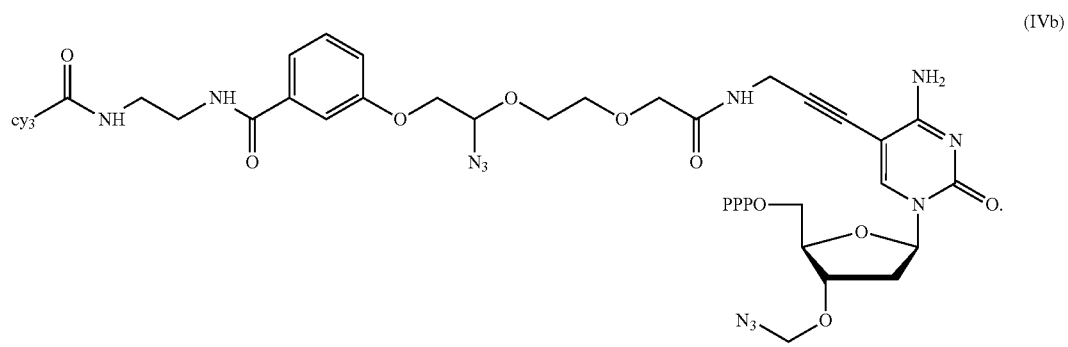

3. A method of sequencing a nucleic acid molecule, comprising the steps of:
  (1) providing a nucleic acid molecule to be sequenced attached onto a support, or attaching a nucleic acid molecule to be sequenced onto a support;
  (2) adding a primer for initiating a nucleotide polymerization, a polymerase for performing the nucleotide polymerization, and the first compound, the second compound, the third compound and the fourth compound having the structures of formula (I), formula (II), formula (III), and formula (IV), respectively, thereby to form a reaction system comprising a solution phase and a solid phase:

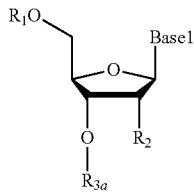

(I)

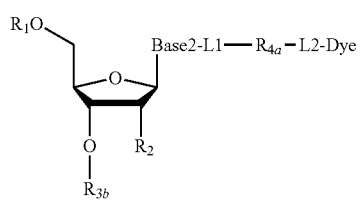

(II)

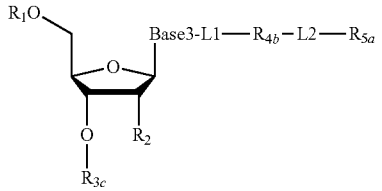

(III)

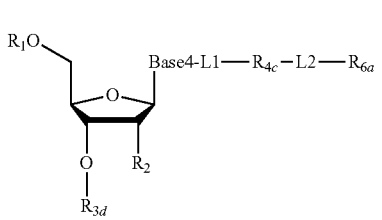

(IV)

wherein, Base1, Base2, Base3, and Base4 represent 4 different bases, and are selected from A, T/U, C, and G;
R$_1$ is independently selected from —H, —PO$_3$H$_2$, —PO$_3$H—PO$_3$H$_2$, —PO$_3$H—PO$_3$H—PO$_3$H$_2$ and —PO$_3$H—PO$_3$H—PO$_3$H—PO$_3$H$_2$;
R$_2$ is independently selected from —H and —OH;
R$_{3a}$, R$_{3b}$, R$_{3c}$ and R$_{3d}$ are —CH$_2$—N$_3$; R$_{4a}$, R$_{4b}$ and R$_{4c}$ are

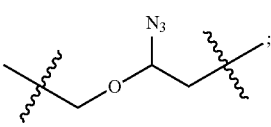 [SMILES: *COC(C*)N=[N+]=[N-]]

$R_{5a}$ is one member of the first binding pair, and is biotin;

L1 are independently a linking group or absent;

L2 are independently a linking group or absent;

$R_{6a}$ is AF532 (Dye$_1$) which has a structure as the following:

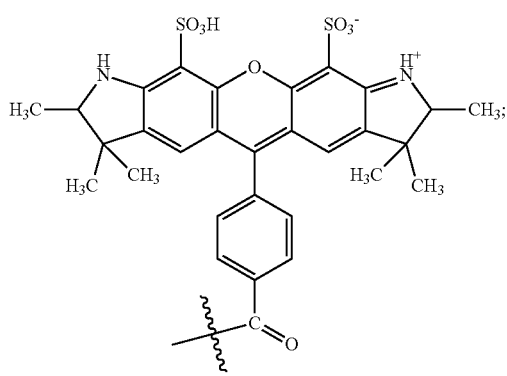

Dye represents a fluorophore capable of emitting a fluorescent signal; and, Dye and Dye$_1$ have the same structure, or have different structures but have the same or substantially the same emission spectrum;

optionally, Dye is AF532 which has a structure as the following:

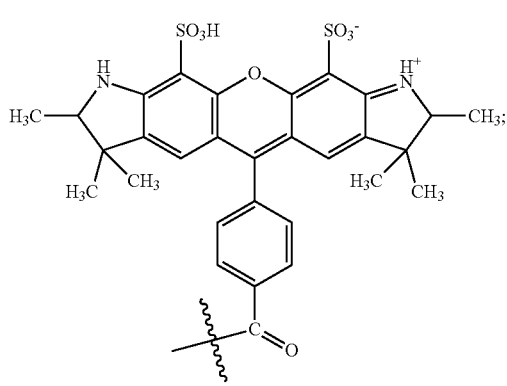

there is a reactive group $R_8$ capable of performing the second bioorthogonal ligation reaction between $R_{4c}$ and $R_{6a}$; $R_8$ is

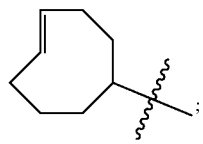 [SMILES: *C1CC/C=C/CCC1]

(3) annealing the primer to the nucleic acid molecule to be sequenced, wherein the primer serves as an initial growing nucleic acid strand, and forms a duplex attached to the support together with the nucleic acid molecule to be sequenced;

(4) performing a nucleotide polymerization reaction using the polymerase under a condition allowing the polymerase to perform the nucleotide polymerization, thereby incorporating one of the four compounds at the 3' end of the growing nucleic acid strand;

(5) removing the solution phase of the reaction system of the previous step, retaining the duplex attached to the support, and detecting whether the chain or the growing nucleic acid strand emits the fluorescent signal;

(6) subjecting the duplex or the growing nucleic acid strand to a treatment in a reaction system containing a solution phase and a solid phase, wherein the treatment has no effect on the first compound and the second compound, and enables $R_{5a}$ in the third compound to specifically bind to the other member of the first binding pair carrying a fluorophore to introduce the fluorophore into the third compound to make the third compound to emit a fluorescent signal; wherein the treatment enables $R_8$ in the fourth compound to perform the second orthogonal ligation reaction with a compound carrying a quenching group, thereby quenching the fluorescent signal emitted by the fluorophore Dye$_1$ in the fourth compound; wherein, the other member of the first binding pair carrying a fluorophore has the following structure: $R_{5b}$-L-Dye$_2$; wherein $R_{5b}$ is streptavidin, L is independently a linking group or absent; Dye$_2$ represents AF532 which has a structure as the following:

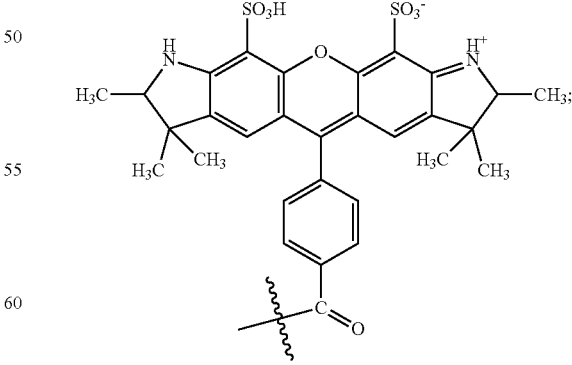

and the compound carrying a quenching group is 1,2,4,5-tetrazine BHQ2 having a structure as the following:

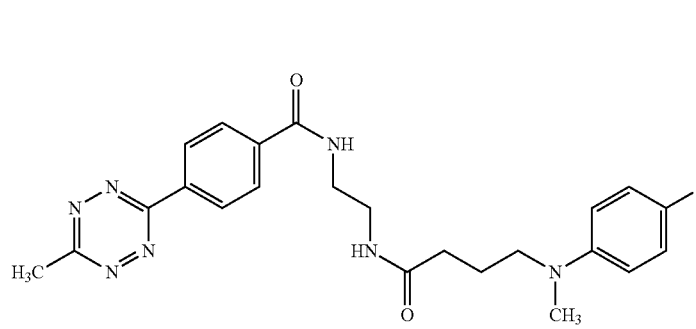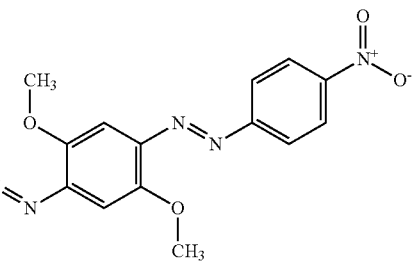

(7) removing the solution phase of the reaction system in the previous step, retaining the duplex attached to the support, and detecting whether the duplex or the growing nucleic acid strand emits the fluorescent signal;

optionally, the method further comprises the steps of:

(8) subjecting the duplex or the growing nucleic acid strand in the previous step to a treatment in a reaction system containing a solution phase and a solid phase, wherein the treatment enables $R_{3a}$, $R_{3b}$, $R_{3c}$, $R_{3d}$, $R_{4a}$ and $R_{4b}$ to perform the bioorthogonal cleavage reaction, thereby allowing the compound incorporated at the 3' end of the growing nucleic acid strand to have a free hydroxyl group at the 3' position of the ribose or deoxyribose, in other words, converting —$OR_{3a}$, —$OR_{3b}$, —$OR_{3c}$ or —$OR_{3d}$ if present into a free hydroxyl group and removing the fluorophore on the duplex or the growing nucleic acid strand, in other words, removing the fluorophore attached to $R_{4a}$ or $R_{4b}$ if present;

(9) removing the solution phase of the reaction system in the previous step;

(10) adding a polymerase for performing a nucleotide polymerization, and the first compound, the second compound, the third compound, and the fourth compound, thereby forming a reaction system containing a solution phase and a solid phase, and then performing the steps (4)-(7);

optionally, the method further comprises the step of:

(11) repeating steps (8)-(10) one or more times;

optionally, the first compound has the structure shown in formula (Ic):

(Ic)

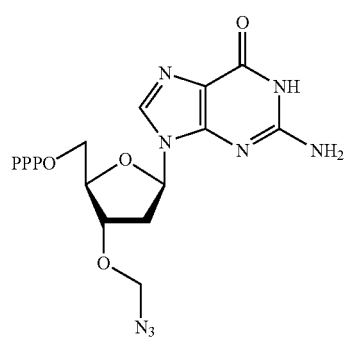

the second compound has the structure shown in formula (IIc):

(IIc)

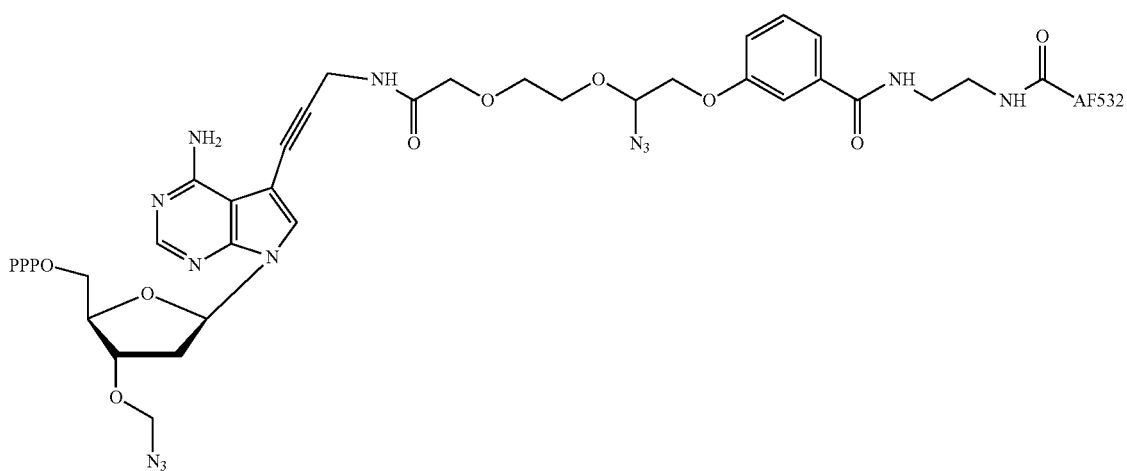

the third compound has the structure shown in formula (IIIc):

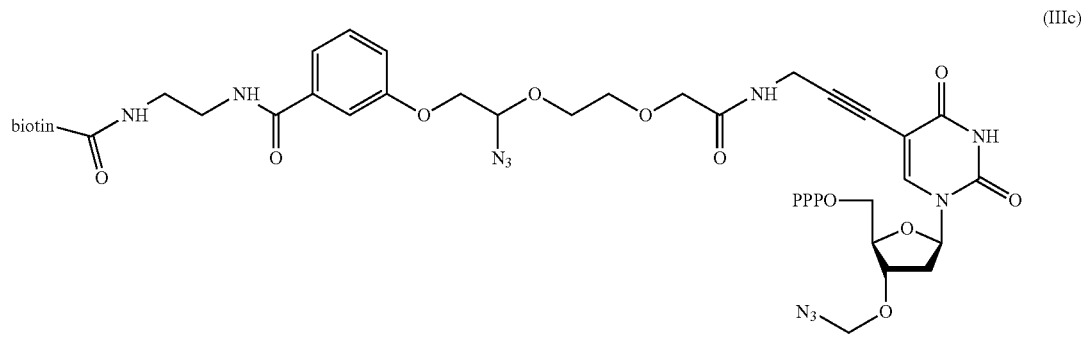
(IIIc)

the fourth compound has the structure shown in formula (IVc):

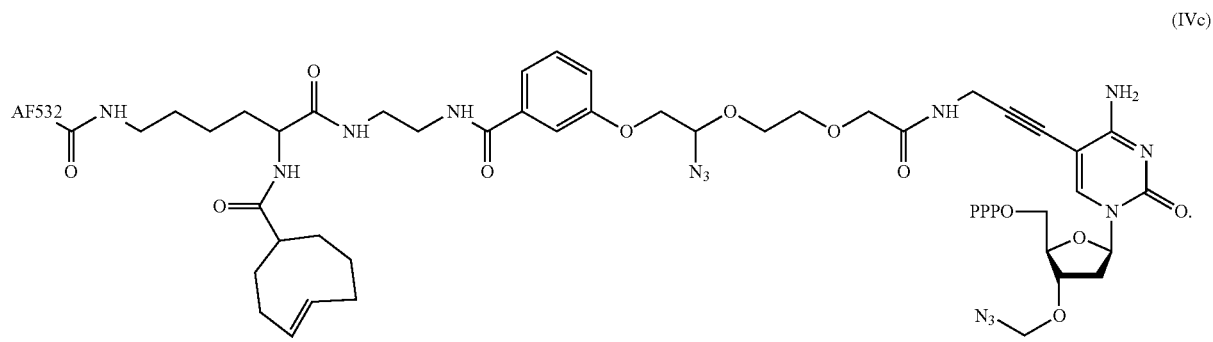
(IVc)

4. A kit comprising the first, second, third and fourth compounds as defined in claim 1,
optionally, the kit further comprises 1,2,4,5-tetrazine derivative having a structure as the following:

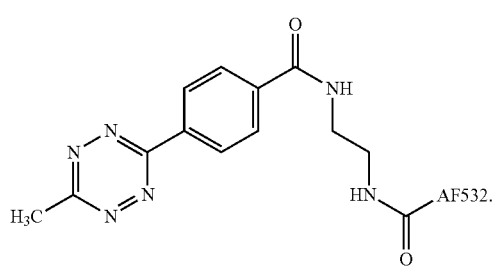

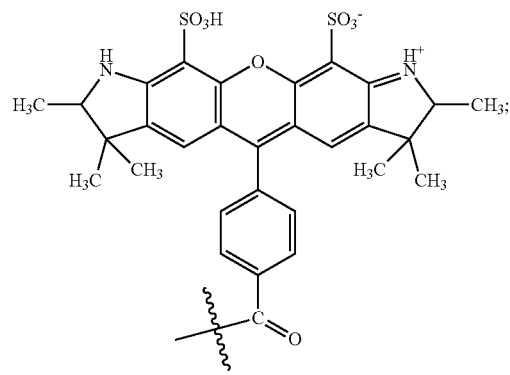

5. A kit comprising the first, second, third and fourth compounds as defined in claim 2,
optionally, the kit further comprises:

$R_{5b}$-L5-Dye$_3$, wherein $R_{5b}$ is streptavidin, L5 is independently a linking group or absent, and Dye$_3$ represents AF532 which has a structure as the following:

and/or $R_{6c}$-L6-Que, wherein $R_{6c}$ is Cy3 antibody, L6 is independently a linking group or absent; Que represents BHQ2 which has a structure of the following:

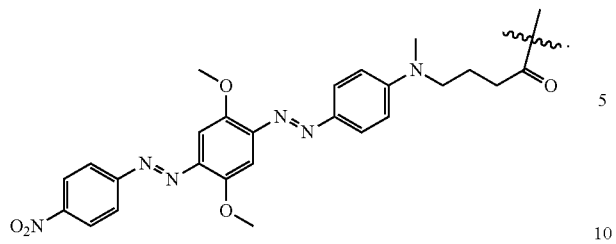
6. A kit comprising the first, second, third and fourth compounds as defined in claim 3,
optionally, the kit further comprises:
$R_{5b}$-L-$Dye_2$, wherein $R_{5b}$ is streptavidin, L is independently a linking group or absent, and $Dye_2$ represents AF532 which has a structure as the following:
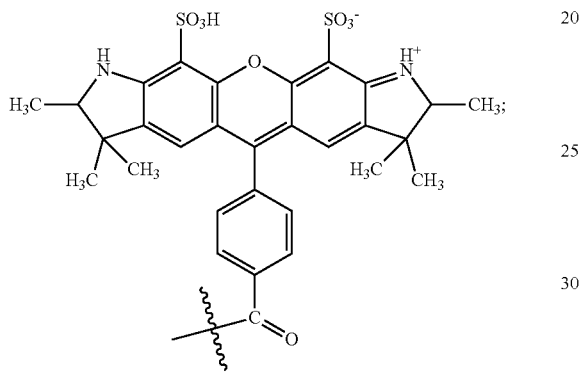
and/or
1,2,4,5-tetrazine BHQ2 having a structure as the following:
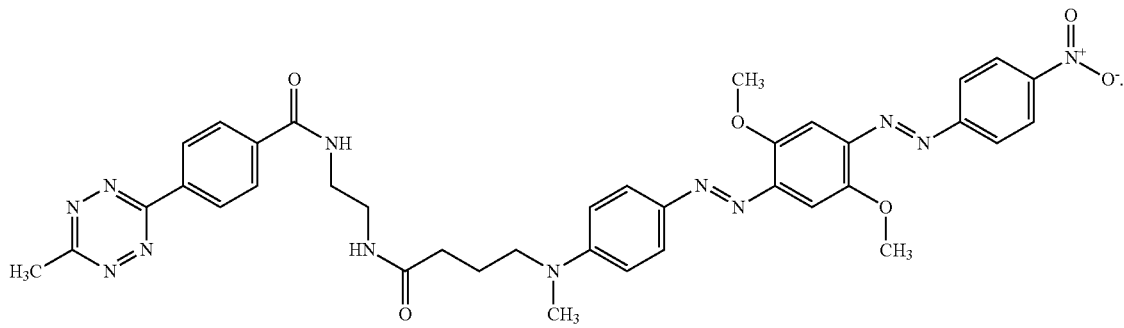
* * * * *

SEQUENCE LISTING

```
<160> NUMBER OF SEQ ID NOS: 36

<210> SEQ ID NO 1
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 1
taggtccgat                                                           10

<210> SEQ ID NO 2
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 2
ggacggaatc                                                           10

<210> SEQ ID NO 3
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 3
cttactgccg                                                           10

<210> SEQ ID NO 4
<211> LENGTH: 10
<212> TYPE: DNA
```

```
<213> ORGANISM: Artificial Sequence
<220> FEATURE:
<223> OTHER INFORMATION: Synthetic oligonucleotide

<400> SEQUENCE: 4
acctaattga                                                              10

<210> SEQ ID NO 5
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 5
ttcgtatccg                                                              10

<210> SEQ ID NO 6
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 6
ggtaacgagc                                                              10

<210> SEQ ID NO 7
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 7
caacgtataa                                                              10

<210> SEQ ID NO 8
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 8
acgtcgcgtt                                                              10

<210> SEQ ID NO 9
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 9
ttctgctagc                                                              10

<210> SEQ ID NO 10
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 10
aggaagatag                                                              10
```

<210> SEQ ID NO 11
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 11
gctcttgctt                                                            10

<210> SEQ ID NO 12
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 12
caagcacgca                                                            10

<210> SEQ ID NO 13
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 13
cggcaatccg                                                            10

<210> SEQ ID NO 14
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 14
atcaggattc                                                            10

<210> SEQ ID NO 15
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 15
tcattccaga                                                            10

<210> SEQ ID NO 16
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 16
gatgctggat                                                            10

<210> SEQ ID NO 17
<211> LENGTH: 10
<212> TYPE: DNA
<213> ORGANISM: Artificial Sequence
<220> FEATURE:

<223> OTHER INFORMATION: Synthetic oligonucleotide

<400> SEQUENCE: 17
gtgagtgatg    10

<210> SEQ ID NO 18
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 18
gagtcagctg    10

<210> SEQ ID NO 19
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 19
tgtctgcgaa    10

<210> SEQ ID NO 20
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 20
attggtacaa    10

<210> SEQ ID NO 21
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 21
cgattgtggt    10

<210> SEQ ID NO 22
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 22
acagacttcc    10

<210> SEQ ID NO 23
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 23
tccacactct    10

```
<210> SEQ ID NO 24
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 24
caccacaagc                                                                 10

<210> SEQ ID NO 25
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 25
tagaggacaa                                                                 10

<210> SEQ ID NO 26
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 26
cctagcgaat                                                                 10

<210> SEQ ID NO 27
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 27
gtagtcatcg                                                                 10

<210> SEQ ID NO 28
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 28
gctgagctgt                                                                 10

<210> SEQ ID NO 29
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 29
aacctagata                                                                 10

<210> SEQ ID NO 30
<211> LENGTH: 10
<212> TYPE: DNA
<213> ORGANISM: Artificial Sequence
<220> FEATURE:
<223> OTHER INFORMATION: Synthetic oligonucleotide
```

```
<400> SEQUENCE: 30
ttgccatctc                                                          10

<210> SEQ ID NO 31
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 31
agatcttgcg                                                          10

<210> SEQ ID NO 32
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 32
cgctatcggc                                                          10

<210> SEQ ID NO 33
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 33
gcaacgatgg                                                          10

<210> SEQ ID NO 34
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 34
taatcgttca                                                          10

<210> SEQ ID NO 35
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 35
gttcgctcta                                                          10

<210> SEQ ID NO 36
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 36
tctcacacat                                                          10
```